US012799220B2

(12) United States Patent
Zhang et al.

(10) Patent No.: US 12,799,220 B2
(45) Date of Patent: Nov. 17, 2026

(54) ANTI-CD73-ANTI-PD-1 BISPECIFIC ANTIBODY AND USE THEREOF

(71) Applicant: Akeso Biopharma, Inc, Zhongshan (CN)

(72) Inventors: Peng Zhang, Zhongshan (CN); Baiyong Li, Zhongshan (CN); Yu Xia, Zhongshan (CN); Zhongmin Wang, Zhongshan (CN)

(73) Assignee: Akeso Biopharma, Inc, Zhongshan (CN)

( * ) Notice: Subject to any disclaimer, the term of this patent is extended or adjusted under 35 U.S.C. 154(b) by 1051 days.

(21) Appl. No.: 17/996,878

(22) PCT Filed: Apr. 22, 2021

(86) PCT No.: PCT/CN2021/089059
§ 371 (c)(1),
(2) Date: Oct. 21, 2022

(87) PCT Pub. No.: WO2021/213475
PCT Pub. Date: Oct. 28, 2021

(65) Prior Publication Data

US 2023/0151111 A1 May 18, 2023

(30) Foreign Application Priority Data

Apr. 22, 2020 (CN) ......................... 202010324783.4
Mar. 12, 2021 (CN) ......................... 202110270671.X

(51) Int. Cl.

| | |
|---|---|
| ***C07K 16/28*** | (2006.01) |
| ***A61K 47/68*** | (2017.01) |
| ***A61P 35/00*** | (2006.01) |
| ***C07K 16/40*** | (2006.01) |
| *A61K 39/00* | (2006.01) |

(52) U.S. Cl.
CPC ...... *C07K 16/2896* (2013.01); *A61K 47/6849* (2017.08); *A61K 47/6871* (2017.08); *A61P 35/00* (2018.01); *C07K 16/2818* (2013.01); *C07K 16/40* (2013.01); *A61K 2039/505* (2013.01); *C07K 2317/24* (2013.01); *C07K 2317/31* (2013.01); *C07K 2317/522* (2013.01); *C07K 2317/565* (2013.01); *C07K 2317/567* (2013.01); *C07K 2317/622* (2013.01); *C07K 2317/76* (2013.01); *C07K 2317/92* (2013.01)

(58) Field of Classification Search
CPC .. C07K 16/2896; C07K 2317/31; A61P 35/00
See application file for complete search history.

(56) References Cited

U.S. PATENT DOCUMENTS

| | | | |
|---|---|---|---|
| 4,816,567 A | 3/1989 | Cabilly et al. | |
| 11,066,465 B2 | 7/2021 | Perlroth et al. | |
| 11,578,128 B2 | 2/2023 | Li et al. | |
| 2016/0129108 A1 | 5/2016 | Sachsenmeier et al. | |
| 2019/0185569 A1 | 6/2019 | Li et al. | |
| 2020/0399389 A1* | 12/2020 | Wang | C07K 16/2896 |
| 2023/0159655 A1 | 5/2023 | Wang et al. | |
| 2024/0010728 A1 | 1/2024 | Li et al. | |

FOREIGN PATENT DOCUMENTS

| | | | | |
|---|---|---|---|---|
| CN | 106967172 | A * | 7/2017 | G01N 33/575 |
| CN | 106977602 | A | 7/2017 | |
| CN | 107001472 | A | 8/2017 | |
| CN | 109476740 | A | 3/2019 | |
| EP | 3505535 | A1 | 7/2019 | |
| EP | 3511346 | A1 | 7/2019 | |
| JP | 2023522365 | A | 5/2023 | |
| KR | 10-2019-0052677 | A | 5/2019 | |
| WO | 2011159877 | A2 | 12/2011 | |
| WO | 2017152085 | A1 | 9/2017 | |
| WO | 2019090347 | A8 | 6/2019 | |
| WO | 2019173291 | A1 | 9/2019 | |
| WO | 2019200256 | A1 | 10/2019 | |

OTHER PUBLICATIONS

Almagro JC, Fransson J. Humanization of antibodies. Front Biosci. Jan. 1, 2008;13:1619-33. (Year: 2008).*
Chen et al., Enhancement and destruction of antibody function by somatic mutation: unequal occurrence is controlled by V gene combinatorial associations. EMBO J. Jun. 15, 1995;14(12):2784-94. (Year: 1995).*
Edwards et al. The remarkable flexibility of the human antibody repertoire; isolation of over one thousand different antibodies to a single protein, BLyS. J Mol Biol Nov. 14, 2003;334(1):103-18. (Year: 2003).*
Koenig et al. Mutational landscape of antibody variable domains reveals a switch modulating the interdomain conformational dynamics and antigen binding. PNAS Jan. 24, 2017 114(4)E486-E495;firstpublished Jan. 5, 2017. (Year: 2017).*
Kussie et al. A single engineered amino acid substitution changes antibody fine specificity.J Immunol. Jan. 1, 1994;152(1):146-52. (Year: 1994).*
Machine translation of CN-106967172-A, published Jul. 21, 2017 << retrieved from Patentscope (WIPO Translate) on Jun. 11, 2026>> (Year: 2017).*
Extended European Search Report of European Patent Application No. 21792313.5, mailed Apr. 29, 2024.
International Search Report and English Translation of International Patent Application No. PCT/CN2021089059, mailed Jul. 21, 2021.
Office Action and English Translation of Japanese Patent Application No. 2022-564073, mailed Apr. 23, 2024.
Acierno et al., "Affinity maturation increases the stability and plasticity of the Fv domain of anti-protein antibodies," J Mol Biol., 2007, 374:130-146.

(Continued)

*Primary Examiner* — Aurora M Fontainhas
*Assistant Examiner* — Jennifer A Benavides
(74) *Attorney, Agent, or Firm* — Medler Ferro Woodhouse & Mills PLLC

(57) ABSTRACT

Provided are an anti-CD73-anti-PD-1 bispecific antibody, a pharmaceutical composition thereof and a use thereof.

25 Claims, 18 Drawing Sheets

Specification includes a Sequence Listing.

(56) References Cited

OTHER PUBLICATIONS

Alfthan et al., "Properties of a single-chain antibody containing different linker peptides," Protein Eng., 1995, 8(7):725-731.
Antonioli et al., "Immunity, inflammation and cancer: a leading role for adenosine," Nat Rev Cancer, 2013, 13(12):842-857.
Araki et al., "Interleukin-8 Is a Molecular Determinant of Androgen Independence and Progression in Prostate Cancer," Cancer Res., 2007, 67(14):6854-6862.
Bergqvist et al., "Vedolizumab treatment for immune checkpoint inhibitor-induced enterocolitis," Cancer Immunol Immunother., 2017, 66:581-592.
Bird et al., "Single-chain antigen-binding proteins," Science, 1988, 242(4877):423-426.
Chen et al., "The endogenous cell-fate factor dachshund restrains prostate epithelial cell migration via repression of cytokine secretion via a CXCL signaling module," Cancer Res., 2015, 75(10):1992-2004.
Choi et al., "Recombinant chimeric OKT3 scFv IgM antibodies mediate immune suppression while reducing T cell activation in vitro," Eur J Immunol., 2001, 31(1):94-106.
Chothia et al., "Conformations of immunoglobin hypervariable regions," Nature, 1989, 342:877-883.
Chothia & Lesk, "Canonical structures for the hypervariable regions of immunoglobins," J Mol Biol., 1987, 196:901-917.
Clark, "Antibody humanization: a case of the 'Emperor's new clothes'?", Immunol Today, 2000, 21(8):397-402.
Coloma & Morrison, "Design and production of novel tetravalent bispecific antibodies," Nat Biotechnol., 1997, 15(2):159-163.
Dahan et al., "FcγRs Modulate the Anti-tumor Activity of Antibodies Targeting the PD-1/PD-L1 Axis," Cancer Cell, 2015, 28(3):285-295.
Dull et al., "A Third-Generation Lentivirus Vector with a Conditional Packaging System," J Virol., 1998, 72(11):8463-8471.
Ehrenmann et al., "IMGT/3Dstructure-DB and IMGT/DomainGapAlign: a database and a tool for immunoglobulins or antibodies, T cell receptors, MHC, IgSF and MhcSF," Nucleic Acids Res., 2010, 38(Database issue):D301-D307.
Escudero-Lourdes et al., "Interleukin-8 (IL-8) over-production and autocrine cell activation are key factors in monomethylarsonous acid [MMA(III)]-induced malignant transformation of urothelial cells," Toxicol Appl Pharmacol., 2012, 258(1):10-18.
Fitzgerald & Lugovskoy, "Rational engineering of antibody therapeutics targeting multiple oncogene pathways," MAbs, 2011, 3(3):299-309.
Gomatou et al., "Immune checkpoint inhibitor-related pneumonitis," Respiration, 2020, 99(11):932-942.
Hage et al., "Crystals of a 1:1 complex between human interleukin-4 and the extracellular domain of its receptor α chain," Eur J Biochem., 1998, 258:831-836.
Hamanishi et al., "Programmed cell death 1 ligand 1 and tumor-infiltrating CD8+ T lymphocytes are prognostic factors of human ovarian cancer," Proc Natl Acad Sci USA, 2007, 104(9):3360-3365.
Held et al., "Advances in immunotherapy of chronic myeloid leukemia CML," Curr Cancer Drug Targets., 2013, 13(7):768-774. Abstract.
Holliger et al., "'Diabodies': Small bivalent and bispecific antibody fragments," Proc Natl Acad Sci USA, 1993, 90:6444-6448.
Homet et al., "Anti-PD-1 therapy in melanoma," Semin Oncol., 2015, 42(3):466-473.
Hu et al., "Minibody: A novel engineered anti-carcinoembryonic antigen antibody fragment (single-chain Fv-CH3) which exhibits rapid, high-level targeting of xenografts," Cancer Res., 1996, 56(13):3055-3061.
Huang et al., "AK131, an anti-PDI/CD73 bispecific antibody for cancer immune therapy," Cancer Res., 2022, 82(12 Suppl):5526:1-2. Abstract.
Huston et al., "Protein engineering of antibody binding sites: Recovery of specific activity in an anti-digoxin single-chain Fv analogue produced in *Escherichia coli*," Proc Natl Acad Sci USA, 1988, 85:5879-5883.
Inoue et al., "Interleukin 8 expression regulates tumorigenicity and metastasis in human bladder cancer," Cancer Res., 2000, 60(8):2290-2299.
Jones et al., "Replacing the complementarity-determining regions of a human antibody with those from a mouse," Nature, 1986, 321:522-525.
Joshi et al., "Immune checkpoint inhibitor-related hypophysitis and endocrine dysfunction: clinical review," Clin Endocrinol (Oxf), 2016, 85(3):331-339.
Kinder et al., "An Fc engineering approach that modulates antibody-dependent cytokine release without altering cell-killing functions," mAbs, 2015, 7(3):494-504.
Kipriyanov et al., "Bispecific Tandem Diabody for Tumor Therapy with Improved Antigen Binding and Pharmacokinetics," J Mol Biol., 1999, 293:41-56.
Köhler & Milstein, "Continuous cultures of fused cells secreting antibody of predefined specificity," Nature, 1975, 256:495-497.
Lo et al., "Role of MIF/CXCL8/CXCR2 signaling in the growth of nasopharyngeal carcinoma tumor spheres," Cancer Lett., 2013, 335(1):81-92.
Martins et al., "New therapeutic perspectives to manage refractory immune checkpoint-related toxicities," Lancet Oncol., 2019, 20(1):e54-e64.
Mian et al., "Fully human anti-interleukin 8 antibody inhibits tumor growth in orthotopic bladder cancer xenografts via down-regulation of matrix metalloproteases and nuclear factor-kappaB," Clin Cancer Res., 2003, 9(8):3167-3175.
Miller et al., "Stability engineering of scFvs for the development of bispecific and multivalent antibodies," Protein Eng Des Sel., 2010, 23(7):549-557.
Müller & Kontermann, "Bispecific antibodies for cancer immunotherapy: Current perspectives," BioDrugs, 2010, 24(2):89-98.
Poljak, "Production and structure of diabodies," Structure, 1994, 2:1121-1123.
Presta, "Antibody engineering," Curr Opin Biotechnol., 1992, 3:394-398.
Prieux-Klotz et al., "Immune Checkpoint Inhibitor-Induced Colitis: Diagnosis and Management," Targ Oncol., 2017, 12:301-308.
Regateiro et al., "CD73 and adenosine generation in the creation of regulatory microenvironments," Clin Exp Immunol., 2013, 171(1):1-7.
Reichmann et al., "Reshaping human antibodies for therapy," Nature, 1988, 332:323-327.
Roovers et al., "In vitro characterization of a monovalent and bivalent form of a fully human anti Ep-CAM phage antibody," Cancer Immunol Immunother., 2001, 50:51-59.
Shinohara et al., "Structure and chromosomal localization of the human PD-1 gene (PDCD1)," Genomics, 1994, 23:704-706.
S & L, "Depletion of intrinsic expression of Interleukin-8 in prostate cancer cells causes cell cycle arrest, spontaneous apoptosis and increases the efficacy of chemotherapeutic drugs," Mol Cancer, 2009, 8:57.
Spain et al., "Management of toxicities of immune checkpoint inhibitors," Cancer Treat Rev., 2016, 44:51-60.
Synnestvedt et al., "Ecto-5'-nucleotidase (CD73) regulation by hypoxia-inducible factor-1 mediates permeability changes in intestinal epithelia," J Clin Invest., 2002, 110(7):993-1002.
Tajiri et al., "Immune checkpoint inhibitor-related myocarditis," Jpn J Clin Oncol., 2017, 2017:1-6.
Zhang et al., "The binding of an anti-PD-1 antibody to FcγRI has a profound impact on its biological functions," Cancer Immunol Immunother., 2018, 67(7):1079-1090.
Zhong et al., "Dual blockade of the PD-1 checkpoint pathway and the adenosinergic negative feedback signaling pathway with a PD-1/CD73 bispecific antibody for cancer immune therapy," J Immunother Cancer, 2020, 8(Suppl 3):A422. Abstract.
Zimmerman, "5'-Nucleotidase: molecular structure and functional aspects," Biochem J., 1992, 285(Pt 2):345-365.

(56) References Cited

OTHER PUBLICATIONS

International Search Report of PCT/CN2021/089059, Jul. 21, 2021.
RN 2550560-20-6, STN Registry, Nov. 8, 2020.
Office Action in Malaysian Patent Application No. PI2022005864, mailed on May 24, 2025.
Office Action in Korean Patent Application No. 10-2022-7040580, mailed on Jun. 20, 2025.
RN 2550560-20-6, STN Registry, Dec. 8, 2020.
Office Action in Australian Patent Application No. 2021261803, mailed on Apr. 28, 2025.
Office Action in New Zealand Patent Application No. 794048, mailed on Jul. 30, 2025.
Delanoy, et al., "Haematological immune-related adverse events induced by anti-PD-1 or anti-PD-L1 immunotherapy: a descriptive observational study" *The Lancet. Haematology* 6(1):1-10 (2018).

* cited by examiner

SEQUENCE LISTING

<160> NUMBER OF SEQ ID NOS: 102

<210> SEQ ID NO 1
<211> LENGTH: 363
<212> TYPE: DNA
<213> ORGANISM: Artificial Sequence
<220> FEATURE:
<223> OTHER INFORMATION: Synthetic Artificial Sequence

<400> SEQUENCE: 1
gaggtgcagc tgcagcagtc cggaccagag ctggtgaagc ctggcgcctc catgcggatg 60
tcttgtaagg cctctggcta cagcttcacc ggctatacaa tgaactgggt gaagcagtct 120
cacggcaaga atctggagtg gatcggcctg atcaaccctt acaatgccgg caccagctat 180
aaccagaagt ttaagggcaa ggccaccctg acagtggaca agagctcctc taccgcctac 240
atggagctgc tgtccctgac atctgaggat agcgccgtgt actattgcgc ccggtccgag 300
tacagatatg gcggcgacta ctttgattat tggggccagg gcaccacact gacagtgagc 360
tcc 363

<210> SEQ ID NO 2
<211> LENGTH: 121
<212> TYPE: PRT
<213> ORGANISM: Artificial Sequence
<220> FEATURE:
<223> OTHER INFORMATION: Synthetic Artificial Sequence

<400> SEQUENCE: 2

Glu Val Gln Leu Gln Gln Ser Gly Pro Glu Leu Val Lys Pro Gly Ala
1 5 10 15

Ser Met Arg Met Ser Cys Lys Ala Ser Gly Tyr Ser Phe Thr Gly Tyr
20 25 30

```
Thr Met Asn Trp Val Lys Gln Ser His Gly Lys Asn Leu Glu Trp Ile
        35                  40                  45

Gly Leu Ile Asn Pro Tyr Asn Ala Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Ser Glu Tyr Arg Tyr Gly Gly Asp Tyr Phe Asp Tyr Trp Gly
            100                 105                 110

Gln Gly Thr Thr Leu Thr Val Ser Ser
        115                 120


<210> SEQ ID NO 3
<211> LENGTH: 8
<212> TYPE: PRT
<213> ORGANISM: Artificial Sequence
<220> FEATURE:
<223> OTHER INFORMATION: Synthetic Artificial Sequence

<400> SEQUENCE: 3

Gly Tyr Ser Phe Thr Gly Tyr Thr
1               5


<210> SEQ ID NO 4
<211> LENGTH: 8
<212> TYPE: PRT
<213> ORGANISM: Artificial Sequence
<220> FEATURE:
<223> OTHER INFORMATION: Synthetic Artificial Sequence

<400> SEQUENCE: 4

Ile Asn Pro Tyr Asn Ala Gly Thr
1               5


<210> SEQ ID NO 5
<211> LENGTH: 14
<212> TYPE: PRT
<213> ORGANISM: Artificial Sequence
<220> FEATURE:
<223> OTHER INFORMATION: Synthetic Artificial Sequence

<400> SEQUENCE: 5

Ala Arg Ser Glu Tyr Arg Tyr Gly Gly Asp Tyr Phe Asp Tyr
1               5                   10


<210> SEQ ID NO 6
<211> LENGTH: 339
<212> TYPE: DNA
<213> ORGANISM: Artificial Sequence
<220> FEATURE:
<223> OTHER INFORMATION: Synthetic Artificial Sequence

<400> SEQUENCE: 6

gacatcgtga tgacccagtc tccaagctcc ctggcaatga gcgtgggaca gaaggtgaca      60

atgtcttgta agtctagcca gagcctgctg aactcctcta atcagaagaa ctacctggcc     120

tggtatcagc agaagccagg ccagtctccc aagctgctgg tgtactttgc cagcaccagg     180

gagtccggag tgcctgacag attcatcggc tccggctctg gcacagactt caccctgaca     240

atcagctccg tgcaggcaga ggacctggca gattatttct gccagcagca ctacgacacc     300

ccttatacat ttggcggcgg caccaagctg gagatcaag                            339
```

<210> SEQ ID NO 7
<211> LENGTH: 113
<212> TYPE: PRT
<213> ORGANISM: Artificial Sequence
<220> FEATURE:
<223> OTHER INFORMATION: Synthetic Artificial Sequence

<400> SEQUENCE: 7

```
Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Asp Thr Pro Tyr Thr Phe Gly Gly Gly Thr Lys Leu Glu Ile
            100                 105                 110

Lys
```

<210> SEQ ID NO 8
<211> LENGTH: 12
<212> TYPE: PRT
<213> ORGANISM: Artificial Sequence
<220> FEATURE:
<223> OTHER INFORMATION: Synthetic Artificial Sequence

<400> SEQUENCE: 8

```
Gln Ser Leu Leu Asn Ser Ser Asn Gln Lys Asn Tyr
1               5                   10
```

<210> SEQ ID NO 9
<211> LENGTH: 3
<212> TYPE: PRT
<213> ORGANISM: Artificial Sequence
<220> FEATURE:
<223> OTHER INFORMATION: Synthetic Artificial Sequence

<400> SEQUENCE: 9

```
Phe Ala Ser
1
```

<210> SEQ ID NO 10
<211> LENGTH: 9
<212> TYPE: PRT
<213> ORGANISM: Artificial Sequence
<220> FEATURE:
<223> OTHER INFORMATION: Synthetic Artificial Sequence

<400> SEQUENCE: 10

```
Gln Gln His Tyr Asp Thr Pro Tyr Thr
1               5
```

<210> SEQ ID NO 11
<211> LENGTH: 25
<212> TYPE: PRT
<213> ORGANISM: Artificial Sequence
<220> FEATURE:
<223> OTHER INFORMATION: Synthetic Artificial Sequence

<400> SEQUENCE: 11

Glu Val Gln Leu Gln Gln Ser Gly Pro Glu Leu Val Lys Pro Gly Ala
1 5 10 15

Ser Met Arg Met Ser Cys Lys Ala Ser
20 25

<210> SEQ ID NO 12
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 12

Met Asn Trp Val Lys Gln Ser His Gly Lys Asn Leu Glu Trp Ile Gly
1 5 10 15

Leu

<210> SEQ ID NO 13
<211> LENGTH: 38
<212> TYPE: PRT
<213> ORGANISM: Artificial Sequence
<220> FEATURE:
<223> OTHER INFORMATION: Synthetic Artificial Sequence

<400> SEQUENCE: 13

Ser Tyr Asn Gln Lys Phe Lys Gly Lys Ala Thr Leu Thr Val Asp Lys
1 5 10 15

Ser Ser Ser Thr Ala Tyr Met Glu Leu Leu Ser Leu Thr Ser Glu Asp
20 25 30

Ser Ala Val Tyr Tyr Cys
35

<210> SEQ ID NO 14
<211> LENGTH: 11
<212> TYPE: PRT
<213> ORGANISM: Artificial Sequence
<220> FEATURE:
<223> OTHER INFORMATION: Synthetic Artificial Sequence

<400> SEQUENCE: 14

Trp Gly Gln Gly Thr Thr Leu Thr Val Ser Ser
1 5 10

<210> SEQ ID NO 15
<211> LENGTH: 26
<212> TYPE: PRT
<213> ORGANISM: Artificial Sequence
<220> FEATURE:
<223> OTHER INFORMATION: Synthetic Artificial Sequence

<400> SEQUENCE: 15

Asp Ile Val Met Thr Gln Ser Pro Ser Ser Leu Ala Met Ser Val Gly
1 5 10 15

Gln Lys Val Thr Met Ser Cys Lys Ser Ser
20 25

<210> SEQ ID NO 16
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 16

Leu Ala Trp Tyr Gln Gln Lys Pro Gly Gln Ser Pro Lys Leu Leu Val
1 5 10 15

Tyr

<210> SEQ ID NO 17
<211> LENGTH: 36
<212> TYPE: PRT
<213> ORGANISM: Artificial Sequence
<220> FEATURE:
<223> OTHER INFORMATION: Synthetic Artificial Sequence

<400> SEQUENCE: 17

Thr Arg Glu Ser Gly Val Pro Asp Arg Phe Ile Gly Ser Gly Ser Gly
1 5 10 15

Thr Asp Phe Thr Leu Thr Ile Ser Ser Val Gln Ala Glu Asp Leu Ala
20 25 30

Asp Tyr Phe Cys
35

<210> SEQ ID NO 18
<211> LENGTH: 10
<212> TYPE: PRT
<213> ORGANISM: Artificial Sequence
<220> FEATURE:
<223> OTHER INFORMATION: Synthetic Artificial Sequence

<400> SEQUENCE: 18

Phe Gly Gly Gly Thr Lys Leu Glu Ile Lys
1 5 10

<210> SEQ ID NO 19
<211> LENGTH: 363
<212> TYPE: DNA
<213> ORGANISM: Artificial Sequence
<220> FEATURE:
<223> OTHER INFORMATION: Synthetic Artificial Sequence

<400> SEQUENCE: 19
caggtgcagc tggtgcagtc tggagcagag gtggtgaagc caggagcctc tgtgaaggtg 60
agctgtaagg ccagcggcta ctccttcacc ggctatacaa tgaactgggt gaggcaggca 120
ccaggacaga atctggagtg gatcggcctg atcaaccctt acaatgccgg cacctcttat 180
aaccagaagt ttcagggcaa ggtgaccctg acagtggaca agtccacctc tacagcctac 240
atggagctga gctccctgcg gagcgaggat acagccgtgt actattgcgc ccggtccgag 300
tacagatatg gcggcgacta ctttgattat tggggccagg gcaccacact gaccgtgtct 360
agc 363

<210> SEQ ID NO 20
<211> LENGTH: 121
<212> TYPE: PRT
<213> ORGANISM: Artificial Sequence
<220> FEATURE:
<223> OTHER INFORMATION: Synthetic Artificial Sequence

<400> SEQUENCE: 20

Gln Val Gln Leu Val Gln Ser Gly Ala Glu Val Val Lys Pro Gly Ala
1 5 10 15

Ser Val Lys Val Ser Cys Lys Ala Ser Gly Tyr Ser Phe Thr Gly Tyr
20 25 30

Thr Met Asn Trp Val Arg Gln Ala Pro Gly Gln Asn Leu Glu Trp Ile
35 40 45

Gly Leu Ile Asn Pro Tyr Asn Ala Gly Thr Ser Tyr Asn Gln Lys Phe
50 55 60

Gln Gly Lys Val Thr Leu Thr Val Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ser Glu Tyr Arg Tyr Gly Gly Asp Tyr Phe Asp Tyr Trp Gly
100 105 110

Gln Gly Thr Thr Leu Thr Val Ser Ser
115 120

<210> SEQ ID NO 21
<211> LENGTH: 339
<212> TYPE: DNA
<213> ORGANISM: Artificial Sequence
<220> FEATURE:
<223> OTHER INFORMATION: Synthetic Artificial Sequence

<400> SEQUENCE: 21
gacatcgtga tgacccagtc cccaagctcc ctggccgtgt ctgtgggaga gcgggtgaca 60
atctcctgta agtctagcca gtctctgctg aactcctcta atcagaagaa ctacctggcc 120
tggtatcagc agaagcccgg ccaggcccct aagctgctga tctacttcgc ctctaccagg 180
gagagcggag tgccagacag attctctggc agcggctccg gcacagactt caccctgaca 240
atcagctccg tgcaggcaga ggacgtggca gattactatt gccagcagca ctacgatacc 300
ccctatacat ttggcggcgg caccaagctg gagatcaag 339

<210> SEQ ID NO 22
<211> LENGTH: 113
<212> TYPE: PRT
<213> ORGANISM: Artificial Sequence
<220> FEATURE:
<223> OTHER INFORMATION: Synthetic Artificial Sequence

<400> SEQUENCE: 22

Asp Ile Val Met Thr Gln Ser Pro Ser Ser Leu Ala Val Ser Val Gly
1 5 10 15

Glu Arg Val Thr Ile Ser Cys Lys Ser Ser Gln Ser Leu Leu Asn Ser
20 25 30

Ser Asn Gln Lys Asn Tyr Leu Ala Trp Tyr Gln Gln Lys Pro Gly Gln
35 40 45

Ala Pro Lys Leu Leu Ile Tyr Phe Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Val Gln Ala Glu Asp Val Ala Asp Tyr Tyr Cys Gln Gln
85 90 95

His Tyr Asp Thr Pro Tyr Thr Phe Gly Gly Gly Thr Lys Leu Glu Ile
100 105 110

Lys

<210> SEQ ID NO 23
<211> LENGTH: 339
<212> TYPE: DNA
<213> ORGANISM: Artificial Sequence
<220> FEATURE:
<223> OTHER INFORMATION: Synthetic Artificial Sequence

<400> SEQUENCE: 23
gacatcgtga tgacccagtc cccaagctcc ctggccgtgt ctgtgggaga gcgggtgaca 60
atctcctgta agtctagcca gtctctgctg aactcctcta atcagaagaa ctacctggcc 120
tggtatcagc agaagcccgg ccaggcccct aagctgctga tctacttcgc ctctaccagg 180
gagagcggag tgccagacag attctctggc agcggctccg gcacagactt caccctgaca 240
atcagctccc tgcaggcaga ggacgtggcc gtgtactatt gccagcagca ctacgatacc 300
ccctatacat ttggcggcgg caccaagctg gagatcaag 339

<210> SEQ ID NO 24
<211> LENGTH: 113
<212> TYPE: PRT
<213> ORGANISM: Artificial Sequence
<220> FEATURE:
<223> OTHER INFORMATION: Synthetic Artificial Sequence

<400> SEQUENCE: 24

Asp Ile Val Met Thr Gln Ser Pro Ser Ser Leu Ala Val Ser Val Gly
1 5 10 15

Glu Arg Val Thr Ile Ser Cys Lys Ser Ser Gln Ser Leu Leu Asn Ser
20 25 30

Ser Asn Gln Lys Asn Tyr Leu Ala Trp Tyr Gln Gln Lys Pro Gly Gln
35 40 45

Ala Pro Lys Leu Leu Ile Tyr Phe Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

His Tyr Asp Thr Pro Tyr Thr Phe Gly Gly Gly Thr Lys Leu Glu Ile
100 105 110

Lys

<210> SEQ ID NO 25
<211> LENGTH: 1356
<212> TYPE: DNA
<213> ORGANISM: Artificial Sequence
<220> FEATURE:
<223> OTHER INFORMATION: Synthetic Artificial Sequence

<400> SEQUENCE: 25
caggtgcagc tggtgcagtc tggagcagag gtggtgaagc caggagcctc tgtgaaggtg 60
agctgtaagg ccagcggcta ctccttcacc ggctatacaa tgaactgggt gaggcaggca 120
ccaggacaga atctggagtg gatcggcctg atcaaccctt acaatgccgg cacctcttat 180
aaccagaagt ttcagggcaa ggtgaccctg acagtggaca agtccacctc tacagcctac 240
atggagctga gctccctgcg gagcgaggat acagccgtgt actattgcgc ccggtccgag 300
tacagatatg gcggcgacta ctttgattat tggggccagg gcaccacact gaccgtgtct 360
agcgcctcca caaaggggcc cagcgtgttt cctctcgccc cctcctccaa aagcaccagc 420
ggaggaaccg ctgctctcgg atgtctggtg aaggactact tccctgaacc cgtcaccgtg 480
agctggaata gcggcgctct gacaagcgga gtccatacat tccctgctgt gctgcaaagc 540
agcggactct attccctgtc cagcgtcgtc acagtgccca gcagcagcct gggcacccag 600

```
acctacatct gtaacgtcaa ccacaagccc tccaacacca aggtggacaa gaaagtggag    660

cccaaatcct gcgacaagac acacacctgt cccccctgtc ctgctcccga agctgctgga    720

ggccctagcg tcttcctctt tcctcccaaa cccaaggaca ccctcatgat cagcagaacc    780

cctgaagtca cctgtgtcgt cgtggatgtc agccatgagg accccgaggt gaaattcaac    840

tggtatgtcg atggcgtcga ggtgcacaac gccaaaacca agcccaggga ggaacagtac    900

aactccacct acagggtggt gtccgtgctg acagtcctcc accaggactg gctgaacggc    960

aaggagtaca agtgcaaggt gtccaacaag gctctccctg cccccattga gaagaccatc   1020

agcaaggcca aaggccaacc cagggagccc caggtctata cactgcctcc ctccagggac   1080

gaactcacca agaaccaggt gtccctgacc tgcctggtca agggctttta tcccagcgac   1140

atcgccgtcg agtgggagtc caacggacag cccgagaata actacaagac cacccctcct   1200

gtcctcgact ccgacggctc cttcttcctg tacagcaagc tgaccgtgga caaaagcagg   1260

tggcagcagg gaaacgtgtt ctcctgcagc gtgatgcacg aagccctcca caaccactac   1320

acccagaaaa gcctgtccct gagccccggc aaatga                              1356
```

```
<210> SEQ ID NO 26
<211> LENGTH: 451
<212> TYPE: PRT
<213> ORGANISM: Artificial Sequence
<220> FEATURE:
<223> OTHER INFORMATION: Synthetic Artificial Sequence

<400> SEQUENCE: 26

Gln Val Gln Leu Val Gln Ser Gly Ala Glu Val Val Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Asn Leu Glu Trp Ile
        35                  40                  45

Gly Leu Ile Asn Pro Tyr Asn Ala Gly Thr Ser Tyr Asn Gln Lys Phe
    50                  55                  60

Gln Gly Lys Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Glu Tyr Arg Tyr Gly Gly Asp Tyr Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

```
Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 27
<211> LENGTH: 660
<212> TYPE: DNA
<213> ORGANISM: Artificial Sequence
<220> FEATURE:
<223> OTHER INFORMATION: Synthetic Artificial Sequence

<400> SEQUENCE: 27

```
gacatcgtga tgacccagtc cccaagctcc ctggccgtgt ctgtgggaga gcgggtgaca     60

atctcctgta agtctagcca gtctctgctg aactcctcta atcagaagaa ctacctggcc    120

tggtatcagc agaagcccgg ccaggcccct aagctgctga tctacttcgc ctctaccagg    180

gagagcggag tgccagacag attctctggc agcggctccg gcacagactt caccctgaca    240

atcagctccc tgcaggcaga ggacgtggcc gtgtactatt gccagcagca ctacgatacc    300

ccctatacat ttggcggcgg caccaagctg gagatcaagc gtacggtggc agccccatct    360

gtcttcattt ttccccctag tgacgagcag ctgaaatccg gaacagcctc tgtggtctgt    420

ctgctgaaca atttctaccc tcgcgaagcc aaggtgcagt ggaaagtcga taacgctctg    480

cagagtggca attcacagga gagcgtgact gaacaggact ccaaggattc tacctatagt    540

ctgagctcca ctctgaccct gtccaaagca gattacgaaa agcacaaagt gtatgcctgt    600

gaggtcaccc accaggggct gagttctcca gtcaccaaat ccttcaacag aggcgaatgt    660
```

<210> SEQ ID NO 28

<211> LENGTH: 220
<212> TYPE: PRT
<213> ORGANISM: Artificial Sequence
<220> FEATURE:
<223> OTHER INFORMATION: Synthetic Artificial Sequence

<400> SEQUENCE: 28

```
Asp Ile Val Met Thr Gln Ser Pro Ser Ser Leu Ala Val Ser Val Gly
1               5                   10                  15

Glu Arg Val Thr Ile Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ala Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Asp Thr Pro Tyr Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 29
<211> LENGTH: 1356
<212> TYPE: DNA
<213> ORGANISM: Artificial Sequence
<220> FEATURE:
<223> OTHER INFORMATION: Synthetic Artificial Sequence

<400> SEQUENCE: 29

```
caggtgcagc tggtgcagtc tggagcagag gtggtgaagc caggagcctc tgtgaaggtg      60

agctgtaagg ccagcggcta ctccttcacc ggctatacaa tgaactgggt gaggcaggca     120

ccaggacaga atctggagtg gatcggcctg atcaaccctt acaatgccgg cacctcttat     180

aaccagaagt ttcagggcaa ggtgaccctg acagtggaca agtccacctc tacagcctac     240

atggagctga gctccctgcg gagcgaggat acagccgtgt actattgcgc ccggtccgag     300

tacagatatg gcggcgacta ctttgattat tggggccagg gcaccacact gaccgtgtct     360

agcgcctcca caaaggggcc cagcgtgttt cctctcgccc cctcctccaa aagcaccagc     420

ggaggaaccg ctgctctcgg atgtctggtg aaggactact tccctgaacc cgtcaccgtg     480

agctggaata gcggcgctct gacaagcgga gtccatacat tccctgctgt gctgcaaagc     540

agcggactct attccctgtc cagcgtcgtc acagtgccca gcagcagcct gggcacccag     600
```

```
acctacatct gtaacgtcaa ccacaagccc tccaacacca aggtggacaa gaaagtggag    660

cccaaatcct gcgacaagac acacacctgt ccccctgtc ctgctcccga agctgctgga    720

gcccctagcg tcttcctctt tcctcccaaa cccaaggaca ccctcatgat cagcagaacc    780

cctgaagtca cctgtgtcgt cgtggatgtc agccatgagg accccgaggt gaaattcaac    840

tggtatgtcg atggcgtcga ggtgcacaac gccaaaacca agcccaggga ggaacagtac    900

aactccacct acagggtggt gtccgtgctg acagtcctcc accaggactg gctgaacggc    960

aaggagtaca agtgcaaggt gtccaacaag gctctccctg cccccattga gaagaccatc   1020

agcaaggcca aaggccaacc cagggagccc caggtctata cactgcctcc ctccagggac   1080

gaactcacca agaaccaggt gtccctgacc tgcctggtca agggctttta tcccagcgac   1140

atcgccgtcg agtgggagtc caacggacag cccgagaata actacaagac cacccctcct   1200

gtcctcgact ccgacggctc cttcttcctg tacagcaagc tgaccgtgga caaaagcagg   1260

tggcagcagg gaaacgtgtt ctcctgcagc gtgatgcacg aagccctcca caaccactac   1320

acccagaaaa gcctgtccct gagccccggc aaatga                             1356
```

<210> SEQ ID NO 30
<211> LENGTH: 451
<212> TYPE: PRT
<213> ORGANISM: Artificial Sequence
<220> FEATURE:
<223> OTHER INFORMATION: Synthetic Artificial Sequence

<400> SEQUENCE: 30

```
Gln Val Gln Leu Val Gln Ser Gly Ala Glu Val Val Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Asn Leu Glu Trp Ile
        35                  40                  45

Gly Leu Ile Asn Pro Tyr Asn Ala Gly Thr Ser Tyr Asn Gln Lys Phe
    50                  55                  60

Gln Gly Lys Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Glu Tyr Arg Tyr Gly Gly Asp Tyr Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

Asp Lys Thr His Thr Cys Pro Pro Cys Pro Ala Pro Glu Ala Ala Gly
225 230 235 240

Ala Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Val
340 345 350

Tyr Thr Leu Pro Pro Ser Arg Asp Glu Leu Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 31
<211> LENGTH: 25
<212> TYPE: PRT
<213> ORGANISM: Artificial Sequence
<220> FEATURE:
<223> OTHER INFORMATION: Synthetic Artificial Sequence

<400> SEQUENCE: 31

Gln Val Gln Leu Val Gln Ser Gly Ala Glu Val Val Lys Pro Gly Ala
1 5 10 15

Ser Val Lys Val Ser Cys Lys Ala Ser
20 25

<210> SEQ ID NO 32
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 32

Met Asn Trp Val Arg Gln Ala Pro Gly Gln Asn Leu Glu Trp Ile Gly
1 5 10 15

Leu

<210> SEQ ID NO 33
<211> LENGTH: 38

<212> TYPE: PRT
<213> ORGANISM: Artificial Sequence
<220> FEATURE:
<223> OTHER INFORMATION: Synthetic Artificial Sequence

<400> SEQUENCE: 33

Ser Tyr Asn Gln Lys Phe Gln Gly Lys Val Thr Leu Thr Val Asp Lys
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 34
<211> LENGTH: 11
<212> TYPE: PRT
<213> ORGANISM: Artificial Sequence
<220> FEATURE:
<223> OTHER INFORMATION: Synthetic Artificial Sequence

<400> SEQUENCE: 34

Trp Gly Gln Gly Thr Thr Leu Thr Val Ser Ser
1               5                   10

<210> SEQ ID NO 35
<211> LENGTH: 26
<212> TYPE: PRT
<213> ORGANISM: Artificial Sequence
<220> FEATURE:
<223> OTHER INFORMATION: Synthetic Artificial Sequence

<400> SEQUENCE: 35

Asp Ile Val Met Thr Gln Ser Pro Ser Ser Leu Ala Val Ser Val Gly
1               5                   10                  15

Glu Arg Val Thr Ile Ser Cys Lys Ser Ser
            20                  25

<210> SEQ ID NO 36
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 36

Leu Ala Trp Tyr Gln Gln Lys Pro Gly Gln Ala Pro Lys Leu Leu Ile
1               5                   10                  15

Tyr

<210> SEQ ID NO 37
<211> LENGTH: 36
<212> TYPE: PRT
<213> ORGANISM: Artificial Sequence
<220> FEATURE:
<223> OTHER INFORMATION: Synthetic Artificial Sequence

<400> SEQUENCE: 37

Thr Arg Glu Ser Gly Val Pro Asp Arg Phe Ser Gly Ser Gly Ser Gly
1               5                   10                  15

Thr Asp Phe Thr Leu Thr Ile Ser Ser Val Gln Ala Glu Asp Val Ala
            20                  25                  30

Asp Tyr Tyr Cys
        35

<210> SEQ ID NO 38
<211> LENGTH: 10
<212> TYPE: PRT
<213> ORGANISM: Artificial Sequence
<220> FEATURE:
<223> OTHER INFORMATION: Synthetic Artificial Sequence

<400> SEQUENCE: 38

Phe Gly Gly Gly Thr Lys Leu Glu Ile Lys
1 5 10

<210> SEQ ID NO 39
<211> LENGTH: 26
<212> TYPE: PRT
<213> ORGANISM: Artificial Sequence
<220> FEATURE:
<223> OTHER INFORMATION: Synthetic Artificial Sequence

<400> SEQUENCE: 39

Asp Ile Val Met Thr Gln Ser Pro Ser Ser Leu Ala Val Ser Val Gly
1 5 10 15

Glu Arg Val Thr Ile Ser Cys Lys Ser Ser
20 25

<210> SEQ ID NO 40
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 40

Leu Ala Trp Tyr Gln Gln Lys Pro Gly Gln Ala Pro Lys Leu Leu Ile
1 5 10 15

Tyr

<210> SEQ ID NO 41
<211> LENGTH: 36
<212> TYPE: PRT
<213> ORGANISM: Artificial Sequence
<220> FEATURE:
<223> OTHER INFORMATION: Synthetic Artificial Sequence

<400> SEQUENCE: 41

Thr Arg Glu Ser Gly Val Pro Asp Arg Phe Ser Gly Ser Gly Ser Gly
1 5 10 15

Thr Asp Phe Thr Leu Thr Ile Ser Ser Leu Gln Ala Glu Asp Val Ala
20 25 30

Val Tyr Tyr Cys
35

<210> SEQ ID NO 42
<211> LENGTH: 10
<212> TYPE: PRT
<213> ORGANISM: Artificial Sequence
<220> FEATURE:
<223> OTHER INFORMATION: Synthetic Artificial Sequence

<400> SEQUENCE: 42

Phe Gly Gly Gly Thr Lys Leu Glu Ile Lys
1 5 10

<210> SEQ ID NO 43
<211> LENGTH: 354

```
<212> TYPE: DNA
<213> ORGANISM: Artificial Sequence
<220> FEATURE:
<223> OTHER INFORMATION: Synthetic Artificial Sequence

<400> SEQUENCE: 43

gaggtcaaac tggtggagag cggcggcggg ctggtgaagc ccggcgggtc actgaaactg      60

agctgcgccg cttccggctt cgcctttagc tcctacgaca tgtcatgggt gaggcagacc     120

cctgagaagc gcctggaatg ggtcgctact atcagcggag gcgggcgata cacctactat     180

cctgactctg tcaaagggag attcacaatt agtcgggata acgccagaaa tactctgtat     240

ctgcagatgt ctagtctgcg gtccgaggat acagctctgt actattgtgc aaaccggtac     300

ggcgaagcat ggtttgccta ttggggacag ggcaccctgg tgacagtctc tgcc           354


<210> SEQ ID NO 44
<211> LENGTH: 118
<212> TYPE: PRT
<213> ORGANISM: Artificial Sequence
<220> FEATURE:
<223> OTHER INFORMATION: Synthetic Artificial Sequence

<400> SEQUENCE: 44

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Thr Ile Ser Gly Gly Gly Arg Tyr Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Leu Tyr Tyr Cys
                85                  90                  95

Ala Asn Arg Tyr Gly Glu Ala Trp Phe Ala Tyr Trp Gly Gln Gly Thr
            100                 105                 110

Leu Val Thr Val Ser Ala
        115


<210> SEQ ID NO 45
<211> LENGTH: 8
<212> TYPE: PRT
<213> ORGANISM: Artificial Sequence
<220> FEATURE:
<223> OTHER INFORMATION: Synthetic Artificial Sequence

<400> SEQUENCE: 45

Gly Phe Ala Phe Ser Ser Tyr Asp
1               5


<210> SEQ ID NO 46
<211> LENGTH: 8
<212> TYPE: PRT
<213> ORGANISM: Artificial Sequence
<220> FEATURE:
<223> OTHER INFORMATION: Synthetic Artificial Sequence

<400> SEQUENCE: 46

Ile Ser Gly Gly Gly Arg Tyr Thr
1               5
```

<210> SEQ ID NO 47
<211> LENGTH: 11
<212> TYPE: PRT
<213> ORGANISM: Artificial Sequence
<220> FEATURE:
<223> OTHER INFORMATION: Synthetic Artificial Sequence

<400> SEQUENCE: 47

Ala Asn Arg Tyr Gly Glu Ala Trp Phe Ala Tyr
1 5 10

<210> SEQ ID NO 48
<211> LENGTH: 321
<212> TYPE: DNA
<213> ORGANISM: Artificial Sequence
<220> FEATURE:
<223> OTHER INFORMATION: Synthetic Artificial Sequence

<400> SEQUENCE: 48
gacattaaga tgacacagtc cccttcctca atgtacgcta gcctgggcga gcgagtgacc 60
ttcacatgca aagcatccca ggacatcaac acatacctgt cttggtttca gcagaagcca 120
ggcaaaagcc ccaagaccct gatctaccgg gccaatagac tggtggacgg ggtccccagc 180
agattctccg gatctggcag tgggcaggat tactccctga ccatcagctc cctggagtat 240
gaagacatgg gcatctacta ttgcctgcag tatgatgagt tccctctgac ctttggagca 300
ggcacaaaac tggaactgaa g 321

<210> SEQ ID NO 49
<211> LENGTH: 107
<212> TYPE: PRT
<213> ORGANISM: Artificial Sequence
<220> FEATURE:
<223> OTHER INFORMATION: Synthetic Artificial Sequence

<400> SEQUENCE: 49

Asp Ile Lys Met Thr Gln Ser Pro Ser Ser Met Tyr Ala Ser Leu Gly
1 5 10 15

Glu Arg Val Thr Phe Thr Cys Lys Ala Ser Gln Asp Ile Asn Thr Tyr
20 25 30

Leu Ser Trp Phe Gln Gln Lys Pro Gly Lys Ser Pro Lys Thr Leu Ile
35 40 45

Tyr Arg Ala Asn Arg Leu Val Asp Gly Val Pro Ser Arg Phe Ser Gly
50 55 60

Ser Gly Ser Gly Gln Asp Tyr Ser Leu Thr Ile Ser Ser Leu Glu Tyr
65 70 75 80

Glu Asp Met Gly Ile Tyr Tyr Cys Leu Gln Tyr Asp Glu Phe Pro Leu
85 90 95

Thr Phe Gly Ala Gly Thr Lys Leu Glu Leu Lys
100 105

<210> SEQ ID NO 50
<211> LENGTH: 6
<212> TYPE: PRT
<213> ORGANISM: Artificial Sequence
<220> FEATURE:
<223> OTHER INFORMATION: Synthetic Artificial Sequence

<400> SEQUENCE: 50

Gln Asp Ile Asn Thr Tyr
1 5

<210> SEQ ID NO 51
<211> LENGTH: 3
<212> TYPE: PRT
<213> ORGANISM: Artificial Sequence
<220> FEATURE:
<223> OTHER INFORMATION: Synthetic Artificial Sequence

<400> SEQUENCE: 51

Arg Ala Asn
1

<210> SEQ ID NO 52
<211> LENGTH: 9
<212> TYPE: PRT
<213> ORGANISM: Artificial Sequence
<220> FEATURE:
<223> OTHER INFORMATION: Synthetic Artificial Sequence

<400> SEQUENCE: 52

Leu Gln Tyr Asp Glu Phe Pro Leu Thr
1 5

<210> SEQ ID NO 53
<211> LENGTH: 25
<212> TYPE: PRT
<213> ORGANISM: Artificial Sequence
<220> FEATURE:
<223> OTHER INFORMATION: Synthetic Artificial Sequence

<400> SEQUENCE: 53

Glu Val Lys Leu Val Glu Ser Gly Gly Gly Leu Val Lys Pro Gly Gly
1 5 10 15

Ser Leu Lys Leu Ser Cys Ala Ala Ser
20 25

<210> SEQ ID NO 54
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 54

Met Ser Trp Val Arg Gln Thr Pro Glu Lys Arg Leu Glu Trp Val Ala
1 5 10 15

Thr

<210> SEQ ID NO 55
<211> LENGTH: 38
<212> TYPE: PRT
<213> ORGANISM: Artificial Sequence
<220> FEATURE:
<223> OTHER INFORMATION: Synthetic Artificial Sequence

<400> SEQUENCE: 55

Tyr Tyr Pro Asp Ser Val Lys Gly Arg Phe Thr Ile Ser Arg Asp Asn
1 5 10 15

Ala Arg Asn Thr Leu Tyr Leu Gln Met Ser Ser Leu Arg Ser Glu Asp
20 25 30

Thr Ala Leu Tyr Tyr Cys
35

<210> SEQ ID NO 56
<211> LENGTH: 11

<212> TYPE: PRT
<213> ORGANISM: Artificial Sequence
<220> FEATURE:
<223> OTHER INFORMATION: Synthetic Artificial Sequence

<400> SEQUENCE: 56

Trp Gly Gln Gly Thr Leu Val Thr Val Ser Ala
1 5 10

<210> SEQ ID NO 57
<211> LENGTH: 26
<212> TYPE: PRT
<213> ORGANISM: Artificial Sequence
<220> FEATURE:
<223> OTHER INFORMATION: Synthetic Artificial Sequence

<400> SEQUENCE: 57

Asp Ile Lys Met Thr Gln Ser Pro Ser Ser Met Tyr Ala Ser Leu Gly
1 5 10 15

Glu Arg Val Thr Phe Thr Cys Lys Ala Ser
20 25

<210> SEQ ID NO 58
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 58

Leu Ser Trp Phe Gln Gln Lys Pro Gly Lys Ser Pro Lys Thr Leu Ile
1 5 10 15

Tyr

<210> SEQ ID NO 59
<211> LENGTH: 36
<212> TYPE: PRT
<213> ORGANISM: Artificial Sequence
<220> FEATURE:
<223> OTHER INFORMATION: Synthetic Artificial Sequence

<400> SEQUENCE: 59

Arg Leu Val Asp Gly Val Pro Ser Arg Phe Ser Gly Ser Gly Ser Gly
1 5 10 15

Gln Asp Tyr Ser Leu Thr Ile Ser Ser Leu Glu Tyr Glu Asp Met Gly
20 25 30

Ile Tyr Tyr Cys
35

<210> SEQ ID NO 60
<211> LENGTH: 10
<212> TYPE: PRT
<213> ORGANISM: Artificial Sequence
<220> FEATURE:
<223> OTHER INFORMATION: Synthetic Artificial Sequence

<400> SEQUENCE: 60

Phe Gly Ala Gly Thr Lys Leu Glu Leu Lys
1 5 10

<210> SEQ ID NO 61
<211> LENGTH: 354
<212> TYPE: DNA
<213> ORGANISM: Artificial Sequence
<220> FEATURE:

<223> OTHER INFORMATION: Synthetic Artificial Sequence

<400> SEQUENCE: 61

```
gaagtgcagc tggtcgagtc tgggggaggg ctggtgcagc ccggcgggtc actgcgactg     60
agctgcgcag cttccggatt cgcctttagc tcctacgaca tgtcctgggt gcgacaggca    120
ccaggaaagg gactggattg ggtcgctact atctcaggag gcgggagata cacctactat    180
cctgacagcg tcaagggccg gttcacaatc tctagagata acagtaagaa caatctgtat    240
ctgcagatga acagcctgag ggctgaggac accgcactgt actattgtgc caaccgctac    300
ggggaagcat ggtttgccta ttgggggcag ggaaccctgg tgacagtctc tagt          354
```

<210> SEQ ID NO 62
<211> LENGTH: 118
<212> TYPE: PRT
<213> ORGANISM: Artificial Sequence
<220> FEATURE:
<223> OTHER INFORMATION: Synthetic Artificial Sequence

<400> SEQUENCE: 62

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Asp Trp Val
        35                  40                  45

Ala Thr Ile Ser Gly Gly Gly Arg Tyr Thr Tyr Tyr Pro Asp Ser Val
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Asn Arg Tyr Gly Glu Ala Trp Phe Ala Tyr Trp Gly Gln Gly Thr
            100                 105                 110

Leu Val Thr Val Ser Ser
        115
```

<210> SEQ ID NO 63
<211> LENGTH: 321
<212> TYPE: DNA
<213> ORGANISM: Artificial Sequence
<220> FEATURE:
<223> OTHER INFORMATION: Synthetic Artificial Sequence

<400> SEQUENCE: 63

```
gacattcaga tgactcagag cccctcctcc atgtccgcct ctgtgggcga cagggtcacc     60
ttcacatgcc gcgctagtca ggatatcaac acctacctga gctggtttca gcagaagcca    120
gggaaaagcc ccaagacact gatctaccgg gctaatagac tggtgtctgg agtcccaagt    180
cggttcagtg gctcagggag cggacaggac tacactctga ccatcagctc cctgcagcct    240
gaggacatgg caacctacta ttgcctgcag tatgatgagt tcccactgac ctttggcgcc    300
gggacaaaac tggagctgaa g                                              321
```

<210> SEQ ID NO 64
<211> LENGTH: 107
<212> TYPE: PRT
<213> ORGANISM: Artificial Sequence
<220> FEATURE:
<223> OTHER INFORMATION: Synthetic Artificial Sequence

<400> SEQUENCE: 64

```
Asp Ile Gln Met Thr Gln Ser Pro Ser Ser Met Ser Ala Ser Val Gly
1               5                   10                  15

Asp Arg Val Thr Phe Thr Cys Arg Ala Ser Gln Asp Ile Asn Thr Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Ser Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Met Ala Thr Tyr Tyr Cys Leu Gln Tyr Asp Glu Phe Pro Leu
                85                  90                  95

Thr Phe Gly Ala Gly Thr Lys Leu Glu Leu Lys
            100                 105
```

<210> SEQ ID NO 65
<211> LENGTH: 1344
<212> TYPE: DNA
<213> ORGANISM: Artificial Sequence
<220> FEATURE:
<223> OTHER INFORMATION: Synthetic Artificial Sequence

<400> SEQUENCE: 65

```
gaagtgcagc tggtcgagtc tgggggaggg ctggtgcagc ccggcgggtc actgcgactg     60
agctgcgcag cttccggatt cgcctttagc tcctacgaca tgtcctgggt gcgacaggca    120
ccaggaaagg gactggattg ggtcgctact atctcaggag gcgggagata cacctactat    180
cctgacagcg tcaagggccg gttcacaatc tctagagata acagtaagaa caatctgtat    240
ctgcagatga acagcctgag ggctgaggac accgcactgt actattgtgc caaccgctac    300
ggggaagcat ggtttgccta ttgggggcag ggaaccctgg tgacagtctc tagtgccagc    360
accaaaggac ctagcgtgtt tcctctcgcc ccctcctcca aaagcaccag cggaggaacc    420
gctgctctcg gatgtctggt gaaggactac ttccctgaac ccgtcaccgt gagctggaat    480
agcggcgctc tgacaagcgg agtccataca ttccctgctg tgctgcaaag cagcggactc    540
tattccctgt ccagcgtcgt cacagtgccc agcagcagcc tgggcaccca gacctacatc    600
tgtaacgtca accacaagcc ctccaacacc aaggtggaca agaaagtgga gcccaaatcc    660
tgcgacaaga cacacacctg tccccccctgt cctgctcccg aactcctcgg aggccctagc    720
gtcttcctct ttcctcccaa acccaaggac accctcatga tcagcagaac ccctgaagtc    780
acctgtgtcg tcgtggatgt cagccatgag gaccccgagg tgaaattcaa ctggtatgtc    840
gatggcgtcg aggtgcacaa cgccaaaacc aagcccaggg aggaacagta caactccacc    900
tacagggtgg tgtccgtgct gacagtcctc caccaggact ggctgaacgg caaggagtac    960
aagtgcaagg tgtccaacaa ggctctccct gcccccattg agaagaccat cagcaaggcc   1020
aaaggccaac ccagggagcc ccaggtctat acactgcctc cctccaggga cgaactcacc   1080
aagaaccagg tgtccctgac ctgcctggtc aagggctttt atcccagcga catcgccgtc   1140
gagtgggagt ccaacggaca gcccgagaat aactacaaga ccacccctcc tgtcctcgac   1200
tccgacggct ccttcttcct gtacagcaag ctgaccgtgg acaaaagcag gtggcagcag   1260
ggaaacgtgt tctcctgcag cgtgatgcac gaagccctcc acaaccacta cacccagaaa   1320
agcctgtccc tgagccccgg caaa                                          1344
```

<210> SEQ ID NO 66
<211> LENGTH: 448
<212> TYPE: PRT
<213> ORGANISM: Artificial Sequence
<220> FEATURE:
<223> OTHER INFORMATION: Synthetic Artificial Sequence

<400> SEQUENCE: 66

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Asp Trp Val
        35                  40                  45

Ala Thr Ile Ser Gly Gly Gly Arg Tyr Thr Tyr Tyr Pro Asp Ser Val
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Asn Arg Tyr Gly Glu Ala Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365
```

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 67
<211> LENGTH: 642
<212> TYPE: DNA
<213> ORGANISM: Artificial Sequence
<220> FEATURE:
<223> OTHER INFORMATION: Synthetic Artificial Sequence

<400> SEQUENCE: 67
gacattcaga tgactcagag cccctcctcc atgtccgcct ctgtgggcga cagggtcacc 60
ttcacatgcc gcgctagtca ggatatcaac acctacctga gctggtttca gcagaagcca 120
gggaaaagcc ccaagacact gatctaccgg gctaatagac tggtgtctgg agtcccaagt 180
cggttcagtg gctcagggag cggacaggac tacactctga ccatcagctc cctgcagcct 240
gaggacatgg caacctacta ttgcctgcag tatgatgagt tcccactgac ctttggcgcc 300
gggacaaaac tggagctgaa gcgaactgtg gccgctccct ccgtcttcat tttcccccct 360
tctgacgaac agctgaaatc aggcacagcc agcgtggtct gtctgctgaa caatttctac 420
cctagagagg caaaagtgca gtggaaggtc gataacgccc tgcagtccgg caacagccag 480
gagagtgtga ctgaacagga ctcaaaagat agcacctatt ccctgtctag tacactgact 540
ctgtccaagg ctgattacga gaagcacaaa gtgtatgcat gcgaagtgac acatcaggga 600
ctgtcaagcc ccgtgactaa gtcttttaac cggggcgaat gt 642

<210> SEQ ID NO 68
<211> LENGTH: 214
<212> TYPE: PRT
<213> ORGANISM: Artificial Sequence
<220> FEATURE:
<223> OTHER INFORMATION: Synthetic Artificial Sequence

<400> SEQUENCE: 68

Asp Ile Gln Met Thr Gln Ser Pro Ser Ser Met Ser Ala Ser Val Gly
1               5                   10                  15

Asp Arg Val Thr Phe Thr Cys Arg Ala Ser Gln Asp Ile Asn Thr Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Ser Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Met Ala Thr Tyr Tyr Cys Leu Gln Tyr Asp Glu Phe Pro Leu
                85                  90                  95

Thr Phe Gly Ala Gly Thr Lys Leu Glu Leu Lys Arg Thr Val Ala Ala
            100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 69
<211> LENGTH: 1344
<212> TYPE: DNA
<213> ORGANISM: Artificial Sequence
<220> FEATURE:
<223> OTHER INFORMATION: Synthetic Artificial Sequence

<400> SEQUENCE: 69

gaagtgcagc tggtcgagtc tggggggaggg ctggtgcagc ccggcgggtc actgcgactg     60

agctgcgcag cttccggatt cgcctttagc tcctacgaca tgtcctgggt gcgacaggca    120

ccaggaaagg gactggattg ggtcgctact atctcaggag gcgggagata cacctactat    180

cctgacagcg tcaagggccg gttcacaatc tctagagata acagtaagaa caatctgtat    240

ctgcagatga acagcctgag ggctgaggac accgcactgt actattgtgc caaccgctac    300

ggggaagcat ggtttgccta ttgggggcag ggaaccctgg tgacagtctc tagtgccagc    360

accaaagggc ccagcgtgtt tcctctcgcc ccctcctcca aaagcaccag cggaggaacc    420

gctgctctcg gatgtctggt gaaggactac ttccctgaac ccgtcaccgt gagctggaat    480

agcggcgctc tgacaagcgg agtccataca ttccctgctg tgctgcaaag cagcggactc    540

tattccctgt ccagcgtcgt cacagtgccc agcagcagcc tgggcaccca gacctacatc    600

tgtaacgtca accacaagcc ctccaacacc aaggtggaca agaaagtgga gcccaaatcc    660

tgcgacaaga cacacacctg tccccccctgt cctgctcccg aagctgctgg agcccctagc    720

gtcttcctct ttcctcccaa acccaaggac accctcatga tcagcagaac ccctgaagtc    780

acctgtgtcg tcgtggatgt cagccatgag gaccccgagg tgaaattcaa ctggtatgtc    840

gatggcgtcg aggtgcacaa cgccaaaacc aagcccaggg aggaacagta caactccacc    900

tacagggtgg tgtccgtgct gacagtcctc caccaggact ggctgaacgg caaggagtac    960

aagtgcaagg tgtccaacaa ggctctccct gcccccattg agaagaccat cagcaaggcc   1020

aaaggccaac ccagggagcc ccaggtctat acactgcctc cctccaggga cgaactcacc   1080

aagaaccagg tgtccctgac ctgcctggtc aagggctttt atcccagcga catcgccgtc   1140

gagtgggagt ccaacggaca gcccgagaat aactacaaga ccacccctcc tgtcctcgac   1200

tccgacggct ccttcttcct gtacagcaag ctgaccgtgg acaaaagcag gtggcagcag   1260

ggaaacgtgt tctcctgcag cgtgatgcac gaagccctcc acaaccacta cacccagaaa   1320

agcctgtccc tgagccccgg caaa                                           1344


<210> SEQ ID NO 70
```

<211> LENGTH: 448
<212> TYPE: PRT
<213> ORGANISM: Artificial Sequence
<220> FEATURE:
<223> OTHER INFORMATION: Synthetic Artificial Sequence

<400> SEQUENCE: 70

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Asp Trp Val
        35                  40                  45

Ala Thr Ile Ser Gly Gly Gly Arg Tyr Thr Tyr Tyr Pro Asp Ser Val
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Asn Arg Tyr Gly Glu Ala Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380
```

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 71
<211> LENGTH: 25
<212> TYPE: PRT
<213> ORGANISM: Artificial Sequence
<220> FEATURE:
<223> OTHER INFORMATION: Synthetic Artificial Sequence

<400> SEQUENCE: 71

Glu Val Gln Leu Val Glu Ser Gly Gly Gly Leu Val Gln Pro Gly Gly
1 5 10 15

Ser Leu Arg Leu Ser Cys Ala Ala Ser
20 25

<210> SEQ ID NO 72
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 72

Met Ser Trp Val Arg Gln Ala Pro Gly Lys Gly Leu Asp Trp Val Ala
1 5 10 15

Thr

<210> SEQ ID NO 73
<211> LENGTH: 38
<212> TYPE: PRT
<213> ORGANISM: Artificial Sequence
<220> FEATURE:
<223> OTHER INFORMATION: Synthetic Artificial Sequence

<400> SEQUENCE: 73

Tyr Tyr Pro Asp Ser Val Lys Gly Arg Phe Thr Ile Ser Arg Asp Asn
1 5 10 15

Ser Lys Asn Asn Leu Tyr Leu Gln Met Asn Ser Leu Arg Ala Glu Asp
20 25 30

Thr Ala Leu Tyr Tyr Cys
35

<210> SEQ ID NO 74
<211> LENGTH: 11
<212> TYPE: PRT
<213> ORGANISM: Artificial Sequence
<220> FEATURE:
<223> OTHER INFORMATION: Synthetic Artificial Sequence

<400> SEQUENCE: 74

Trp Gly Gln Gly Thr Leu Val Thr Val Ser Ser
1 5 10

<210> SEQ ID NO 75
<211> LENGTH: 26

<212> TYPE: PRT
<213> ORGANISM: Artificial Sequence
<220> FEATURE:
<223> OTHER INFORMATION: Synthetic Artificial Sequence

<400> SEQUENCE: 75

Asp Ile Gln Met Thr Gln Ser Pro Ser Ser Met Ser Ala Ser Val Gly
1 5 10 15

Asp Arg Val Thr Phe Thr Cys Arg Ala Ser
20 25

<210> SEQ ID NO 76
<211> LENGTH: 17
<212> TYPE: PRT
<213> ORGANISM: Artificial Sequence
<220> FEATURE:
<223> OTHER INFORMATION: Synthetic Artificial Sequence

<400> SEQUENCE: 76

Leu Ser Trp Phe Gln Gln Lys Pro Gly Lys Ser Pro Lys Thr Leu Ile
1 5 10 15

Tyr

<210> SEQ ID NO 77
<211> LENGTH: 36
<212> TYPE: PRT
<213> ORGANISM: Artificial Sequence
<220> FEATURE:
<223> OTHER INFORMATION: Synthetic Artificial Sequence

<400> SEQUENCE: 77

Arg Leu Val Ser Gly Val Pro Ser Arg Phe Ser Gly Ser Gly Ser Gly
1 5 10 15

Gln Asp Tyr Thr Leu Thr Ile Ser Ser Leu Gln Pro Glu Asp Met Ala
20 25 30

Thr Tyr Tyr Cys
35

<210> SEQ ID NO 78
<211> LENGTH: 10
<212> TYPE: PRT
<213> ORGANISM: Artificial Sequence
<220> FEATURE:
<223> OTHER INFORMATION: Synthetic Artificial Sequence

<400> SEQUENCE: 78

Phe Gly Ala Gly Thr Lys Leu Glu Leu Lys
1 5 10

<210> SEQ ID NO 79
<211> LENGTH: 20
<212> TYPE: PRT
<213> ORGANISM: Artificial Sequence
<220> FEATURE:
<223> OTHER INFORMATION: Synthetic Artificial Sequence

<400> SEQUENCE: 79

Gly Gly Gly Gly Ser Gly Gly Gly Gly Ser Gly Gly Gly Gly Ser Gly
1 5 10 15

Gly Gly Gly Ser
20

<210> SEQ ID NO 80
<211> LENGTH: 60

<212> TYPE: DNA
<213> ORGANISM: Artificial Sequence
<220> FEATURE:
<223> OTHER INFORMATION: Synthetic Artificial Sequence

<400> SEQUENCE: 80
ggcggcggcg gcagcggcgg cggcggctcc ggaggaggcg gctctggcgg cggcggcagc 60

<210> SEQ ID NO 81
<211> LENGTH: 15
<212> TYPE: PRT
<213> ORGANISM: Artificial Sequence
<220> FEATURE:
<223> OTHER INFORMATION: Synthetic Artificial Sequence

<400> SEQUENCE: 81

Gly Gly Gly Gly Ser Gly Gly Gly Gly Ser Gly Gly Gly Gly Ser
1 5 10 15

<210> SEQ ID NO 82
<211> LENGTH: 45
<212> TYPE: DNA
<213> ORGANISM: Artificial Sequence
<220> FEATURE:
<223> OTHER INFORMATION: Synthetic Artificial Sequence

<400> SEQUENCE: 82
ggcggcggcg gctccggagg aggcggctct ggcggcggcg gcagc 45

<210> SEQ ID NO 83
<211> LENGTH: 717
<212> TYPE: PRT
<213> ORGANISM: Artificial Sequence
<220> FEATURE:
<223> OTHER INFORMATION: Synthetic Artificial Sequence

<400> SEQUENCE: 83

Gln Val Gln Leu Val Gln Ser Gly Ala Glu Val Val Lys Pro Gly Ala
1 5 10 15

Ser Val Lys Val Ser Cys Lys Ala Ser Gly Tyr Ser Phe Thr Gly Tyr
20 25 30

Thr Met Asn Trp Val Arg Gln Ala Pro Gly Gln Asn Leu Glu Trp Ile
35 40 45

Gly Leu Ile Asn Pro Tyr Asn Ala Gly Thr Ser Tyr Asn Gln Lys Phe
50 55 60

Gln Gly Lys Val Thr Leu Thr Val Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ser Glu Tyr Arg Tyr Gly Gly Asp Tyr Phe Asp Tyr Trp Gly
100 105 110

Gln Gly Thr Thr Leu Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

```
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Gly Gly Gly Gly Ser Glu Val Gln Leu Val Glu Ser Gly Gly
465                 470                 475                 480

Gly Leu Val Gln Pro Gly Gly Ser Leu Arg Leu Ser Cys Ala Ala Ser
                485                 490                 495

Gly Phe Ala Phe Ser Ser Tyr Asp Met Ser Trp Val Arg Gln Ala Pro
            500                 505                 510

Gly Lys Gly Leu Asp Trp Val Ala Thr Ile Ser Gly Gly Gly Arg Tyr
        515                 520                 525

Thr Tyr Tyr Pro Asp Ser Val Lys Gly Arg Phe Thr Ile Ser Arg Asp
    530                 535                 540

Asn Ser Lys Asn Asn Leu Tyr Leu Gln Met Asn Ser Leu Arg Ala Glu
545                 550                 555                 560

Asp Thr Ala Leu Tyr Tyr Cys Ala Asn Arg Tyr Gly Glu Ala Trp Phe
                565                 570                 575

Ala Tyr Trp Gly Gln Gly Thr Leu Val Thr Val Ser Ser Gly Gly Gly
            580                 585                 590

Gly Ser Gly Gly Gly Gly Ser Gly Gly Gly Gly Ser Gly Gly Gly Gly
        595                 600                 605
```

```
Ser Asp Ile Gln Met Thr Gln Ser Pro Ser Ser Met Ser Ala Ser Val
    610                 615                 620

Gly Asp Arg Val Thr Phe Thr Cys Arg Ala Ser Gln Asp Ile Asn Thr
625                 630                 635                 640

Tyr Leu Ser Trp Phe Gln Gln Lys Pro Gly Lys Ser Pro Lys Thr Leu
                645                 650                 655

Ile Tyr Arg Ala Asn Arg Leu Val Ser Gly Val Pro Ser Arg Phe Ser
            660                 665                 670

Gly Ser Gly Ser Gly Gln Asp Tyr Thr Leu Thr Ile Ser Ser Leu Gln
        675                 680                 685

Pro Glu Asp Met Ala Thr Tyr Tyr Cys Leu Gln Tyr Asp Glu Phe Pro
    690                 695                 700

Leu Thr Phe Gly Ala Gly Thr Lys Leu Glu Leu Lys Arg
705                 710                 715
```

<210> SEQ ID NO 84
<211> LENGTH: 2151
<212> TYPE: DNA
<213> ORGANISM: Artificial Sequence
<220> FEATURE:
<223> OTHER INFORMATION: Synthetic Artificial Sequence

<400> SEQUENCE: 84

```
caggtgcagc tggtgcagtc tggagcagag gtggtgaagc caggagcctc tgtgaaggtg     60

agctgtaagg ccagcggcta ctccttcacc ggctatacaa tgaactgggt gaggcaggca    120

ccaggacaga atctggagtg gatcggcctg atcaaccctt acaatgccgg cacctcttat    180

aaccagaagt ttcagggcaa ggtgaccctg acagtggaca agtccacctc tacagcctac    240

atggagctga gctccctgcg gagcgaggat acagccgtgt actattgcgc ccggtccgag    300

tacagatatg gcggcgacta ctttgattat tggggccagg gcaccacact gaccgtgtct    360

agcgcctcca caaaggggcc cagcgtgttt cctctcgccc cctcctccaa aagcaccagc    420

ggaggaaccg ctgctctcgg atgtctggtg aaggactact tccctgaacc cgtcaccgtg    480

agctggaata gcggcgctct gacaagcgga gtccatacat tccctgctgt gctgcaaagc    540

agcggactct attccctgtc cagcgtcgtc acagtgccca gcagcagcct gggcacccag    600

acctacatct gtaacgtcaa ccacaagccc tccaacacca aggtggacaa gaaagtggag    660

cccaaatcct gcgacaagac acacacctgt ccccccctgtc ctgctcccga agctgctgga    720

gcccctagcg tcttcctctt tcctcccaaa cccaaggaca ccctcatgat cagcagaacc    780

cctgaagtca cctgtgtcgt cgtggatgtc agccatgagg accccgaggt gaaattcaac    840

tggtatgtcg atggcgtcga ggtgcacaac gccaaaacca agcccaggga ggaacagtac    900

aactccacct acagggtggt gtccgtgctg acagtcctcc accaggactg gctgaacggc    960

aaggagtaca agtgcaaggt gtccaacaag gctctccctg cccccattga gaagaccatc   1020

agcaaggcca aaggccaacc cagggagccc caggtctata cactgcctcc ctccagggac   1080

gaactcacca agaaccaggt gtccctgacc tgcctggtca agggctttta tcccagcgac   1140

atcgccgtcg agtgggagtc caacggacag cccgagaata actacaagac cacccctcct   1200

gtcctcgact ccgacggctc cttcttcctg tacagcaaac tgaccgtcga taaatctagg   1260

tggcagcagg gcaacgtgtt ctcttgttcc gtgatgcatg aagcactgca caaccattat   1320

acccagaagt ctctgagcct gtcccccggc aagggcggcg gcggctctgg aggaggaggc   1380

agcggcggag gaggctccgg aggcggcggc tctgaggtgc agctggtgga gtctggagga   1440
```

```
ggactggtgc agcctggagg ctccctgagg ctgtcttgcg cagcaagcgg attcgccttt   1500

agctcctacg acatgagctg ggtgcggcag gcacctggca agggtctgga ttgggtggca   1560

accatcagcg gaggcggcag atacacatac tatcccgact ccgtgaaggg caggttcacc   1620

atctcccgcg ataactctaa gaacaatctg tatctgcaga tgaacagcct gagggccgag   1680

gacacagccc tgtactattg cgccaaccgc tacggcgagg cctggtttgc ctattggggc   1740

cagggcaccc tggtgacagt gtctagcggc ggcggcggca gcggcggcgg cggctccgga   1800

ggaggcggct ctggcggcgg cggcagcgat atccagatga cccagtcccc ctcctctatg   1860

tctgccagcg tgggcgaccg ggtgaccttc acatgtagag cctcccagga tatcaacacc   1920

tacctgtctt ggtttcagca gaagcccggc aagagcccta agacactgat ctatcgggcc   1980

aatagactgg tgagcggagt gccttcccgg ttctccggct ctggcagcgg acaggactat   2040

accctgacaa tcagctccct gcagccagag gatatggcca catactattg cctgcagtat   2100

gacgagttcc ccctgacctt cggggctggc actaagctgg agctgaaaag a            2151
```

<210> SEQ ID NO 85
<211> LENGTH: 712
<212> TYPE: PRT
<213> ORGANISM: Artificial Sequence
<220> FEATURE:
<223> OTHER INFORMATION: Synthetic Artificial Sequence

<400> SEQUENCE: 85

```
Gln Val Gln Leu Val Gln Ser Gly Ala Glu Val Val Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Asn Leu Glu Trp Ile
        35                  40                  45

Gly Leu Ile Asn Pro Tyr Asn Ala Gly Thr Ser Tyr Asn Gln Lys Phe
    50                  55                  60

Gln Gly Lys Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Glu Tyr Arg Tyr Gly Gly Asp Tyr Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240
```

```
Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Gly Gly Gly Gly Ser Glu Val Gln Leu Val Glu Ser Gly Gly
465                 470                 475                 480

Gly Leu Val Gln Pro Gly Gly Ser Leu Arg Leu Ser Cys Ala Ala Ser
                485                 490                 495

Gly Phe Ala Phe Ser Ser Tyr Asp Met Ser Trp Val Arg Gln Ala Pro
            500                 505                 510

Gly Lys Gly Leu Asp Trp Val Ala Thr Ile Ser Gly Gly Gly Arg Tyr
        515                 520                 525

Thr Tyr Tyr Pro Asp Ser Val Lys Gly Arg Phe Thr Ile Ser Arg Asp
    530                 535                 540

Asn Ser Lys Asn Asn Leu Tyr Leu Gln Met Asn Ser Leu Arg Ala Glu
545                 550                 555                 560

Asp Thr Ala Leu Tyr Tyr Cys Ala Asn Arg Tyr Gly Glu Ala Trp Phe
                565                 570                 575

Ala Tyr Trp Gly Gln Gly Thr Leu Val Thr Val Ser Ser Gly Gly Gly
            580                 585                 590

Gly Ser Gly Gly Gly Gly Ser Gly Gly Gly Gly Ser Asp Ile Gln Met
        595                 600                 605

Thr Gln Ser Pro Ser Ser Met Ser Ala Ser Val Gly Asp Arg Val Thr
    610                 615                 620

Phe Thr Cys Arg Ala Ser Gln Asp Ile Asn Thr Tyr Leu Ser Trp Phe
625                 630                 635                 640

Gln Gln Lys Pro Gly Lys Ser Pro Lys Thr Leu Ile Tyr Arg Ala Asn
                645                 650                 655

Arg Leu Val Ser Gly Val Pro Ser Arg Phe Ser Gly Ser Gly Ser Gly
```

```
            660                 665                 670

Gln Asp Tyr Thr Leu Thr Ile Ser Ser Leu Gln Pro Glu Asp Met Ala
        675                 680                 685

Thr Tyr Tyr Cys Leu Gln Tyr Asp Glu Phe Pro Leu Thr Phe Gly Ala
    690                 695                 700

Gly Thr Lys Leu Glu Leu Lys Arg
705                 710


<210> SEQ ID NO 86
<211> LENGTH: 2148
<212> TYPE: DNA
<213> ORGANISM: Artificial Sequence
<220> FEATURE:
<223> OTHER INFORMATION: Synthetic Artificial Sequence

<400> SEQUENCE: 86

caggtgcagc tggtgcagtc tggagcagag gtggtgaagc caggagcctc tgtgaaggtg     60

agctgtaagg ccagcggcta ctccttcacc ggctatacaa tgaactgggt gaggcaggca    120

ccaggacaga atctggagtg gatcggcctg atcaaccctt acaatgccgg cacctcttat    180

aaccagaagt ttcagggcaa ggtgaccctg acagtggaca agtccacctc tacagcctac    240

atggagctga gctccctgcg gagcgaggat acagccgtgt actattgcgc ccggtccgag    300

tacagatatg gcggcgacta ctttgattat tggggccagg gcaccacact gaccgtgtct    360

agcgcctcca caaaggggcc cagcgtgttt cctctcgccc cctcctccaa aagcaccagc    420

ggaggaaccg ctgctctcgg atgtctggtg aaggactact tccctgaacc cgtcaccgtg    480

agctggaata gcggcgctct gacaagcgga gtccatacat tccctgctgt gctgcaaagc    540

agcggactct attccctgtc cagcgtcgtc acagtgccca gcagcagcct gggcacccag    600

acctacatct gtaacgtcaa ccacaagccc tccaacacca aggtggacaa gaaagtggag    660

cccaaatcct gcgacaagac acacacctgt ccccccctgtc ctgctcccga agctgctgga    720

gcccctagcg tcttcctctt tcctcccaaa cccaaggaca ccctcatgat cagcagaacc    780

cctgaagtca cctgtgtcgt cgtggatgtc agccatgagg accccgaggt gaaattcaac    840

tggtatgtcg atggcgtcga ggtgcacaac gccaaaacca agcccaggga ggaacagtac    900

aactccacct acagggtggt gtccgtgctg acagtcctcc accaggactg gctgaacggc    960

aaggagtaca agtgcaaggt gtccaacaag gctctccctg cccccattga gaagaccatc   1020

agcaaggcca aaggccaacc cagggagccc caggtctata cactgcctcc ctccagggac   1080

gaactcacca agaaccaggt gtccctgacc tgcctggtca agggctttta tcccagcgac   1140

atcgccgtcg agtgggagtc caacggacag cccgagaata actacaagac cacccctcct   1200

gtcctcgact ccgacggctc cttcttcctg tacagcaaac tgaccgtcga taaatctagg   1260

tggcagcagg gcaacgtgtt ctcttgttcc gtgatgcatg aagcactgca caaccattat   1320

acccagaagt ctctgagcct gtcccccggc aagggcggcg gcggctctgg aggaggaggc   1380

agcggcggag gaggctccgg aggcggcggc tctgaggtgc agctggtgga gtctggagga   1440

ggactggtgc agcctggagg ctccctgagg ctgtcttgcg cagcaagcgg attcgccttt   1500

agctcctacg acatgagctg ggtgcggcag gcacctggca agggtctgga ttgggtggca   1560

accatcagcg gaggcggcag atacacatac tatcccgact ccgtgaaggg caggttcacc   1620

atctcccgcg ataactctaa gaacaatctg tatctgcaga tgaacagcct gagggccgag   1680

gacacagccc tgtactattg cgccaaccgc tacggcgagg cctggtttgc ctattggggc   1740
```

cagggcaccc tggtgacagt gtctagcggc ggcggcggct ccggaggagg cggctctggc 1800
ggcggcggca gcgatatcca gatgacccag tccccctcct ctatgtctgc cagcgtgggc 1860
gaccgggtga ccttcacatg tagagcctcc caggatatca acacctacct gtcttggttt 1920
cagcagaagc ccggcaagag ccctaagaca ctgatctatc gggccaatag actggtgagc 1980
ggagtgcctt cccggttctc cggctctggc agcggacagg actataccct gacaatcagc 2040
tccctgcagc cagaggatat ggccacatac tattgcctgc agtatgacga gttccccctg 2100
accttcgggg ctggcactaa gctggagctg aaaagatgat aagaattc 2148

<210> SEQ ID NO 87
<211> LENGTH: 558
<212> TYPE: PRT
<213> ORGANISM: Artificial Sequence
<220> FEATURE:
<223> OTHER INFORMATION: Synthetic Artificial Sequence

<400> SEQUENCE: 87

Met Cys Pro Arg Ala Ala Arg Ala Pro Ala Thr Leu Leu Leu Ala Leu
1 5 10 15

Gly Ala Val Leu Trp Pro Ala Ala Gly Ala Trp Glu Leu Thr Ile Leu
20 25 30

His Thr Asn Asp Val His Ser Arg Leu Glu Gln Thr Ser Glu Asp Ser
35 40 45

Ser Lys Cys Val Asn Ala Ser Arg Cys Met Gly Gly Val Ala Arg Leu
50 55 60

Phe Thr Lys Val Gln Gln Ile Arg Arg Ala Glu Pro Asn Val Leu Leu
65 70 75 80

Leu Asp Ala Gly Asp Gln Tyr Gln Gly Thr Ile Trp Phe Thr Val Tyr
85 90 95

Lys Gly Ala Glu Val Ala His Phe Met Asn Ala Leu Arg Tyr Asp Ala
100 105 110

Met Ala Leu Gly Asn His Glu Phe Asp Asn Gly Val Glu Gly Leu Ile
115 120 125

Glu Pro Leu Leu Lys Glu Ala Lys Phe Pro Ile Leu Ser Ala Asn Ile
130 135 140

Lys Ala Lys Gly Pro Leu Ala Ser Gln Ile Ser Gly Leu Tyr Leu Pro
145 150 155 160

Tyr Lys Val Leu Pro Val Gly Asp Glu Val Val Gly Ile Val Gly Tyr
165 170 175

Thr Ser Lys Glu Thr Pro Phe Leu Ser Asn Pro Gly Thr Asn Leu Val
180 185 190

Phe Glu Asp Glu Ile Thr Ala Leu Gln Pro Glu Val Asp Lys Leu Lys
195 200 205

Thr Leu Asn Val Asn Lys Ile Ile Ala Leu Gly His Ser Gly Phe Glu
210 215 220

Met Asp Lys Leu Ile Ala Gln Lys Val Arg Gly Val Asp Val Val Val
225 230 235 240

Gly Gly His Ser Asn Thr Phe Leu Tyr Thr Gly Asn Pro Pro Ser Lys
245 250 255

Glu Val Pro Ala Gly Lys Tyr Pro Phe Ile Val Thr Ser Asp Asp Gly
260 265 270

Arg Lys Val Pro Val Val Gln Ala Tyr Ala Phe Gly Lys Tyr Leu Gly
275 280 285

Tyr Leu Lys Ile Glu Phe Asp Glu Arg Gly Asn Val Ile Ser Ser His

```
    290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Asn Leu Arg His Thr Asp Glu Met Phe Trp Asn His Val
    370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
        435                 440                 445

Phe Leu Gln Val Gly Gly Ile His Val Val Tyr Asp Leu Ser Arg Lys
    450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
        515                 520                 525

Ser Thr Tyr Ile Ser Lys Met Lys Val Ile Tyr Pro Ala Val Glu Gly
    530                 535                 540

Arg Ile Lys Phe Ser Thr Gly Ser His His His His His His
545                 550                 555
```

<210> SEQ ID NO 88
<211> LENGTH: 1674
<212> TYPE: DNA
<213> ORGANISM: Artificial Sequence
<220> FEATURE:
<223> OTHER INFORMATION: Synthetic Artificial Sequence

<400> SEQUENCE: 88

```
atgtgtccta gagccgccag agctccagct acactgctgc tggctctggg agcagtcctc     60

tggccagcag caggagcttg ggaactgacc atcctgcaca ccaacgacgt gcacagcagg    120

ctggaacaga ccagcgagga cagcagcaag tgcgtgaacg ccagtcgctg tatgggagga    180

gtggcaaggc tgttcaccaa ggtgcagcag atccggagag ccgaacctaa cgtgctgctg    240

ctggacgccg gagatcagta tcagggaacc atctggttca ccgtgtacaa gggcgccgaa    300

gtggcccact tcatgaacgc tctgcgctac gacgctatgg ccctgggcaa tcacgagttc    360

gataacggcg tggagggact gatcgagcct ctgctgaagg aggccaagtt ccccatcctg    420

agcgccaaca tcaaggccaa gggacctctg gctagccaga ttagcggcct gtacctgcct    480

tacaaggtgc tgcccgtggg agacgaagtg gtgggaatcg tgggctacac cagcaaggag    540

acccctttcc tgagcaaccc aggcaccaac ctggtgttcg aggacgagat caccgctctg    600
```

cagccagagg tggacaagct gaagaccctg aacgtgaaca agatcatcgc cctgggacac 660
agcggcttcg agatggacaa gctgatcgcc cagaaagtgc gaggagtgga cgtggtcgtg 720
ggcggacaca gcaacacctt cctgtacacc ggcaaccctc cttctaagga agtgccagcc 780
ggcaagtacc ccttcatcgt gaccagcgac gacggaagaa aggtgccagt ggtgcaggct 840
tacgccttcg gcaagtacct gggctacctg aagatcgagt tcgacgagcg gggcaacgtg 900
atctctagcc acggcaaccc catcctgctg aacagcagca tcccagagga ccccagcatc 960
aaggccgaca tcaacaagtg gcggatcaag ctggacaact acagcaccca ggagctggga 1020
aagaccatcg tgtacctgga cggcagctct cagtcttgcc ggttccgcga gtgcaacatg 1080
ggcaacctga tttgcgacgc catgatcaac aacaacctgc ggcacaccga cgagatgttt 1140
tggaaccacg tcagcatgtg catcctgaac ggcggaggca tcagaagccc tattgacgag 1200
cggaacaacg gcaccatcac ttgggagaac ctggcagcag tgctgccttt tggcggaaca 1260
ttcgacctgg tgcagctgaa gggcagcaca ctgaagaagg ccttcgagca cagcgtgcac 1320
agatacggcc agagcacagg cgagttcctg caggtcggag gaatccacgt ggtgtacgac 1380
ctgagcagga agccaggaga cagagtggtg aagctggacg tgctctgcac caagtgtcgg 1440
gtgccaagct acgacccccct gaagatggac gaggtgtaca aggtcatcct gcccaacttc 1500
ctggctaacg gaggagacgg cttccagatg atcaaggacg agctgctgag gcacgacagc 1560
ggagaccagg acatcaacgt cgtgtccacc tacatcagca agatgaaggt catctacccc 1620
gccgtggaag gcaggatcaa gttcagcacc ggctctcacc accaccatca ccac 1674

<210> SEQ ID NO 89
<211> LENGTH: 232
<212> TYPE: PRT
<213> ORGANISM: Artificial Sequence
<220> FEATURE:
<223> OTHER INFORMATION: Synthetic Artificial Sequence

<400> SEQUENCE: 89

Pro Arg Gly Pro Thr Ile Lys Pro Cys Pro Pro Cys Lys Cys Pro Ala
1 5 10 15

Pro Asn Leu Leu Gly Gly Pro Ser Val Phe Ile Phe Pro Pro Lys Ile
20 25 30

Lys Asp Val Leu Met Ile Ser Leu Ser Pro Ile Val Thr Cys Val Val
35 40 45

Val Asp Val Ser Glu Asp Asp Pro Asp Val Gln Ile Ser Trp Phe Val
50 55 60

Asn Asn Val Glu Val His Thr Ala Gln Thr Gln Thr His Arg Glu Asp
65 70 75 80

Tyr Asn Ser Thr Leu Arg Val Val Ser Ala Leu Pro Ile Gln His Gln
85 90 95

Asp Trp Met Ser Gly Lys Glu Phe Lys Cys Lys Val Asn Asn Lys Asp
100 105 110

Leu Pro Ala Pro Ile Glu Arg Thr Ile Ser Lys Pro Lys Gly Ser Val
115 120 125

Arg Ala Pro Gln Val Tyr Val Leu Pro Pro Pro Glu Glu Glu Met Thr
130 135 140

Lys Lys Gln Val Thr Leu Thr Cys Met Val Thr Asp Phe Met Pro Glu
145 150 155 160

Asp Ile Tyr Val Glu Trp Thr Asn Asn Gly Lys Thr Glu Leu Asn Tyr
165 170 175

Lys Asn Thr Glu Pro Val Leu Asp Ser Asp Gly Ser Tyr Phe Met Tyr
180 185 190

Ser Lys Leu Arg Val Glu Lys Lys Asn Trp Val Glu Arg Asn Ser Tyr
195 200 205

Ser Cys Ser Val Val His Glu Gly Leu His Asn His His Thr Thr Lys
210 215 220

Ser Phe Ser Arg Thr Pro Gly Lys
225 230

<210> SEQ ID NO 90
<211> LENGTH: 249
<212> TYPE: PRT
<213> ORGANISM: Artificial Sequence
<220> FEATURE:
<223> OTHER INFORMATION: Synthetic Artificial Sequence

<400> SEQUENCE: 90

Gln Val Gln Leu Gln Gln Ser Gly Ala Glu Val Val Lys Pro Gly Ala
1 5 10 15

Ser Met Lys Met Ser Cys Lys Ala Ser Gly Tyr Ser Phe Thr Gly Tyr
20 25 30

Thr Met Asn Trp Val Lys Gln Ala His Gly Gln Asn Leu Glu Trp Ile
35 40 45

Gly Leu Ile Asn Pro Tyr Asn Ala Gly Thr Ser Tyr Asn Gln Lys Phe
50 55 60

Gln Gly Lys Ala Thr Leu Thr Val Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ser Glu Tyr Arg Tyr Gly Gly Asp Tyr Phe Asp Tyr Trp Gly
100 105 110

Gln Gly Thr Thr Leu Thr Val Ser Ser Gly Gly Gly Gly Ser Gly Gly
115 120 125

Gly Gly Ser Gly Gly Gly Gly Ser Asp Ile Val Met Thr Gln Ser Pro
130 135 140

Ser Ser Leu Ala Val Ser Val Gly Glu Arg Val Thr Ile Ser Cys Lys
145 150 155 160

Ser Ser Gln Ser Leu Leu Asn Ser Ser Asn Gln Lys Asn Tyr Leu Ala
165 170 175

Trp Tyr Gln Gln Lys Pro Gly Gln Ala Pro Lys Leu Leu Ile Tyr Phe
180 185 190

Ala Ser Thr Arg Glu Ser Gly Val Pro Asp Arg Phe Ser Gly Ser Gly
195 200 205

Ser Gly Thr Asp Phe Thr Leu Thr Ile Ser Ser Val Gln Ala Glu Asp
210 215 220

Val Ala Asp Tyr Tyr Cys Gln Gln His Tyr Asp Thr Pro Tyr Thr Phe
225 230 235 240

Gly Gly Gly Thr Lys Leu Glu Ile Lys
245

<210> SEQ ID NO 91
<211> LENGTH: 837
<212> TYPE: DNA
<213> ORGANISM: Artificial Sequence
<220> FEATURE:
<223> OTHER INFORMATION: Synthetic Artificial Sequence

<400> SEQUENCE: 91
caggtgcagc tgcagcagtc tggagcagag gtggtgaagc caggagcctc tatgaagatg 60
agctgtaagg ccagcggcta ctccttcacc ggctatacaa tgaactgggt gaagcaggcc 120
cacggccaga atctggagtg gatcggcctg atcaaccctt acaatgccgg cacctcttat 180
aaccagaagt ttcagggcaa ggccaccctg acagtggaca agtccacctc tacagcctac 240
atggagctga gctccctgcg gagcgaggat acagccgtgt actattgcgc ccggtccgag 300
tacagatatg gcggcgacta ctttgattat tggggccagg gcaccacact gaccgtgtct 360
agcggcctgt acggcctgta cggcctgtac ggcctgtaca gcgagagggg cctgtacggc 420
ctgtacggcc tgtacggcct gtacagcgag aggggcctgt acggcctgta cggcctgtac 480
ggcctgtaca gcgagaggga catcgtgatg acccagtccc caagctccct ggccgtgtct 540
gtgggagagc gggtgacaat ctcctgtaag tctagccagt ctctgctgaa ctcctctaat 600
cagaagaact acctggcctg gtatcagcag aagcccggcc aggcccctaa gctgctgatc 660
tacttcgcct ctaccaggga gagcggagtg ccagacagat tctctggcag cggctccggc 720
acagacttca ccctgacaat cagctccgtg caggcagagg acgtggcaga ttactattgc 780
cagcagcact acgatacccc ctatacattt ggcggcggca ccaagctgga gatcaag 837

<210> SEQ ID NO 92
<211> LENGTH: 363
<212> TYPE: DNA
<213> ORGANISM: Artificial Sequence
<220> FEATURE:
<223> OTHER INFORMATION: Synthetic Artificial Sequence

<400> SEQUENCE: 92
caggtgcagc tgcagcagtc tggagcagag gtggtgaagc caggagcctc tatgaagatg 60
agctgtaagg ccagcggcta ctccttcacc ggctatacaa tgaactgggt gaagcaggcc 120
cacggccaga atctggagtg gatcggcctg atcaaccctt acaatgccgg cacctcttat 180
aaccagaagt ttcagggcaa ggccaccctg acagtggaca agtccacctc tacagcctac 240
atggagctga gctccctgcg gagcgaggat acagccgtgt actattgcgc ccggtccgag 300
tacagatatg gcggcgacta ctttgattat tggggccagg gcaccacact gaccgtgtct 360
agc 363

<210> SEQ ID NO 93
<211> LENGTH: 121
<212> TYPE: PRT
<213> ORGANISM: Artificial Sequence
<220> FEATURE:
<223> OTHER INFORMATION: Synthetic Artificial Sequence

<400> SEQUENCE: 93

Gln Val Gln Leu Gln Gln Ser Gly Ala Glu Val Val Lys Pro Gly Ala
1 5 10 15

Ser Met Lys Met Ser Cys Lys Ala Ser Gly Tyr Ser Phe Thr Gly Tyr
20 25 30

Thr Met Asn Trp Val Lys Gln Ala His Gly Gln Asn Leu Glu Trp Ile
35 40 45

Gly Leu Ile Asn Pro Tyr Asn Ala Gly Thr Ser Tyr Asn Gln Lys Phe
50 55 60

Gln Gly Lys Ala Thr Leu Thr Val Asp Lys Ser Thr Ser Thr Ala Tyr
65 70 75 80

```
Met Glu Leu Ser Ser Leu Arg Ser Glu Asp Thr Ala Val Tyr Tyr Cys
                85                  90                  95

Ala Arg Ser Glu Tyr Arg Tyr Gly Gly Asp Tyr Phe Asp Tyr Trp Gly
            100                 105                 110

Gln Gly Thr Thr Leu Thr Val Ser Ser
        115                 120


<210> SEQ ID NO 94
<211> LENGTH: 339
<212> TYPE: DNA
<213> ORGANISM: Artificial Sequence
<220> FEATURE:
<223> OTHER INFORMATION: Synthetic Artificial Sequence

<400> SEQUENCE: 94

gacatcgtga tgacccagtc cccaagctcc ctggcaatgt ctgtgggaga gagggtgaca      60

atgtcctgta agtctagcca gtctctgctg aactcctcta atcagaagaa ctacctggcc     120

tggtatcagc agaagcccgg ccaggcccct aagctgctgg tgtactttgc ctctaccagg     180

gagagcggag tgccagacag attctctggc agcggctccg gcacagactt caccctgaca     240

atcagctccg tgcaggcaga ggacctggca gattatttct gccagcagca ctacgatacc     300

ccctatacat ttggcggcgg caccaagctg gagatcaag                            339


<210> SEQ ID NO 95
<211> LENGTH: 113
<212> TYPE: PRT
<213> ORGANISM: Artificial Sequence
<220> FEATURE:
<223> OTHER INFORMATION: Synthetic Artificial Sequence

<400> SEQUENCE: 95

Asp Ile Val Met Thr Gln Ser Pro Ser Ser Leu Ala Met Ser Val Gly
1               5                   10                  15

Glu Arg Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ala Pro Lys Leu Leu Val Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Asp Thr Pro Tyr Thr Phe Gly Gly Gly Thr Lys Leu Glu Ile
            100                 105                 110

Lys


<210> SEQ ID NO 96
<211> LENGTH: 220
<212> TYPE: PRT
<213> ORGANISM: Artificial Sequence
<220> FEATURE:
<223> OTHER INFORMATION: Synthetic Artificial Sequence

<400> SEQUENCE: 96

Asp Ile Val Met Thr Gln Ser Pro Ser Ser Leu Ala Val Ser Val Gly
1               5                   10                  15

Glu Arg Val Thr Ile Ser Cys Lys Ser Ser Gln Ser Leu Leu Asn Ser
            20                  25                  30
```

```
Ser Asn Gln Lys Asn Tyr Leu Ala Trp Tyr Gln Gln Lys Pro Gly Gln
        35                  40                  45

Ala Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Asp Tyr Tyr Cys Gln Gln
                85                  90                  95

His Tyr Asp Thr Pro Tyr Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 97
<211> LENGTH: 121
<212> TYPE: PRT
<213> ORGANISM: Artificial Sequence
<220> FEATURE:
<223> OTHER INFORMATION: Synthetic Artificial Sequence

<400> SEQUENCE: 97

Gln Val Gln Leu Val Gln Ser Gly Ala Glu Val Val Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Asn Leu Glu Trp Ile
        35                  40                  45

Gly Leu Ile Asn Pro Tyr Asn Ala Gly Thr Ser Tyr Asn Gln Lys Phe
    50                  55                  60

Gln Gly Lys Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Glu Tyr Arg Tyr Gly Gly Asp Tyr Phe Asp Tyr Trp Gly
            100                 105                 110

Gln Gly Thr Thr Leu Thr Val Ser Ser
        115                 120


<210> SEQ ID NO 98
<211> LENGTH: 113
<212> TYPE: PRT
<213> ORGANISM: Artificial Sequence
<220> FEATURE:
<223> OTHER INFORMATION: Synthetic Artificial Sequence
```

<400> SEQUENCE: 98

```
Asp Ile Val Met Thr Gln Ser Pro Ser Ser Leu Ala Val Ser Val Gly
1               5                   10                  15

Glu Arg Val Thr Ile Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ala Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Asp Tyr Tyr Cys Gln Gln
                85                  90                  95

His Tyr Asp Thr Pro Tyr Thr Phe Gly Gly Gly Thr Lys Leu Glu Ile
            100                 105                 110

Lys
```

<210> SEQ ID NO 99
<211> LENGTH: 113
<212> TYPE: PRT
<213> ORGANISM: Artificial Sequence
<220> FEATURE:
<223> OTHER INFORMATION: Synthetic Artificial Sequence

<400> SEQUENCE: 99

```
Asp Ile Val Met Thr Gln Ser Pro Ser Ser Leu Ala Val Ser Val Gly
1               5                   10                  15

Glu Arg Val Thr Ile Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ala Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Asp Thr Pro Tyr Thr Phe Gly Gly Gly Thr Lys Leu Glu Ile
            100                 105                 110

Lys
```

<210> SEQ ID NO 100
<211> LENGTH: 660
<212> TYPE: DNA
<213> ORGANISM: Artificial Sequence
<220> FEATURE:
<223> OTHER INFORMATION: Synthetic Artificial Sequence

<400> SEQUENCE: 100

```
gacatcgtga tgacccagtc cccaagctcc ctggccgtgt ctgtgggaga gcgggtgaca     60

atctcctgta agtctagcca gtctctgctg aactcctcta atcagaagaa ctacctggcc    120

tggtatcagc agaagcccgg ccaggcccct aagctgctga tctacttcgc ctctaccagg    180

gagagcggag tgccagacag attctctggc agcggctccg gcacagactt caccctgaca    240

atcagctccg tgcaggcaga ggacgtggca gattactatt gccagcagca ctacgatacc    300

ccctatacat ttggcggcgg caccaagctg gagatcaagc gtacggtggc agccccatct    360
```

-continued

```
gtcttcattt ttccccctag tgacgagcag ctgaaatccg gaacagcctc tgtggtctgt    420

ctgctgaaca atttctaccc tcgcgaagcc aaggtgcagt ggaaagtcga taacgctctg    480

cagagtggca attcacagga gagcgtgact gaacaggact ccaaggattc tacctatagt    540

ctgagctcca ctctgaccct gtccaaagca gattacgaaa agcacaaagt gtatgcctgt    600

gaggtcaccc accaggggct gagttctcca gtcaccaaat ccttcaacag aggcgaatgt    660


<210> SEQ ID NO 101
<211> LENGTH: 5
<212> TYPE: PRT
<213> ORGANISM: Artificial Sequence
<220> FEATURE:
<221> NAME/KEY: misc_feature
<222> LOCATION: 1..5
<223> OTHER INFORMATION: (GGGGS)n linker peptide, wherein n is any
      positive integer.
<220> FEATURE:
<223> OTHER INFORMATION: Synthetic Artificial Sequence

<400> SEQUENCE: 101

Gly Gly Gly Gly Ser


<210> SEQ ID NO 102
<211> LENGTH: 5
<212> TYPE: PRT
<213> ORGANISM: Artificial Sequence
<220> FEATURE:
<223> OTHER INFORMATION: Synthetic Artificial Sequence

<400> SEQUENCE: 102

Gly Gly Gly Gly Ser
```

ANTI-CD73-ANTI-PD-1 BISPECIFIC ANTIBODY AND USE THEREOF

SEQUENCE LISTING

This application contains a Sequence Listing which has been submitted electronically in ASCII format and is hereby incorporated by reference in its entirety. Said ASCII copy, created on Jun. 18, 2026, is named "FP220366-Sequence Listing-revised" and is 100,126 bytes in size.

TECHNICAL FIELD

The present invention relates to the fields of tumor treatment and molecular immunology, and particularly to an anti-CD73/anti-PD-1 bispecific antibody, a pharmaceutical composition thereof, and use thereof.

BACKGROUND

Ecto-5'-nucleotidase, namely CD73 protein, is a multi-functional glycoprotein encoded by NT5E gene and having a molecular weight of 70 KD, which is anchored on a cell membrane by glyocsyl phosphatidy linositol (GPI) (Zimmermann H., 5'-Nucleotidase: molecular structure and functional aspects, *Biochem J.,* 1992; 285:345-365).

CD73 is widely distributed on the surface of human tissue cells, and it has been found in research that CD73 is highly expressed in various solid tumors, specifically in cancer cells, dendritic cells, regulatory T cells (Tregs), natural killer cells (NK cells), myeloid-derived suppressor cells (MDSCs), tumor-associated macrophages (TAMs) and the like in a tumor micro environment. The expression of CD73 is regulated by TGF-β, EGFR, AKT, β-catenin and other molecules, especially HIF-1, which exerts the function of a transcription factor, is the most critical. An important feature of the tumor microenvironment is hypoxia, which induces the up-regulation of hypoxia-inducible factor-1 (HIF-1) and other molecules, thereby leading to the widespread expression of CD73 in the tumor micro environment (Synnestvedt K, et al., Ecto-5'-nucleotidase (CD73) regulation by hypoxia-inducible factor-1 mediates permeability changes in intestinal epithelia. *J Clin Invest.,* 2002; 110:993-1002). Analysis of clinical tumor samples has shown that high expression of CD73 is a potential biomarker and is closely related to adverse prognosis of various types of tumors, including breast cancer, lung cancer, ovarian cancer, kidney cancer, gastric cancer, head and neck cancer and the like.

CD73 has hydrolase activity and non-hydrolase activity. The enzyme and non-enzyme functions of CD73 simultaneously work in the related process in tumors, and mutually promote and maintain the progression of tumors. More and more studies have found that CD73 is a key regulatory molecule for tumor cell proliferation, metastasis and invasion in vitro, and tumor angiogenesis and tumor immune escape mechanism in vivo, wherein an important mechanism of immune suppression is mediated by CD73-adenosine metabolic signaling pathway. CD39 at the upstream of CD73 can catalyze ATP to generate adenosine monophosphate (AMP), the generated AMP is converted into adenosine by CD73, and adenosine binds to a downstream adenosine receptor (A2AR). A2AR inhibits a series of signaling pathways related to immune activation, such as LCK, MAPK, PKC, and inhibits the immune killing effect of T cells by activating protein kinase A (PKA) and Csk kinase, thereby playing an immune suppression role to enable the tumor to achieve immune escape (Antonioli L, et al., Immunity, inflammation and cancer: a leading role for adenosine. *Nat Rev Cancer.,* 2013; 13:842-857). Preclinical animal model studies have shown that CD73 expressed in immune cells and non-immune cells can promote the immune escape, development and metastasis of tumors, wherein the inhibition of cytotoxic T cell (CTL) and NK cell functions by Treg cell-related CD73-adenosine signals is the most significant.

For the treatment of solid tumors, one important aspect of overcoming drug resistance and improving the therapeutic effect is to relieve the inhibition effect of the tumor micro environment (TME) on immune effector cells. TME is a very complex system composed of various cells, intercellular matrix, enzymes, cytokines, metabolites, etc. It features significant low hydrogen, low pH and high pressure, and is greatly different from normal tissues. Hypoxia or ATP enrichment caused by chemoradiotherapy for killing tumor cells promotes the cascade reaction of CD39-CD73 adenosine signals, which is beneficial to the proliferation and function of various cancer-promoting cells, but is not beneficial to cancer-inhibiting cells. (Regateiro, F. S., Cobbold, S. P. & Waldmann, H., CD73 and adenosine generation in the creation of regulatory microenvironments. *Clin. Exp. Immunol.,* 2013; 171:1-7).

The use of antibodies targeting CD73 or gene knock-out of CD73 in animal models can effectively block the growth and metastasis of tumors. Recently, the use of CD73 monoclonal antibody, small interfering RNA technology, specific inhibitor APCP and the like has achieved remarkable therapeutic effect in anti-tumor treatment of animal experiments, providing a new way for anti-tumor treatment. Evidence from in vivo studies has shown that targeted blockade of CD73 will be an effective treatment means for tumor patients.

The relation between CD73 overexpression and tumor subtype, prognosis and response in patients has shown that CD73 can be an important marker for future tumor treatment and detection of individuals. Therefore, the study of the CD73 target is indispensable.

The transmembrane receptor PD-1 (programmed cell death protein 1) is a member of the CD28 family, and is expressed in activated T cells, B cells and myeloid cells. The receptors of PD-1, PDL1 and PDL2, are members of the B7 superfamily. PDL1 is expressed in a variety of cells including T cells, B cells, endothelial cells and epithelial cells, and PDL2 is expressed only in antigen presenting cells such as dendritic cells and macrophages.

PD-1 plays a very important role in down-regulating the activation of T cells, and the PD-1-mediated down-regulation of T cells is one of the important mechanisms of tumor immune escape. PDL-1 expressed on the surface of tumors can bind to PD-1 on the surface of immune cells, thereby inhibiting the killing of tumor tissues by the immune cells through the PD-1/PDL-1 signaling pathway, and tumors with high expression of PD-L1 are associated with cancers that are difficult to detect (Hamanishi et al., *Proc. Natl. Acad. Sci. USA,* 2007; 104:3360-5). An effective way to antagonize PD-1 and thus inhibit PD-1/PDL-1 signaling pathway is injection of anti-PDL-1 antibody.

Due to the broad anti-tumor prospect and surprising efficacy of PD-1 antibodies, it is widely accepted that antibodies targeting the PD-1 pathway will bring about breakthroughs in the treatment of a variety of tumors: non-small cell lung cancer, renal cell carcinoma, ovarian cancer and melanoma (Homet M. B., Parisi G., et al., Anti-PD-1 therapy in melanoma. *Semin Oncol.,* 2015 June; 42(3): 466-473), and hematological tumor and anemia (Held S A, Heine A, et al., Advances in immunotherapy of chronic myeloid leukemia CML. *Curr Cancer Drug Targets,* 2013 September; 13(7): 768-74).

Bifunctional antibodies, also known as bispecific antibodies, are specific antibody drugs that target two different antigens simultaneously, and can be produced by immunosorting and purification, or can be obtained by genetic engineering. The genetic engineering has flexibility in aspects of binding site optimization, synthetic form, yield and the like, thus having certain advantages. Currently, over 45 forms of the bispecific antibody have been demonstrated (Müller D, Kontermann R E. Bispecific antibodies for cancer immunotherapy: current perspectives. *BioDrugs* 2010; 24:89-98). The IgG-ScFv form, namely the Morrison form (Coloma M J, Morrison S L. Design and production of novel tetravalent bispecific antibodies. *Nat Biotechnol. Nature Biotechnology,* 1997; 15:159-163), has been demonstrated to be an ideal form of the bifunctional antibody due to its similarity to the naturally existing IgG form and advantages in antibody engineering, expression and purification (Miller B R, Demarest S J, et al., Stability engineering of scFvs for the development of bispecific and multivalent antibodies. *Protein Eng Des Sel* 2010; 23:549-57; Fitzgerald J, Lugovskoy A. Rational engineering of antibody therapeutics targeting multiple oncogene pathways. *MAbs* 2011; 3:299-309).

ADCC (antibody-dependent cell-mediated cytotoxicity) refers to killing of a target cell by a killer cell (NK cell, macrophage, etc.) that is mediated by binding of the Fab fragment of an antibody to an epitope of a virus-infected cell or a tumor cell and binding of the Fc fragment of the antibody to an Fc receptor (FcR) on the surface of the killer cell.

CDC (complement dependent cytotoxicity) refers to a lytic effect on target cells by a membrane-attacking complex that is formed by the bindings of an antibody to a corresponding antigen on a cell membrane surface and later to the complement C1q and activation of C2-C9.

The IgG family comprises four members, IgG1, IgG2, IgG3 and IgG4, which differ in amino acids in the fragment crystallizable (Fc) region of the heavy chain constant region, resulting in their varying affinities for FcγRs. Wild-type IgG1 can bind to various FcγRs and elicit ADCC and CDC effects. Zhang et al. (Zhang T et al, *Cancer Immunol Immunother.,* 2018; 67(7): 1079-1090) and Dahan et al. (Dahan R et al., *Cancer cell,* 2015, 28(3): 285-95) reported that the binding of Fc fragments of antibodies targeting immune checkpoints such as PD-1 to Fc receptors negatively affects antibody-mediated anti-cancer activity, possibly because Fc-dependent effector function-induced immune cell damage, including antibody-dependent cell-mediated cytotoxicity, is an important mechanism leading to immune cell damage.

Interleukin-8 (IL-8) is a chemotactic cytokine and is mainly secreted by monocytes and the like. IL-8 plays an important role in the proliferation of normal cells and tumor cells, especially in promoting the development and progression of tumors. Studies have shown that IL-8 can promote the development of tumors; and the tumor cells themselves also secrete IL-8 to promote tumor growth and metastasis (Lo M C et al., *Cancer letters,* 2013, 335(1): 81-92). Therefore, IL-8 has become an important inflammatory factor indispensable in the tumor micro environment.

As a pro-inflammatory factor, IL-8 is closely related to the development and progression of tumors. During the methylarsonate-induced malignant transformation of non-renal cancer cells, the expression of IL-8 gene is increased. Gene silencing of IL-8 can significantly inhibit the growth of transplanted tumors in mice, and in addition, the reduction of IL-8 level can inhibit the expression of matrix metalloproteinase-9, cyclin D1, pro-apoptotic protein Bcl-2 and vascular endothelial growth factor (VEGF), which are related to the growth and metastasis of tumors (Escudero-Lourdes C et al., *Toxicology and applied pharmacology,* 2012, 258(1): $10^{-18}$). Inoue et al. found that IL-8 can induce malignant transformation of non-neoplastic bladder cell line (233JP) and increases its aggressiveness, while the incidence of malignant transformation of 233JP cells is significantly reduced in IL-8 knock-out mice (Inoue K et al., *Cancer Res,* 2000, 60(8): 2290-2299). Furthermore, in prostate cancer, IL-8 can promote the development of castration-resistant prostate cancer (CRPC) in patients (Chen K et al., *Cancer research,* 2015, 75(10): 1992-2004), and is associated with drug resistance to tumor treatment (Araki S et al., *Cancer Res,* 2007, 67(14): 6854-6862); gene silencing of IL-8 or its receptor can induce cell cycle arrest in tumor cells and inhibit tumor proliferation (Singh R K, Lokeshwar B L., *Molecul Cancer,* 2009, 8:57). The above studies have shown that the level of IL-8 is closely related to the development and progression of tumors. Further studies (Mian B M et al. *Clin Cancer Res,* 2003, 9(8): 3167-3175) have shown that IL-8 can be a novel target for tumor treatment. In a tumor model of bladder cancer, the use of anti-IL-8 antibodies can significantly inhibit the growth of tumors.

IL-6 is mainly produced rapidly by macrophages in response to pathogen-associated molecular patterns (PAMPs) or damage-associated molecular patterns (DAMPs), and plays a protective role by removing infectious agents and inducing acute phase and immune responses to cure the damaged tissues. Although IL-6 plays an important role in infection and the resistance to and repair of tissue damage, a high level of IL-6 can activate the coagulation pathway and vascular endothelial cells, thereby inhibiting myocardial function, and can even cause a “cytokine storm”, resulting in severe acute systemic inflammatory responses. Cytokine storm is a fatal complication and adverse effect in viral infection, tumor immunotherapy and the like.

Immune-related adverse effect is a common and dangerous adverse effect in the anti-tumor treatment with immune checkpoint inhibitors (ICIs) (Spain L et al., *Cancer Treat Rev.,* 2016; 44:51-60). In recent years, immune checkpoint inhibitors have achieved great success in tumor immunotherapy, but also led to a brand-new toxicity profile due to off-target effects, among which the severe immune-related adverse events (irAEs) in major organs (including heart, lung and brain) are especially life-threatening (Bergqvist V, et al., *Cancer Immunol Immunother.,* 2017; 66(5): 581-592; Gomatou G et al., *Respiration.,* 2020; 1:1-11; Joshi M N et al., *Clin Endocrinol* (*Oxf*), 2016; 85(3): 331-9; Prieux-Klotz C et al., *Target Oncol.,* 2017; 12(3): 301-308; Tajiri K et al., *Jpn J Clin Oncol.,* 2018; 48(1): 7-12). Existing data have shown that ICIs can induce off-target effects by 4 mechanisms, including direct binding to immune checkpoint molecules expressed on the surface of normal cells, and activating complement hypersensitivity; the presence of homologous antigens/epitopes in normal tissues and tumor cells; producing autoantibodies; increasing the level of pro-inflammatory cytokines, such as IL-6 and the like (Martins F et al., *The Lancet Oncology,* 20(1), e54-e64).

Currently, anti-IL-6 therapy, such as tocilizumab, a recombinant humanized anti-IL-6R monoclonal antibody, has been used to treat severe irAEs, severe or refractory arthritis, large vessel vasculitis, uveitis, myocarditis, pneumonia, myasthenia gravis and the like in the acute phase (Martins F et al., *The Lancet Oncology,* 20(1), e54-e64).

Binding of FcγRIa on macrophages to wild-type IgG1 or IgG4 antibodies can induce the macrophages to secrete IL-8 and IL-6 (Kinder M et al., *mAbs.,* 2015), while inducing mutations in the Fc segments of antibodies and eliminating their binding to FcγRIa can effectively inhibit the secretion of IL-8, thereby improving the safety and efficacy of the antibodies.

SUMMARY

The inventors used mammalian cell expression systems to express recombinant human CD73 and PD-1 as antigens to immunize mice, and obtained hybridoma cells by fusion of mouse spleen cells and myeloma cells. The inventors obtained the following hybridoma cell lines by screening a large number of the samples:

- hybridoma cell line LT014 (also called CD73-19F3) deposited at China Center for Type Culture Collection (CCTCC) on Jun. 19, 2018 with an accession number of CCTCC NO: C2018137; and
- hybridoma cell line LT003 (also called PD-1-14C12) deposited at China Center for Type Culture Collection (CCTCC) on Jun. 16, 2015 with an accession number of CCTCC NO: C2015105.

The inventors surprisingly found that:

- the hybridoma cell line LT014 can secrete a specific monoclonal antibody (named as 19F3) specifically binding to human CD73, and the monoclonal antibody can effectively inhibit the enzyme activity reaction of CD73 in a non-substrate competition mode, reduce the production of adenosine, and promote the activity and the tumor inhibitory effect of T cells; and
- the hybridoma cell line LT003 may secrete a specific monoclonal antibody (named as 14C12) specifically binding to PD-1, and the monoclonal antibody can effectively block the binding of PD-1 to PDL1.

Furthermore, the inventors creatively prepared humanized anti-CD73 antibodies (named as 19F3H2L2, 19F3H2L3, 19F3H2L3(hG1M) and 19F3H2L3(hG1TM), respectively) and humanized anti-PD-1 antibodies (named as 14C12H1L1 and 14C12H1L1(hG1TM)).

Furthermore, the inventors creatively fused two types of humanized antibodies into new antibodies through protein recombination, and obtained humanized bifunctional antibodies (named as P1D7V01, P1D7V03, NTPDV1, NTPDV2, NTPDV3 and NTPDV4, respectively (also written as NTPDV1(hG1TM), NTPDV2(hG1TM), NTPDV3 (hG1TM) and NTPDV4(hG1TM) herein and in the Chinese Patent Application NO. 202110270671.X)) capable of binding to CD73 and PD-1, inhibiting the activity of CD73 and blocking the binding of PD-1 to PDL1, and having the potential for use in preparing a medicament for preventing and treating of solid tumors and hematological tumors.

The present invention is detailed below.

One aspect of the present invention relates to an anti-CD73/anti-PD-1 bispecific antibody comprising:

- a first protein functional region targeting PD-1, and
- a second protein functional region targeting CD73.

In one embodiment of the present invention, in the bispecific antibody, the first protein functional region comprises: HCDR1, HCDR2 and HCDR3 contained in a heavy chain variable region having an amino acid sequence set forth in SEQ ID NO: 44, wherein preferably the amino acid sequences of HCDR1, HCDR2 and HCDR3 are sequences set forth in SEQ ID NOs: 45-47, respectively, or sequences having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequences set forth in SEQ ID NOs: 45-47, or amino acid sequences having one or more (preferably 1, 2 or 3) conservative amino acid mutations (preferably substitutions, insertions or deletions) compared with the sequences set forth in SEQ ID NOs: 45-47; and

- LCDR1, LCDR2 and LCDR3 contained in a light chain variable region having an amino acid sequence set forth in SEQ ID NO: 49, wherein preferably the amino acid sequences of LCDR1, LCDR2 and LCDR3 are sequences set forth in SEQ ID NOs: 50-52, respectively, or sequences having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequences set forth in SEQ ID NOs: 50-52, or amino acid sequences having one or more (preferably 1, 2 or 3) conservative amino acid mutations (preferably substitutions, insertions or deletions) compared with the sequences set forth in SEQ ID NOs: 50-52;
- the second protein functional region comprises: HCDR1, HCDR2 and HCDR3 contained in a heavy chain variable region having an amino acid sequence set forth in SEQ ID NO: 2, wherein preferably the amino acid sequences of HCDR1, HCDR2 and HCDR3 are sequences set forth in SEQ ID NOs: 3-5, or sequences having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequences set forth in SEQ ID NOs: 3-5, or amino acid sequences having one or more (preferably 1, 2 or 3) conservative amino acid mutations (preferably substitutions, insertions or deletions) compared with the sequences set forth in SEQ ID NOs: 3-5; and
- LCDR1, LCDR2 and LCDR3 contained in a light chain variable region having an amino acid sequence set forth in SEQ ID NO: 7, wherein preferably the amino acid sequences of LCDR1, LCDR2 and LCDR3 are sequences set forth in SEQ ID NOs: 8-10, respectively, or sequences having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequences set forth in SEQ ID NOs: 8-10, or amino acid sequences having one or more (preferably 1, 2 or 3) conservative amino acid mutations (preferably substitutions, insertions or deletions) compared with the sequences set forth in SEQ ID NOs: 8-10.

In one embodiment of the present invention, in the anti-CD73/anti-PD-1 bispecific antibody, the first protein functional region comprises:

- a sequence having an amino acid sequence set forth in SEQ ID NO: 44 or SEQ ID NO: 62, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 44 or 62, or an amino acid sequence having one or more (preferably 1, 2 or 3) conservative amino acid mutations (preferably substitutions, insertions or deletions) compared with the sequences set forth in SEQ ID NO: 44 or 62; and
- a sequence having an amino acid sequence correspondingly set forth in SEQ ID NO: 49 or SEQ ID NO: 64, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 49 or 64, or an amino acid sequence having one or more (preferably 1, 2 or 3) conservative amino acid mutations (preferably substitutions, insertions or deletions) compared with the sequences set forth in SEQ ID NO: 49 or 64;

and/or, the second protein functional region comprises a sequence having an amino acid sequence set forth in SEQ ID NO: 2 or SEQ ID NO: 20, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 2 or 20, or an amino acid sequence having one or more (preferably 1, 2 or 3) conservative amino acid mutations (preferably substitutions, insertions or deletions) compared with the sequences set forth in SEQ ID NO: 2 or 20; and a sequence having an amino acid sequence correspondingly set forth in SEQ ID NO: 7 or SEQ ID NO: 22, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 7 or 22, or an amino acid sequence having one or more (preferably 1, 2 or 3) conservative amino acid mutations (preferably substitutions, insertions or deletions) compared with the sequences set forth in SEQ ID NO: 7 or 22;

or the second protein functional region comprises a sequence having an amino acid sequence set forth in SEQ ID NO: 20, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 20, or an amino acid sequence having one or more (preferably 1, 2 or 3) conservative amino acid mutations (preferably substitutions, insertions or deletions) compared with the sequences set forth in SEQ ID NO: 20; and a sequence having an amino acid sequence set forth in SEQ ID NO: 24, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 24, or an amino acid sequence having one or more (preferably 1, 2 or 3) conservative amino acid mutations (preferably substitutions, insertions or deletions) compared with the sequences set forth in SEQ ID NO: 24.

One aspect of the present invention relates to an anti-CD73/anti-PD-1 bispecific antibody comprising:

a first protein functional region targeting CD73, and a second protein functional region targeting PD-1.

In one embodiment of the present invention, in the bispecific antibody, the first protein functional region comprises: HCDR1, HCDR2 and HCDR3 contained in a heavy chain variable region having an amino acid sequence set forth in SEQ ID NO: 2, wherein preferably the amino acid sequences of HCDR1, HCDR2 and HCDR3 are sequences set forth in SEQ ID NOs: 3-5, respectively, or sequences having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequences set forth in SEQ ID NOs: 3-5, or amino acid sequences having one or more (preferably 1, 2 or 3) conservative amino acid mutations (preferably substitutions, insertions or deletions) compared with the sequences set forth in SEQ ID NOs: 3-5; and LCDR1, LCDR2 and LCDR3 contained in a light chain variable region having an amino acid sequence set forth in SEQ ID NO: 7, wherein preferably the amino acid sequences of LCDR1, LCDR2 and LCDR3 are sequences set forth in SEQ ID NOs: 8-10, respectively, or sequences having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequences set forth in SEQ ID NOs: 8-10, or amino acid sequences having one or more (preferably 1, 2 or 3) conservative amino acid mutations (preferably substitutions, insertions or deletions) compared with the sequences set forth in SEQ ID NOs: 8-10;

the second protein functional region comprises: HCDR1, HCDR2 and HCDR3 contained in a heavy chain variable region having an amino acid sequence set forth in SEQ ID NO: 44, wherein preferably the amino acid sequences of HCDR1, HCDR2 and HCDR3 are sequences set forth in SEQ ID NOs: 45-47, respectively, or sequences having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequences set forth in SEQ ID NOs: 45-47, or amino acid sequences having one or more (preferably 1, 2 or 3) conservative amino acid mutations (preferably substitutions, insertions or deletions) compared with the sequences set forth in SEQ ID NOs: 45-47; and LCDR1, LCDR2 and LCDR3 contained in a light chain variable region having an amino acid sequence set forth in SEQ ID NO: 49, wherein preferably the amino acid sequences of LCDR1, LCDR2 and LCDR3 are sequences set forth in SEQ ID NOs: 50-52, respectively, or sequences having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequences set forth in SEQ ID NOs: 50-52, or amino acid sequences having one or more (preferably 1, 2 or 3) conservative amino acid mutations (preferably substitutions, insertions or deletions) compared with the sequences set forth in SEQ ID NOs: 50-52.

In one embodiment of the present invention, in the anti-CD73/anti-PD-1 bispecific antibody, the first protein functional region comprises:

a sequence having an amino acid sequence set forth in SEQ ID NO: 2 or SEQ ID NO: 20, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 2 or 20, or an amino acid sequence having one or more (preferably 1, 2 or 3) conservative amino acid mutations (preferably substitutions, insertions or deletions) compared with the sequences set forth in SEQ ID NO: 2 or 20; and a sequence having an amino acid sequence correspondingly set forth in SEQ ID NO: 7, SEQ ID NO: 22 or SEQ ID NO: 24, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 7, SEQ ID NO: 22 or SEQ ID NO: 24, or an amino acid sequence having one or more (preferably 1, 2 or 3) conservative amino acid mutations (preferably substitutions, insertions or deletions) compared with the sequences set forth in SEQ ID NO: 7, 22 or 24;

and/or, the second protein functional region comprises a sequence having an amino acid sequence set forth in SEQ ID NO: 44 or SEQ ID NO: 62, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 44 or SEQ ID NO: 62, or an amino acid sequence having one or more (preferably 1, 2 or 3) conservative amino acid mutations (preferably substitutions, insertions or deletions) compared with the sequences set forth in SEQ ID NO: 44 or SEQ ID NO: 62; and a sequence having an amino acid sequence correspondingly set forth in SEQ ID NO: 49 or 64, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 49 or 64, or an amino acid sequence having one or more (preferably 1, 2 or 3) conservative amino acid mutations (preferably substitutions, insertions or deletions) compared with the sequences set forth in SEQ ID NO: 49 or 64.

In one embodiment of the present invention, in the anti-CD73/anti-PD-1 bispecific antibody, the first protein functional region and the second protein functional region are linked directly or via a linker; preferably, the linker is (GGGGS) n represented by SEQ ID NO: 101, and n is a positive integer, e.g., 1, 2, 3, 4, 5 or 6.

In one embodiment of the present invention, the first protein functional region and the second protein functional region in the anti-CD73/anti-PD-1 bispecific antibody are independently an immunoglobulin or an antigen-binding fragment, such as a half-antibody, Fab, $F(ab')_2$ or a single-chain variable fragment, preferably, the first protein functional region is an immunoglobulin and the second protein functional region is an antigen-binding fragment; or the first protein functional region is an antigen-binding fragment and the second protein functional region is an immunoglobulin.

In one embodiment of the present invention, the N terminus of the heavy chain variable region of the antigen-binding fragment is linked directly (or via a linker) to the C terminus of CH1 of the immunoglobulin, and the N terminus of the light chain variable region of the antigen-binding fragment is linked directly (or via a linker) to the C terminus of the light chain variable region CL of the immunoglobulin; or the N terminus of the heavy chain variable region of the antigen-binding fragment is linked directly (or via a linker) to the C terminus of the light chain variable region CL of the immunoglobulin, and the N terminus of the light chain variable region of the antigen-binding fragment is linked directly (or via a linker) to the C terminus of the heavy chain variable region CH1 of the immunoglobulin.

In one embodiment of the present invention, the C terminus of the heavy chain variable region of the antigen-binding fragment is linked directly (or via a linker) to the N terminus of the heavy chain of the immunoglobulin, and the C terminus of the light chain variable region of the antigen-binding fragment is linked directly (or via a linker) to the N terminus of the light chain of the immunoglobulin; or the C terminus of the heavy chain variable region of the antigen-binding fragment is linked directly (or via a linker) to the N terminus of the light chain of the immunoglobulin, and the C terminus of the light chain variable region of the antigen-binding fragment is linked directly (or via a linker) to the N terminus of the heavy chain of the immunoglobulin.

In one embodiment of the present invention, the antigen-binding fragment is a single-chain variable fragment; preferably, the first protein functional region is an immunoglobulin and the second protein functional region is a single-chain variable fragment; or the first protein functional region is a single-chain variable fragment and the second protein functional region is an immunoglobulin.

In one embodiment of the present invention, the bispecific antibody is provided, wherein the numbers of the first protein functional region and the second protein functional region are each independently 1, 2 or more.

In one embodiment of the present invention, in the anti-CD73/anti-PD-1 bispecific antibody, the single-chain variable fragment is a molecule formed by connecting an antibody heavy chain variable region ($V_H$) and an antibody light chain variable region ($V_L$) via a linker; preferably, the single-chain variable fragment may have a general structure: $NH_2$-$V_L$-linker-$V_H$-COOH or $NH_2$-$V_H$-linker-$V_L$-COOH.

In one embodiment of the present invention, in the anti-CD73/anti-PD-1 bispecific antibody, when the single-chain variable fragment is linked to the C terminus of the heavy chain of the immunoglobulin (CH) (or the N terminus of the heavy chain, the C terminal of CH1 of the heavy chain variable region) by a linker, the antibody heavy chain variable region ($V_H$) of the single-chain variable fragment may be firstly linked, or the antibody light chain variable region ($V_L$) of the may be firstly linked; preferably, the single-chain variable fragment may have a general structure: CH-linker-$V_H$-linker-$V_L$-COOH, or CH-linker-$V_L$-linker-$V_H$-COOH, preferably, the heavy chain variable region of the immunoglobulin comprises CDRs having amino acid sequences set forth in SEQ ID NOs: 3-5, and the light chain variable region of the immunoglobulin comprises CDRs having amino acid sequences set forth in SEQ ID NOs: 8-10;

the heavy chain variable region of the single-chain variable fragment comprises CDRs having amino acid sequences set forth in SEQ ID NOs: 45-47, and the light chain variable region of the single-chain variable fragment comprises CDRs having amino acid sequences set forth in SEQ ID NOs: 50-52, preferably, when the single-chain variable fragment (such as $NH_2$-$V_L$-linker-$V_H$-COOH or $NH_2$-$V_H$-linker-$V_L$-COOH) is linked to the C terminus of the heavy chain of the immunoglobulin via a linker, the antibody heavy chain variable region ($V_H$) of the single-chain variable fragment comprising CDRs having amino acid sequences set forth in SEQ ID NOs: 45-47 may be firstly linked, or the antibody light chain variable region ($V_L$) of the single-chain variable fragment comprising CDRs having amino acid sequences set forth in SEQ ID NOs: 50-52 may be firstly linked, or preferably, the heavy chain variable region of the immunoglobulin comprises CDRs having amino acid sequences set forth in SEQ ID NOs: 45-47, and the light chain variable region of the immunoglobulin comprises CDRs having amino acid sequences set forth in SEQ ID NOs: 50-52;

and/or, the heavy chain variable region of the single-chain variable fragment comprises CDRs having amino acid sequences set forth in SEQ ID NOs: 3-5, and the light chain variable region of the single-chain variable fragment comprises CDRs having amino acid sequences set forth in SEQ ID NOs: 8-10, wherein, when the single-chain variable fragment (such as $NH_2$-$V_L$-linker-$V_H$-COOH or $NH_2$-$V_H$-linker-$V_L$-COOH) is linked to the C terminus of the heavy chain of the immunoglobulin via a linker, the antibody heavy chain variable region ($V_H$) of the single-chain variable fragment comprising CDRs having amino acid sequences set forth in SEQ ID NOs: 3-5 may be firstly linked, or the antibody light chain variable region ($V_L$) of the single-chain variable fragment comprising CDRs having amino acid sequences set forth in SEQ ID NOs: 8-10 may be firstly linked, preferably, one immunoglobulin molecule is linked to two single-chain variable fragment molecules, and more preferably, the two single-chain variable fragment molecules are identical.

In one embodiment of the present invention, in the anti-CD73/anti-PD-1 bispecific antibody, the immunoglobulin is IgG, IgA, IgD, IgE or IgM, preferably IgG, e.g., IgG1, IgG2, IgG3 or IgG4.

In one embodiment of the present invention, in the anti-CD73/anti-PD-1 bispecific antibody, the single-chain variable fragment is linked to the C terminus of the heavy chain of the immunoglobulin. Since an immunoglobulin consists of two heavy chains, two single-chain variable fragment molecules are linked to one immunoglobulin molecule. Preferably, the two single-chain variable fragment molecules are identical.

In one embodiment of the present invention, in the anti-CD73/anti-PD-1 bispecific antibody, the heavy chain variable region of the immunoglobulin comprises CDRs having amino acid sequences set forth in SEQ ID NOs: 3-5, and the light chain variable region of the immunoglobulin comprises CDRs having amino acid sequences set forth in SEQ ID NOs: 8-10;

and/or, the heavy chain variable region of the single-chain variable fragment comprises CDRs having amino acid sequences set forth in SEQ ID NOs: 45-47, and the light chain variable region of the single-chain variable fragment comprises CDRs having amino acid sequences set forth in SEQ ID NOs: 50-52, preferably, when the single-chain variable fragment (such as $NH_2$-$V_L$-linker-$V_H$-COOH or $NH_2$-$V_H$-linker-$V_L$-COOH) is linked to the C terminus of the heavy chain of the immunoglobulin via a linker, the antibody heavy chain variable region ($V_H$) of the single-chain variable fragment comprising CDRs having amino acid sequences set forth in SEQ ID NOs: 45-47 may be firstly linked, or the antibody light chain variable region ($V_L$) of the single-chain variable fragment comprising CDRs having amino acid sequences set forth in SEQ ID NOs: 50-52 may be firstly linked.

In another embodiment of the present invention, in the anti-CD73/anti-PD-1 bispecific antibody, the heavy chain variable region of the immunoglobulin comprises CDRs having amino acid sequences set forth in SEQ ID NOs: 45-47, and the light chain variable region of the immunoglobulin comprises CDRs having amino acid sequences set forth in SEQ ID NOs: 50-52;

and/or, the heavy chain variable region of the single-chain variable fragment comprises CDRs having amino acid sequences set forth in SEQ ID NOs: 3-5, and the light chain variable region of the single-chain variable fragment comprises CDRs having amino acid sequences set forth in SEQ ID NOs: 8-10, wherein, when the single-chain variable fragment (such as $NH_2$-$V_L$-linker-$V_H$-COOH or $NH_2$-$V_H$-linker-$V_L$-COOH) is linked to the C terminus of the heavy chain of the immunoglobulin via a linker, the antibody heavy chain variable region ($V_H$) of the single-chain variable fragment comprising CDRs having amino acid sequences set forth in SEQ ID NOs: 3-5 may be firstly linked, or the antibody light chain variable region ($V_L$) of the single-chain variable fragment comprising CDRs having amino acid sequences set forth in SEQ ID NOs: 8-10 may be firstly linked.

In one embodiment of the present invention, in the anti-CD73/anti-PD-1 bispecific antibody, the heavy chain variable region of the immunoglobulin has an amino acid sequence selected from SEQ ID NO: 2 and SEQ ID NO: 20, and the light chain variable region of the immunoglobulin has an amino acid sequence correspondingly selected from SEQ ID NO: 7 and SEQ ID NO: 22; or the heavy chain variable region of the immunoglobulin has an amino acid sequence set forth in SEQ ID NO. 20, and the light chain variable region of the immunoglobulin has an amino acid sequence set forth in SEQ ID NO. 24;

and/or, the heavy chain variable region of the single-chain variable fragment has an amino acid sequence selected from SEQ ID NO: 44 and SEQ ID NO: 62, and the light chain variable region of the single-chain variable fragment has an amino acid sequence correspondingly selected from SEQ ID NO: 49 and SEQ ID NO: 64;

wherein, when the single-chain variable fragment is linked to the C terminus of the heavy chain of the immunoglobulin via a linker, the antibody heavy chain variable region ($V_H$) of the single-chain variable fragment may be firstly linked, or the antibody light chain variable region ($V_L$) of the single-chain variable fragment may be firstly linked.

In another embodiment of the present invention, in the anti-CD73/anti-PD-1 bispecific antibody, the heavy chain variable region of the immunoglobulin has an amino acid sequence selected from SEQ ID NO: 44 and SEQ ID NO: 62; the light chain variable region of the immunoglobulin has an amino acid sequence correspondingly selected from SEQ ID NO: 49 and SEQ ID NO: 64, or the heavy chain variable region of the single-chain variable fragment has an amino acid sequence selected from SEQ ID NO: 2 and SEQ ID NO: 20, the light chain variable region of the single-chain variable fragment has an amino acid sequence correspondingly selected from SEQ ID NO: 7 and SEQ ID NO: 22, or the heavy chain variable region of the single-chain antibody has an amino acid sequence set forth in SEQ ID NO: 20, and the light chain variable region of the single-chain variable fragment has an amino acid sequence set forth in SEQ ID NO: 24.

Another aspect of the present invention relates to an isolated nucleic acid molecule comprising a nucleotide sequence capable of encoding a heavy chain variable region of a bispecific antibody, wherein, the heavy chain variable region of the antibody comprises:

a CDR having an amino acid sequence of SEQ ID NOs: 3-5, a CDR having an amino acid sequence of SEQ ID NOs: 45-47, and a CDR having an amino acid sequence of SEQ ID NOs: 50-52;

and the heavy chain variable region of the bispecific antibody specifically binds to CD73 and PD-1 antigens as a part of the bispecific antibody, and the bispecific antibody further comprises a light chain variable region comprising:

a CDR having an amino acid sequence of SEQ ID NOs: 8-10;

preferably, the CDRs of the light chain variable region are different from the CDRs of the heavy chain variable region.

In one embodiment of the present invention, in the bispecific antibody, the immunoglobulin comprises a non-CDR region derived from a species other than murine, such as from a human antibody.

In one embodiment of the present invention, the constant regions of the immunoglobulin are humanized. For example, the heavy chain constant region is Ig gamma-1 chain C region, ACCESSION: P01857; and the light chain constant region is Ig kappa chain C region, ACCESSION: P01834.

In one embodiment of the present invention, the constant regions of the immunoglobulin are humanized. For example, the heavy chain constant region is Ig gamma-1 chain C region, ACCESSION: P01857; and the light chain constant region is Ig kappa chain C region, ACCESSION: P01834; wherein, according to the EU numbering system, the heavy chain constant region of the immunoglobulin comprises mutations at any 2 or 3 of positions 234, 235 and 237, and the affinity constant of the bispecific antibody for FcγRIa, FcγRIIIa and/or C1q is reduced after the mutations as compared to that before the mutations; preferably, the affinity constants are measured by a Fortebio Octet system.

In one or more embodiments of the present invention, for the bispecific antibody, according to the EU numbering system, the heavy chain constant region of the immunoglobulin has the following mutations at positions 234, 235 and/or 237:

L234A and L235A;

L234A and G237A;

L235A and G237A;

or

L234A, L235A and G237A.

In the present invention, letters before the position number represent amino acids before mutation, and letters after the position number represent amino acids after mutation, unless otherwise specified.

In one or more embodiments of the present invention, for the bispecific antibody, according to the EU numbering system, the heavy chain constant region of the immunoglobulin has one or more mutations selected from:

N297A, D265A, D270A, P238D, L328E, E233D, H268D, P271G, A330R, C226S, C229S, E233P, P331S, S267E, L328F, A330L, M252Y, S254T, T256E, N297Q, P238S, P238A, A327Q, A327G, P329A, K322A, T394D, G236R, G236A, L328R, A330S, P331S, H268A, E318A and K320A.

In a specific embodiment, the anti-CD73/anti-PD-1 bispecific antibody has a structure shown as heavy chain-light chain-linker 1-scFv, and the scFv is selected from 14C12H1V-linker 2-14C12L1V, 14C12H1V-linker 1-14C12L1V, 14C12H1V-linker 2-14C12L1V and 14C12H1V-linker 1-14C12L1V, particularly selected from the group consisting of:

(1) NTPDV1, of which the heavy chain has an amino acid sequence set forth in SEQ ID NO: 85, the light chain has an amino acid sequence set forth in SEQ ID NO: 28, the linker 1 has an amino acid sequence set forth in SEQ ID NO: 79, 14C12H1V has an amino acid sequence set forth in SEQ ID NO: 62, the linker 2 has an amino acid sequence set forth in SEQ ID NO: 81, and 14C12L1V has an amino acid sequence set forth in SEQ ID NO: 64;

(2) NTPDV2, of which the heavy chain has an amino acid sequence set forth in SEQ ID NO: 83, the light chain has an amino acid sequence set forth in SEQ ID NO: 28, the linker 1 has an amino acid sequence set forth in SEQ ID NO: 79, 14C12H1V has an amino acid sequence set forth in SEQ ID NO: 62, the linker 1 has an amino acid sequence set forth in SEQ ID NO: 79, and 14C12L1V has an amino acid sequence set forth in SEQ ID NO: 64;

(3) NTPDV3, of which the heavy chain has an amino acid sequence set forth in SEQ ID NO: 85, the light chain has an amino acid sequence set forth in SEQ ID NO: 96, the linker 1 has an amino acid sequence set forth in SEQ ID NO: 79, 14C12H1V has an amino acid sequence set forth in SEQ ID NO: 62, the linker 2 has an amino acid sequence set forth in SEQ ID NO: 81, and 14C12L1V has an amino acid sequence set forth in SEQ ID NO: 64; and (4) NTPDV4, of which the heavy chain has an amino acid sequence set forth in SEQ ID NO: 83, the light chain has an amino acid sequence set forth in SEQ ID NO: 96, the linker 1 has an amino acid sequence set forth in SEQ ID NO: 79, 14C12H1V has an amino acid sequence set forth in SEQ ID NO: 62, the linker 1 has an amino acid sequence set forth in SEQ ID NO: 79, and 14C12L1V has an amino acid sequence set forth in SEQ ID NO: 64.

In one embodiment of the present invention, the bispecific antibody binds to CD73 protein and/or PD-1 protein with a $K_D$ of less than about $10^{-5}$ M, e.g., less than about $10^{-6}$ M, $10^{-7}$ M, $10^{-8}$ M, $10^{-9}$ M, $10^{-10}$ M or less.

Yet another aspect of the present invention relates to a vector comprising the isolated nucleic acid molecule disclosed herein.

Yet another aspect of the present invention relates to a host cell comprising the isolated nucleic acid molecule or the vector disclosed herein.

Yet another aspect of the present invention relates to a method for preparing the bispecific antibody disclosed herein, comprising culturing the host cell disclosed herein in a suitable condition and isolating the bispecific antibody from the cell cultures.

Yet another aspect of the present invention relates to a conjugate comprising a bispecific antibody and a conjugated moiety, wherein the bispecific antibody is the bispecific antibody disclosed herein and the conjugated moiety is a detectable label; specifically, the conjugated moiety is a radioisotope, a fluorescent substance, a chemiluminescent substance, a colored substance or an enzyme.

Yet another aspect of the present invention relates to a kit comprising the bispecific antibody disclosed herein or comprising the conjugate disclosed herein; preferably, the kit further comprises a secondary antibody that specifically recognizes the bispecific antibody; optionally, the secondary antibody further comprises a detectable label, e.g., a radioisotope, a fluorescent substance, a chemiluminescent substance, a colored substance or an enzyme.

Yet another aspect of the present invention relates to use of the bispecific antibody disclosed herein in preparing a kit for detecting the presence or level of CD73 and/or PD-1 in a sample.

Yet another aspect of the present invention relates to a pharmaceutical composition comprising the bispecific antibody disclosed herein or the conjugate disclosed herein; optionally, the pharmaceutical composition further comprises a pharmaceutically acceptable carrier and/or excipient.

Yet another aspect of the present invention relates to use of the bispecific antibody disclosed herein or the conjugate disclosed herein in preventing and/or treating a tumor or anemia, or in diagnosing a tumor or anemia.

Yet another aspect of the present invention relates to use of the bispecific antibody disclosed herein or the conjugate disclosed herein in preparing a medicament for preventing and/or treating a tumor or anemia, or in preparing a medicament for diagnosing a tumor or anemia.

Yet another aspect of the present invention relates to use of the bispecific antibody disclosed herein or the conjugate disclosed herein in preparing:

- a medicament for detecting the level of CD73 in a sample,
- a medicament for inhibiting the enzyme activity reaction of CD73;

and/or

- a medicament for blocking the binding of PD-1 to PD-L1,
- a medicament for down-regulating (e.g., down-regulating) the activity or level of PD-1,
- a medicament for relieving the immunosuppression of PD-1 in an organism,
- a medicament for elevating IL-2 expression in T lymphocytes, or
- a medicament for elevating IFN-γexpression in T lymphocytes.

Yet another aspect of the present invention relates to an in vivo or in vitro method comprising administering to a cell or administering to a subject in need an effective amount of the bispecific antibody disclosed herein or the conjugate disclosed herein.

The anti-CD73/anti-PD-1 bispecific antibodies disclosed herein can inhibit the enzyme activity of CD73 a cell membrane surface, and can induce the secretion of IFNγ and IL-2 to activate the immune response.

The variable regions of the light chain and the heavy chain determine the binding of the antigen; the variable region of each chain contains three hypervariable regions called complementarity determining regions (CDRs) (CDRs of the heavy chain (H) comprise HCDR1, HCDR2 and HCDR3, and CDRs of the light chain (L) comprise LCDR1, LCDR2 and LCDR3, which are named by Kabat et al., see Bethesda M.d., *Sequences of Proteins of Immunological Interest*, Fifth Edition, NIH Publication 1991; 1-3:91-3242.

Preferably, CDRs may also be defined by the IMGT numbering system, see Ehrenmann F, Kaas Q, and Lefranc M P., IMGT/3Dstructure-DB and IMGT/DomainGapAlign: a database and a tool for immunoglobulins or antibodies, T cell receptors, MHC, IgSF and MhcSF[J]. Nucleic acids research 2009; 38(suppl_1): D301-D307.

The amino acid sequences of the CDRs of the monoclonal antibody in (1) to (11) below are analyzed by technical means well known to those skilled in the art, for example, according to the IMGT definition, and the results are as follows:

(1) 19F3

The heavy chain variable region has an amino acid sequence set forth in SEQ ID NO: 2, and the light chain variable region has an amino acid sequence set forth in SEQ ID NO: 7.

The 3 CDRs of the heavy chain variable region have the following amino acid sequences:

```
HCDR1:
                              (SEQ ID NO: 3)
GYSFTGYT,

HCDR2:
                              (SEQ ID NO: 4)
INPYNAGT, and

HCDR3:
                              (SEQ ID NO: 5)
ARSEYRYGGDYFDY;
```

the 3 CDRs of the light chain variable region have the following amino acid sequences:

```
LCDR1:
                              (SEQ ID NO: 8)
QSLLNSSNQKNY,

LCDR2:
                              (SEQ ID NO: 9)
FAS, and

LCDR3:
                             (SEQ ID NO: 10)
QQHYDTPYT.
```

(2) 19F3H2L2

The heavy chain variable region has an amino acid sequence set forth in SEQ ID NO: 20, and the light chain variable region has an amino acid sequence set forth in SEQ ID NO: 22.

The 3 CDRs of the heavy chain variable region have the same amino acid sequences as 19F3.

The 3 CDRs of the light chain variable region have the same amino acid sequences as 19F3.

(3) 19F3H2L3

The heavy chain variable region has an amino acid sequence set forth in SEQ ID NO: 20, and the light chain variable region has an amino acid sequence set forth in SEQ ID NO: 24.

The 3 CDRs of the heavy chain variable region have the same amino acid sequences as 19F3.

The 3 CDRs of the light chain variable region have the same amino acid sequences as 19F3.

(4) 14C12

The heavy chain variable region has an amino acid sequence set forth in SEQ ID NO: 44, and the light chain variable region has an amino acid sequence set forth in SEQ ID NO: 49.

The 3 CDRs of the heavy chain variable region have the following amino acid sequences:

```
HCDR1:
                             (SEQ ID NO: 45)
GFAFSSYD

HCDR2:
                             (SEQ ID NO: 46)
ISGGGRYT
```

-continued

HCDR3: (SEQ ID NO: 47)
ANRYGEAWFAY the 3 CDRs of the light chain variable region have the following amino acid sequences:

LCDR1: (SEQ ID NO: 50)
QDINTY

LCDR2: (SEQ ID NO: 51)
RAN

LCDR3: (SEQ ID NO: 52)
LQYDEFPLT (5) 14C12H1L1

The heavy chain variable region has an amino acid sequence set forth in SEQ ID NO: 62, and the light chain variable region has an amino acid sequence set forth in SEQ ID NO: 64.

The 3 CDRs of the heavy chain variable region have the same amino acid sequences as 14C12.

The 3 CDRs of the light chain variable region have the same amino acid sequences as 14C12.

(6) The 9 CDRs of the heavy chain of NTPDV1, NTPDV2, NTPDV3 and NTPDV4 has the same amino acid sequences as those of the CDRs of 13F9 heavy chain, 14C12 heavy chain and 14C12 light chain regions, respectively, in the order from N terminus to C terminus. The sequences, in the order described above, are as follows:

HCDR1: (SEQ ID NO: 3)
GYSFTGYT

HCDR2: (SEQ ID NO: 4)
INPYNAGT

HCDR3: (SEQ ID NO: 5)
ARSEYRYGGDYFDY

HCDR4: (SEQ ID NO: 45)
GFAFSSYD

HCDR5: (SEQ ID NO: 46)
ISGGGRYT

HCDR6: (SEQ ID NO: 47)
ANRYGEAWFAY

HCDR7: (SEQ ID NO: 50)
QDINTY

HCDR8: (SEQ ID NO: 51)
RAN

HCDR9: (SEQ ID NO: 52)
LQYDEFPLT

The 3 CDRs of the light chain has the same amino acid sequences as those of the three CDRs of 19F3 light chain, and the sequences are as follows:

LCDR1: (SEQ ID NO: 8)
QSLLNSSNQKNY

LCDR2: (SEQ ID NO: 9)
FAS

LCDR3: (SEQ ID NO: 10)
QQHYDTPYT

Yet another aspect of the present invention relates to hybridoma cell line LT014 deposited at China Center for Type Culture Collection (CCTCC) with a collection number of CCTCC NO: C2018137. Yet another aspect of the present invention relates to hybridoma cell line LT003 deposited at China Center for Type Culture Collection (CCTCC) with a collection number of CCTCC NO: C2015105.

In the present invention, unless otherwise specified, the scientific and technical terms used herein have the meanings generally understood by those skilled in the art. In addition, the laboratory operations of cell culture, molecular genetics, nucleic acid chemistry and immunology used herein are the routine procedures widely used in the corresponding fields. Meanwhile, in order to better understand the present invention, the definitions and explanations of the relevant terms are provided below.

As used herein, the term $EC_{50}$ refers to the concentration for 50% of maximal effect, i.e., the concentration that can cause 50% of the maximal effect.

As used herein, the term “antibody” refers to an immunoglobulin molecule that generally consists of two pairs of polypeptide chains (each pair with one “light” (L) chain and one “heavy” (H) chain).

Antibody light chains are classified as κ and λ light chains. Heavy chains are classified as μ, δ, γ, α, or ε. Isotypes of antibodies are defined as IgM, IgD, IgG, IgA, and IgE. In light chains and heavy chains, the variable region and constant region are linked by a “J” region of about 12 or more amino acids, and the heavy chain further comprises a “D” region of about 3 or more amino acids. Each heavy chain consists of a heavy chain variable region (VH) and a heavy chain constant region (CH). The heavy chain constant region consists of 3 domains (CH1, CH2, and CH3). Each light chain consists of a light chain variable region (VL) and a light chain constant region (CL). The light chain constant region consists of one domain CL. The constant region of the antibody can mediate the binding of immunoglobulins to host tissues or factors, including the binding of various cells of the immune system (e.g., effector cells) to the first component (C1q) of classical complement system. The VH and VL regions can be further subdivided into highly variable regions (called complementarity determining regions (CDRs)), between which conservative regions called framework regions (FRs) are distributed. Each VH and VL consists of 3 CDRs and 4 FRs arranged from amino terminus to carboxyl terminus in the following order: FR1, CDR1, FR2, CDR2, FR3, CDR3 and FR4. The variable regions (VH and VL) of each heavy chain/light chain pair form an antibody-binding site. The assignment of amino acids to the regions or domains is based on Bethesda M.d., Kabat Sequences of Proteins of Immunological Interest (*National Institutes of Health*, (1987 and 1991)), or Chothia & Lesk *J. Mol. Biol.,* 1987; 196:901-917; Chothia et al., *Nature,* 1989; 342:878-883, or the definition of the IMGT numbering system, see the definition in Ehrenmann F, Kaas Q, Lefranc M P., IMGT/3Dstructure-DB and IMGT/DomainGapAlign:

a database and a tool for immunoglobulins or antibodies, T cell receptors, MHC, IgSF and MhcSF[J], *Nucleic acids research,* 2009; 38 (suppl_1): D301-D307.

In particular, the heavy chain may also comprise more than 3 CDRs, such as 6, 9 or 12. For example, in the bispecific antibody disclosed herein, the heavy chain may be a heavy chain of IgG antibody with the C terminus linked to one ScFv, and in this case, the heavy chain comprises 9 CDRs.

The term "antibody" is not limited by any specific method for producing antibody. For example, the antibody includes a recombinant antibody, a monoclonal antibody and a polyclonal antibody. The antibody may be antibodies of different isotypes, such as IgG (e.g., subtype IgG1, IgG2, IgG3 or IgG4), IgA1, IgA2, IgD, IgE or IgM.

As used herein, the terms "mAb" and "monoclonal antibody" refer to an antibody or a fragment of an antibody that is derived from a group of highly homologous antibodies, i.e., from a group of identical antibody molecules, except for natural mutations that may occur spontaneously. The monoclonal antibody is highly specific for a single epitope on an antigen. The polyclonal antibody, relative to the monoclonal antibody, generally comprises at least 2 or more different antibodies which generally recognize different epitopes on an antigen. Monoclonal antibodies can generally be obtained using hybridoma technology first reported by Kohler et al (Köhler G, Milstein C. Continuous cultures of fused cells secreting antibody of predefined specificity [J]. *Nature,* 1975; 256(5517): 495), but can also be obtained using recombinant DNA technology (see, e.g., U.S. Pat. No. 4,816,567).

As used herein, the term "humanized antibody" refers to an antibody or an antibody fragment obtained when all or a part of CDR regions of a human immunoglobulin (receptor antibody) are replaced by the CDR regions of a non-human antibody (donor antibody), wherein the donor antibody may be a non-human (e.g., mouse, rat or rabbit) antibody having expected specificity, affinity or reactivity. In addition, some amino acid residues in the framework regions (FRs) of the receptor antibody can also be replaced by the amino acid residues of corresponding non-human antibodies or by the amino acid residues of other antibodies to further improve or optimize the performance of the antibody. For more details on humanized antibodies, see, e.g., Jones et al., *Nature,* 1986; 321:522 525; Reichmann et al., *Nature,* 1988; 332:323 329; Presta, *Curr. Op. Struct. Biol.,* 1992; 2:593-596; and Clark, *Immunol. Today,* 2000; 21:397-402. In some cases, the antigen-binding fragments of the antibodies are diabodies, in which the $V_H$ and $V_L$ domains are expressed on a single polypeptide chain. However, the linker used is too short to allow the pairing of the two domains on the same chain. Thereby the domains are forced to pair with the complementary domains on the other chain and two antigen-binding sites are generated (see, e.g., Holliger P. et al., *Proc. Natl. Acad. Sci. USA,* 1993; 90:6444-6448 and Poljak R. J. et al., *Structure,* 1994; 2:1121-1123).

As used herein, the term "single-chain variable fragment (ScFv)" refers to a molecule in which the antibody heavy chain variable region ($V_H$) and the antibody light chain variable region ($V_L$) are linked by a linker. The $V_L$ and $V_H$ domains are paired to form a monovalent molecule by a linker that enable them to produce a single polypeptide chain (see, e.g., Bird et al, *Science,* 1988; 242:423-426 and Huston et al, *Proc. Natl. Acad. Sci. USA,* 1988; 85:5879-5883). Such scFv molecules may have a general structure: $NH_2$-$V_L$-linker-$V_H$-COOH or $NH_2$-$V_H$-linker-$V_L$-COOH. An appropriate linker in the prior art consists of a repeating GGGGS amino acid sequence (SEQ ID NO: 102) or a variant thereof. For example, a linker having the amino acid sequence (GGGGS) 4 may be used, but variants thereof may also be used (Holliger et al., *Proc. Natl. Acad. Sci. USA,* 1993; 90:6444-6448). Other linkers that can be used in the present invention are described by Alfthan et al., *Protein Eng.,* 1995; 8:725-731, Choi et al., *Eur. J. Immunol.,* 2001; 31:94-106, Hu et al., *Cancer Res.,* 1996; 56:3055-3061, Kipriyanov et al., *J. Mol. Biol.,* 1999; 293:41-56 and Roovers et al., *Cancer Immunology, Immunotherapy,* 2001, 50(1): 51-59.

As used herein, the term "isolated" refers to obtaining by artificial means from natural state. If a certain "isolated" substance or component appears in nature, it may be the case that change occurs in its natural environment, or that it is isolated from the natural environment, or both. For example, a certain non-isolated polynucleotide or polypeptide naturally occurs in a certain living animal, and the same polynucleotide or polypeptide with high purity isolated in such a natural state is referred to as an isolated polynucleotide or polypeptide. The term "isolated" does not exclude the existence of artificial or synthetic substances or other impurities that do not affect the activity of the substance.

As used herein, the term "vector" refers to a nucleic acid vehicle into which a polynucleotide can be inserted. When a vector allows the expression of the protein encoded by the inserted polynucleotide, the vector is referred to as an expression vector. The vector can be introduced into a host cell by transformation, transduction or transfection, such that the genetic substance elements carried by the vector can be expressed in the host cell. Vectors are well known to those skilled in the art, including but not limited to: plasmids; phagemids; cosmids; artificial chromosomes, such as yeast artificial chromosome (YAC), bacterial artificial chromosome (BAC), or P1-derived artificial chromosome (PAC); phages such as lambda phages or M13 phages; and animal viruses. Animal viruses that can be used as vectors include, but are not limited to retroviruses (including lentiviruses), adenoviruses, adeno-associated viruses, herpes viruses (such as herpes simplex virus), poxviruses, baculoviruses, papillomaviruses, and papovaviruses (such as SV40). A vector may comprise a variety of elements that control expression, including, but not limited to promoter sequences, transcription initiation sequences, enhancer sequences, selection elements and reporter genes. In addition, the vector may further comprise a replication initiation site.

As used herein, the term "host cell" refers to cells to which vectors can be introduced, including, but not limited to, prokaryotic cells such as *E. coli* or *Bacillus subtilis*, fungal cells such as yeast cells or *aspergillus*, insect cells such as S2 drosophila cells or Sf9, or animal cells such as fibroblasts, CHO cells, GS cells, COS cells, NSO cells, HeLa cells, BHK cells, HEK 293 cells, or human cells.

As used herein, the term "specifically bindi" refers to a non-random binding reaction between two molecules, such as a reaction between an antibody and an antigen it targets. In some embodiments, an antibody that specifically binds to an antigen (or an antibody that is specific for an antigen) means that the antibody binds to the antigen with an affinity ($K_D$) of less than about $10^{-5}$ M, such as less than about $10^{-6}$ M, $10^{-7}$ M, $10^{-8}$ M, $10^{-9}$ M or $10^{-10}$ M or less.

As used herein, the term "$K_D$" refers to a dissociation equilibrium constant for a specific antibody-antigen interaction, which is used to describe the binding affinity between the antibody and the antigen. A smaller dissociation equilibrium constant indicates a stronger antibody-antigen binding and a higher affinity between the antibody and the antigen. Typically, the antibody binds to the antigen (e.g., PD-1 protein) with a dissociation equilibrium constant ($K_D$) of less than about $10^{-5}$ M, such as less than about $10^{-6}$ M, $10^{-7}$ M, $10^{-8}$ M, $10^{-9}$ M or $10^{-10}$ M or less. $K_D$ can be determined using methods known to those skilled in the art, for example, using a Fortebio system.

As used herein, the terms "monoclonal antibody" and "mAb" have the same meaning and can be used interchangeably; the terms "polyclonal antibody" and "pAb" have the same meaning and can be used interchangeably. Besides, herein, amino acids are generally represented by single-letter and three-letter abbreviations known in the art. For example, alanine can be represented by A or Ala.

As used herein, the term "pharmaceutically acceptable carrier and/or excipient" refers to a carrier and/or excipient that is pharmacologically and/or physiologically compatible with the subject and the active ingredient. Such carriers and/or excipients are well known in the art (see, e.g., *Remington's Pharmaceutical Sciences*, edited by Gennaro A R, 19$^{th}$ Ed., Pennsylvania: Mack Publishing Company, 1995), including, but not limited to: pH regulators, surfactants, adjuvants, and ionic strength enhancers. For example, the pH regulators include, but are not limited to, phosphate buffer; the surfactants include, but are not limited to, cationic, anionic, or non-ionic surfactants, such as Tween-80; the ionic strength enhancers include, but are not limited to, sodium chloride.

As used herein, the term "effective amount" refers to an amount sufficient to obtain or at least partially obtain desired effects. For example, a prophylactically effective amount against a disease (e.g., a tumor) refers to an amount sufficient to prevent, stop, or delay the onset of a disease (e.g., a tumor); a therapeutically effective amount refers to an amount sufficient to cure or at least partially stop a disease and complications thereof in patients suffering from the disease. It is undoubtedly within the ability of those skilled in the art to determine such an effective amount. For example, the amount effective for therapeutic purpose will depend on the severity of the disease to be treated, the overall state of the patient's own immune system, the general condition of the patient such as age, body weight and gender, the route of administration, and other treatments given concurrently, etc.

Beneficial Effects

The monoclonal antibody of the present invention (such as 13F9H2L3) can well and specifically bind to CD73, and can effectively inhibit the enzyme activity reaction of CD73 in a non-substrate competition mode, reduce the production of adenosine, promote the activity of T cells and the tumor inhibitory effect.

The bispecific antibody disclosed herein, such as NTPDV1, NTPDV2, NTPDV3 and NTPDV4, can well and specifically bind to PD-1 and CD73, can effectively block the binding of PD-1 to PDL1, specifically relieve the immunosuppression of PD-1 in an organism, inhibit the catalytic activity of CD73, relieve the inhibition on immune cells by adenosine, activate T lymphocytes, and does not cause the release of cytokines IL-8 and IL-6, showing effectively increased safety and efficacy.

The bifunctional antibody disclosed herein has the potential for use in preparing an anti-tumor drug.

COLLECTION INFORMATION OF BIOLOGICAL MATERIALS

Figure 1:
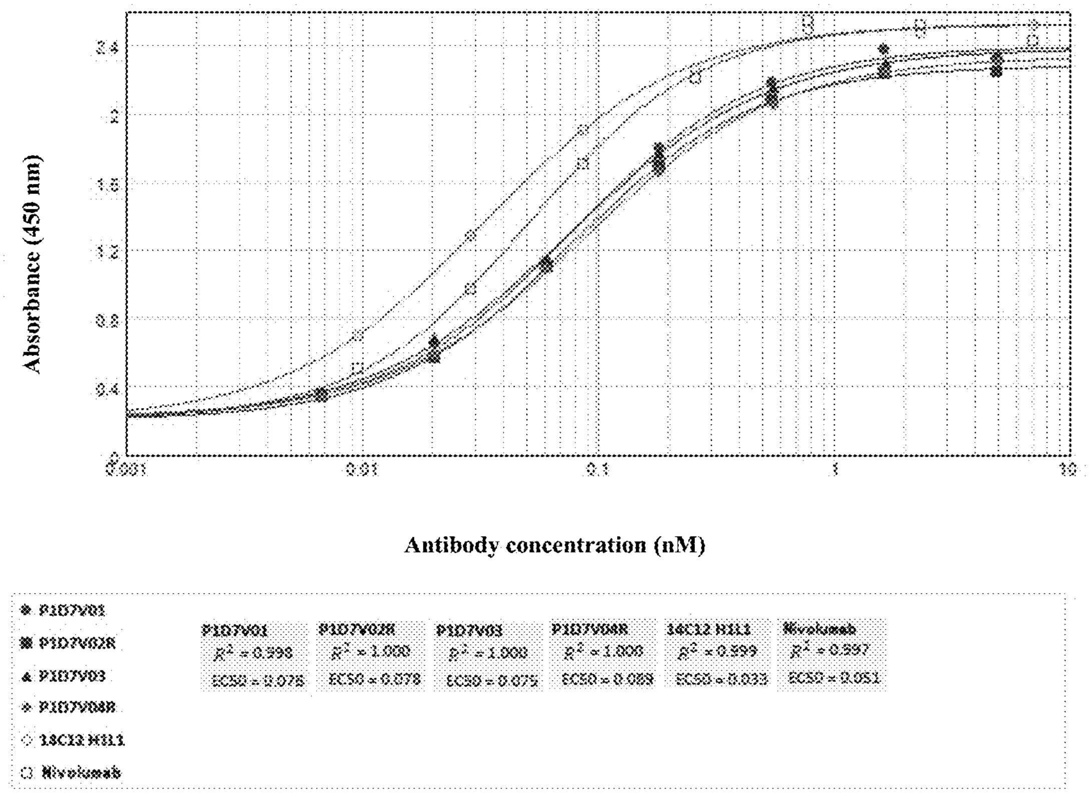
FIG. 1. Binding of P1D7V01, P1D7V02R, P1D7V03, P1D7V04R, 14C12H1L1 and nivolumab to PD-1-mFc determined by ELISA.

The hybridoma cell line LT003 (also called PD-1-14C12), which was deposited at China Center for Type Culture Collection (CCTCC) on Jun. 16, 2015 with a collection number of CCTCC NO: C2015105 and a collection address of Wuhan University, Wuhan, China, postal code: 430072. The hybridoma cell line LT014 (also called CD73-19F3), which was deposited at China Center for Type Culture Collection (CCTCC) on Jun. 21, 2018 with a collection number of CCTCC NO: C2018137 and a collection address of Wuhan University, Wuhan, China, postal code: 430072.

DETAILED DESCRIPTION

The embodiments of the present invention will be described in detail below with reference to the examples. Those skilled in the art will understand that the following examples are only for illustrating the present invention, and should not be construed as limitations on the scope of the present invention. In the cases where the techniques or conditions are not specified, the examples were implemented according to the techniques or conditions described in the literature in the art (e.g., see, *Molecular Cloning: A Laboratory Manual*, authored by J. Sambrook et al., and translated by Peitang Huang et al., $3^{rd}$ Edition, Science Press) or according to the product manual. Reagents or instruments used are commercially available conventional products if the manufacturers thereof are not specified. For example, MDA-MB-231 cells and U87-MG cells can be purchased from ATCC.

In the following examples of the present invention, BALB/c mice used were purchased from Guangdong Medical Laboratory Animal Center.

In the following examples of the present invention, the positive control antibody MEDI9447 (generic name: Oleclumab) used was produced by Zhongshan Akesobio Co. Ltd., the sequence of which is identical to the antibody SEQ ID NOs: 21-24 described in the Medmmune Limited's Patent Publication No. US20160129108A1.

In the following examples of the present invention, the marketed antibody nivolumab (trade name: Opdivo) for the same target was used, which was purchased from Bristol-Myers Squibb.

In the following examples of the present invention, the cell line 293T-PD1 used was constructed by Zhongshan Akesobio Co. Ltd. The cell line 293T-PD1 was prepared by viral infection of HEK293T cells using 3rd Generation Lentiviral Systems (see, e.g., A Third Generation Lentivirus Vector with a Conditional Packaging System. Dull T, Zufferey R, Kelly M, Mandel R J, Nguyen M, Trono D, and Naldini L., *J Virol.,* 1998. 72(11): 8463-8471), wherein the lentivirus expression vector used was pCDH-CMV-PD-1FL-Puro (PD1, Genebank ID: NM_005018; vector pCDH-CMV-Puro, purchased from Youbio, Cat. No. VT1480).

In the following examples of the present invention, the cell line Raji-PDL1 used was constructed by Zhongshan Akesobio Co. Ltd. The cell line Raji-PDL1 was prepared by viral infection of Raji cells using 3rd Generation Lentiviral Systems (see, e.g., A Third Generation Lentivirus Vector with a Conditional Packaging System. Dull T, Zufferey R, Kelly M, Mandel R J, Nguyen M, Trono D, and Naldini L., *J Virol.,* 1998. 72(11): 8463-8471), wherein the lentivirus expression vector used was plenti6.3-PDL1 (PDL1, Genebank ID: NP_054862.1; vector plenti6.3, purchased from Invitrogen, Cat. No. K5315-20).

In the following examples of the present invention, the cell line CHO-K1-PD1 used was constructed by Zhongshan Akesobio Co. Ltd. The cell line CHO-K1-PD1 was prepared by viral infection of CHO-K1 cells using 3rd Generation Lentiviral Systems (see, e.g., A Third Generation Lentivirus Vector with a Conditional Packaging System. Dull T, Zufferey R, Kelly M, Mandel R J, Nguyen M, Trono D, and Naldini L., *J Virol.,* 1998. 72(11): 8463-8471), wherein the lentivirus expression vector used was pCDH-CMV-PD-1FL-Puro (PD1, Genebank ID: NM_005018; vector pCDH-CMV-Puro, purchased from Youbio, Cat. No. VT1480).

Nivolumab (trade name: Opdivo), an IgG4 subtype anti-PD-1 antibody carrying S228P mutation, was used as a control antibody in the examples and was purchased from Bristol-Myers Squibb. In the following examples of the present invention, the isotype control antibodiy used, i.e., hIgG1, was an antibody targeting human anti-hen egg lysozyme (HEL), and the variable region sequence of the antibody is from the study reported by Acierno et al., entitled "Affinity maturation increases the stability and plasticity of the Fv domain of anti-protein antibodies" (Acierno et al., *J Mol biol.,* 2007; 374(1): 130-46). In the constant region fragment of hIgG1, the heavy chain constant region is Ig gamma-1 chain C region, ACCESSION: P01857, and the light chain constant region is Ig kappa chain C region, ACCESSION: P01834; the hIgG1 was prepared in the laboratory of Zhongshan Akesobio Co. Ltd.

Example 1: Preparation of Anti-CD73 Antibody 19F3

1. Preparation of Hybridoma Cell Line LT014

The antigen used to prepare the anti-CD73 antibody was human NT5E-his (for NT5E, Genbank ID: NP_002517.1, position: 1-552). Spleen cells of immunized mice were fused with myeloma cells of the mice to prepare hybridoma cells. With human NT5E-Biotin (for NT5E, Genbank ID: NP_002517.1, position: 1-552) taken as an antigen, the hybridoma cells were screened by indirect ELISA to obtain hybridoma cells capable of secreting antibodies that can specifically bind to CD73. The hybridoma cells obtained by ELISA screening were subjected to limiting dilution to obtain a stable hybridoma cell line. The above hybridoma cell line was named as hybridoma cell line LT014, and the monoclonal antibody secreted therefrom was named 19F3.

The hybridoma cell line LT014 (also called CD73-19F3) was deposited at China Center for Type Culture Collection (CCTCC) on Jun. 21, 2018 with a collection number of CCTCC NO: C2018137 and a collection address of Wuhan University, Wuhan, China, postal code: 430072.

2. Preparation of Anti-CD73 Antibody 19F3

The cell line LT014 prepared above was cultured with a chemical defined medium (CD medium, containing 1% Penicillin-Streptomycin) in a 5% $CO_2$, 37 °C incubator. After 7 days, the supernatants were collected and purified by high-speed centrifugation, vacuum filtration through a microfiltration membrane and a HiTrap protein A HP column to obtain an antibody 19F3.

Example 2: Sequence Analysis of Anti-CD73 Antibody 19F3 mRNA was extracted from the cell line LT014 prepared in Example 1 according to the method described in the manual of RNAprep pure Cell/Bacteria Kit (Tiangen, Cat. No. DP430).

cDNA was synthesized according to the manual of Invitrogen SuperScript® III First-Strand Synthesis System for RT-PCR and amplified by PCR.

The PCR-amplified products were directly subjected to TA cloning according to the manual of the pEASY-T1 Cloning Kit (Transgen CT101).

The TA-cloned products were directly sequenced, and the sequencing results are as follows:

The nucleotide sequence (363 bp) of 19F3 heavy chain variable region is set forth in SEQ ID NO: 1, and the encoded amino acid sequence (121 aa) is set forth in SEQ ID NO: 2.

According to the IMGT numbering system, the heavy chain CDR1 has a sequence set forth in SEQ ID NO: 3, the heavy chain CDR2 has a sequence set forth in SEQ ID NO: 4, and the heavy chain CDR3 has a sequence set forth in SEQ ID NO: 5.

The nucleotide sequence (339 bp) of 19F3 light chain variable region is set forth in SEQ ID NO: 6, and the encoded amino acid sequence (113 aa) is set forth in SEQ ID NO: 7.

According to the IMGT numbering system, the light chain CDR1 has a sequence set forth in SEQ ID NO: 8, the light chain CDR2 has a sequence set forth in SEQ ID NO: 9, and the light chain CDR3 has a sequence set forth in SEQ ID NO: 10.

The amino acid sequences of 4 framework regions (FR-H1 to FR-H4) of the 19F3 heavy chain are set forth in SEQ ID NO: 11 to SEQ ID NO: 14, respectively; the amino acid sequences of 4 framework regions (FR-H1 to FR-H4) of the 19F3 light chain are set forth in SEQ ID NO: 15 to SEQ ID NO: 18, respectively.

Example 3: Design, Preparation and Detection of Humanized Anti-Human CD73 Antibodies 1. Design of Light and Heavy Chain Sequences of Humanized Antibodies 19F3H2L3 and 19F3H2L2

Based on the three-dimensional crystal structure of human CD73 protein (Hage T, Reinemer P, Sebald W., Crystals of a 1:1 complex between human interleukin-4 and the extracellular domain of its receptor alpha chain, *Eur J Biochem.*, 1998; 258(2): 831-6) and the sequence of murine antibody 19F3 obtained in Example 2, the variable region sequences of antibodies 19F3H1L1, 19F3H2L3 and 19F3H2L3 were obtained by computer modeling and mutation design. The corresponding heavy chain variable region sequences were 19F3H1 and 19F3H2, respectively (with amino acid sequences set forth in SEQ ID NO: 93 and SEQ ID NO: 97, respectively), and the light chain variable region sequences were 19F3L1, 19F3L2 and 19F3L3, respectively (with amino acid sequences set forth in SEQ ID NO: 95, SEQ ID NO: 98 and SEQ ID NO: 99, respectively). The antibody constant region sequences are from NCBI database: the heavy chain constant region is Ig gamma-1 chain C region, ACCESSION: P01857; the light chain constant region is Ig kappa chain C region, ACCESSION: P01834. 19F3H2L3 is also known as 19F3H2L3(hG1WT) in the Chinese Patent Application No. 202110270671.X, wherein the light and heavy chain variable regions of 19F3H1L1, 19F3H2L2 and 19F3H2L3 can further be noted as 19F3H1V (or 19F3H$1_V$), 19F3H2V (or 19F3H$2_V$), 19F3L1V (or 19F3L$1_V$), 19F3L2V (or 19F3L$2_V$) and 19F3L3V (or 19F3L$3_V$).

(1) Heavy chain variable region and light chain variable region sequences of humanized monoclonal antibody 19F3H1L1 are as follows:

The nucleotide sequence (363 bp) of the heavy chain variable region is set forth in SEQ ID NO: 92, and the encoded amino acid sequence (121 aa) is set forth in SEQ ID NO: 93.

The nucleotide sequence (339 bp) of the light chain variable region is set forth in SEQ ID NO: 94, and the encoded amino acid sequence (113 aa) is set forth in SEQ ID NO: 95.

(2) Heavy chain variable region and light chain variable region sequences of humanized monoclonal antibody 19F3H2L2 are as follows:

The nucleotide sequence (363 bp) of the heavy chain variable region 19F3H2 is set forth in SEQ ID NO: 19, and the encoded amino acid sequence (121 aa) is set forth in SEQ ID NO: 20.

The nucleotide sequence (339 bp) of the light chain variable region 19F3L3 is set forth in SEQ ID NO: 21, and the encoded amino acid sequence (113 aa) is set forth in SEQ ID NO: 22.

(3) Heavy chain variable region and light chain variable region sequences of humanized monoclonal antibody 19F3H2L3 are as follows:

The nucleotide sequence (363 bp) of the heavy chain variable region 19F3H2 is set forth in SEQ ID NO: 19, and the encoded amino acid sequence (121 aa) is set forth in SEQ ID NO: 20.

The nucleotide sequence (339 bp) of the light chain variable region 19F3L3 is set forth in SEQ ID NO: 23, and the encoded amino acid sequence (113 aa) is set forth in SEQ ID NO: 24.

2. Preparation of humanized antibodies 19F3H1L1, 19F3H2L2 and 19F3H2L3

Heavy chain constant regions used Ig gamma-1 chain C region, ACCESSION: P01857; the light chain constant regions used Ig kappa chain C region, ACCESSION: P01834.

The heavy chain cDNA and light chain cDNA of 19F3H1L1, 19F3H2L2 and 19F3H2L3 were separately cloned into pUC57simple (provided by GenScript) vectors to obtain pUC57simple-19F3H1, pUC57simple-19F3L1, pUC57simple-19F3H2, pUC57simple-19F3L2 and pUC57simple-19F3L3. Referring to the standard techniques described in *Molecular Cloning: A Laboratory Manual* (Second Edition), the heavy and light chain full-length genes synthesized by EcoRI&HindIII digestion were subcloned into an expression vector pcDNA3.1 through digestion by an restriction enzyme (EcoRI&HindIII) to obtain expression plasmids pcDNA3.1-19F3H1, pcDNA3.1-19F3L1, pcDNA3.1-19F3H2, pcDNA3.1-19F3L2, and pcDNA3.1-19F3L3, and the heavy/light chain genes of the recombinant expression plasmids were further subjected to sequencing analysis. Then the designed gene combinations comprising the corresponding light and heavy chain recombinant plasmids (pcDNA3.1-19F3H1/pcDNA3.1-19F3L1, pcDNA3.1-19F3H2/pcDNA3.1-19F3L2, and pcDNA3.1-19F3H2/pcDNA3.1-19F3L3) were separately co-transfected into 293F cells, and the culture solutions were collected and purified. After the sequences were verified, endotoxin-free expression plasmids were prepared, and were transiently transfected into HEK293 cells for antibody expression. The culture solutions were collected after 7 days, and subjected to affinity purification on a Protein A column to obtain humanized antibodies.

3. Design of Light and Heavy Chain Sequences of Humanized Antibodies 19F3H2L3(hG1M) and 19F3H2L3 (hG1TM)

On the basis of 19F3H2L3 obtained in of Example 3 1, 19F3H2L3(hG1M) was obtained by introducing a leucine-to-alanine point mutation at position 234 (L234A) and a leucine-to-alanine point mutation at position 235 (L235A) of the heavy chain. The nucleotide and amino acid sequences of the heavy chain of 19F3H2L3(hG1M) are set forth in SEQ ID NO: 25 and SEQ ID NO: 26, respectively; the light chain constant region of 19F3H2L3(hG1M) is an Ig kappa chain C region, ACCESSION: P01834, and the nucleotide and amino acid sequences of the light chain of 19F3H2L3 (hG1M) are set forth in SEQ ID NO: 27 and SEQ ID NO: 28, respectively.

On the basis of 19F3H2L3 obtained in step 1 of Example 3, 19F3H2L3(hG1TM) was obtained by introducing a leucine-to-alanine point mutation at position 234 (L234A), a leucine-to-alanine point mutation at position 235 (L235A), and a glycine-to-alanine point mutation at position 237 (G237A) in the heavy chain. The nucleotide and amino acid sequences of the heavy chain are set forth in SEQ ID NO: 29 and SEQ ID NO: 30, respectively; and the light chain is identical to 19F3H2L3(hG1M).

The amino acid sequences of 4 framework regions (FR-H1 to FR-H4) of 19F3H2 are set forth in SEQ ID NO: 31 to SEQ ID NO: 34, respectively;

the amino acid sequences of 4 framework regions (FR-H1 to FR-H4) of the 19F3L2 light chain are set forth in SEQ ID NO: 35 to SEQ ID NO: 38, respectively; and the amino acid sequences of 4 framework regions (FR-H1 to FR-H4) of the 19F3L3 light chain are set forth in SEQ ID NO: 39 to SEQ ID NO: 42, respectively.

4. Preparation of Humanized Antibody 19F3H2L3(hG1M)

The heavy chain cDNA and light chain cDNA of 19F3H2L3(hG1M) were separately cloned into vector pUC57simple (provided by Genscript) to obtain pUC57simple-19F3H2(hG1M) and pUC57simple-19F3L3, respectively. Referring to the standard techniques described in *Molecular Cloning: A Laboratory Manual* (Second Edition), the heavy and light chain full-length genes synthesized by EcoRI&HindIII digestion were subcloned into an expression vector pcDNA3.1 through digestion by an restriction enzyme (EcoRI&HindIII) to obtain expression plasmids pcDNA3.1-19F3H2(hG1M) and pcDNA3.1-19F3L3, and the heavy/light chain genes of the recombinant expression plasmids were further subjected to sequencing analysis. Then the designed gene combination comprising the corresponding light and heavy chain recombinant plasmids pcDNA3.1-19F3H2(hG1M)/pcDNA3.1-19F3L3 was co-transfected into 293F cells, and the culture solutions were collected and purified. After the sequences were verified, endotoxin-free expression plasmids were prepared, and were transiently transfected into HEK293 cells for antibody expression. The culture solutions were collected after 7 days, and subjected to affinity purification on a Protein A column to obtain a humanized antibody 19F3H2L3(hG1M).

Example 4: Preparation of Anti-PD-1 Antibody 14C12

1. Preparation of the Hybridoma Cell Line LT003

Using PD-1-mFc fusion protein (PD-1 GenBank: NM-005018, mFc SEQ ID NO: 89) as an antigen, spleen cells of an immunized BALB/c mice (purchased from Guangdong Medical Laboratory Animal Center) and mouse myeloma cells were fused into hybridoma cells, and the established methods (e.g., Stewart, S. J., "Monoclonal Antibody Production", in Basic Methods in Antibody Production and Characterization, Eds. G. C. Howard and D. R. Bethell, Boca Raton: CRC Press, 2000) were referred to.

The plate was coated with PD-1-hFc (PD-1, Genbank ID: NM_005018, hFc is a human IgG Fc purification tag, specifically Ig gamma-1 chain C region, Genbank ID: P01857, positions 114-330) for indirect ELISA. By screening, hybridoma cells secreting new antibodies specifically binding to PD-1 were obtained.

Hybridoma cell lines capable of secreting a monoclonal antibody that competes with the ligand PD-L1-hFc (PD-L1 Genbank ID: NP_054862.1) for binding to PD-1 were screened by competitive ELISA, and a stable hybridoma cell line was obtained by limiting dilution. The LT003 stable cell line (PD-1-14C12) was obtained by limiting dilution, and the secreted monoclonal antibody was named as 14C12.

The hybridoma cell line LT003 (also called PD-1-14C12) was deposited at China Center for Type Culture Collection (CCTCC) on Jun. 16, 2015 with a collection number of CCTCC NO: C2015105 and a collection address of Wuhan University, Wuhan, China, postal code: 430072.

2. Preparation of Anti-PD-1 Antibody 14C12

The LT003 cells prepared above were cultured in an IMDM medium containing 10% low IgG fetal bovine serum (IMDM medium containing 1% Penicillin-Streptomycin, cultured in a 5% $CO_2$, 37 °C cell incubator). After 7 days, the cell culture supernatant was collected and purified to obtain antibody 14C12.

Example 5: Sequence Analysis of Anti-PD-1 Antibody 14C12 mRNA was extracted from the hybridoma cell line LT003 prepared in Example 1 according to the method described in the manual of RNAprep pure Cell/Bacteria Kit (Tiangen, Cat. No. DP430). cDNA was synthesized according to the manual of Invitrogen SuperScript® III First-Strand Synthesis System for RT-PCR and amplified by PCR.

The PCR-amplified products were directly subjected to TA cloning according to the manual of the pEASY-T1 Cloning Kit (Transgen CT101).

The TA-cloned products were directly sequenced, and the sequencing results are as follows: The nucleotide sequence (354 bp) of the heavy chain variable region is set forth in SEQ ID NO: 43, and the encoded amino acid sequence (118 aa) is set forth in SEQ ID NO: 44.

According to the IMGT numbering system, the heavy chain CDR1 has a sequence set forth in SEQ ID NO: 45, the heavy chain CDR2 has a sequence set forth in SEQ ID NO: 46, and the heavy chain CDR3 has a sequence set forth in SEQ ID NO: 47.

The nucleotide sequence (321 bp) of the light chain variable region is set forth in SEQ ID NO: 48, and the encoded amino acid sequence (107 aa) is set forth in SEQ ID NO: 49.

According to the IMGT numbering system, the light chain CDR1 has a sequence set forth in SEQ ID NO: 50, the light chain CDR2 has a sequence set forth in SEQ ID NO: 51, and the light chain CDR3 has a sequence set forth in SEQ ID NO: 52.

The amino acid sequences of 4 framework regions (FR-H1 to FR-H4) of the 14C12 heavy chain are set forth in SEQ ID NO: 53 to SEQ ID NO: 56, respectively; the amino acid sequences of 4 framework regions (FR-H1 to FR-H4) of the 14C12 light chain are set forth in SEQ ID NO: 57 to SEQ ID NO: 60, respectively.

Example 6: Design and Preparation of Humanized Anti-PD-1 Antibodies 14C12H1L1 and 14C12H1L1(hG1TM)

1. Design of Humanized Anti-PD-1 Antibody 14C12H1L1

The light and heavy chain sequences of the humanized antibody 14C12H1L1 were designed according to the three-dimensional crystal structure of PD-1 protein (Shinohara T, et al., Structure and chromosomal localization of the human PD-1 gene (PDCD1). *Genomics* 1995, 23(3): 704-6) and the sequence of antibody 14C12 obtained in Example 5 by computer simulation of antibody model and designing mutations according to the model to obtain the variable region sequences of antibody 14C12H1L1.

The designed variable region sequences are as follows.

The nucleotide sequence (354 bp) of the heavy chain variable region 14C12H1 of the humanized monoclonal antibody 14C12H1L1 is set forth in SEQ ID NO: 61, and the encoded amino acid sequence (118 aa) is set forth in SEQ ID NO: 62.

The nucleotide sequence (321 bp) of the light chain variable region 14C12L1 of the humanized monoclonal antibody 14C12H1L1 is set forth in SEQ ID NO: 63, and the encoded amino acid sequence (107 aa) is set forth in SEQ ID NO: 64.

The constant region of the antibody 14C12H1L1 is from NCBI database (the heavy chain constant region is Ig gamma-1 chain C region, ACCESSION: P01857; the light chain constant region is Ig kappa chain C region, ACCESSION: P01834). The nucleotide sequence and amino acid sequence of the 14C12H1L1 heavy chain are set forth in SEQ ID NOs: 65 and 66, respectively, and the nucleotide sequence and amino acid sequence of the 14C12H1L1 light chain are set forth in SEQ ID NOs: 67 and 68, respectively. 14C12H1L1 is also known as 14C12H1L1(hG1WT) herein and in Chinese Patent Application No. 202110270671.X, wherein the heavy chain variable region and the light chain variable region of 14C12H1L1 are also known as 14C12H1V (or $14C12H1_V$) and $14C12L1_V$ (or $14C12L1_V$) herein and in Chinese Patent Application No. 202110270671.X.

2. Design of Light and Heavy Chain Sequences of Humanized Antibody 14C12H1L1(hG1TM)

On the basis of 14C12H1L1 obtained in step 1 of Example 6, 14C12H1L1(hG1TM) was obtained by introducing a leucine-to-alanine point mutation at position 234 (L234A), a leucine-to-alanine point mutation at position 235 (L235A), and a glycine-to-alanine point mutation at position 237 (G237A) in the heavy chain. The nucleotide and amino acid sequences of the heavy chain of 14C12H1L1(hG1TM) are set forth in SEQ ID NO: 69 and SEQ ID NO: 70, respectively; and the light chain is identical to 14C12H1L1.

The amino acid sequences of 4 framework regions (FR-H1 to FR-H4) of 14C12H1 are set forth in SEQ ID NO: 71 to SEQ ID NO: 74, respectively;

the amino acid sequences of 4 framework regions (FR-H1 to FR-H4) of the 14C12L1 light chain are set forth in SEQ ID NO: 75 to SEQ ID NO: 78, respectively.

3. Preparation of Humanized Antibodies 14C12H1L1 and 14C12H1L1(hG1TM)

The heavy chain cDNA and light chain cDNA of 14C12H1L1(hG1TM) and 14C12H1L1 were separately cloned into pUC57simple (provided by GenScript) vectors to obtain pUC57simple-14C12H1, pUC57simple-14C12L1 and pUC57simple-14C12H1(hG1TM). Referring to the standard techniques described in *Molecular Cloning: A Laboratory Manual* (Second Edition), the heavy and light chain full-length genes synthesized by EcoRI&HindIII digestion were subcloned into an expression vector pcDNA3.1 through digestion by an restriction enzyme (EcoRI&HindIII) to obtain expression plasmids pcDNA3.1-14C12H1, pcDNA3.1-14C12L1 and pcDNA3.1-14C12H1 (hG1TM), and the heavy/light chain genes of the recombinant expression plasmids were further subjected to sequencing analysis. Then the designed gene combinations comprising the corresponding light and heavy chain recombinant plasmids (pcDNA3.1-14C12H1(hG1TM)/pcDNA3.1-14C12L1, and pcDNA3.1-14C12H1/pcDNA3.1-14C12L1) were separately co-transfected into 293F cells, and the culture solutions were collected and purified. After the sequences were verified, endotoxin-free expression plasmids were prepared, and were transiently transfected into HEK293 cells for antibody expression. The culture solutions were collected after 7 days, and subjected to affinity purification on a Protein A column to obtain humanized antibodies.

Example 7: Sequence Design and Expression of Anti-PD-1/CD73 Bifunctional Antibodies 1. Sequence Design The structure of the bifunctional antibody described herein is in the Morrison form (IgG-scFv), i.e., C-termini of two heavy chains of an IgG antibody are each linked to a scFv fragment of another antibody, and the main composition design of the heavy and light chains is as shown in Table 1 below.

TABLE 1

Table 1. Composition design of heavy and light chains of P1D7V01, P1D7V02R, P1D7V03, P1D7V04R, PID7V07 and P1D7V08.

| Bispecific antibody No. | Heavy chain IgG moiety | Linker | scFv moiety | Light chain |
|---|---|---|---|---|
| P1D7V01 | 14C12H1 | Linker1 | 19F3H2v-Linker1-19F3L3v | 14C12L1 |
| P1D7V02R | 14C12H1 | Linker1 | 19F3L3v-Linker1-19F3H2v | 14C12L1 |
| P1D7V03 | 14C12H1 | Linker2 | 19F3H2v-Linker1-19F3L3v | 14C12L1 |
| P1D7V04R | 14C12H1 | Linker2 | 19F3L3v-Linker1-19F3H2v | 14C12L1 |
| P1D7V07 | 19F3H2 | Linker1 | 14C12H1 v-Linker1-14C12L1v | 19F3L3 |
| P1D7V08 | 19F3H2 | Linker2 | 14C12H1 v-Linker1-14C12L1v | 19F3L3 |

In the Table 1 above:

(1) Those with "V" label at lower right corner refer to the variable region of corresponding heavy chain or the variable region of corresponding light chain. For those without "V" label, the corresponding heavy or light chain is the full length comprising the constant region. The corresponding sequences described in the above examples are referred to for the amino acid sequences of these variable regions or the full length and the nucleotide sequences encoding them.

(2) The amino acid sequence of linker 1 is $(GGGGS)_4$ (the nucleotide sequence is SEQ ID NO: 80, and the amino acid sequence is SEQ ID NO: 79), and the amino acid sequence of linker 2 is $(GGGGS)_3$ (the nucleotide sequence is SEQ ID NO: 82, and the amino acid sequence is SEQ ID NO: 81).

2. Expression and Purification of Antibodies

The heavy chain cDNA sequence and the light chain cDNA sequence of P1D7V01 were each cloned into vector pUC57simple (provided by Genscript) to obtain plasmids pUC57simple-VP101H and pUC57simple-VP101L, respectively.

Plasmids pUC57simple-VP101H and pUC57simple-VP101L were enzyme-digested (HindIII&EcoRI), and heavy and light chains isolated by electrophoresis were subcloned into vector pcDNA3.1, and recombinant plasmids were extracted to co-transfect 293F cells. After 7 days of cell culture, the culture medium was separated by centrifugation at high speed, and the supernatant was concentrated and loaded onto a HiTrap MabSelect SuRe column. The protein was eluted in one step with an elution buffer. The target sample was isolated and the buffer was exchanged into PBS.

The purified antibodies P1D7V02R, P1D7V03, P1D7V04R, P1D7V07 and P1D7V08 were obtained according to the above expression and purification methods for P1D7V01.

Example 8: Assay for Binding Activity of Anti-CD73/Anti-PD-1 Bispecific Antibodies to Antigens by ELISA 1. Binding Activity of P1D7V01, P1D7V02R, P1D7V03 and P1D7V04R to Antigen PD-1-mFc Determined by ELISA the Method is Specifically as Follows.

A microplate was coated with PD-1-mFc at 0.5 μg/mL and incubated at 4 °C overnight. Then the microplate coated with antigens was washed once with PBST, and then blocked with a PBS solution containing 1% BSA as blocking solution at 37 °C for 2 h. After blocking, the microplate was washed 3 times with PBST. The antibodies serially diluted with PBST solution (the dilution gradients for the antibody are shown in Table 2) were added. The microplate containing the test antibodies was incubated at 37 °C for 30 min, and then washed 3 times with PBST. After washing, HRP-labeled goat anti-human IgG (H+L) (Jackson, Cat. No. 109-035-088) secondary antibody working solution diluted in a ratio of 1:5000 was added, and then the microplate was incubated at 37 °C for 30 min. After incubation, the plate was washed 4 times with PBST, TMB (Neogen, 308177) was added in the dark for chromogenesis for 5 min, and then a stop solution was added to terminate chromogenic reaction. The microplate was put into a microplate reader immediately, and the OD value of each well in the microplate was read at 450 nm. The data were analyzed and processed by SoftMax Pro 6.2.1.

The results are shown in Table 2 and FIG. 1. It can be seen from the figure that P1D7V01, P1D7V02R, P1D7V03 and P1D7V04R can effectively bind to the antigen PD-1-mFc in a dose-dependent manner. The absorbance intensity of each dose is shown in Table 2. By quantitative analysis of the absorbance of the bound antibodies, the binding efficiency $EC_{50}$ values of the antibodies P1D7V01, P1D7V02R, P1D7V03, P1D7V04R, 14C12H1L1 and nivolumab (as a control) obtained by curve fitting were 0.078 nM, 0.078 nM, 0.075 nM, 0.089 nM, 0.033 nM and 0.051 nM, respectively.

The above experimental results showed that in the same experimental condition, the binding activities of P1D7V01, P1D7V02R, P1D7V03 and P1D7V04R to PD-1-mFc are comparable to that of the reference drugs 14C12H1L1 and nivolumab for the same target, suggesting that P1D7V01, P1D7V02R, P1D7V03, P1D7V04R have the activity of effectively binding to PD-1-mFc.

2. Binding Activity of P1D7V01, P1D7V02R, P1D7V03 and P1D7V04R to Antigen Human NT5E-Biotin Determined by ELISA A microplate was coated with streptavidin at 2 μg/mL and then incubated at 4 °C overnight. After incubation, the microplate coated with streptavidin was washed once with PBST, and blocked with a PBS solution containing 1% BSA as a microplate blocking solution at 37 °C for 2 h. After blocking, the microplate was washed 3 times with PBST. Then, 0.5 g/mL antigen human NT5E-Biotin was added and incubated at 37 °C for 30 min. Then, the plate was washed 3 times with PBST. The antibodies serially diluted with PBST solution (the dilution gradients for the antibody are shown in Table 3) were added to wells of the microplate. The microplate containing the test antibodies was incubated at 37 °C for 30 min, and then washed 3 times with PBST. After washing, HRP-labeled goat anti-human IgG (H+L) (Jackson, Cat. No. 109-035-088) secondary antibody working solution diluted in a ratio of 1:5000 was added, and the microplate was incubated at 37 °C for 30 min. After incubation, the plate was washed 4 times with PBST, TMB (Neogen, 308177) was added in the dark for chromogenesis for 5 min, and then a stop solution was added to terminate chromogenic reaction. The microplate was put into a microplate reader immediately, and the OD value of each well in the microplate was read at 450 nm. The data were analyzed and processed by SoftMax Pro 6.2.1.

Figure 2:
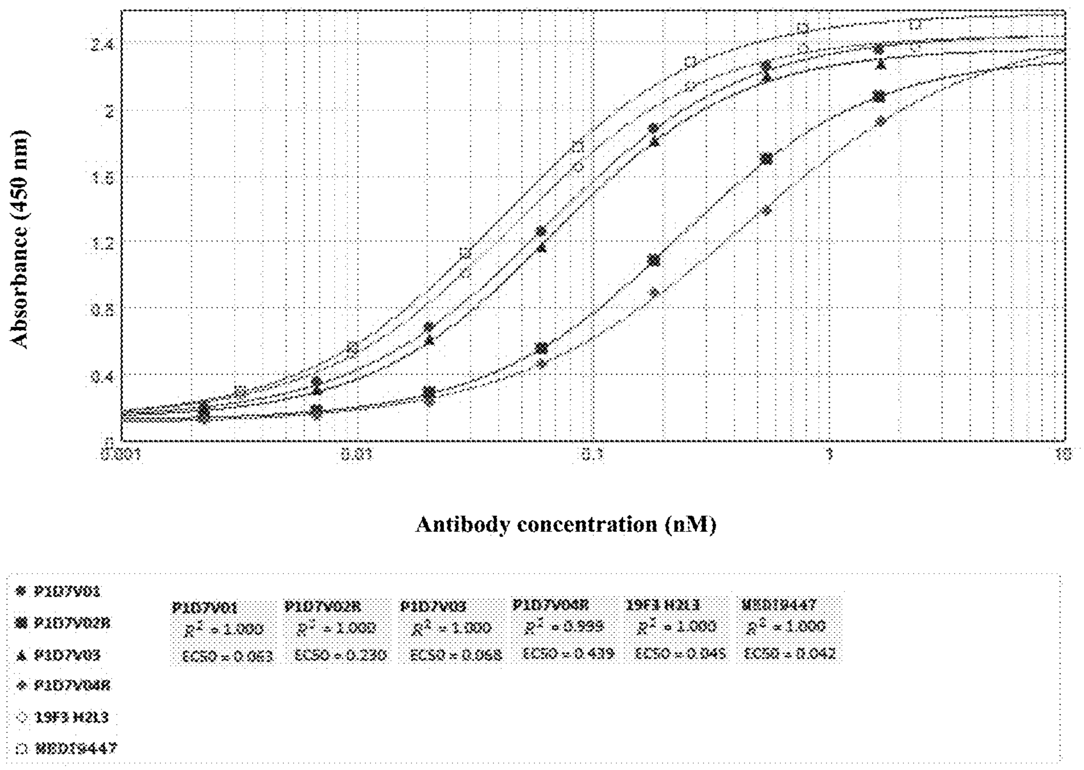
FIG. 2. Binding of P1D7V01, P1D7V02R, P1D7V03, P1D7V04R, 19F3 H2L3 and MEDI9447 to human NT5E-Biotin determined by ELISA.

The results are shown in Table 3 and FIG. 2. It can be seen from the figure that P1D7V01, P1D7V02R, P1D7V03 and P1D7V04R can effectively bind to the antigen human NT5E-biotin in a dose-dependent manner. The absorbance intensity of each dose is shown in Table 3. By quantitative analysis of the absorbance of the bound antibodies, the binding efficiency $EC_{50}$ values of the antibodies P1D7V01, P1D7V02R, P1D7V03, P1D7V04R, 19F3H2L3 and MEDI9447 (as a control antibody) obtained by curve fitting were 0.063 nM, 0.230 nM, 0.068 nM, 0.439 nM, 0.045 nM and 0.042 nM, respectively.

The above experimental results showed that in the same experimental condition, the binding activities of bispecific antibodies P1D7V01, P1D7V02R, P1D7V03 and P1D7V04R to human NT5E-biotin are comparable to that of the reference drugs 19F3H2L3 and MEDI9447 for the same target, suggesting that P1D7V01, P1D7V02R, P1D7V03 and P1D7V04R have the activity of effectively binding to human NT5E-biotin.

TABLE 2

Binding of P1D7V01, P1D7V02R, P1D7V03, P1D7V04R, 14C12H1L1 and nivolumab to PD-1-mFc determined by ELISA

| Antibody dilution concentration | Antigen coating PD-1-mFc 0.5 μg/mL | | | | | | | | | | | |
|---|---|---|---|---|---|---|---|---|---|---|---|---|
| (μg/mL) | P1D7V01 | | P1D7V02R | | P1D7V03 | | P1D7V04R | | 14C12H1L1 | | Nivolumab | |
| 1 | 2.345 | 2.300 | 2.169 | 2.323 | 2.406 | 2.292 | 2.225 | 2.393 | 2.441 | 2.609 | 2.386 | 2.473 |
| 1:3 | 2.461 | 2.295 | 2.114 | 2.361 | 2.288 | 2.303 | 2.199 | 2.302 | 2.414 | 2.548 | 2.441 | 2.600 |
| 1:9 | 2.279 | 2.085 | 2.063 | 2.094 | 2.135 | 2.178 | 2.075 | 2.043 | 2.461 | 2.525 | 2.519 | 2.572 |
| 1:27 | 1.838 | 1.765 | 1.701 | 1.696 | 1.777 | 1.764 | 1.659 | 1.659 | 2.236 | 2.295 | 2.196 | 2.219 |
| 1:81 | 1.153 | 1.097 | 1.089 | 1.120 | 1.149 | 1.154 | 1.062 | 1.131 | 1.858 | 1.954 | 1.711 | 1.712 |
| 1:243 | 0.629 | 0.684 | 0.570 | 0.582 | 0.675 | 0.686 | 0.584 | 0.592 | 1.251 | 1.318 | 0.980 | 0.965 |
| 1:729 | 0.361 | 0.364 | 0.334 | 0.349 | 0.360 | 0.370 | 0.340 | 0.341 | 0.683 | 0.709 | 0.521 | 0.498 |
| 0 | 0.201 | 0.198 | 0.187 | 0.210 | 0.197 | 0.197 | 0.213 | 0.257 | 0.208 | 0.199 | 0.196 | 0.190 |
| Secondary antibody | Goat anti-human IgG (H + L), HRP (1:5000) | | | | | | | | | | | |
| EC50(nM) | 0.078 | | 0.078 | | 0.075 | | 0.089 | | 0.033 | | 0.051 | |

TABLE 3

Binding of P1D7V01, P1D7V02R, P1D7V03, P1D7V04R, 19F3H2L3 and MEDI9447 to human NT5E-biotin determined by ELISA

| Antibody dilution concentration | Antigen coating: SA (2 μg/mL) Human NT5E-biotin (0.5 μg/mL) | | | | | | | | | | | |
|---|---|---|---|---|---|---|---|---|---|---|---|---|
| (μg/mL) | P1D7V01 | | P1D7V02R | | P1D7V03 | | P1D7V04R | | 19F3 H2L3 | | MEDI9447 | |
| 0.333 | 2.465 | 2.254 | 2.125 | 2.024 | 2.245 | 2.311 | 1.992 | 1.864 | 2.345 | 2.413 | 2.460 | 2.570 |
| 1:3 | 2.310 | 2.207 | 1.718 | 1.680 | 2.202 | 2.194 | 1.385 | 1.397 | 2.366 | 2.376 | 2.434 | 2.528 |
| 1:9 | 1.899 | 1.856 | 1.090 | 1.086 | 1.834 | 1.782 | 0.886 | 0.898 | 2.164 | 2.120 | 2.219 | 2.345 |
| 1:27 | 1.276 | 1.239 | 0.556 | 0.554 | 1.199 | 1.132 | 0.464 | 0.465 | 1.681 | 1.631 | 1.729 | 1.810 |
| 1:81 | 0.704 | 0.654 | 0.289 | 0.279 | 0.610 | 0.601 | 0.235 | 0.230 | 1.048 | 0.978 | 1.091 | 1.166 |
| 1:243 | 0.363 | 0.333 | 0.183 | 0.178 | 0.308 | 0.302 | 0.155 | 0.156 | 0.548 | 0.504 | 0.547 | 0.587 |
| 1:729 | 0.199 | 0.197 | 0.138 | 0.141 | 0.183 | 0.184 | 0.130 | 0.122 | 0.283 | 0.278 | 0.288 | 0.305 |
| 0 | 0.135 | 0.119 | 0.115 | 0.117 | 0.116 | 0.119 | 0.115 | 0.111 | 0.120 | 0.126 | 0.121 | 0.121 |
| Secondary antibody | Goat anti-human IgG (H + L), HRP (1:5000) | | | | | | | | | | | |
| EC50(nM) | 0.063 | | 0.230 | | 0.068 | | 0.439 | | 0.045 | | 0.042 | |

Example 9: Activity of Anti-CD73/Anti-PD-1 Bispecific Antibodies Completing with Human PD-L1-mFc for Binding to Human PD-1-mFc-Biotin Determined by Competitive ELISA A microplate was coated with human PD-L1-mFc (PD-L1 Genbank ID: NP_054862.1, mFc SEQ ID NO: 143) at 2 μg/mL and incubated at 4 °C overnight. After incubation, the microplate was blocked with a PBS solution containing 1% BSA at 37 °C for 2 h. After blocking, the plate was washed three times and dried. The antibody was serially diluted to 7 concentrations in a gradient ratio of 1:3 on a dilution plate with 10 μg/mL as the starting concentration, and a blank control was set. Then an equal volume of 0.3 μg/mL human PD-1-mFc-biotin solution was added, and the system was mixed well and incubated at room temperature for 20 min. Then the mixture after reaction was added to the coated microplate, and the microplate was incubated for at 37 °C for 30 min. After incubation, the plate was washed three times with PBST and dried. SA-HRP (KPL, 14-30-00) working solution was added, and the plate was incubated at 37 °C for 30 min. After incubation, the plate was washed four times and patted dry. Then TMB (Neogen, 308177) was added in the dark for chromogenesis for 5 min, and a stop solution was added to terminate chromogenic reaction. Then the microplate was put into a microplate reader immediately, and the OD value of each well in the microplate was read at 450 nm. The data were analyzed and processed by SoftMax Pro 6.2.1.

Figure 3:
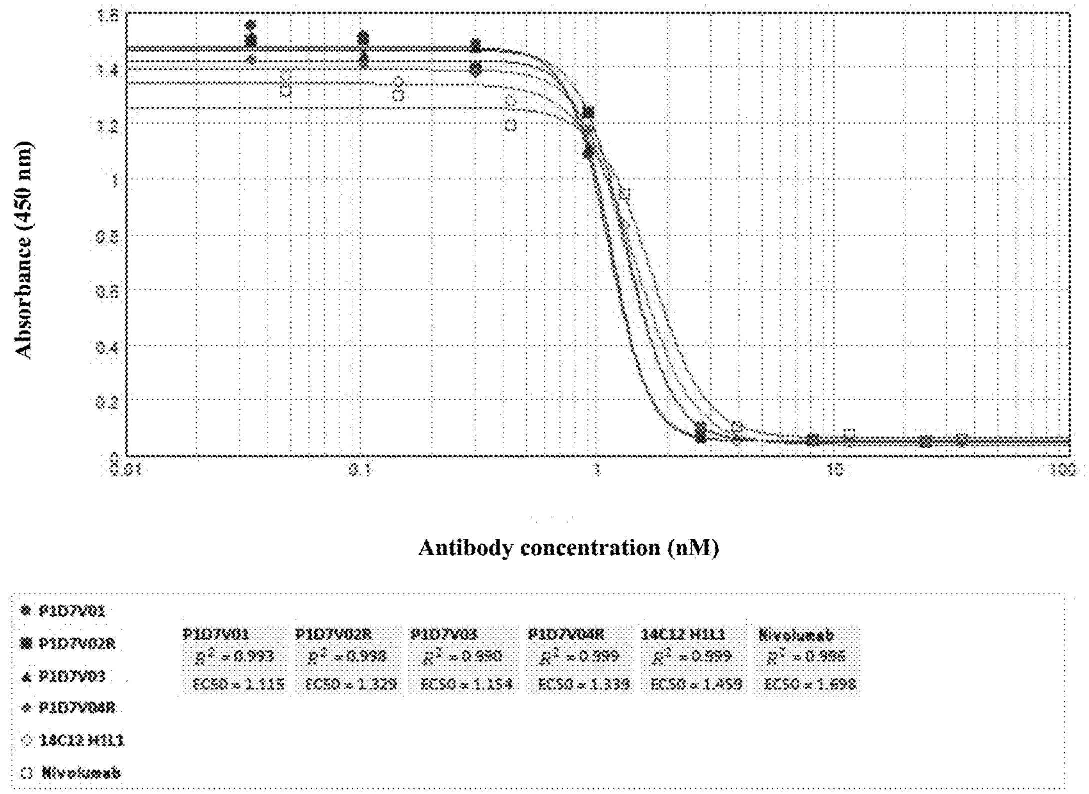
FIG. 3. Activity of P1D7V01, P1D7V02R, P1D7V03, P1D7V04R, 14C12H1L1 and nivolumab competing with human PD-L1-mFc for binding to human PD-1-mFc-Biotin.

The results are shown in FIG. 3. The OD values for all the dosages are shown in Table 4. By quantitative analysis of the absorbance intensity of the bound antibody, the curve simulation was performed to give the binding efficiency $EC_{50}$ of the antibody (Table 4).

The results showed that P1D7V01, P1D7V02R, P1D7V03, P1D7V04R, 14C12H1L1 and nivolumab (as a control) can effectively block the binding of the antigen human PD-1-mFc-biotin to its receptor human PD-L1-mFc in a dose-dependent manner. The $EC_{50}$ values of P1D7V01, P1D7V02R, P1D7V03, P1D7V04R, 14C12H1L1 and nivolumab for blocking the binding of human PD-1-mFc-biotin to its ligand human PD-L1-mFc were 1.115 nM, 1.329 nM, 1.154 nM, 1.339 nM, 1.459 nM and 1.698 nM, respectively.

TABLE 4

Activity of P1D7V01, P1D7V02R, P1D7V03, P1D7V04R, 14C12H1L1 and nivolumab competing with human PD-L1-mFc for binding to human PD-1-mFc-biotin

| Antibody dilution | Antigen coating: human PD-L1-mFc 2 μg/mL | | | | | | | | | | | |
|---|---|---|---|---|---|---|---|---|---|---|---|---|
| (μg/mL) | P1D7V01 | | P1D7V02R | | P1D7V03 | | P1D7V04R | | 14C12 H1L1 | | Nivolumab | |
| 5 | 0.049 | 0.047 | 0.047 | 0.048 | 0.048 | 0.048 | 0.048 | 0.051 | 0.046 | 0.047 | 0.057 | 0.057 |
| 1:3 | 0.050 | 0.050 | 0.051 | 0.051 | 0.052 | 0.050 | 0.052 | 0.054 | 0.048 | 0.050 | 0.075 | 0.076 |
| 1:9 | 0.070 | 0.065 | 0.097 | 0.104 | 0.067 | 0.068 | 0.105 | 0.107 | 0.053 | 0.055 | 0.107 | 0.100 |
| 1:27 | 1.056 | 1.109 | 1.253 | 1.216 | 1.109 | 1.121 | 1.187 | 1.158 | 0.817 | 0.849 | 1.014 | 0.875 |
| 1:81 | 1.460 | 1.505 | 1.414 | 1.372 | 1.453 | 1.491 | 1.424 | 1.337 | 1.263 | 1.299 | 1.235 | 1.152 |
| 1:243 | 1.474 | 1.551 | 1.503 | 1.505 | 1.449 | 1.447 | 1.442 | 1.382 | 1.316 | 1.383 | 1.387 | 1.207 |
| 1:729 | 1.499 | 1.604 | 1.501 | 1.493 | 1.569 | 1.452 | 1.436 | 1.424 | 1.336 | 1.403 | 1.347 | 1.284 |
| 0 | 1.399 | 1.283 | 1.467 | 1.456 | 1.288 | 1.252 | 1.343 | 1.342 | 1.302 | 1.391 | 1.265 | 1.156 |
| | Human PD-1-mFc-biotin: 0.3 μg/mL | | | | | | | | | | | |
| Secondary antibody | SA-HRP(1:4000) | | | | | | | | | | | |
| EC50(nM) | 1.115 | | 1.329 | | 1.154 | | 1.339 | | 1.459 | | 1.698 | |

Example 10: Kinetic Parameters for Binding of Anti-CD73/Anti-PD-1 Bispecific Antibodies to Antigen Human PD-1-mFc Determined by Fortebio System The sample dilution buffer was PBST, 0.1% BSA, pH 7.4. The antibody was immobilized on an AHC sensor at a concentration of 5 μg/mL with an immobilization height of about 0.4 nm. The sensor was equilibrated in a buffer for 60 s, and the binding of the immobilized antibody on the sensor to the antigen PD-1-mFc at concentrations of 0.6-50 nM (three-fold dilution) was determined in 120 s. The protein was dissociated in the buffer for 180 s. The detection temperature was 37 °C, the detection frequency was 0.3 Hz, and the sample plate shaking rate was 1000 rpm.

The data were analyzed by 1:1 model fitting to obtain affinity constants.

Figure 4:
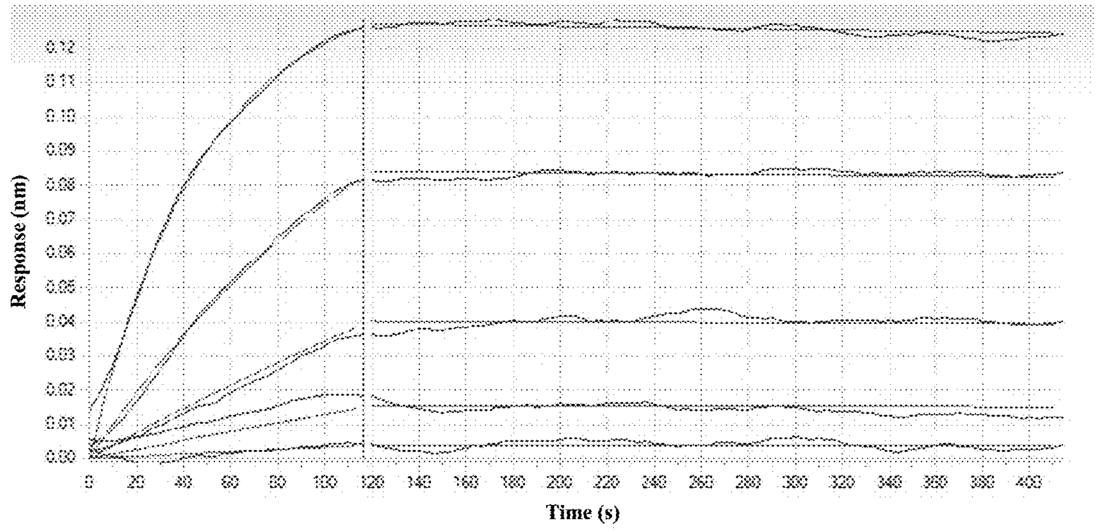
FIG. 4. Affinity constant of P1D7V01 for PD-1-mFc.
Figure 5:
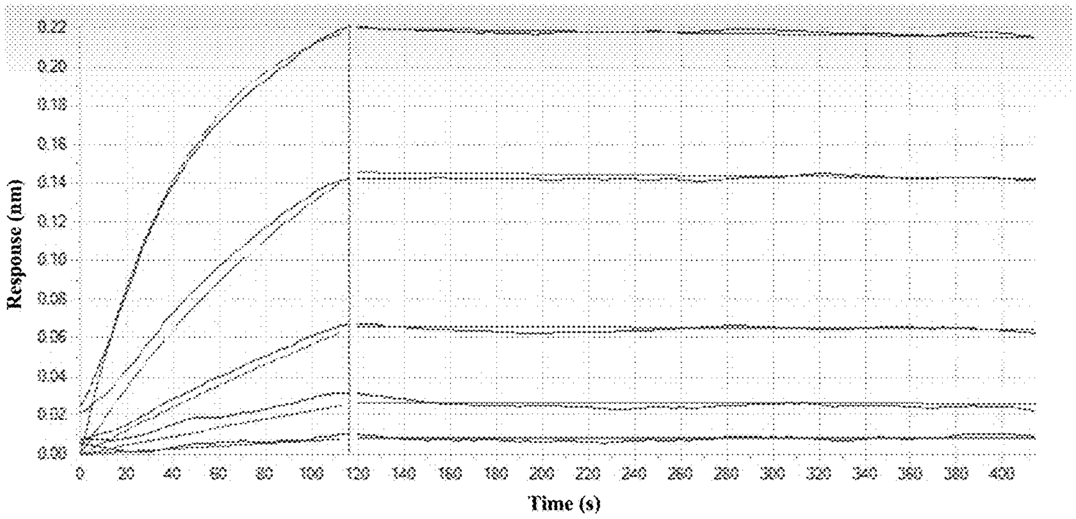
FIG. 5. Affinity constant of 14C12H1L1 for PD-1-mFc.
Figure 6:
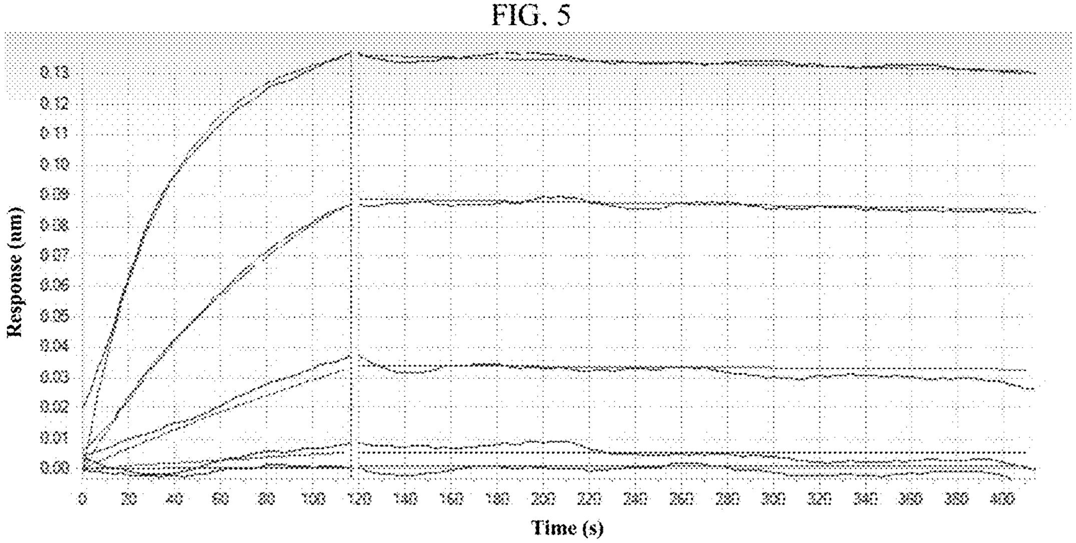
FIG. 6. Affinity constant of nivolumab for PD-1-mFc.

The determination results of the affinity constants of the humanized antibodies P1D7V01, 14C12H1L1 and nivolumab (as a control antibody) for human PD-1-mFc are shown in Table 5, and the detection results are shown in FIG. 4, FIG. 5 and FIG. 6. The affinity constants of the humanized antibodies P1D7V01, 14C12H1L1 and nivolumab for human PD-1-mFc were 1.76E-10 M, 1.64E-10 M and 2.32E-10 M, respectively. The above experimental results show that the binding ability of P1D7V01 is comparable to that of 14C12H1L1 and nivolumab, suggesting that the humanized antibody P1D7V01 has stronger binding ability to human PD-1-mFc.

TABLE 5

Determination of affinity constants of P1D7V01, 14C12H1L1 and nivolumab for PD-1-mFc

| Test antibodies | KD (M) | Kon (1/Ms) | SE (kon) | Kdis (1/s) | S E (kdis) | Rmax (nm) |
|---|---|---|---|---|---|---|
| P1D7V01 | 1.76E−10 | 4.19E+05 | 1.52E+04 | 7.37E−05 | 3.12E−05 | 0.13-0.17 |
| 14C12H1L1 | 1.64E−10 | 4.55E+05 | 1.61E+04 | 7.47E−05 | 2.98E−05 | 0.24-0.28 |
| Nivolumab | 2.32E−10 | 5.85E+05 | 2.03E+04 | 1.36E−04 | 3.47E−05 | 0.02-0.14 |

$K_D$ is the affinity constant;
$K_D$ = kdis/kon

Example 11: Kinetic Parameters for Binding of Anti-CD73/Anti-PD-1 Bispecific Antibodies to Antigen Human NT5E (1-552)-his Determined by Fortebio System The sample dilution buffer was PBST, pH 7.4. The antibody was immobilized on a Protein A sensor at a concentration of 5 μg/mL with the immobilization time of about 15 s. The sensor was equilibrated in a buffer for 120 s, and the binding of the immobilized antibody on the sensor to the antigen human NT5E(1-552)-his at concentrations of 3.125-200 nM (two-fold dilution) was determined for 120 s. The protein was dissociated in the buffer for 600 s. The sensor was refreshed with 10 mM Gly solution, pH 1.5. The detection temperature was 37 °C, the detection frequency was 0.6 Hz, and the sample plate shaking rate was 1000 rpm. The data were analyzed by 1:1 model fitting to obtain affinity constants.

Figure 7:
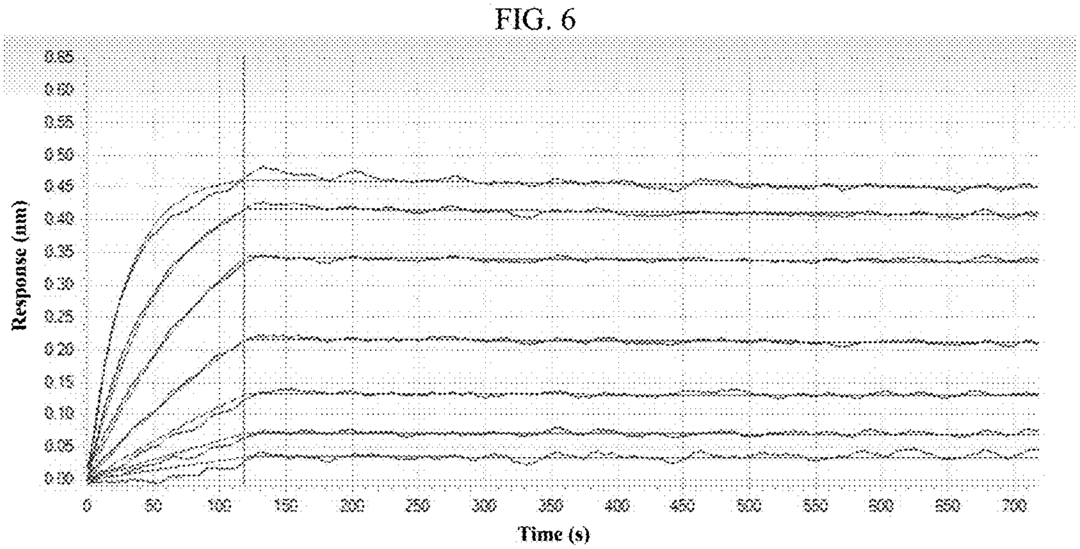
FIG. 7. Affinity constant of P1D7V01 for human NT5E (1-552)-his.
Figure 8:
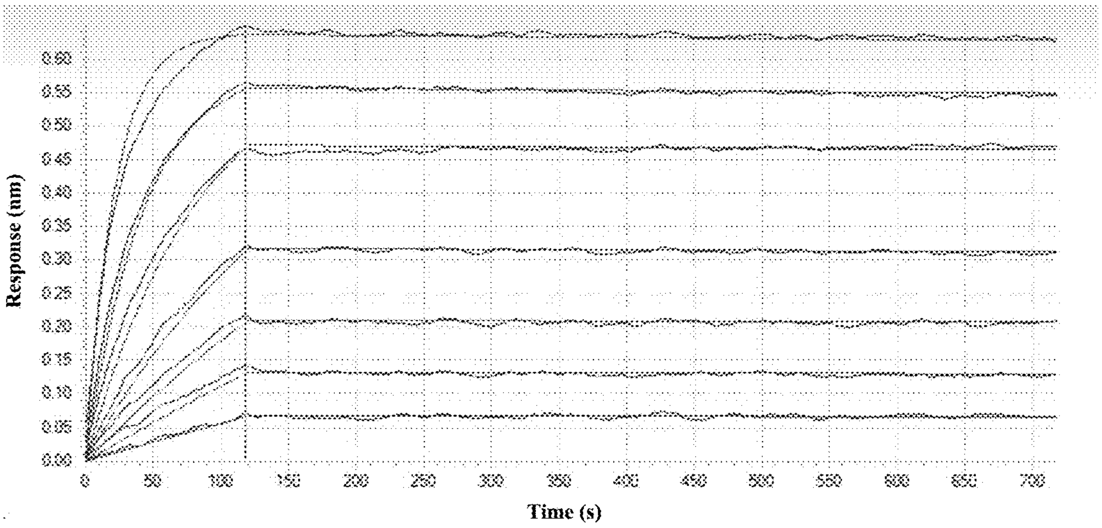
FIG. 8. Affinity constant of MEDI 9447 for human NT5E(1-552)-his.

The determination results of the affinity constants of the humanized antibodies P1D7V01 and MEDI9447 (as a control antibody) for human NT5E(1-552)-his are shown in Table 6, and the detection results are shown in FIG. 7 and FIG. 8. The affinity constants of the humanized antibodies P1D7V01 and MEDI9447 for human NT5E(1-552)-his are 2.29E-10 M and 1.04E-10 M respectively.

The above experimental results showed that the binding ability of P1D7V01 is comparable to that of MEDI9447, suggesting that the humanized antibody P1D7V01 has stronger binding ability to human NT5E(1-552)-his.

TABLE 6

Affinity constants of P1D7V01 and MEDI9447 for NTSE(1-552)-his

| Test antibodies | KD (M) | Kon (1/Ms) | S E (kon) | Kdis (1/s) | S E (kdis) | Rmax (nm) |
|---|---|---|---|---|---|---|
| P1D7V01 | 2.29E−10 | 1.81E+05 | 2.30E+03 | 4.13E−05 | 4.54E−06 | 0.47-0.57 |
| MEDI 9447 | 1.04E−10 | 2.34E+05 | 3.20E+03 | 2.44E−05 | 5.02E−06 | 0.59-0.82 |

$K_D$ is the affinity constant;
$K_D$ = kdis/kon

Example 12: Binding Activity of Anti-CD73/Anti-PD-1 Bispecific Antibodies Determined by FACS 1. Binding Activity of Anti-CD73/Anti-PD-1 Bispecific Antibody to PD-1 on 293T-PD1 Membrane Surface Determined by FACS 293T-PD1 cells in logarithmic growth phase were collected and transferred to a 1.5 mL centrifuge tube at $3\times10^5$ cells/tube. 500 μL of PBSA was added, and the mixture was centrifuged at 5600 rpm for 5 min to remove the supernatant. 100 μL of antibodies diluted by PBSA (at the final concentrations of 100 nM, 33.33 nM, 11.11 nM, 3.7 nM, 1.23 nM, 0.41 nM, 0.14 nM and 0.05 nM, respectively) were added, respectively. The system was mixed gently and uniformly, and then was incubated on ice for 1 h. Then 500 μL of PBSA was added, and the mixture was centrifuged at 5600 rpm for 5 min to remove the supernatant. The 500-fold diluted FITC labeled goat anti-human IgG secondary antibody (Jackson, Cat. No. 109-095-098) was added to resuspend and mix well, and the mixture was incubated on ice in the dark for 0.5 h. 500 μL of PBSA was added, and the mixture was centrifuged at 5600 rpm for 5 min to remove the supernatant. At last, 200 μL of PBSA was added to resuspend cell precipitates, and the mixture was transferred to a flow tube for FACSCalibur detection.

Figure 9:
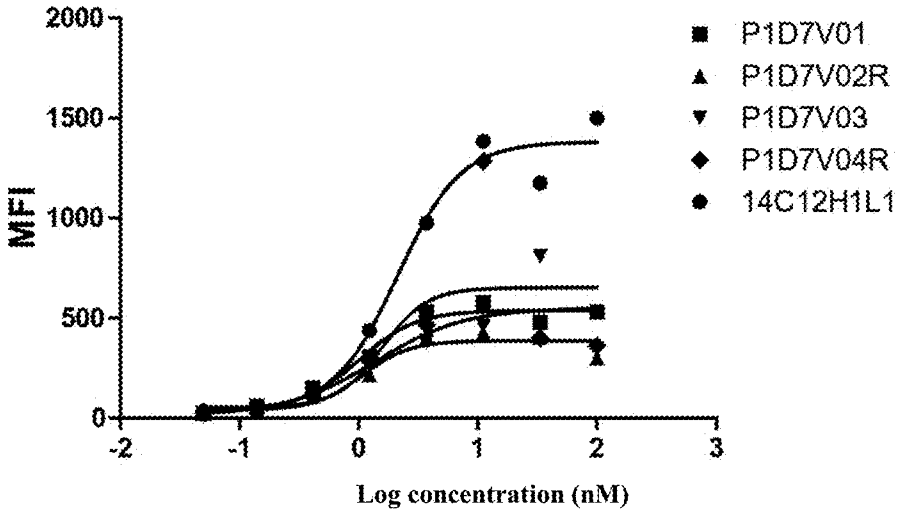
FIG. 9. Binding activity of P1D7V01, P1D7V02R, P1D7V03, P1D7V04R and 14C12H1L1 to PD-1 on 293T-PD1 cell surface determined by FACS.

The experimental results are shown in Table 7 and FIG. 9, and P1D7V01, P1D7V02R, P1D7V03, and P1D7V04R can specifically bind to PD-1 on the 293T-PD1 membrane surface in a dose-dependent manner, and compared with PD1 single-target control antibody 14C12H1L1, it is stronger than that of 14C12H1L1.

Under the same experimental conditions, $EC_{50}$ values of P1D7V01, P1D7V02R, P1D7V03 and P1D7V04R binding to 293T-PD1 were 1.000 nM, 1.075 nM, 1.377 nM and 1.57 nM, respectively, and the $EC_{50}$ value of 14C12H1L1 binding to 293T-PD1 was 2.111 nM.

The above experimental results showed that in the same experimental condition, P1D7V01, P1D7V02R, P1D7V03, P1D7V04R and 293T-PD1 all have binding activity superior to that of the PD1 single-target control antibody 14C12H1L1, suggesting that P1D7V01, P1D7V02R, P1D7V03 and P1D7V04R have the activity of effectively binding to PD-1 on the 293T-PD1 membrane surface.

TABLE 7

Binding activity of P1D7V01, P1D7V02R, P1D7V03, P1D7V04R and 14C12H1L1 to PD-1 on 293T-PD1 cell surface determined by FACS.

| Concentration (nM) | 0.05 | 0.14 | 0.41 | 1.23 | 3.70 | 11.11 | 33.33 | 100.00 | EC50 |
|---|---|---|---|---|---|---|---|---|---|
| 14C12H1L1 | 35.69 | 57.70 | 129.42 | 437.62 | 974.97 | 1384.91 | 1174.75 | 1500.20 | 2.111 |
| P1D7V01 | 26.65 | 58.65 | 150.57 | 307.19 | 530.77 | 577.76 | 479.34 | 531.15 | 1.000 |
| P1D7V02R | 23.44 | 42.98 | 108.44 | 217.56 | 404.33 | 426.06 | 405.29 | 301.40 | 1.075 |
| P1D7V03 | 24.05 | 49.21 | 118.03 | 289.08 | 384.62 | 459.40 | 808.38 | 343.48 | 1.377 |
| P1D7V04R | 24.79 | 52.43 | 112.56 | 288.79 | 466.72 | 1284.73 | 400.33 | 360.79 | 1.57.0 |

2. Binding Activity of Anti-CD73/Anti-PD-1 Bispecific Antibody to CD73 on MDA-MB-231 Membrane Surface Determined by FACS MDA-MB-231 cells in logarithmic phase were digested with conventional trypsin and transferred to a 1.5 mL centrifuge tube at $3\times10^5$ cells/tube. 500 μL of PBSA was added, and the mixture was centrifuged at 5600 rpm for 5 min to remove the supernatant. 100 μL of antibodies diluted by PBSA (at the final concentrations of 100 nM, 33.33 nM, 11.11 nM, 3.7 nM, 1.23 nM, 0.41 nM, 0.14 nM and 0.05 nM, respectively) were added, respectively. The system was mixed gently and uniformly, and then was incubated on ice for 1 h. Then 500 μL of PBSA was added, and the mixture was centrifuged at 5600 rpm for 5 min to remove the supernatant. The 500-fold diluted FITC labeled goat anti-human IgG secondary antibody (Jackson, Cat. No. 109-095-098) was added to resuspend and mix well, and the mixture was incubated on ice in the dark for 0.5 h. 500 μL of PBSA was added, and the mixture was centrifuged at 5600 rpm for 5 min to remove the supernatant. At last, 200 μL of PBSA was added to resuspend cell precipitates, and the mixture was transferred to a flow tube for FACSCalibur detection.

Figure 10:
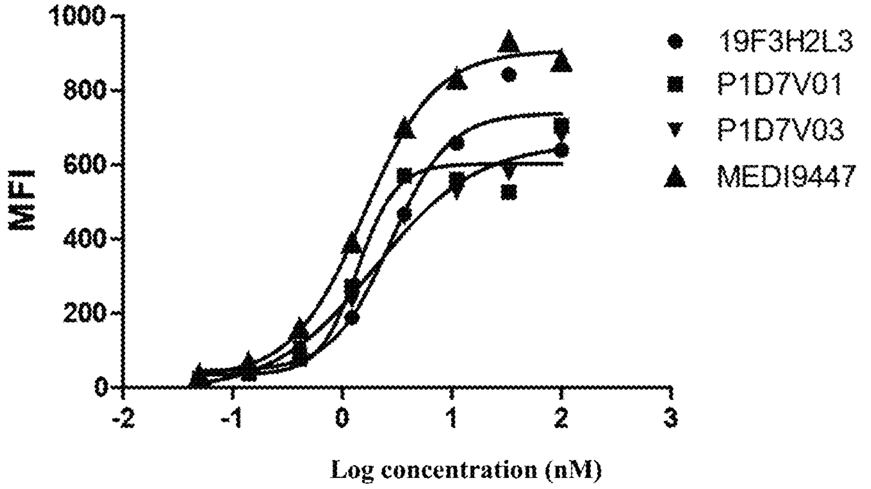
FIG. 10. Binding activity of P1D7V01, P1D7V03, MEDI9447 and 19F3H2L3 to CD73 on MDA-MB-231 cell surface determined by FACS.

The experimental results are as shown in Table 8 and FIG. 10. The binding activities of P1D7V01 and P1D7V03 to CD73 on the MDA-MB-231 membrane surface were superior to that of 19F3H2L3, wherein P1D7V01 was superior to the reference drug MEDI9447 for the same target.

In the same experimental condition, the $EC_{50}$ values of P1D7V01 and P1D7V03 binding to CD73 on the MDA-MB-231 membrane surface were 1.384 nM and 2.009 nM, respectively, and the $EC_{50}$ values of MEDI9447 and 19F3H2L3 binding to CD73 on MDA-MB-231 membrane surface were 1.589 nM and 2.773 nM, respectively.

The above experimental results showed that P1D7V01, P1D7V03, 19F3H2L3 and the reference drug MEDI9447 for the same target can specifically bind to CD73 on the MDA-MB-231 membrane surface in a dose-dependent manner. The binding activities of P1D7V01 and P1D7V03 were superior to that of 19F3H2L3, wherein P1D7V01 was superior to the reference drug MEDI9447 for the same target. It was suggested that P1D7V01 and P1D7V03 have the activity of effectively binding to CD73 on the MDA-MB-231 membrane surface.

TABLE 8

Binding activity of P1D7V01, P1D7V03, MEDI9447 and 19F3H2L3 to CD73 on the MDA-MB-231 cell surface determined by FACS

| Concentration (nM) | 0.05 | 0.14 | 0.41 | 1.23 | 3.70 | 11.11 | 33.33 | 100.00 | EC50 |
|---|---|---|---|---|---|---|---|---|---|
| MEDI9447 | 32.59 | 64.38 | 157.75 | 388.51 | 697.80 | 829.29 | 930.26 | 878.04 | 1.589 |
| 19F3H2L3 | 25.95 | 45.13 | 102.56 | 189.07 | 466.87 | 658.72 | 843.09 | 639.57 | 2.773 |
| P1D7V01 | 23.37 | 38.02 | 76.84 | 271.72 | 571.56 | 560.81 | 525.91 | 705.50 | 1.384 |
| P1D7V03 | 16.96 | 44.05 | 106.39 | 233.32 | 457.61 | 525.37 | 576.19 | 677.66 | 2.009 |

Example 13: Detection of Inhibition of Anti-CD73/Anti-PD-1 Bispecific Antibody on Enzyme Activity of CD73 on Cell Membrane Surface 1. Detection of Inhibition of Anti-CD73/Anti-PD-1 Bispecific Antibody on Enzyme Activity of CD73 on MDA-MB-231 Membrane Surface The experimental procedures were as follows. MDA-MB-231 cells in logarithmic phase in good condition were taken, resuspended in a serum-free RPMI-1640 culture solution, and then counted. The MDA-MB-231 cells were seeded into a 96-well plate at $2\times10^4$ cells/100 μL/well. The antibody was diluted with the serum-free RPMI-1640 culture solution (serial 2.5-fold dilution). The antibody was added to the 96-well plate at 50 μL/well, and the plate was incubated at 37 °C for 1 h. After 1 h, 50 μL of 1200 μM RPMI-1640-diluted AMP (TCL, Cat. No. A0157) was added to each well. After 3 h, 25 μL of cell culture supernatant was taken and transferred to a new 96-well plate, and 25 μL of 100 μM ATP (TCL, Cat. No. A0158) was added to each well. 50 μL of CTG (CellTiterGlo, promega, Cat. No. G8641) chromogenic solution was added to each well for chromogenesis, and relative fluorescence intensity RLU was read by a multi-label microplate tester (PerkinElmer 2140-0020).

Figure 11:
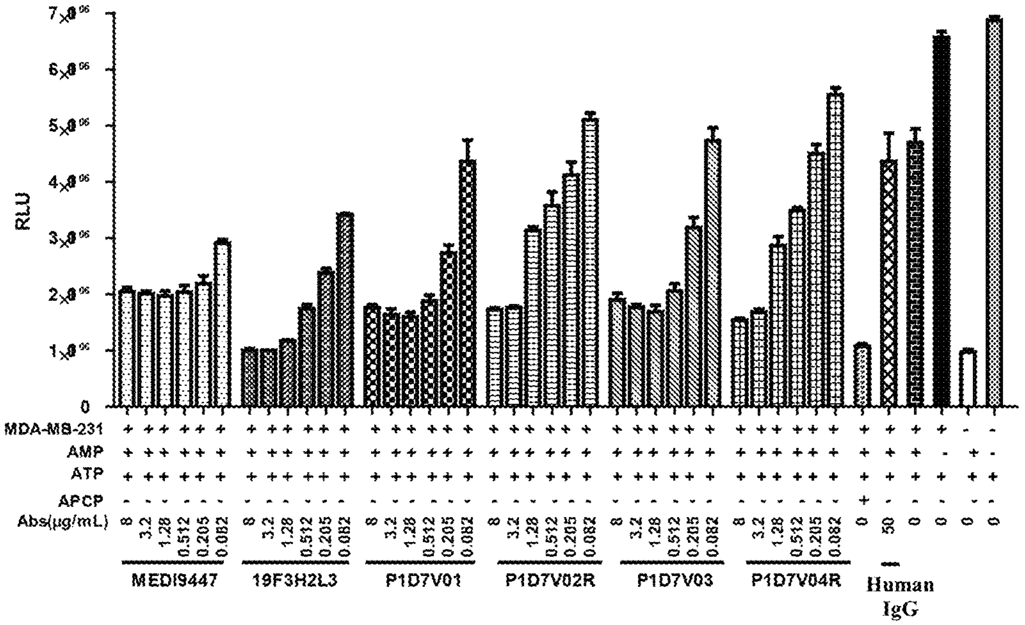
FIG. 11. Inhibition of anti-CD73/anti-PD-1 bispecific antibodies on the enzyme activity of CD73 on MDA-MB-231 membrane surface.

The experimental results are as shown in FIG. 11. The AMP amounts of P1D7V01, P1D7V02R, P1D7V03 and P1D7V04R are comparable to that of the positive control MEDI9447 in concentration-dependent manners.

The above experimental results showed that the added AMP can be converted into adenosine A without antibodies by the enzyme activity of CD73 on the MDA-MB-231 cell surface, and that after the addition of the antibody, the enzyme-catalyzed activity was decreased due to the binding of antibodiesP1D7V01, P1D7V02R, P1D7V03 and P1D7V04R to CD73, so that the AMP was not converted into adenosine A. It was suggested that the antibodies effectively inhibit the enzyme activity reaction thereof in a non-substrate competition mode and reduce the production of adenosine.

Figure 12:
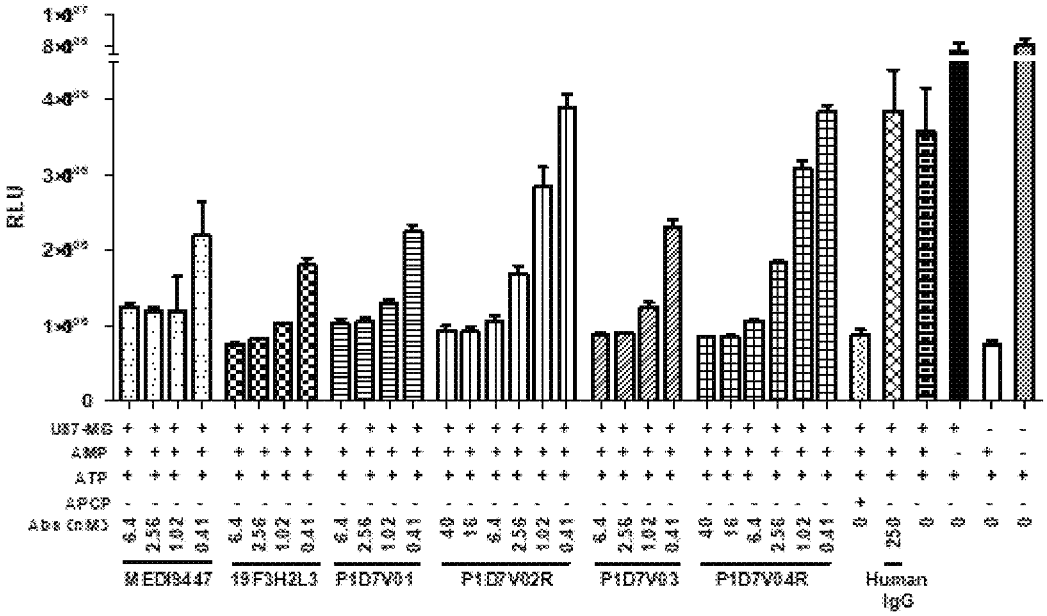
FIG. 12. Inhibition of anti-CD73/anti-PD-1 bispecific antibodies on the enzyme activity of CD73 on U87-MG membrane surface.

2. Detection of Inhibition of Anti-CD73/Anti-PD-1 Bispecific Antibody on Enzyme Activity of CD73 on U87-MG Membrane Surface U87-MG cells in logarithmic phase in good condition were taken, resuspended in a serum-free RPMI-1640 culture solution, and then counted. The U87-MG cells were seeded into a 96-well plate at $2\times10^4$ cells/100 μL/well. The antibody was diluted with the serum-free RPMI-1640 culture solution (serial 2.5-fold dilution). The antibody was added to the 96-well plate at 50 μL/well, and the plate was incubated at 37 °C for 1 h. After 1 h, 50 μL of 1200 μM RPMI-1640-diluted AMP was added to each well. After 3 h, 25 μL of cell culture supernatant was taken and transferred to a new 96-well plate, and 25 μL of 100 μM ATP was added to each well. 50 μL of CTG (CellTiterGlo) chromogenic solution was added to each well for chromogenesis, and relative fluorescence intensity RLU were read by a multi-label microplate tester (PerkinElmer 2140-0020). The experimental results are as shown in FIG. 12. The AMP amounts of P1D7V01, P1D7V02R, P1D7V03 and P1D7V04R are comparable to that of the positive control MEDI9447 in concentration-dependent manners.

The above experimental results showed that the added AMP can be converted into adenosine A without antibodies by the enzyme activity of CD73 on the U87-MG cell surface, and that after the addition of the antibody, the enzyme-catalyzed function was decreased due to the binding of antibodiesP1D7V01, P1D7V02R, P1D7V03 and P1D7V04R to CD73, so that the AMP was not converted into adenosine A. It was suggested that the antibodies effectively inhibit the enzyme activity reaction thereof in a non-substrate competition mode and reduce the production of adenosine.

Example 14: Biological Activity of Anti-CD73/Anti-PD-1 Bispecific Antibodies for Promoting IFN-γ and IL-2 Secretion Determined by Mixed Lymphocyte Reaction (MLR)

1. Biological Activity of Anti-CD73/Anti-PD-1 Bispecific Antibodies for Promoting IFN-γ Secretion in Raji-PDL1 Mixed Lymphocyte Reaction System Raji-PDL1 cells were normally subcultured. PBMCs were thawed, incubated with 10 mL of a 1640 complete medium, and stimulated with 0.5 g/mL SEB (Dianotech, Cat. No. S010201) for two days. Raji-PDL1 cells were treated with 25 μg/mL MMC (Sigma, Cat. No. M4287) and placed in a 37 °C incubator for 1 h. PBMCs (peripheral blood mononuclear cells) stimulated with SEB for 2 days and Raji-PDL1 cells treated with MMC for 1 h were collected, washed twice with PBS, resuspended in the complete medium, and counted. The cells were separately added to a U-shaped 96-well plate at 100,000 cells/well. The antibodies were added according to the study design and cultured in an incubator for 3 days. After 3 days, the cell culture supernatant was collected and determined for IFN-γ by ELISA.

Figure 13:
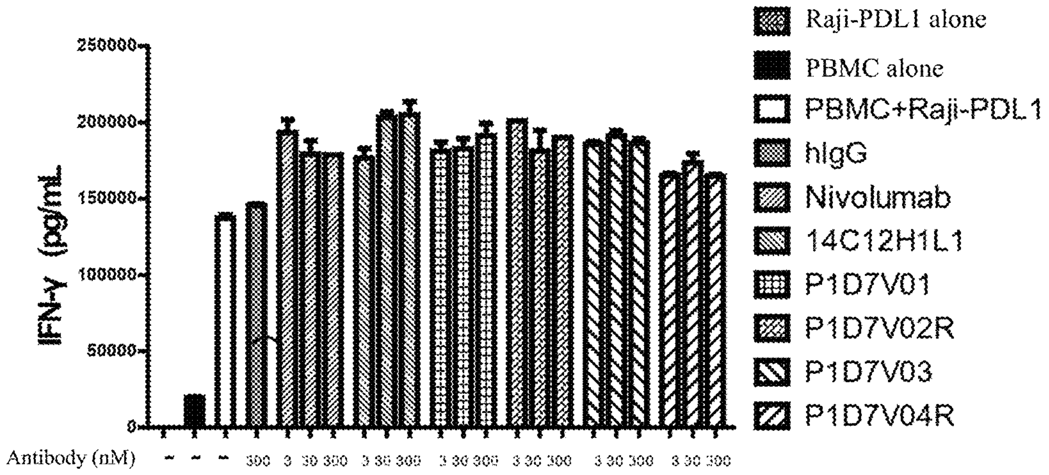
FIG. 13. Biological activity of anti-CD73/anti-PD-1 bispecific antibodies for promoting IFN-γ secretion in Raji-PDL1 mixed lymphocyte reaction system.

As shown in FIG. 13, the mixed culture of human PBMCs and Raji-PDL1 cells significantly promoted the secretion of IFN-γ from PBMCs, and the addition of antibodies to the mixed culture system significantly induced secretion of IFN-γ in PBMCs. In terms of the level of promoting IFN-γ secretion activity, the antibodies P1D7V01, P1D7V02R, P1D7V03 and P1D7V04R have the activity comparable to that of the parent PD-1 single-target antibody 14C12H1L1.

2. Biological Activity of Anti-CD73/Anti-PD-1 Bispecific Antibodies for Promoting IL-2 Secretion in Raji-PDL1 Mixed Lymphocyte Reaction System Raji-PDL1 cells were normally subcultured. PBMCs were thawed, incubated with 10 mL of a 1640 complete medium, and stimulated with SEB (0.5 μg/mL) for two days. Raji-PDL1 cells were treated with 25 g/mL MMC and placed in a 37 °C incubator for 1 h. PBMCs (peripheral blood mononuclear cells) stimulated with SEB for 2 days and Raji-PDL1 cells treated with MMC for 1 h were collected, washed twice with PBS, resuspended in the complete medium, and counted. The cells were separately added to a U-shaped 96-well plate at 100,000 cells/well. The antibodies were added according to the study design and cultured for 3 days. The cell culture supernatant was collected and determined for IL-2 by ELISA.

Figure 14:
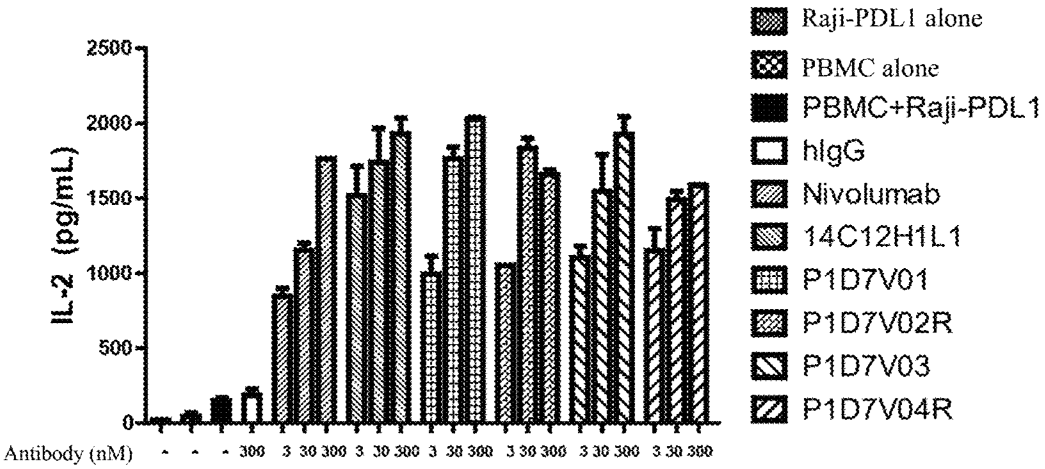
FIG. 14. Biological activity of anti-CD73/anti-PD-1 bispecific antibodies for promoting IL-2 secretion in Raji-PDL1 mixed lymphocyte reaction system.

As shown in FIG. 14, the mixed culture of human PBMCs and Raji-PDL1 cells had certain promoting effect on the secretion of IL-2 in PBMCs, and the simultaneous addition of antibodies to the mixed culture system significantly induced IL-2 secretion in PBMCs in a significant dose-dependent manner. In terms of the level of promoting IL-2 secretion activity, the bifunctional antibodies P1D7V01, P1D7V02R, P1D7V03 and P1D7V04R have the activity at low concentrations slightly lower than that of the parent PD-1 single-target antibody 14C12H1L1, and the activity at medium-high concentrations comparable to that of the parent PD-1 single-target antibody 14C12H1L1. Compared with the PD1 target positive control drug nivolumab, P1D7V01, P1D7V02R, P1D7V03 and P1D7V04R have better IL-2 secretion promotion potential at three different antibody concentration levels.

3. Bioactivity Detection of Anti-CD73/Anti-PD-1 Bispecific Antibody Promoting DC Mixed Lymph Reaction System to Secrete IFN-γ

PBMCs in normal human peripheral blood were isolated, resuspended in a complete medium, and seed into a culture dish. The culture dish was placed in an incubator overnight for culture. The suspended PBMCs were collected and removed. The adherent cells at the bottom of the dish were washed with PBS buffer and then subjected to DC maturation induction. 10 mL of RPMI1640 complete medium containing GM-CSF and IL-4 was added to each dish with GM-CSF and IL-4 each at a concentration of 1000 U/mL. The dishes were cultured in a 37 °C, 5% carbon dioxide incubator for three days. Then half of the medium was exchanged, 1000 U/mL GM-CSF and IL-4 each was added, and the dishes were put into a 37 °C, 5% carbon dioxide incubator for continuous culture for three days. After three days, half amount of the medium was changed again, 1000 U/mL GM-CSF and IL-4 each, and 100 U/mL TNF-α were added, and the dishes were cultured for another two days. PBMCs from other donors were freshly isolated and seeded into a 96-well plate at 100,000 cells/well after cell counting. DCs induced to mature were collected and washed once with the complete medium. The cells were counted and seed into the 96-well plate containing PBMC at 10,000 cells/well. The antibodies were added according to the study design. The system was mixed well and cultured in a 37 °C, 5% carbon dioxide incubator for 5 days for co-culture. After 5 days, the cell culture supernatant was collected and quantitatively determined for IFN-γ by ELISA.

Figure 15:
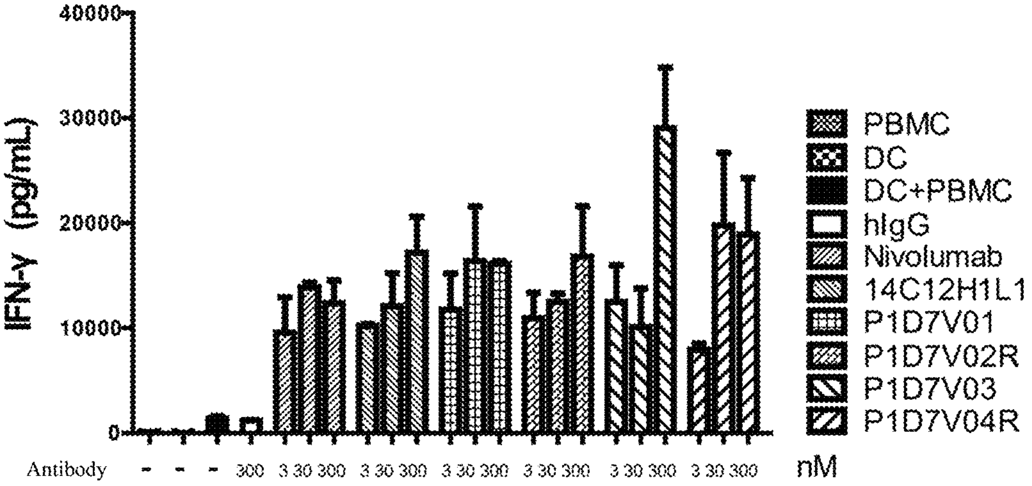
FIG. 15. Biological activity of anti-CD73/anti-PD-1 bispecific antibodies for promoting IFN-γ secretion in DC mixed lymphocyte reaction system.
Figure 16:
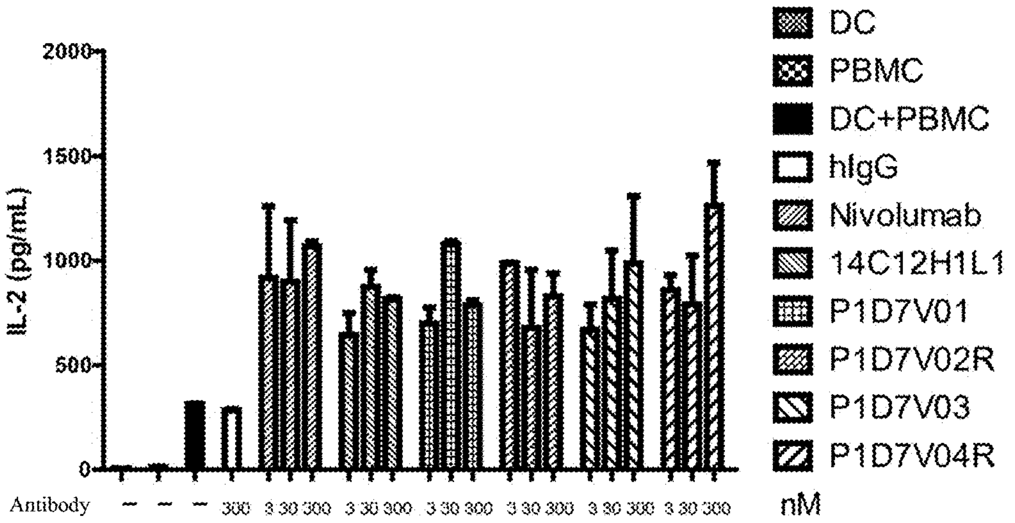
FIG. 16. Biological activity of anti-CD73/anti-PD-1 bispecific antibodies for promoting IL-2 secretion in DC mixed lymphocyte reaction system.
Figure 17:
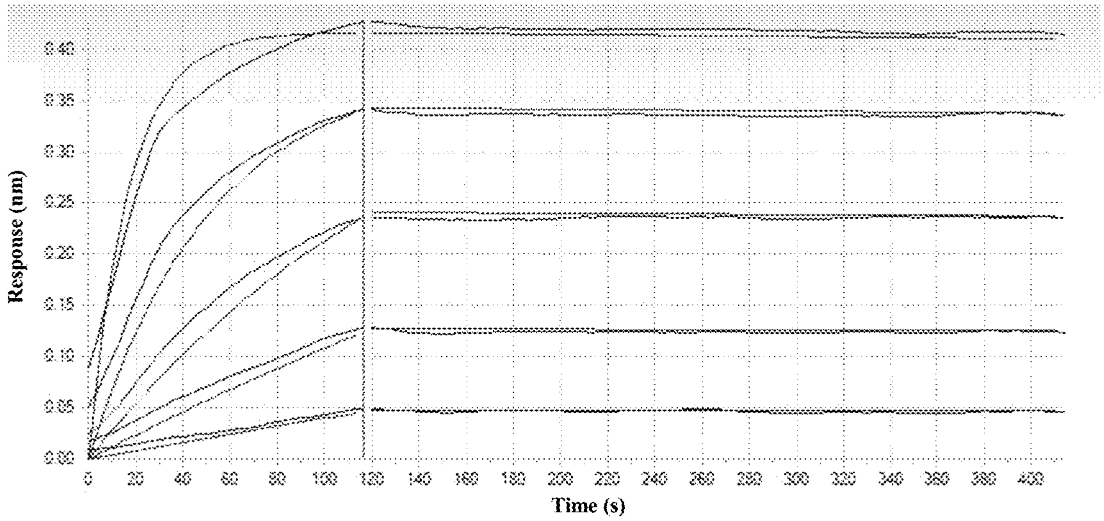
FIG. 17. Affinity constant of 14C12H1L1(hG1TM) for PD-1-mFc.
Figure 18:
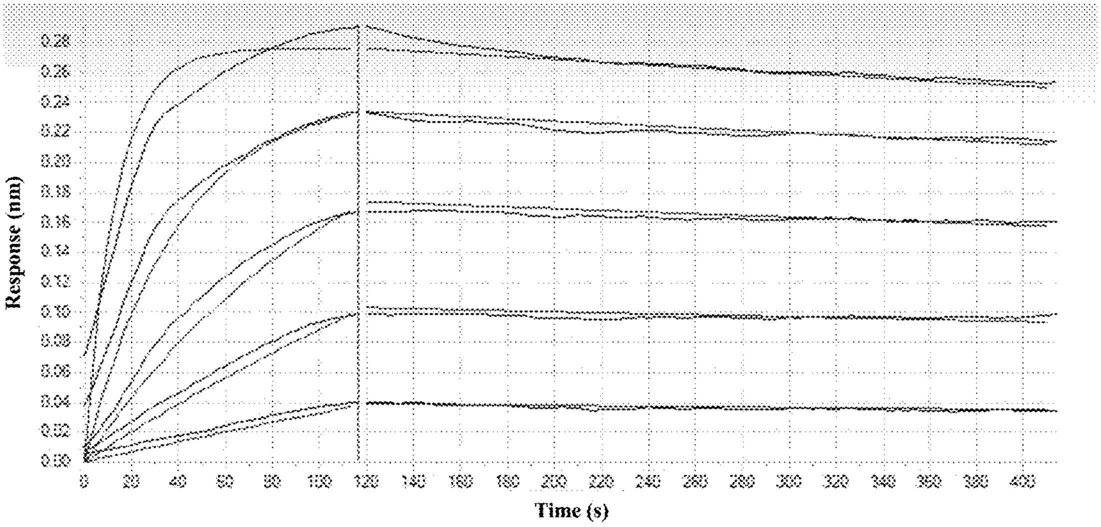
FIG. 18. Affinity constant of nivolumab for PD-1-mFc.
Figure 19:
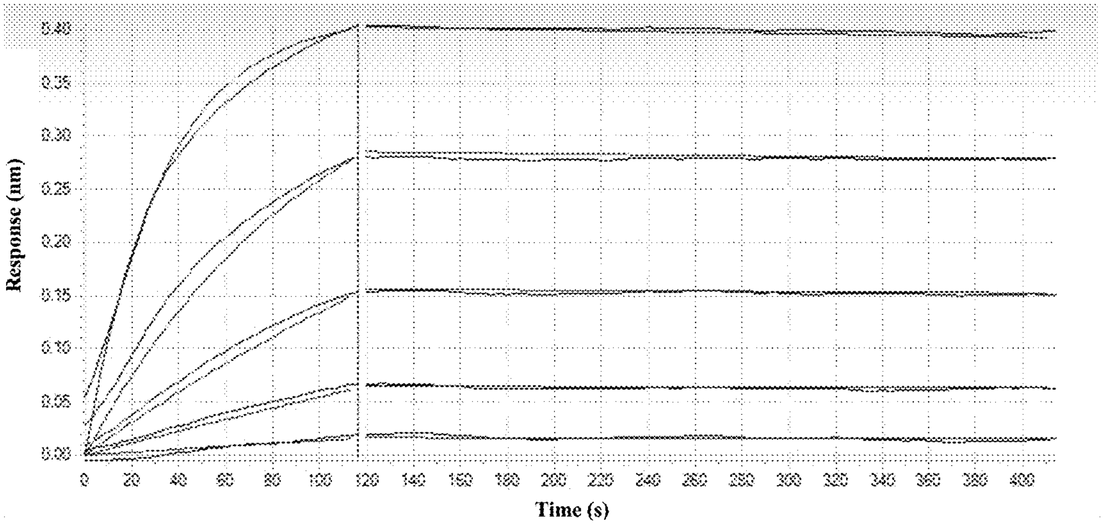
FIG. 19. Affinity constant of NTPDV1 for PD-1-mFc.
Figure 20:
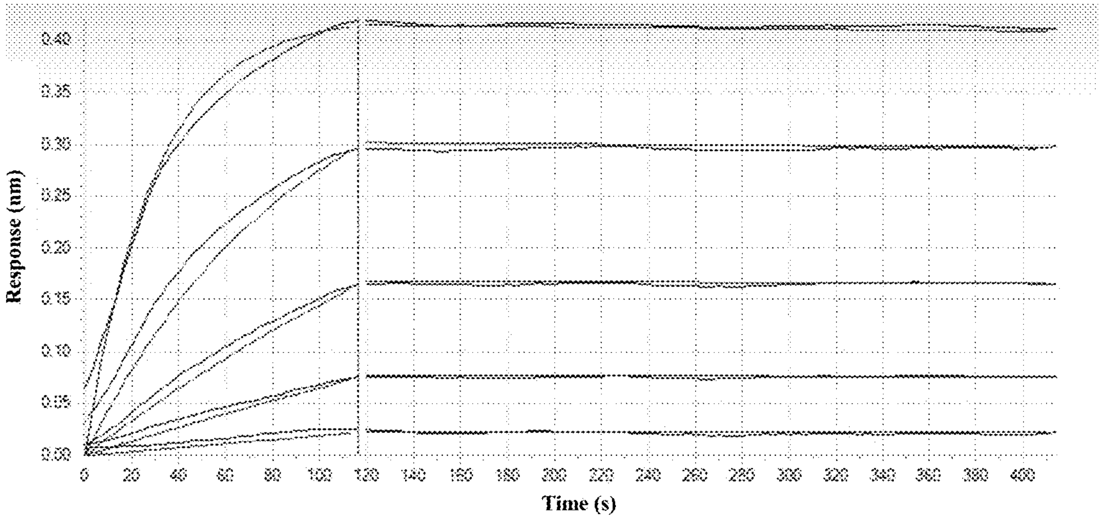
FIG. 20. Affinity constant of NTPDV2 for PD-1-mFc.
Figure 21:
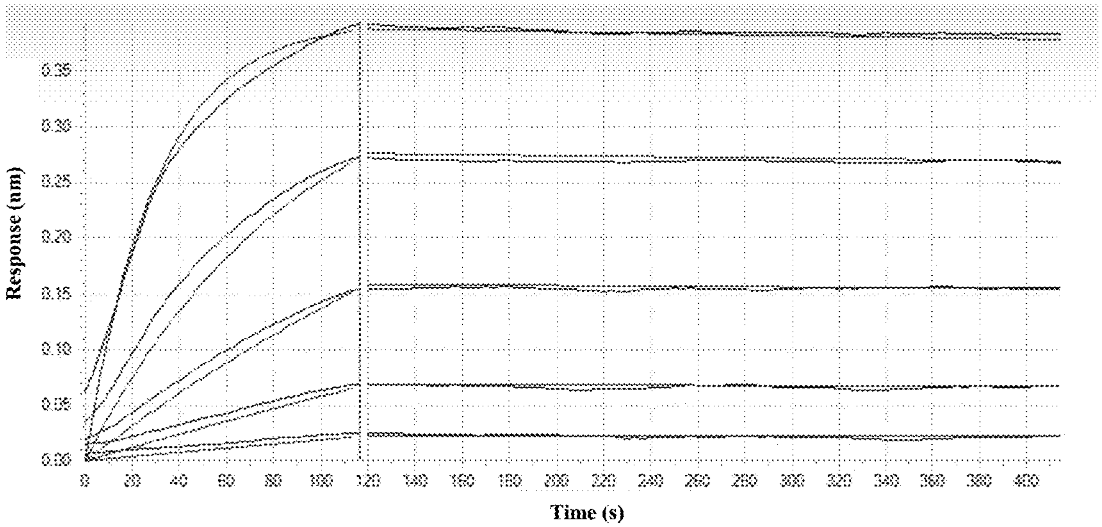
FIG. 21. Affinity constant of NTPDV3 for PD-1-mFc.
Figure 22:
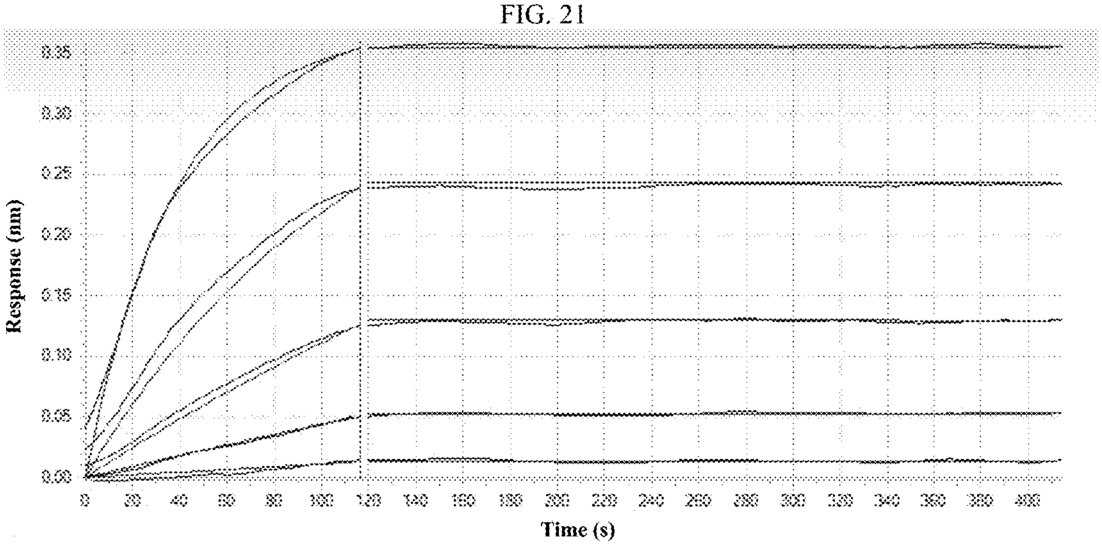
FIG. 22. Affinity constant of NTPDV4 for PD-1-mFc.
Figure 23:
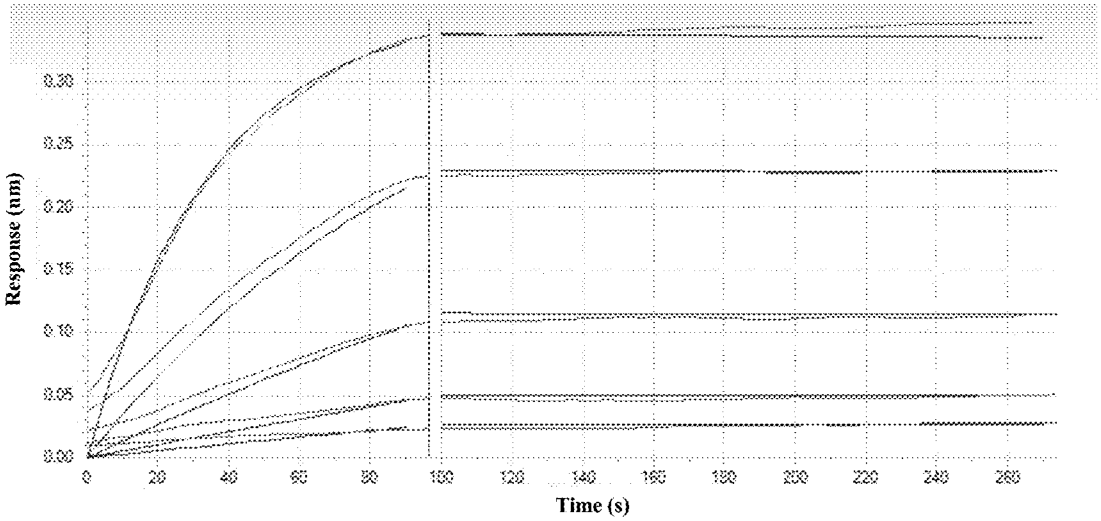
FIG. 23. Affinity constant of 19F3H2L3(hG1M) for human NT5E(1-552)-his.
Figure 24:
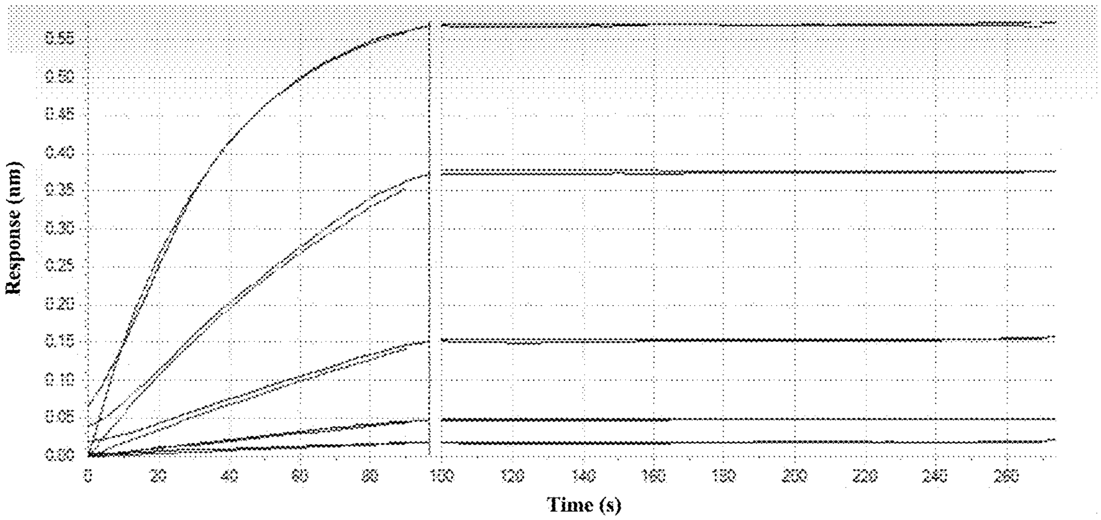
FIG. 24. Affinity constant of NTPDV1 for human NT5E (1-552)-his.
Figure 25:
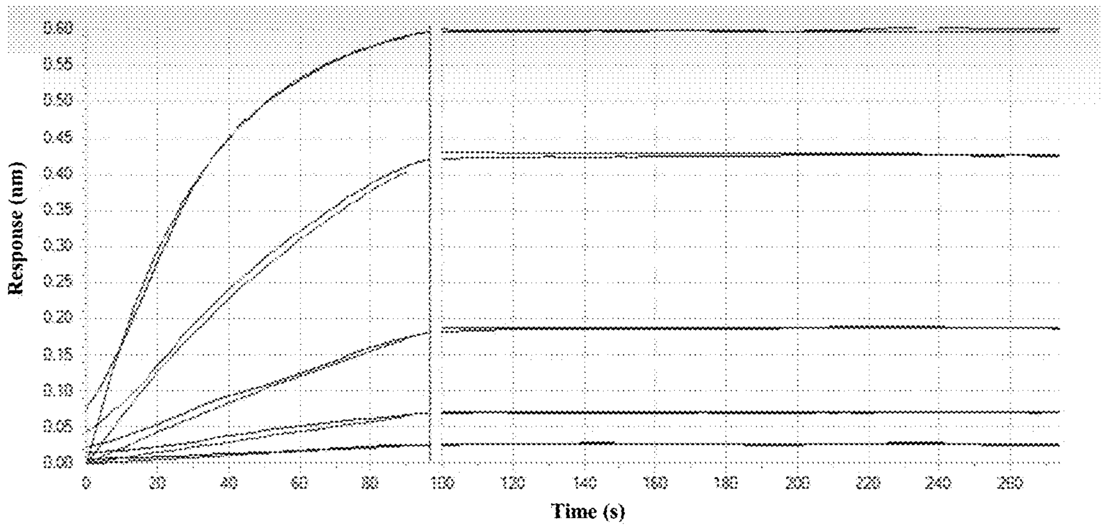
FIG. 25. Affinity constant of NTPDV2 for human NT5E (1-552)-his.
Figure 26:
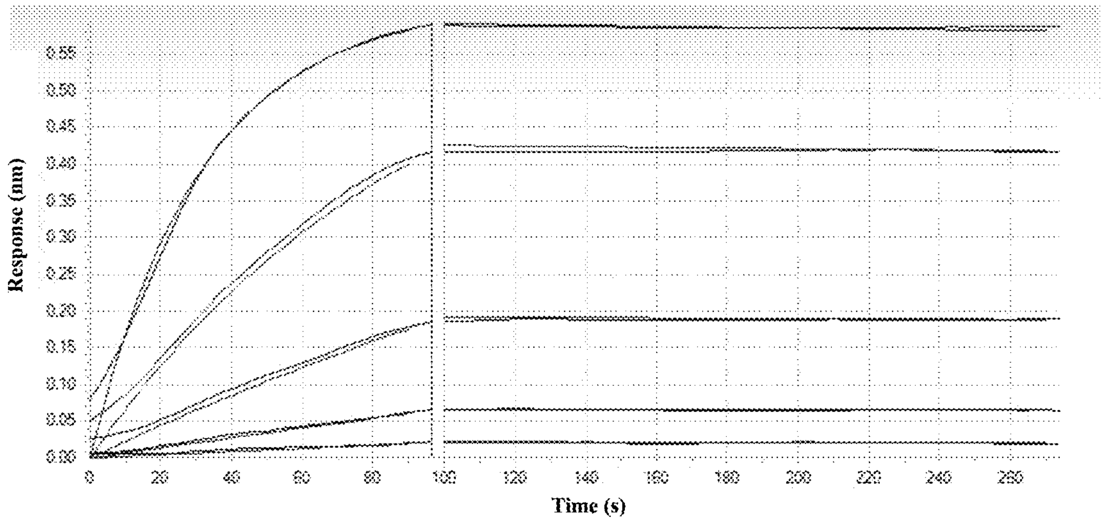
FIG. 26. Affinity constant of NTPDV3 for human NT5E (1-552)-his.
Figure 27:
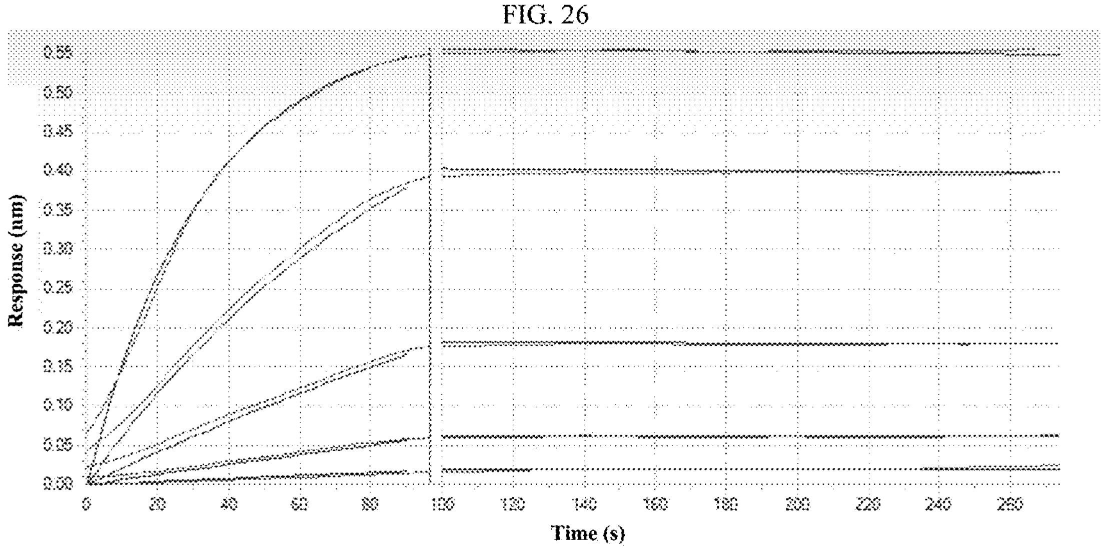
FIG. 27. Affinity constant of NTPDV4 for human NT5E (1-552)-his.

The results are as shown in FIG. 15. Compared with the culture of DCs or PBMCs alone, the mixed culture of DCs and PBMCs significantly promoted the secretion of IFN-γ; and compared with an isotype control, IFN-γ secretion level was further significantly improved by the addition of the anti-CD73/anti-PD-1 bispecific antibody based on the mixed culture of DCs and PBMCs. Biological activity of anti-CD73/anti-PD-1 bispecific antibodies for promoting IL-2 secretion in DC mixed lymphocyte reaction system PBMCs in normal human peripheral blood were isolated, resuspended in a complete medium, and seed into a culture dish. The culture dish was placed in an incubator overnight for culture. The suspended PBMCs were collected and removed. The adherent cells at the bottom of the dish were washed with PBS buffer and then subjected to DC maturation induction. 10 mL of RPMI1640 complete medium containing GM-CSF and IL-4 was added to each dish with GM-CSF and IL-4 each at a concentration of 2000 U/mL. The dishes were cultured in a 37 °C, 5% carbon dioxide incubator for three days. Then half amount of the medium was changed, 50 ng/ml IFN-γ and 100 ng/ml LPS were added, and the dishes were cultured for another two days. PBMCs from other donors were thawed and seeded into a 96-well plate at 100,000 cells/well after cell counting. DCs induced to mature were collected and washed once with the complete medium. The cells were counted and seed into the 96-well plate containing PBMCs at 10,000 cells/well. The antibodies were added according to the study design. The system was mixed well and cultured in a 37 °C, 5% carbon dioxide incubator for 5 days for co-culture. After 5 days, the cell culture supernatant was collected and quantitatively determined for IL-2 by ELISA. The results are as shown in FIG. 16. Compared with the culture of DCs or PBMCs alone, the mixed culture of DCs and PBMCs significantly promoted the secretion of IL-2; and compared with an isotype control, IL-2 secretion level was further significantly improved by the addition of the anti-CD73/anti-PD-1 bispecific antibody based on the mixed culture of DCs and PBMCs.

Example 15: Preparation of Anti-PD-1/CD73 Bispecific Antibodies NTPDV1, NTPDV2, NTPDV3 and NTPDV4

The structural patterns of the bispecific antibodies NTPDV1, NTPDV2, NTPDV3 and NTPDV4 are in the Morrison format (IgG-scFv), i.e., C termini of two heavy chains of one IgG antibody are separately linked to the scFv fragment of another antibody via linkers. The components for the heavy and light chain design are shown in Table 9 below.

NTPDV1, NTPDV2, NTPDV3 and NTPDV4 are known as NTPDV1(hG1TM), NTPDV2(hG1TM), NTPDV3 (hG1TM) and NTPDV4(hG1TM) herein and in Chinese Patent Application No. 202110270671.X, because the constant regions of the immunoglobulin moieties thereof have introduced amino acid mutations to eliminate their binding activity to FcγR.

TABLE 9

Sequence design of NTPDV1, NTPDV2, NTPDV3 and NTPDV4

| | Heavy chain | | | |
|---|---|---|---|---|
| | Immunoglobulin moiety | Linker | scFv moiety | Light chain |
| NTPDV1 | 19F3H2 (hGITM) | Linker1 | 14C12H1v-Linker 2-14C2L1v | 19F3L3 |
| NTPDV2 | | | 14C12H1v-Linker 1-14C2L1v | |
| NTPDV3 | | | 14C12H1v-Linker 2-14C2L1v | 19F3L2 |
| NTPDV4 | | | 14C12H1v-Linker1-14C12L1v | |

In the Table 9 above:

Those with "V" label at lower right corner refer to the variable region of corresponding heavy chain or the variable region of corresponding light chain. For those without "V" label, the corresponding heavy or light chain is the full length comprising the constant region. The corresponding sequences described in the above examples are referred to for the amino acid sequences of these variable regions or the full length and the nucleotide sequences encoding them. The amino acid sequence of linker1 consists of 4 repeats of (GGGGS), i.e., $(GGGGS)_4$ or $(G_4S)_4$ (nucleotide sequence SEQ ID NO: 80, and amino acid sequence SEQ ID NO: 79).

The amino acid sequence of linker2 consists of 3 repeats of (GGGGS), i.e., $(GGGGS)_3$ or $(G_4S)_3$ (nucleotide sequence SEQ ID NO: 82, and amino acid sequence SEQ ID NO: 81).

The 3 CDR sequences of the light chains 19F3L2 and 19F3L3 of the immunoglobulin moiety in NTPDV1, NTPDV2, NTPDV3 and NTPDV4 are identical to the light chain CDR sequences of 19F3.

The 3 CDR sequences of 19F3H2(hG1TM) of the immunoglobulin moiety in NTPDV1, NTPDV2, NTPDV3 and NTPDV4 are identical to the heavy chain CDR sequences of 19F3.

The CDR sequences of 14C12H1V-Linker2-14C12L1V and 14C12H1V-Linker1-14C12L1V of the scFv moiety in NTPDV1, NTPDV2, NTPDV3 and NTPDV4 are identical to the heavy chain CDRs and light chain CDRs of 14C12.

The amino acid sequences of the heavy chains of NTPDV2 and NTPDV4 are identical and are marked as NTPDH2/4 (SEQ ID NO: 83), and the nucleotide sequence of the heavy chains of NTPDV2 or NTPDV4 is SEQ ID NO: 84.

The amino acid sequences of the heavy chains of NTPDV1 and NTPDV3 are identical and are marked as NTPDH1/3 (SEQ ID NO: 85), and the nucleotide sequence of the heavy chains of NTPDV1 or NTPDV3 is SEQ ID NO: 86.

The 3 CDR sequences of 19F3L3 and 19F3L2 of the immunoglobulin moiety in NTPDV1, NTPDV2, NTPDV3 and NTPDV4 are identical to the three CDRs of the light chain of antibody 19F3.

The amino acid sequence of the light chain 19F3L3 of the immunoglobulin moiety in NTPDV1 or NTPDV2 is identical to the light chain sequence (SEQ ID NO: 28) of antibody 19F3H2L3 (G1M), and the nucleotide sequence of the light chain 19F3L3 of the immunoglobulin moiety in NTPDV1 or NTPDV2 is SEQ ID NO: 27. The amino acid sequence of the light chain 19F3L2 of the immunoglobulin moiety in NTPDV3 or NTPDV4 is SEQ ID NO: 96, and the nucleotide sequence of the light chain 19F3L2 of the immunoglobulin moiety in NTPDV3 or NTPDV4 is SEQ ID NO: 100.

(1) NTPDV1, of which the heavy chain has an amino acid sequence set forth in SEQ ID NO: 85, the light chain has an amino acid sequence set forth in SEQ ID NO: 28, the linker 1 has an amino acid sequence set forth in SEQ ID NO: 79, 14C12H1V has an amino acid sequence set forth in SEQ ID NO: 62, the linker 2 has an amino acid sequence set forth in SEQ ID NO: 81, and 14C12L1V has an amino acid sequence set forth in SEQ ID NO: 64;

(2) NTPDV2, of which the heavy chain has an amino acid sequence set forth in SEQ ID NO: 83, the light chain has an amino acid sequence set forth in SEQ ID NO: 28, the linker 1 has an amino acid sequence set forth in SEQ ID NO: 79, 14C12H1V has an amino acid sequence set forth in SEQ ID NO: 62, the linker 1 has an amino acid sequence set forth in SEQ ID NO: 79, and 14C12L1V has an amino acid sequence set forth in SEQ ID NO: 64;

(3) NTPDV3, of which the heavy chain has an amino acid sequence set forth in SEQ ID NO: 85, the light chain has an amino acid sequence set forth in SEQ ID NO: 96, the linker 1 has an amino acid sequence set forth in SEQ ID NO: 79, 14C12H1V has an amino acid sequence set forth in SEQ ID NO: 62, the linker 2 has an amino acid sequence set forth in SEQ ID NO: 81, and 14C12L1V has an amino acid sequence set forth in SEQ ID NO: 64; and (4) NTPDV4, of which the heavy chain has an amino acid sequence set forth in SEQ ID NO: 83, the light chain has an amino acid sequence set forth in SEQ ID NO: 96, the linker 1 has an amino acid sequence set forth in SEQ ID NO: 79, 14C12H1V has an amino acid sequence set forth in SEQ ID NO: 62, the linker 1 has an amino acid sequence set forth in SEQ ID NO: 79, and 14C12L1V has an amino acid sequence set forth in SEQ ID NO: 64.

Expression and Purification of Antibodies

The heavy chain cDNA sequences of NTPDV1 and NTPDV3, the heavy chain cDNA sequences of NTPDV2 and NTPDV4, and the light chain cDNA sequences thereof were separately cloned into vector pUC57simple (provided by Genscript) to obtain plasmids pUC57simple-NTPDH2/4, pUC57simple-NTPDH1/3, pUC57simple-19F3L3 and pUC57simple-19F3L2, respectively.

Plasmid pUC57simple-NTPDH2/4 and plasmid pUC57simple-19F3L3, plasmid pUC57simple-NTPDH2/4 and plasmid pUC57simple-19F3L2, plasmid pUC57simple-NTPDH1/3 and plasmid pUC57simple-19F3L3, and plasmid pUC57simple-NTPDH1/3 and plasmid pUC57simple-19F3L2 were digested (HindIII&EcoRI). The recovered heavy and light chains were separately subcloned into vector pcDNA3.1 to obtain plasmids pcDNA3.1-NTPDH2/4 and pcDNA3.1-19F3L3, plasmids pcDNA3.1-NTPDH2/4 and pcDNA3.1-19F3L2, plasmids pcDNA3.1-NTPDH1/3 and pcDNA3.1-19F3L3, and plasmids pcDNA3.1-NTPDH1/3 and pcDNA3.1-19F3L2. The recombinant plasmids were extracted and co-transfected into 293F cells. After 7 days of cell culture, the culture medium was separated by centrifugation at high speed, and the supernatant was concentrated and loaded onto a HiTrap MabSelect SuRe column. The protein was eluted in one step with an elution buffer. The target sample was isolated and the buffer was exchanged into PBS.

The purified antibodies NTPDV1, NTPDV2, NTPDV3 and NTPDV4 were obtained according to the expression and purification methods mentioned in the above preparation examples.

Example 16: Assay for Binding Activity of Anti-CD73/Anti-PD-1 Bispecific Antibodies to Antigens by ELISA 1. Binding Activity of NTPDV1, NTPDV2, NTPDV3 and NTPDV4 to Antigen PD-1-mFc Determined by ELISA A microplate was coated with PD-1-mFc (0.5 g/mL) and incubated at 4 °C overnight. Then the microplate coated with antigens was washed once with PBST, and then blocked with a PBS solution containing 1% BSA as blocking solution at 37 °C for 2 h. After blocking, the microplate was washed 3 times with PBST. The antibodies serially diluted with PBST solution (the dilution gradients for the antibody are shown in Table 2) were added. The microplate containing the test antibodies was incubated at 37 °C for 30 min, and then washed 3 times with PBST. After washing, HRP-labeled goat anti-human IgG Fc (Jackson, Cat. No. 109-035-098) secondary antibody working solution diluted in a ratio of 1:5000 was added, and then the microplate was incubated at 37 °C for 30 min. After incubation, the plate was washed 4 times with PBST, TMB (Neogen, 308177) was added in the dark for chromogenesis for 8 min, and then a stop solution was added to terminate chromogenic reaction. The microplate was put into a microplate reader immediately, and the OD value of each well in the microplate was read at 450 nm. The data were analyzed and processed by SoftMax Pro 6.2.1.

The results are shown in Table 10. It can be seen that NTPDV1, NTPDV2, NTPDV3 and NTPDV4 can effectively bind to the antigen PD-1-mFc in a dose-dependent manner. The absorbance intensity of each dose is shown in Table 10. By quantitative analysis of the absorbance of the bound antibodies, the binding efficiency $EC_{50}$ values of the antibodies NTPDV1, NTPDV2, NTPDV3, NTPDV4 and 14C12H1L1(hG1TM) (as a control) obtained by curve fitting were 0.101 nM, 0.119 nM, 0.110 nM, 0.123 nM and 0.031 nM, respectively.

The above experimental results showed that in the same experimental condition, the binding activities of NTPDV1, NTPDV2, NTPDV3 and NTPDV4 to PD-1-mFc are comparable to that of the reference drugs 14C12H1L1(hG1TM) for the same target, suggesting that NTPDV1, NTPDV2, NTPDV3 and NTPDV4 have the activity of effectively binding to PD-1-mFc.

TABLE 10

Binding of NTPDV1, NTPDV2, NTPDV3, NTPDV4 and 14C12H1L1(hG1TM) to PD-1-mFc determined by ELISA

| Antibody dilution concentration | Antigen coating PD-1-mFc 0.5 μg/mL | | | | | | | | | |
|---|---|---|---|---|---|---|---|---|---|---|
| (nM) | NTPDV1 | | NTPDV2 | | NTPDV3 | | NTPDV4 | | 14C12H1L1 (hG1TM) | |
| 5 | 2.222 | 2.231 | 2.249 | 2.249 | 2.204 | 2.171 | 2.244 | 2.289 | 2.399 | 2.524 |
| 1:3 | 2.206 | 2.195 | 2.160 | 2.223 | 2.211 | 2.167 | 2.222 | 2.209 | 2.361 | 2.441 |
| 1:9 | 2.039 | 2.027 | 1.922 | 2.013 | 2.010 | 1.971 | 1.920 | 1.944 | 2.273 | 2.401 |
| 1:27 | 1.514 | 1.530 | 1.425 | 1.446 | 1.489 | 1.414 | 1.417 | 1.464 | 2.071 | 2.091 |
| 1:81 | 0.880 | 0.844 | 0.804 | 0.802 | 0.829 | 0.807 | 0.794 | 0.804 | 1.644 | 1.691 |
| 1:243 | 0.400 | 0.396 | 0.363 | 0.369 | 0.386 | 0.381 | 0.373 | 0.379 | 1.006 | 1.059 |
| 1:729 | 0.183 | 0.184 | 0.176 | 0.174 | 0.175 | 0.174 | 0.170 | 0.178 | 0.503 | 0.531 |
| 0 | 0.053 | 0.056 | 0.055 | 0.056 | 0.056 | 0.056 | 0.054 | 0.059 | 0.057 | 0.059 |
| Secondary antibody | HRP-labeled goat anti-human IgG Fc (1:5000) | | | | | | | | | |
| EC50 (nM) | 0.101 | | 0.119 | | 0.110 | | 0.123 | | 0.031 | |

2. Binding Activity of NTPDV1, NTPDV2, NTPDV3 and NTPDV4 to Antigen Human NT5E-Biotin Determined ELISA A microplate was coated with streptavidin SA (2 μg/mL) and then incubated at 4 °C overnight. After incubation, the microplate coated with streptavidin was washed once with PBST, and blocked with a PBS solution containing 1% BSA as a microplate blocking solution at 37 °C for 2 h. After blocking, the microplate was washed 3 times with PBST. Then, 0.5 μg/mL antigen human NT5E-Biotin was added and incubated at 37 °C for 30 min. Then, the plate was washed 3 times with PBST. The antibodies serially diluted with PBST solution (the dilution gradients for the antibody are shown in Table 11) were added to wells of the microplate. The microplate containing the test antibodies was incubated at 37 °C for 30 min, and then washed 3 times with PBST. After washing, HRP-labeled goat anti-human IgG Fc (Jackson, Cat. No. 109-035-098) secondary antibody working solution diluted in a ratio of 1:5000 was added, and the microplate was incubated at 37 °C for 30 min. After incubation, the plate was washed 4 times with PBST, TMB (Neogen, 308177) was added in the dark for chromogenesis for 7 min, and then a stop solution was added to terminate chromogenic reaction. The microplate was put into a microplate reader immediately, and the OD value of each well in the microplate was read at 450 nm. The data were analyzed and processed by SoftMax Pro 6.2.1.

The results are shown in Table 11. It can be seen that NTPDV1, NTPDV2, NTPDV3, NTPDV4 and 19F3H2L3 (hG1M) can effectively bind to the antigen human NT5E-biotin in a dose-dependent manner (the absorbance intensity of each dose is shown in Table 11). By quantitative analysis of the absorbance of the bound antibodies, the binding efficiency $EC_{50}$ values of the antibodies NTPDV1, NTPDV2, NTPDV3, NTPDV4 and 19F3H2L3(hG1M) (as a control antibody) obtained by curve fitting were 0.079 nM, 0.082 nM, 0.084 nM, 0.077 nM and 0.029 nM, respectively.

The above experimental results showed that in the same experimental condition, the binding activities of bispecific antibodies NTPDV1, NTPDV2, NTPDV3 and NTPDV4 to human NT5E-biotin are comparable to that of the reference drug 19F3H2L3(hG1M) for the same target, suggesting that NTPDV1, NTPDV2, NTPDV3 and NTPDV4 have the activity of effectively binding to human NT5E-biotin.

TABLE 11

Binding of NTPDV1, NTPDV2, NTPDV3, NTPDV4 and 19F3H2L3(hG1M) to human NT5E-biotin determined by ELISA

| Antibody dilution concentration | Antigen coating SA: 2 μg/mL Human NT5E-biotin (0.5 μg/mL) | | | | | | | | | |
|---|---|---|---|---|---|---|---|---|---|---|
| (nM) | NTPDV1 | | NTPDV2 | | NTPDV3 | | NTPDV4 | | 19F3H2L3 (hG1M) | |
| 5 | 2.286 | 2.300 | 2.322 | 2.333 | 2.364 | 2.286 | 2.298 | 2.291 | 2.371 | 2.383 |
| 1:3 | 2.412 | 2.347 | 2.450 | 2.409 | 2.381 | 2.412 | 2.427 | 2.421 | 2.420 | 2.506 |
| 1:9 | 2.227 | 2.177 | 2.226 | 2.238 | 2.230 | 2.081 | 2.186 | 2.222 | 2.322 | 2.345 |
| 1:27 | 1.795 | 1.729 | 1.744 | 1.746 | 1.768 | 1.698 | 1.734 | 1.759 | 2.125 | 2.162 |
| 1:81 | 1.071 | 1.070 | 1.103 | 1.058 | 1.068 | 1.025 | 1.095 | 1.125 | 1.649 | 1.752 |
| 1:243 | 0.528 | 0.527 | 0.540 | 0.551 | 0.552 | 0.534 | 0.552 | 0.611 | 1.067 | 1.143 |
| 1:729 | 0.273 | 0.274 | 0.271 | 0.275 | 0.279 | 0.267 | 0.275 | 0.309 | 0.542 | 0.601 |
| 0 | 0.092 | 0.092 | 0.090 | 0.087 | 0.092 | 0.090 | 0.092 | 0.095 | 0.112 | 0.206 |
| Secondary antibody | HRP-labeled goat anti-human IgG Fc (1:5000) | | | | | | | | | |
| EC50 (nM) | 0.079 | | 0.082 | | 0.084 | | 0.077 | | 0.029 | |

Example 17: Activity of Anti-CD73/Anti-PD-1 Bispecific Antibodies Completing with Human PD-L1-mFc for Binding to Human PD-1-mFc-Biotin Determined by Competitive ELISA A microplate was coated with human PD-L1-mFc (PD-L1 Genbank ID: NP_054862.1, mFc SEQ ID NO: 89) at 2 μg/mL and incubated at 4 °C overnight. After incubation, the microplate was blocked with a PBS solution containing 1% BSA at 37 °C for 2 h. After blocking, the plate was washed once and dried. The antibody was serially diluted to 7 concentrations in a gradient ratio of 1:3 on a dilution plate with 10 μg/mL as the starting concentration, and a blank control was set.

Then an equal volume of 0.3 μg/mL human PD-1-mFc-biotin solution was added, and the system was mixed well and incubated at room temperature for 10 min. Then the mixture after reaction was added to the coated microplate, and the microplate was incubated for at 37 °C for 30 min. After incubation, the plate was washed three times with PBST and dried. SA-HRP (KPL, 14-30-00) working solution was added, and the plate was incubated at 37 °C for 30 min. After incubation, the plate was washed four times and patted dry. Then TMB (Neogen, 308177) was added in the dark for chromogenesis for 5 min, and a stop solution was added to terminate chromogenic reaction. Then the microplate was put into a microplate reader immediately, and the OD value of each well in the microplate was read at 450 nm. The data were analyzed and processed by SoftMax Pro 6.2.1.

The OD values for all the dosages are shown in Table 12. By quantitative analysis of the absorbance intensity of the bound antibody, the curve simulation was performed to give the binding efficiency $EC_{50}$ of the antibody (Table 12).

The results showed that NTPDV1, NTPDV2, NTPDV3, NTPDV4 and 14C12H1L1(hG1TM) (as a control) can effectively block the binding of the antigen human PD-1-mFc-biotin to its receptor human PD-L1-mFc in a dose-dependent manner. The $EC_{50}$ values of NTPDV1, NTPDV2, NTPDV3, NTPDV4 and 14C12H1L1(hG1TM) for blocking the binding of human PD-1-mFc-biotin to its ligand human PD-L1-mFc were 2.249 nM, 2.253 nM, 2.332 nM, 2.398 nM, 2.216 nM and 2.231 nM, respectively.

TABLE 12

Activity of NTPDV1, NTPDV2, NTPDV3, NTPDV4 and 14C12H1L1(hG1TM) competing with human PD-L1-mFc for binding to human PD-1-mFc-biotin

| Antibody | Antigen coating: human PD-L1-mFc 2 μg/mL | | | | | | | | | |
|---|---|---|---|---|---|---|---|---|---|---|
| dilution (nM) | NTPDV1 | | NTPDV2 | | NTPDV3 | | NTPDV4 | | 14C12H1L1 (hG1TM) | |
| 50 | 0.086 | 0.082 | 0.084 | 0.081 | 0.077 | 0.087 | 0.076 | 0.076 | 0.081 | 0.077 |
| 1:3 | 0.083 | 0.083 | 0.083 | 0.084 | 0.083 | 0.085 | 0.084 | 0.090 | 0.087 | 0.082 |
| 1:9 | 0.202 | 0.195 | 0.204 | 0.204 | 0.195 | 0.183 | 0.189 | 0.214 | 0.120 | 0.119 |
| 1:27 | 0.604 | 0.616 | 0.564 | 0.593 | 0.628 | 0.598 | 0.521 | 0.584 | 0.576 | 0.634 |
| 1:81 | 0.837 | 0.821 | 0.790 | 0.809 | 0.816 | 0.884 | 0.782 | 0.768 | 0.797 | 0.871 |
| 1:243 | 0.946 | 0.938 | 0.822 | 0.929 | 0.895 | 0.851 | 0.926 | 0.891 | 0.880 | 0.934 |
| 1:729 | 0.956 | 0.938 | 0.884 | 0.878 | 0.928 | 0.923 | 0.854 | 0.902 | 0.901 | 0.964 |
| 0 | 1.012 | 0.952 | 0.891 | 0.966 | 0.918 | 0.983 | 0.919 | 0.966 | 0.904 | 0.954 |
| | Human PD-1-mFc-biotin: 0.3 μg/mL<br>Secondary antibody SA-HRP (1:4000) | | | | | | | | | |
| EC50 (nM) | 2.253 | | 2.332 | | 2.398 | | 2.216 | | 2.231 | |

Example 18: Kinetic Parameters for Binding of Anti-CD73/Anti-PD-1 Bispecific Antibodies to Antigen Human PD-1-mFc Determined by Fortebio System The sample dilution buffer was PBS (0.02% Tween-20, 0.1% BSA, pH 7.4). PD1-mFc was immobilized on the AMC sensor at a concentration of 5 g/mL with an immobilization height of about 0.1 nM (time 60 s). The sensor was equilibrated in a buffer for 60 s, and the binding of the immobilized PD1-mFc on the sensor to the antibodies at concentrations of 0.62-50 nM (three-fold dilution) was determined for 120 s. The protein was dissociated in the buffer for 300 s. The detection temperature was 30 °C, the detection frequency was 0.3 Hz, and the sample plate shaking rate was 1000 rpm. The data were analyzed by 1:1 model fitting to obtain affinity constants.

The determination results of the affinity constants of humanized antibodies NTPDV1, NTPDV2, NTPDV3, NTPDV4 and nivolumab (as control antibody) for human PD-1-mFc are shown in Table 13, and the detection results are shown in FIGS. 19, 20, 21, 22 and 18. The affinity constants of the humanized antibodies NTPDV1, NTPDV2, NTPDV3, NTPDV4 and nivolumab for human PD-1-mFc were 1.40E-10 M, 7.39E-11 M, 1.25E-10 M, 1.13E-11 M and 2.26E-10 M, respectively. The above experimental results showed that the binding ability of NTPDV1, NTPDV3 and nivolumab is comparable, and the binding ability of NTPDV2 and NTPDV4 is superior to that of nivolumab, suggesting that the humanized antibodies NTPDV1, NTPDV2, NTPDV3 and NTPDV4 have stronger binding ability to human PD-1-mFc.

TABLE 13

Affinity constants of 14C12H1L1(hG1TM), NTPDV1, NTPDV2, NTPDV3, NTPDV4 and nivolumab for PD-1-mFc

| Test antibodies | KD (M) | Kon (1/Ms) | S E (kon) | Kdis (1/s) | S E (kdis) | Rmax (nm) |
|---|---|---|---|---|---|---|
| 14C12H1L1(hG1TM) | 4.45E−11 | 1.18E+06 | 5.74E+04 | 5.23E−05 | 4.47E−05 | 0.38-0.57 |
| Nivolumab | 2.26E−10 | 1.52E+06 | 7.79E+04 | 3.43E−04 | 4.66E−05 | 0.25-0.37 |
| NTPDV1 | 1.40E−10 | 6.09E+05 | 2.01E+04 | 8.55E−05 | 3.18E−05 | 0.38-0.52 |
| NTPDV2 | 7.39E−11 | 6.83E+05 | 2.47E+04 | 5.05E−05 | 3.50E−05 | 0.40-0.55 |
| NTPDV3 | 1.25E−10 | 6.68E+05 | 2.52E+04 | 8.35E−05 | 3.44E−05 | 0.38-0.50 |
| NTPDV4 | 1.13E−11 | 5.35E+05 | 1.59E+04 | 6.03E−06 | 2.77E−05 | 0.35-0.47 |

$K_D$ is the affinity constant;

$K_D$ = kdis/kon

Example 19: Kinetic Parameters for Binding of Anti-CD73/Anti-PD-1 Bispecific Antibodies to Antigen Human NT5E (1-552)-his Determined by Fortebio System The sample dilution buffer was PBS (0.02% Tween-20, 0.1% BSA, pH 7.4). HNT5E(1-552)-his was immobilized on the HIS1K sensor at a concentration of 5 μg/mL with an immobilization height of about 0.4 nM (time 50 s). The sensor was equilibrated in a buffer for 60 s, and the binding of the immobilized HNT5E (1-552)-his on the sensor to the antibodies at concentrations of 0.31-25 nM (three-fold dilution) was determined for 100 s. The protein was dissociated in the buffer for 180 s. The detection temperature was 30 °C, the detection frequency was 0.3 Hz, and the sample plate shaking rate was 1000 rpm. The data were analyzed by 1:1 model fitting to obtain affinity constants.

The determination results of the affinity constants of the humanized antibodies 19F3H2L3(hG1M) (as a control antibody), NTPDV1, NTPDV2, NTPDV3 and NTPDV4 for human NT5E(1-552)-his are shown in Table 14, and the detection results are shown in FIGS. 24-27. The affinity constants of the humanized antibodies NTPDV1, NTPDV2, NTPDV3 and NTPDV4 for human NT5E(1-552)-his were 3.29E-11 M, 2.88E-11 M, 7.92E-11 M and 5.77E-11 M, respectively.

The above experimental results showed that the binding ability of 19F3H2L3(hG1M), NTPDV1, NTPDV2, NTPDV3 and NTPDV4 is comparable, suggesting that the humanized antibodies NTPDV1, NTPDV2, NTPDV3 and NTPDV4 has stronger binding ability to human NT5E(1-552)-his.

TABLE 14

| Affinity constants of 19F3H2L3(hG1M), NTPDV1, NTPDV2, NTPDV3 and NTPDV4 for human NTSE(1-552)-his | | | | | | |
|---|---|---|---|---|---|---|
| Test antibodies | KD (M) | kon (1/Ms) | S E (kon) | kdis (1/s) | S E (kdis) | Rmax (nm) |
| 19F3H2L3 (hG1M) | 4.05E−11 | 1.16E+06 | 6.50E+04 | 4.68E−05 | 8.96E−05 | 0.36-0.77 |
| NTPDV1 | 3.29E−11 | 1.16E+06 | 3.27E+04 | 3.80E−05 | 4.63E−05 | 0.49-0.61 |
| NTPDV2 | 2.88E−11 | 1.27E+06 | 3.84E+04 | 3.66E−05 | 4.88E−05 | 0.63-0.71 |
| NTPDV3 | 7.92E−11 | 1.28E+06 | 4.08E+04 | 1.02E−04 | 5.29E−05 | 0.55-0.65 |
| NTPDV4 | 5.77E−11 | 1.23E+06 | 3.82E+04 | 7.09E−05 | 4.95E−05 | 0.52-0.63 |

$K_D$ is the affinity constant;
$K_D$ = kdis/kon

Example 20: Detection of Inhibition of Anti-CD73/Anti-PD-1 Bispecific Antibody on Enzyme Activity of CD73 on U87-MG Cell Membrane Surface U87-MG cells in logarithmic phase in good condition were taken, resuspended in a serum-free RPMI-1640 culture solution, and then counted. The U87-MG cells were seeded into a 96-well plate at $2.5\times10^4$ cells/60 μL/well. The antibody was diluted according to the study design with the serum-free RPMI-1640 culture solution. The antibody was added to the 96-well plate at 60 μL/well, and the plate was incubated at 37 °C for 1 h. After 1 h, 60 μL of 600 μM RPMI-1640-diluted AMP was added to each well. After 3 h, 100 μL of cell culture supernatant was taken and transferred to a new 96-well plate, 40 μL of CTG (CellTiterGlo) chromogenic solution was added to each well, and the plate was placed in the dark at room temperature for 5 min. After 5 min, 10 μL of 300 μM ATP was added to each well for chromogenesis. Relative fluorescence intensity RLU were read by a multi-label microplate tester (PerkinElmer 2140-0020).

Figure 28:
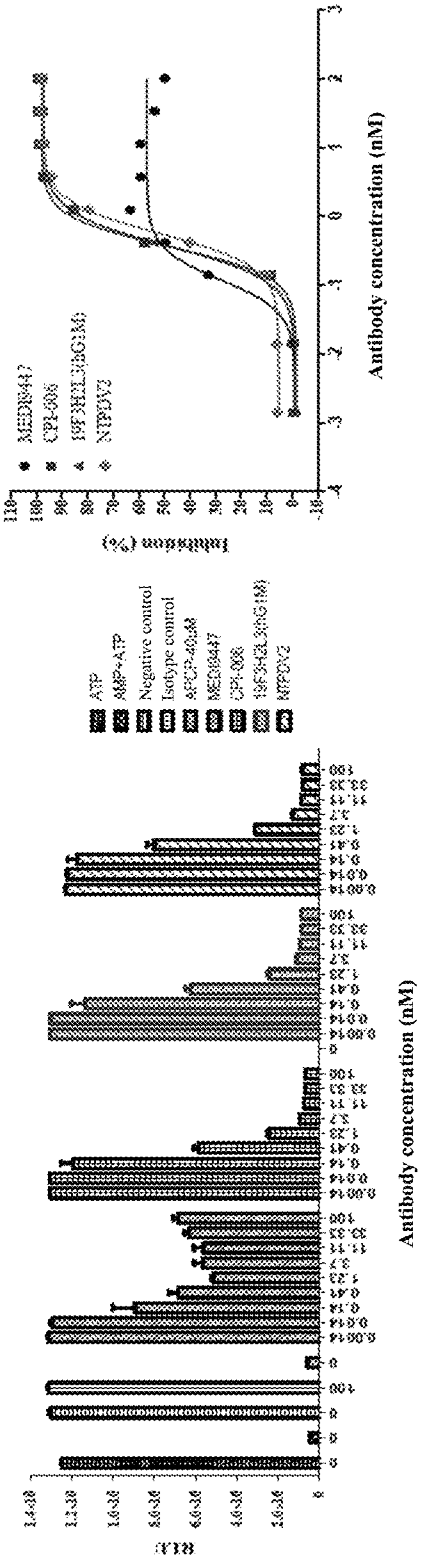
FIG. 28. Inhibition of the enzyme activity of CD73 on U87-MG cell membrane surface by anti-CD73/anti-PD-1 bispecific antibodies.

The experimental results are as shown in Table 15 and FIG. 28, the AMP amount of NTPDV2 is comparable to that of the positive control MEDI9447.

The above experimental results showed that the added AMP can be converted into adenosine A without antibodies by the enzyme activity of CD73 on the U87-MG cell surface, and that after the addition of the antibody, the enzyme-catalyzed function was decreased due to the binding of antibody NTPDV2 to CD73, so that the AMP was not converted into adenosine A. It was suggested that the antibodies effectively inhibit the enzyme activity reaction thereof in a non-substrate competition mode and reduce the production of adenosine.

TABLE 15

| Detection of inhibition of anti-CD73/anti-PD-1 bispecific antibody on enzyme activity of CD73 on U87-MG cell membrane surface | | | |
|---|---|---|---|
| Name of antibody | MEDI9447 | 19E3H2L3(hG1M) | NTPDV2 |
| IC50 (nM) | 0.1189 | 0.3647 | 0.5551 |

Example 21: Biological Activity of Anti-CD73/Anti-PD-1 Bispecific Antibodies for Promoting IFN-γ and IL-2 Secretion Determined by Mixed Lymphocyte Reaction (MLR)

1. Biological Activity of Anti-CD73/Anti-PD-1 Bispecific Antibodies for Promoting IFN-γ Secretion in Raji-PDL1 Mixed Lymphocyte Reaction System Raji-PDL1 cells were normally subcultured. PBMCs were thawed, incubated with 10 mL of a 1640 complete medium, and stimulated with 0.5 μg/mL SEB (Dianotech, Cat. No. S010201) for two days. Raji-PDL1 cells were treated with 25 μg/mL MMC (mitomycin C, Stressmarq, catalog: SIH-246, Cat. No. SM286474) and placed in a 37 °C incubator for 1 h. PBMCs (peripheral blood mononuclear cells) stimulated with SEB for 2 days and Raji-PDL1 cells treated with MMC for 1 h were collected, washed twice with PBS, resuspended in the complete medium, and counted. The cells were separately added to a U-shaped 96-well plate at $1\times10^5$ cells/well. The antibodies were added according to the study design and cultured in an incubator for 3 days. After 3 days, the cell culture supernatant was collected and determined for IFN-γ by ELISA.

Figure 29:
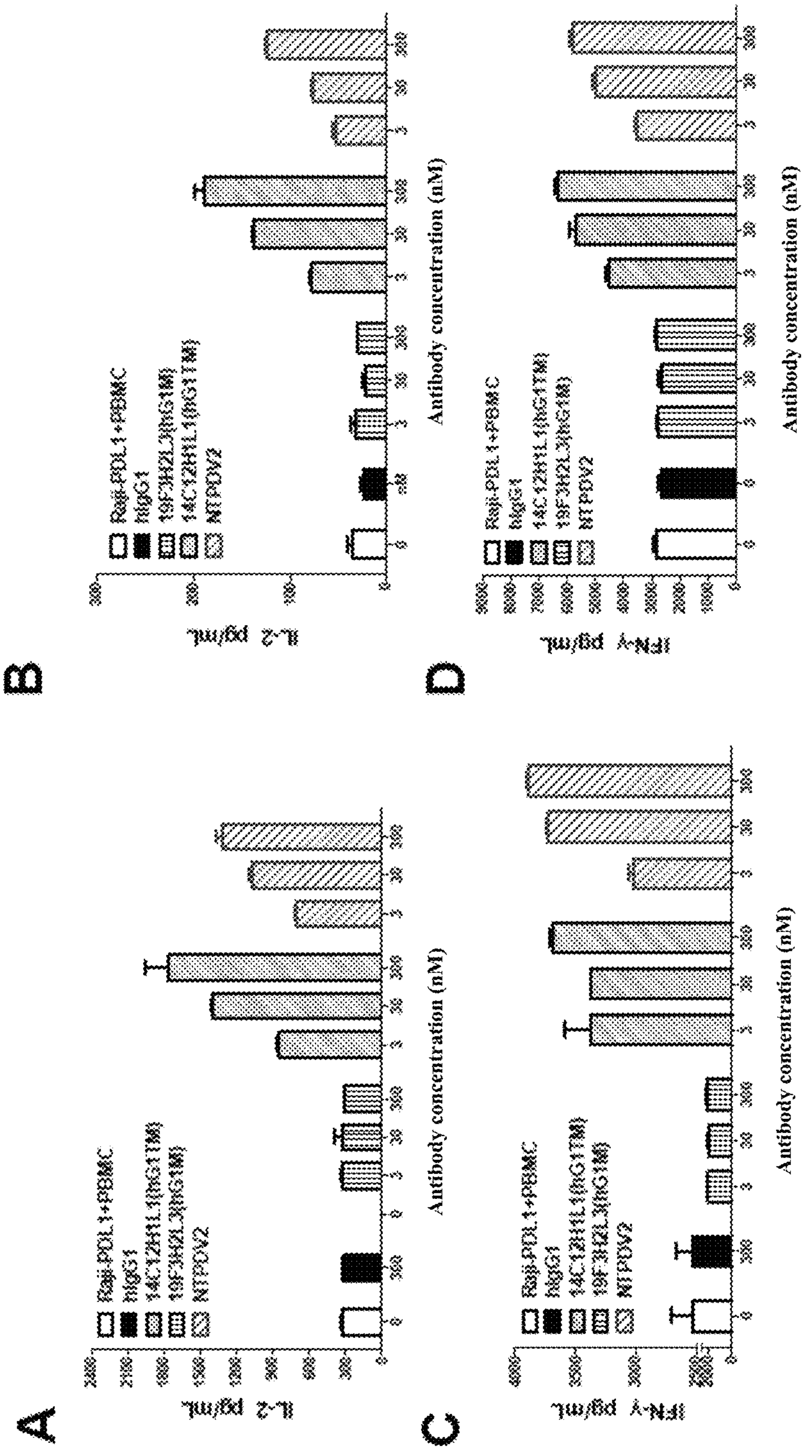
FIG. 29. Biological activity of anti-CD73/anti-PD-1 bispecific antibodies for promoting IFN-γ and IL-2 secretion determined by mixed lymphocyte reaction (MLR).

As shown in FIG. 29, the mixed culture of human PBMCs and Raji-PDL1 cells significantly promoted the secretion of IFN-γ from PBMCs, and the addition of antibodies to the mixed culture system significantly induced secretion of IFN-γ in PBMCs. In terms of the level of promoting IFN-γ secretion activity, the antibody NTPDV2 has the activity comparable to that of the parent PD-1 single-target antibody 14C12H1L1.

2. Biological Activity of Anti-CD73/Anti-PD-1 Bispecific Antibodies for Promoting IL-2 Secretion in Raji-PDL1 Mixed Lymphocyte Reaction System Raji-PDL1 cells were normally subcultured. PBMCs were thawed, incubated with 10 mL of a 1640 complete medium, and stimulated with SEB (0.5 μg/mL) for two days. Raji-PDL1 cells were treated with 25 μg/mL MMC and placed in a 37 °C incubator for 1 h. PBMCs (peripheral blood mononuclear cells) stimulated with SEB for 2 days and Raji-PDL1 cells treated with MMC for 1 h were collected, washed twice with PBS, resuspended in the complete medium, and counted. The cells were separately added to a U-shaped 96-well plate at $1\times10^5$ cells/well. The antibodies were added according to the study design and cultured for 3 days. The cell culture supernatant was collected and determined for IL-2 by ELISA.

As shown in FIG. 29, the mixed culture of human PBMCs and Raji-PDL1 cells had certain promoting effect on the secretion of IL-2 from PBMCs, and the simultaneous addition of antibodies to the mixed culture system significantly induced IL-2 secretion in PBMCs in a significant dose-dependent manner. In terms of the level of promoting IL-2 secretion activity, the bifunctional antibody NTPDV2 has the activity at low a concentration comparable to that of the parent PD-1 single-target antibody 14C12H1L1, and the activity at a medium-high concentration slightly lower than that of the parent PD-1 single-target antibody 14C12H1L1.

Example 22: Experiment of Inhibition of Tumor Growth In Vivo by Anti-CD73/Anti-PD-1 Bispecific Antibody In order to determine the anti-tumor activity in vivo of the anti-CD73/anti-PD-1 bispecific antibody, firstly, MC38-hPDL1/hCD73 cells (from GemPharmatech Co., Ltd.) were subcutaneously inoculated into female C57BL6-hPD1hPDL1hCD73 triple-transgenic mice aged 5-7 weeks (from GemPharmatech Co., Ltd.). The modeling and specific administration methods are shown in Table 16. After the administration, the length and width of each group of tumors were measured, and the tumor volume was calculated.

TABLE 16

Study design

| Grouping | n | Tumor xenograft | Condition of administration |
|---|---|---|---|
| Isotype control | 8 | MC38-hPDL1/hCD73, 1 million cells/mouse, s.c. | Isotype control antibody hIgG, 10 mg/kg<br>Twice weekly, for three weeks |
| 19F3H2L3 (hG1M) | 8 | | 19F3H2L3(hG1M)m 10 mg/kg<br>Twice weekly, for three weeks |
| NTPDV2 | 8 | | NTPDV2, 13.3 mg/kg<br>Twice weekly, for three weeks |
| NTPDV2 | 8 | | NTPDV2, 1.33 mg/kg<br>Twice weekly, for three weeks |

Figure 30:
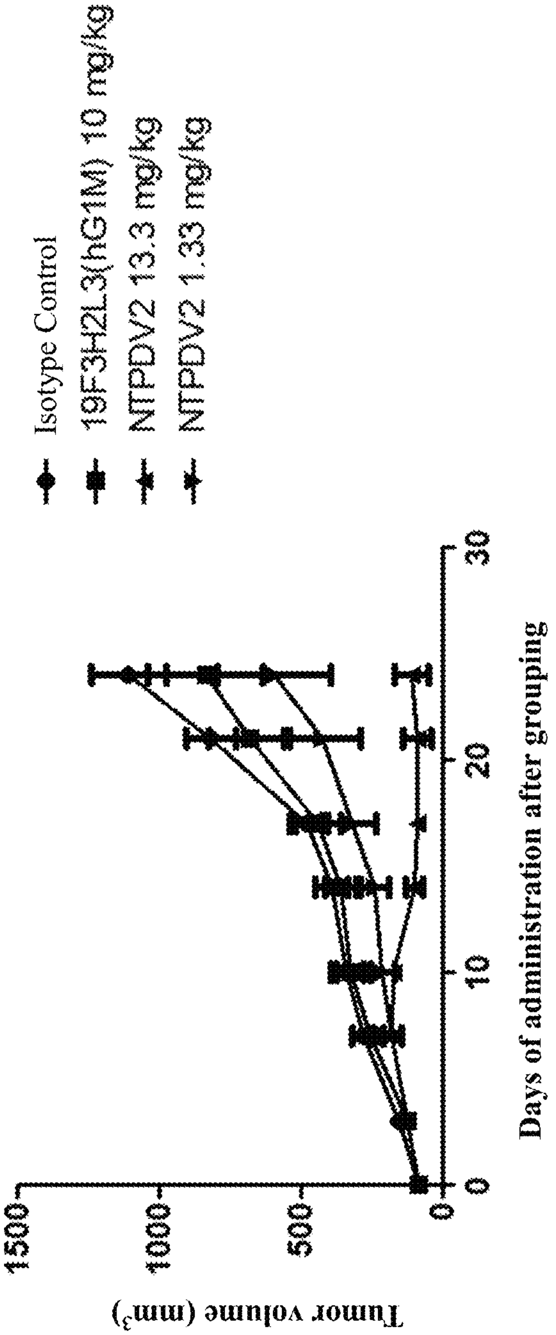
FIG. 30. Effect of isotype control, 19F3H2L3(hG1M) and different doses of NTPDV2 on tumor volume in mice.
Figure 31:
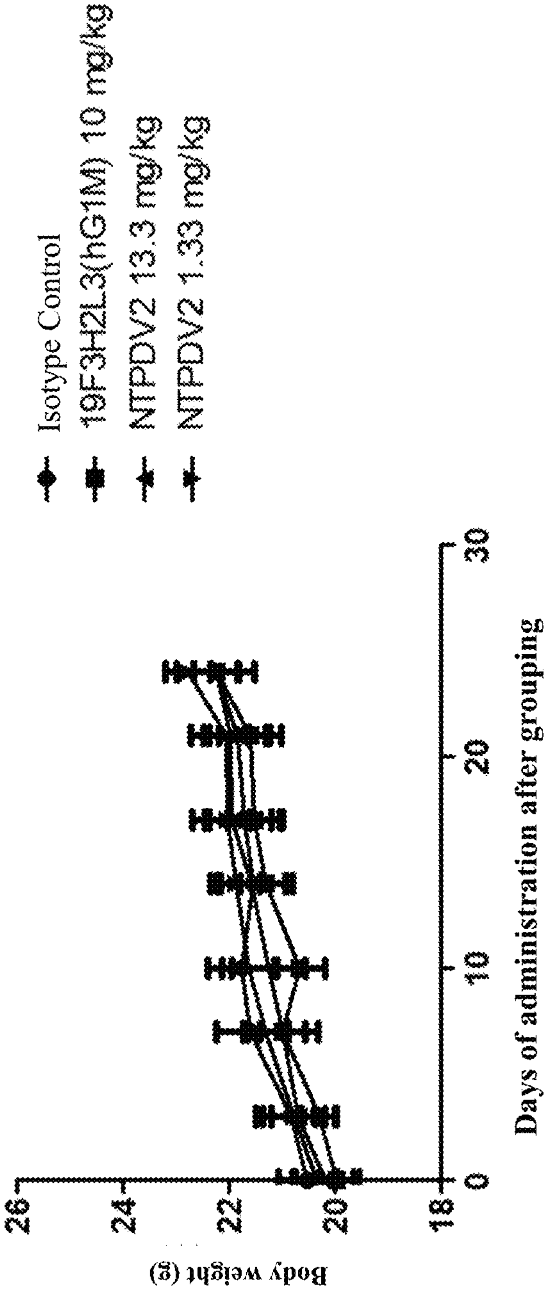
FIG. 31. Effect of isotype control, 19F3H2L3(hG1M) and different doses of NTPDV2 on body weight of mice.
Figure 32:
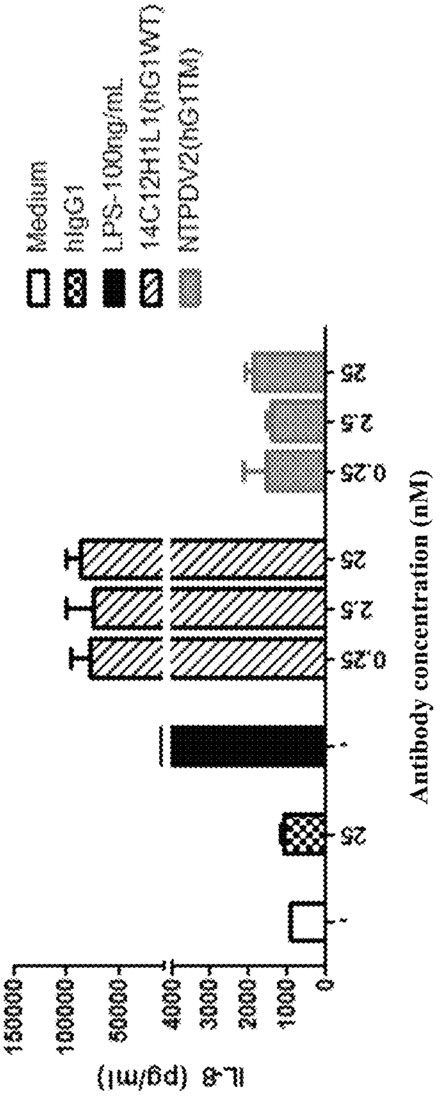
FIG. 32. Effective elimination of PD-1/CD73 bispecific antibody-mediated IL-8 secretion in human macrophages by the amino acid mutations of Fc segments in a co-culture system of CHO-K1-PD1 cells and human macrophages.
Figure 33:
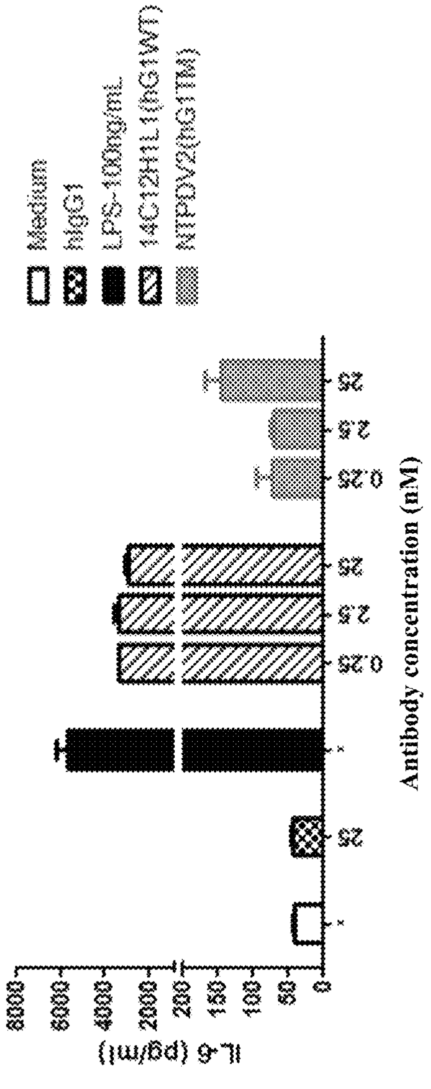
FIG. 33. Effective elimination of PD-1/CD73 bispecific antibody-mediated IL-6 secretion in human macrophages by the amino acid mutations of Fc segments in a co-culture system of CHO-K1-PD1 cells and human macrophages.
Figure 34:
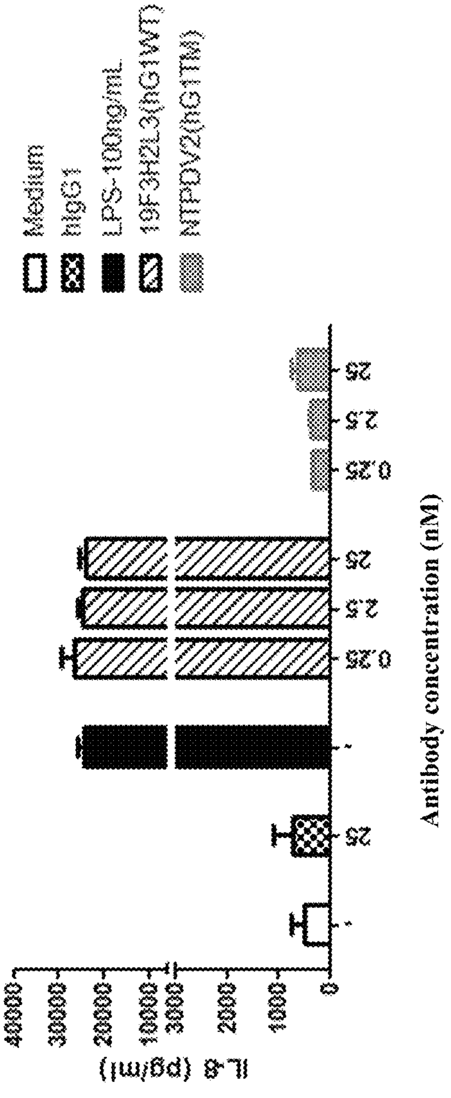
FIG. 34. Effective elimination of PD-1/CD73 bispecific antibody-mediated IL-8 secretion in human macrophages by the amino acid mutations of Fc segments in a co-culture system of U87-MG cells and human macrophages.
Figure 35:
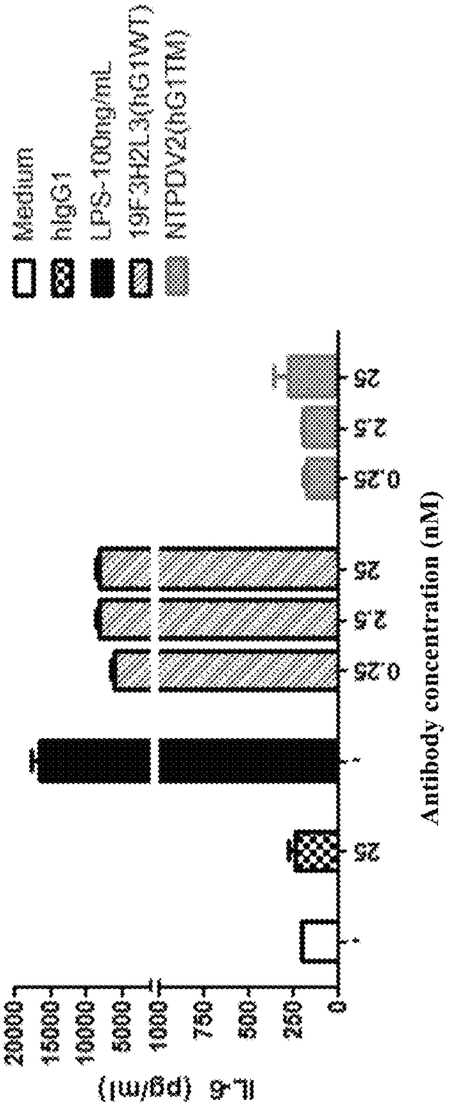
FIG. 35. Effective elimination of PD-1/CD73 bispecific antibody-mediated IL-6 secretion in human macrophages by the amino acid mutations of Fc segments in a co-culture system of U87-MG cells and human macrophages.

The experimental results are as shown in FIG. 30 and FIG. 31. The results showed that compared with an isotype control antibodies hIgG and 19F3H2L3(hG1M), NTPDV2 at different doses can effectively inhibit the growth of mouse tumors, and NTPDV2 at high dose is superior to NTPDV2 at low-dose in inhibiting tumors. In addition, NTPDV2 had no effect on the body weight of the tumor-bearing mouse.

Experimental Example 23: Effective Elimination of Bispecific Immune Checkpoint Inhibitor PD-1/CD73 Bispecific Antibody-Mediated IL-8 and IL-6 Secretions in Human Macrophages by the Amino Acid Mutations of Fc Segments HPMMs were prepared by induction of PBMCs. PBMCs used in this study were isolated and prepared in Zhongshan Akesobio Co. Ltd., with informed consent of the donor.

Ficoll-Paque PLUS lymphocyte isolation solution (GE, Cat. No. 17-1440-03); RPMI 1640 (Gibco, Cat. No. 22400-105); CHO-K1-PD1 cells (constructed by Zhongshan Akesobio Co. Ltd.); U87-MG cells (cells from ATCC, purchased from Beijing Zhongyuan Ltd.); FBS (Fetal Bovine Serum, Excell bio, Cat. No. FSP 500); human IFN-γ protein (Sinobio, Cat. No. 11725-HNAS-100); LPS (lipopolysaccharide) (Sigma, Cat. No. L4391); a 96-well cell culture plate (Corning). Healthy human PBMCs were isolated according to the instructions of insolation solution Ficoll-Paque™ Plus reagent and resuspended in a 1640 medium containing 2% FBS. The plate was incubated in a 5% $CO_2$ cell incubator at 37 °C. After 2 h, the supernatant was removed, and the adherent cells were washed twice with PBS and 1640 complete medium (containing 10% FBS) and 100 ng/ml human M-CSF were added for 7 days of induction. On day 3 and day 5, the medium was exchanged, and M-CSF was added to induce HPMM. On day 7, after induction of HPMM, the cells were collected, adjusted to the concentration of 0.1 million cells/mL with the complete medium, and filled into a 96-well plate. The recombinant human IFN-γ (50 ng/mL) was added, and incubated in an incubator for 24 h. After 24 h, CHO-K1-PD1 cells expressing human PD-1 or U87-MG cells constitutively expressing human CD73 in logarithmic phase were collected. The cells were resuspended and then adjusted to the concentration of 0.3 million cells/mL with the complete medium. The antibody was diluted with the complete medium to working concentrations of 25 nM, 2.5 nM and 0.25 nM. An isotype control antibody and a blank control were designed simultaneously. The supernatant in the 96-well plate was removed, the CHO-K1-PD1 or U87-MG cell suspension and antibodies were added (with a final volume of 200 μL). The system was mixed well and incubated in an incubator for 24 h. The mixture was centrifuged at 500×g for 5 min, the supernatant was collected, and the secretion amounts of IL-8 and IL-6 were determined with a Dakewe kit. LPS was used as a positive control and was adjusted to a concentration of 100 ng/ml with the complete medium in the experiment.

In this example, the co-culture of CHO-K1-PD1 and U87-MG cells as target cells with HPMM induced the activation of HPMM, and after the activated HPMM was linked to the target cells by antibody Fab, the Fc fragment of the antibody interacted with FcγR on HPMM, causing the secretion of cytokine by HPMM.

3. Experimental Results

The results are shown in FIGS. 32-35.

The results showed that compared with the wild-type IgG1 subtype PD-1 antibody or CD73 antibody, the anti-PD-1/CD73 bispecific antibody carrying the Fc fragment mutation is able to effectively eliminate the secretion of IL-6 and/or IL-8 in immune cells.

The preferred embodiments of the present invention have been described above in detail, but the present invention is not limited to the embodiments. Those skilled in the art can make various equivalent modifications or replacements without violating the spirit of the present invention. These equivalent modifications or replacements are included in the scope defined by the claims of the present application.

SEQUENCE LISTING

Nucleotide sequence of 19F3 heavy chain variable region:
(SEQ ID NO: 1, with CDR sequences underlined)
GAGGTGCAGCTGCAGCAGTCCGGACCAGAGCTGGTGAAGCCTGGCGCCTCCATGCGGATGTCTT

GTAAGGCCTCTGGCTACAGCTTCACCGGCTATACAATGAACTGGGTGAAGCAGTCTCACGGCA

AGAATCTGGAGTGGATCGGCCTGATCAACCCTTACAATGCCGGCACCAGCTATAACCAGAAGT

TTAAGGGCAAGGCCACCCTGACAGTGGACAAGAGCTCCTCTACCGCCTACATGGAGCTGCTGTCC

CTGACATCTGAGGATAGCGCCGTGTACTATTGCGCCCGGTCCGAGTACAGATATGGCGGCGAC

TACTTTGATTATTGGGGCCAGGGCACCACACTGACAGTGAGCTCC

Amino acid sequence of 19F3 heavy chain variable region:
(SEQ ID NO: 2, with CDR sequences underlined)
EVQLQQSGPELVKPGASMRMSCKASGYSFTGYTMNWVKQSHGKNLEWIGLINPYNAGTSYNQKFK

GKATLTVDKSSSTAYMELLSLTSEDSAVYYCARSEYRYGGDYFDYWGQGTTLTVSS

-continued

HCDR1 of 19F3:
(SEQ ID NO: 3)
GYSFTGYT

HCDR2 of 19F3:
(SEQ ID NO: 4)
INPYNAGT

HCDR3 of 19F3:
(SEQ ID NO: 5)
ARSEYRYGGDYFDY

Nucleotide sequence of 19F3 light chain variable region:
(SEQ ID NO: 6, with CDR sequences underlined)
GACATCGTGATGACCCAGTCTCCAAGCTCCCTGGCAATGAGCGTGGGACAGAAGGTGACAATGT

CTTGTAAGTCTAGCCAGAGCCTGCTGAACTCCTCTAATCAGAAGAACTACCTGGCCTGGTATC

AGCAGAAGCCAGGCCAGTCTCCCAAGCTGCTGGTGTACTTTGCCAGCACCAGGGAGTCCGGAGT

GCCTGACAGATTCATCGGCTCCGGCTCTGGCACAGACTTCACCCTGACAATCAGCTCCGTGCAGG

CAGAGGACCTGGCAGATTATTTCTGCCAGCAGCACTACGACACCCCTTATACATTTGGCGGCG

GCACCAAGCTGGAGATCAAG

Amino acid sequence of 19F3 light chain variable region:
(SEQ ID NO: 7, with CDR sequences underlined)
DIVMTQSPSSLAMSVGQKVTMSCKSSQSLLNSSNQKNYLAWYQQKPGQSPKLLVYFASTRESGVPD

RFIGSGSGTDFTLTISSVQAEDLADYFCQQHYDTPYTFGGGTKLEIK

LCDR1 amino acid sequence of 19F3:
(SEQ ID NO: 8)
QSLLNSSNQKNY

LCDR2 amino acid sequence of 19F3:
(SEQ ID NO: 9)
FAS

LCDR3 amino acid sequence of 19F3:
(SEQ ID NO: 10)
QQHYDTPYT

Amino add sequences of 19F3 heavy chain framework regions:
FR-H1:
(SEQ ID NO: 11)
EVQLQQSGPELVKPGASMRMSCKAS

FR-H2:
(SEQ ID NO: 12)
MNWVKQSHGKNLEWIGL

FR-H3:
(SEQ ID NO: 13)
SYNQKFKGKATLTVDKSSSTAYMELLSLTSEDSAVYYC

FR-H4:
(SEQ ID NO: 14)
WGQGTTLTVSS

Amino acid sequences of 19F3 light chain framework regions:
FR-L1:
(SEQ ID NO: 15)
DIVMTQSPSSLAMSVGQKVTMSCKSS

FR-L2:
(SEQ ID NO: 16)
LAWYQQKPGQSPKLLVY

FR-L3:
(SEQ ID NO: 17)
TRESGVPDRFIGSGSGTDFTLTISSVQAEDLADYFC

FR-L4:
(SEQ ID NO: 18)
FGGGTKLEIK

-continued

Nucleotide sequence of 19F3H2:
(SEQ ID NO: 19, with CDR sequences underlined)
CAGGTGCAGCTGGTGCAGTCTGGAGCAGAGGTGGTGAAGCCAGGAGCCTCTGTGAAGGTGAGCT

GTAAGGCCAGCGGCTACTCCTTCACCGGCTATACAATGAACTGGGTGAGGCAGGCACCAGGAC

AGAATCTGGAGTGGATCGGCCTGATCAACCCTTACAATGCCGGCACCTCTTATAACCAGAAGTT

TCAGGGCAAGGTGACCCTGACAGTGGACAAGTCCACCTCTACAGCCTACATGGAGCTGAGCTCCC

TGCGGAGCGAGGATACAGCCGTGTACTATTGCGCCCGGTCCGAGTACAGATATGGCGGCGAC

TACTTTGATTATTGGGGCCAGGGCACCACACTGACCGTGTCTAGC

Amino acid sequence of 19F3H2:
(SEQ ID NO: 20, with CDR sequences underlined)
QVQLVQSGAEVVKPGASVKVSCKASGYSFTGYTMNWVRQAPGQNLEWIGLINPYNAGTSYNQKFQ

GKVTLTVDKSTSTAYMELSSLRSEDTAVYYCARSEYRYGGDYFDYWGQGTTLTVSS

Nucleotide sequence of 19F3L2:
(SEQ ID NO: 21, with CDR sequences underlined)
GACATCGTGATGACCCAGTCCCCAAGCTCCCTGGCCGTGTCTGTGGGAGAGCGGGTGACAATCTC

CTGTAAGTCTAGCCAGTCTCTGCTGAACTCCTCTAATCAGAAGAACTACCTGGCCTGGTATCA

GCAGAAGCCCGGCCAGGCCCCTAAGCTGCTGATCTACTTCGCCTCTACCAGGGAGAGCGGAGTG

CCAGACAGATTCTCTGGCAGCGGCTCCGGCACAGACTTCACCCTGACAATCAGCTCCGTGCAGGC

AGAGGACGTGGCAGATTACTATTGCCAGCAGCACTACGATACCCCCTATACATTTGGCGGCGG

CACCAAGCTGGAGATCAAG

Amino acid sequence of 19F3L2:
(SEQ ID NO: 22, with CDR sequences underlined)
DIVMTQSPSSLAVSVGERVTISCKSSQSLLNSSNQKNYLAWYQQKPGQAPKLLIYFASTRESGVPDRF

SGSGSGTDFTLTISSVQAEDVADYYCQQHYDTPYTFGGGTKLEIK

Nucleotide sequence of 19F3L3:
(SEQ ID NO: 23, with CDR sequences underlined)
GACATCGTGATGACCCAGTCCCCAAGCTCCCTGGCCGTGTCTGTGGGAGAGCGGGTGACAATCTC

CTGTAAGTCTAGCCAGTCTCTGCTGAACTCCTCTAATCAGAAGAACTACCTGGCCTGGTATCA

GCAGAAGCCCGGCCAGGCCCCTAAGCTGCTGATCTACTTCGCCTCTACCAGGGAGAGCGGAGTG

CCAGACAGATTCTCTGGCAGCGGCTCCGGCACAGACTTCACCCTGACAATCAGCTCCCTGCAGGC

AGAGGACGTGGCCGTGTACTATTGCCAGCAGCACTACGATACCCCCTATACATTTGGCGGCGG

CACCAAGCTGGAGATCAAG

Amino acid sequence of 19F3L3:
(SEQ ID NO: 24, with CDR sequences underlined)
DIVMTQSPSSLAVSVGERVTISCKSSQSLLNSSNQKNYLAWYQQKPGQAPKLLIYFASTRESGVPDRF

SGSGSGTDFTLTISSLQAEDVAVYYCQQHYDTPYTFGGGTKLEIK

Nucleotide sequence of 19F3H2L3(G1M) heavy chain
(SEQ ID NO: 25, with non-variable region sequences
underlined)
CAGGTGCAGCTGGTGCAGTCTGGAGCAGAGGTGGTGAAGCCAGGAGCCTCTGTGAAGGTGAGCT

GTAAGGCCAGCGGCTACTCCTTCACCGGCTATACAATGAACTGGGTGAGGCAGGCACCAGGACA

GAATCTGGAGTGGATCGGCCTGATCAACCCTTACAATGCCGGCACCTCTTATAACCAGAAGTTTC

AGGGCAAGGTGACCCTGACAGTGGACAAGTCCACCTCTACAGCCTACATGGAGCTGAGCTCCCT

GCGGAGCGAGGATACAGCCGTGTACTATTGCGCCCGGTCCGAGTACAGATATGGCGGCGACTAC

TTTGATTATTGGGGCCAGGGCACCACACTGACCGTGTCTAGCGCCTCCACAAAG ggG ccC agc gtg ttt cct ctc gcc ccc tcc tcc aaa a gcaccagcggaggaaccgctgctctcggatgtctggtgaaggactacttccctgaacccgtcaccgtgagctgg aatagcggcgctctgacaagcggagtccatacattccctgctgtgctgcaaagcagcggactctattccctgtc -continued cagcgtcgtcacagtgcccagcagcagcctgggcacccagacctacatctgtaacgtcaaccacaagccctcca acaccaaggtggacaagaaagtggagcccaaatcctgcgacaagacacacacctgtccccctgtcctgctccc gaaGCTGCTggaggccctagcgtcttcctctttcctcccaaacccaaggacaccctcatgatcagcagaaccc ctgaagtcacctgtgtcgtcgtggatgtcagccatgaggaccccgaggtgaaattcaactggtatgtcgatggc gtcgaggtgcacaacgccaaaaccaagcccagggaggaacagtacaactccacctacagggtggtgtccgtgct gacagtcctccaccaggactggctgaacggcaaggagtacaagtgcaaggtgtccaacaaggctctccctgccc ccattgagaagaccatcagcaaggccaaaggccaacccagggagccccaggtctatacactgcctccctccagg gacgaactcaccaagaaccaggtgtccctgacctgcctggtcaagggcttttatcccagcgacatcgccgtcga gtgggagtccaacggacagcccgagaataactacaagaccacccctcctgtcctcgactccgacggctccttct tcctgtacagcaagctgaccgtggacaaaagcaggtggcagcagggaaacgtgttctcctgcagcgtgatgcac gaagccctccacaaccactacacccagaaaagcctgtccctgagccccggcaaatga Amino acid sequence of 19F3H2L3(G1M) heavy chain
(SEQ ID NO: 26, with non-variable region sequences
underlined)
QVQLVQSGAEVVKPGASVKVSCKASGYSFTGYTMNWVRQAPGQNLEWIGLINPYNAGTSYNQKFQGKVTLTVDK

STSTAYMELSSLRSEDTAVYYCARSEYRYGGDYFDYWGQGTTLTVSSASTKGPSVFPLAPSSKSTSGGTAALGC

LVKDYFPEPVTVSWNSGALTSGVHTFPAVLQSSGLYSLSSVVTVPSSSLGTQTYICNVNHKPSNTKVDKKVEPK

SCDKTHTCPPCPAPEAAGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSRWQQGNVFSCSVMHEALHNHYTQKS

LSLSPGK

Nucleotide sequence of 19F3H2L3(G1M) light chain.
(SEQ ID NO: 27, with non-variable region sequences
underlined)
GACATCGTGATGACCCAGTCCCCAAGCTCCCTGGCCGTGTCTGTGGGAGAGCGGGTGACAATCTC

CTGTAAGTCTAGCCAGTCTCTGCTGAACTCCTCTAATCAGAAGAACTACCTGGCCTGGTATCAGC

AGAAGCCCGGCCAGGCCCCTAAGCTGCTGATCTACTTCGCCTCTACCAGGGAGAGCGGAGTGCC

AGACAGATTCTCTGGCAGCGGCTCCGGCACAGACTTCACCCTGACAATCAGCTCCCTGCAGGCAG

AGGACGTGGCCGTGTACTATTGCCAGCAGCACTACGATACCCCCTATACATTTGGCGGCGGCACC

AAGCTGGAGATCAAGCGTACGGTGGCAGCCCCATCTGTCTTCATTTTTCCCCCTAGTGACGAGCAGCTGAA

ATCCGGAACAGCCTCTGTGGTCTGTCTGCTGAACAATTTCTACCCTCGCGAAGCCAAGGTGCAGTGGAAAGTCG

ATAACGCTCTGCAGAGTGGCAATTCACAGGAGAGCGTGACTGAACAGGACTCCAAGGATTCTACCTATAGTCTG

AGCTCCACTCTGACCCTGTCCAAAGCAGATTACGAAAAGCACAAAGTGTATGCCTGTGAGGTCACCCACCAGGG

GCTGAGTTCTCCAGTCACCAAATCCTTCAACAGAGGCGAATGT

Amino acid sequence of 19F3H2L3(G1M) light chain
(SEQ ID NO: 28, with non-variable region sequences
underlined)
DIVMTQSPSSLAVSVGERVTISCKSSQSLLNSSNQKNYLAWYQQKPGQAPKLLIYFASTRESGVPDRFSGSGSG

TDFTLTISSLQAEDVAVYYCQQHYDTPYTFGGGTKLEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVTKSFNRGEC

Nucleotide sequence of 19F3H2L3(hG1TM) heavy chain
(SEQ ID NO: 29, with non-variable region
sequences underlined)
CAGGTGCAGCTGGTGCAGTCTGGAGCAGAGGTGGTGAAGCCAGGAGCCTCTGTGAAGGTGAGCT

GTAAGGCCAGCGGCTACTCCTTCACCGGCTATACAATGAACTGGGTGAGGCAGGCACCAGGACA

GAATCTGGAGTGGATCGGCCTGATCAACCCTTACAATGCCGGCACCTCTTATAACCAGAAGTTTC

AGGGCAAGGTGACCCTGACAGTGGACAAGTCCACCTCTACAGCCTACATGGAGCTGAGCTCCCT

-continued

GCGGAGCGAGGATACAGCCGTGTACTATTGCGCCCGGTCCGAGTACAGATATGGCGGCGACTAC

TTTGATTATTGGGGCCAGGGCACCACACTGACCGTGTCTAGCGCCTCCACAAAG ggG ccC agc gtg ttt cct ctc gcc ccc tcc tcc aaa a gcaccagcggaggaaccgctgctctcggatgtctggtgaaggactacttccctgaacccgtcaccgtgagctgg aatagcggcgctctgacaagcggagtccatacattccctgctgtgctgcaaagcagcggactctattccctgtc cagcgtcgtcacagtgcccagcagcagcctgggcacccagacctacatctgtaacgtcaaccacaagccctcca acaccaaggtggacaagaaagtggagcccaaatcctgcgacaagacacacacctgtccccctgtcctgctccc gaaGCTGCTggaGCCcctagcgtcttcctctttcctcccaaacccaaggacaccctcatgatcagcagaaccc ctgaagtcacctgtgtcgtcgtggatgtcagccatgaggaccccgaggtgaaattcaactggtatgtcgatggc gtcgaggtgcacaacgccaaaaccaagcccagggaggaacagtacaactccacctacagggtggtgtccgtgct gacagtcctccaccaggactggctgaacggcaaggagtacaagtgcaaggtgtccaacaaggctctccctgccc ccattgagaagaccatcagcaaggccaaaggccaacccagggagccccaggtctatacactgcctccctccagg gacgaactcaccaagaaccaggtgtccctgacctgcctggtcaagggcttttatcccagcgacatcgccgtcga gtgggagtccaacggacagcccgagaataactacaagaccacccctcctgtcctcgactccgacggctccttct tcctgtacagcaagctgaccgtggacaaaagcaggtggcagcagggaaacgtgttctcctgcagcgtgatgcac gaagccctccacaaccactacacccagaaaagcctgtccctgagccccggcaaatga Amino acid sequence of 19F3H2L3(hG1TM) heavy chain variable region:
(SEQ ID NO: 30)
QVQLVQSGAEVVKPGASVKVSCKASGYSFTGYTMNWVRQAPGQNLEWIGLINPYNAGTSYNQKFQ

GKVTLTVDKSTSTAYMELSSLRSEDTAVYYCARSEYRYGGDYFDYWGQGTTLTVSSASTKGPSVFPL

APSSKSTSGGTAALGCLVKDYFPEPVTVSWNSGALTSGVHTFPAVLQSSGLYSLSSVVTVPSSSLGTQT

YICNVNHKPSNTKVDKKVEPKSCDKTHTCPPCPAPEAAGAPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVEWESNGQPENNYKTTPPVLD

SDGSEFLYSKLTVDKSRWQQGNVFSCSVMHEALHNHYTQKSLSLSPGK

Amino acid sequences of 19F3H2 framework regions:
FR-H1:
(SEQ ID NO: 31)
QVQLVQSGAEVVKPGASVKVSCKAS

FR-H2:
(SEQ ID NO: 32)
MNWVRQAPGQNLEWIGL

FR-H3:
(SEQ ID NO: 33)
SYNQKFQGKVTLTVDKSTSTAYMELSSLRSEDTAVYYC

FR-H4:
(SEQ ID NO: 34)
QVQLVQSGAEVVKPGASVKVSCKAS

Amino acid sequences of 19F3L2 framework regions:
FR-L1:
(SEQ ID NO: 35)
DIVMTQSPSSLAVSVGERVTISCKSS

FR-L2:
(SEQ ID NO: 36)
LAWYQQKPGQAPKLLIY

FR-L3:
(SEQ ID NO: 37)
TRESGVPDRFSGSGSGTDFTLTISSVQAEDVADYYC

-continued

FR-L4:
(SEQ ID NO: 38)
FGGGTKLEIK

Amino acid sequences of 19F3L3 framework regions:
FR-L1:
(SEQ ID NO: 39)
DIVMTQSPSSLAVSVGERVTISCKSS

FR-L2:
(SEQ ID NO: 40)
LAWYQQKPGQAPKLLIY

FR-L3:
(SEQ ID NO: 41)
TRESGVPDRFSGSGSGTDFTLTISSLQAEDVAVYYC

FR-L4:
(SEQ ID NO: 42)
FGGGTKLEIK

Nucleotide sequence of 14C12 heavy chain variable region:
(SEQ ID NO: 43)
GAGGTCAAACTGGTGGAGAGCGGCGGCGGGCTGGTGAAGCCCGGCGGGTCACTGAAACTGAGCT

GCGCCGCTTCCGGCTTCGCCTTTAGCTCCTACGACATGTCATGGGTGAGGCAGACCCCTGAGAAG

CGCCTGGAATGGGTCGCTACTATCAGCGGAGGCGGGCGATACACCTACTATCCTGACTCTGTCAA

AGGGAGATTCACAATTAGTCGGGATAACGCCAGAAATACTCTGTATCTGCAGATGTCTAGTCTGC

GGTCCGAGGATACAGCTCTGTACTATTGTGCAAACCGGTACGGCGAAGCATGGTTTGCCTATTGG

GGACAGGGCACCCTGGTGACAGTCTCTGCC

Amino acid sequence of 14C12 heavy chain variable region:
(SEQ ID NO: 44)
EVKLVESGGGLVKPGGSLKLSCAASGFAFSSYDMSWVRQTPEKRLEWVATISGGGRYTYYPDSVKG

RFTISRDNARNTLYLQMSSLRSEDTALYYCANRYGEAWFAYWGQGTLVTVSA

HCDR1 amino acid sequence of 14C12:
(SEQ ID NO: 45)
GFAFSSYD

HCDR2 amino acid sequence of 14C12:
(SEQ ID NO: 46)
ISGGGRYT

HCDR3 amino acid sequence of 14C12:
(SEQ ID NO: 47)
ANRYGEAWFAY

Nucleotide sequence of 14C12 light chain variable region:
(SEQ ID NO: 48)
GACATTAAGATGACACAGTCCCCTTCCTCAATGTACGCTAGCCTGGGCGAGCGAGTGACCTTCAC

ATGCAAAGCATCCCAGGACATCAACACATACCTGTCTTGGTTTCAGCAGAAGCCAGGCAAAAGC

CCCAAGACCCTGATCTACCGGGCCAATAGACTGGTGGACGGGGTCCCCAGCAGATTCTCCGGATC

TGGCAGTGGGCAGGATTACTCCCTGACCATCAGCTCCCTGGAGTATGAAGACATGGGCATCTACT

ATTGCCTGCAGTATGATGAGTTCCCTCTGACCTTTGGAGCAGGCACAAAACTGGAACTGAAG

Amino acid sequence of 14C12 light chain variable region:
(SEQ ID NO: 49)
DIKMTQSPSSMYASLGERVTFTCKASQDINTYLSWFQQKPGKSPKTLIYRANRLVDGVPSRFSGSGSG

QDYSLTISSLEYEDMGIYYCLQYDEFPLTFGAGTKLELK

LCDR1 amino acid sequence of 14C12:
(SEQ ID NO: 50)
QDINTY

LCDR2 amino acid sequence of 14C12:
(SEQ ID NO: 51)
RAN

-continued

LCDR3 amino acid sequence of 14C12:
(SEQ ID NO: 52)
LQYDEFPLT

Amino acid sequences of 14C12 heavy chain framework regions:
FR-H1:
(SEQ ID NO: 53)
EVKLVESGGGLVKPGGSLKLSCAAS

FR-H2:
(SEQ ID NO: 54)
MSWVRQTPEKRLEWVAT

FR-H3:
(SEQ ID NO: 55)
YYPDSVKGRFTISRDNARNTLYLQMSSLRSEDTALYYC

FR-H4:
(SEQ ID NO: 56)
WGQGTLVTVSA

Amino acid sequences of 14C12 light chain framework regions:
HR-L1:
(SEQ ID NO: 57)
DIKMTQSPSSMYASLGERVTFTCKAS

HR-L2:
(SEQ ID NO: 58)
LSWFQQKPGKSPKTLIY

HR-L3:
(SEQ ID ND: 59)
RLVDGVPSRFSGSGSGQDYSLLISSLEYEDMGIYYC

HR-L4:
(SEQ ID NO: 60)
FGAGTKLELK

Nucleotide sequence of 14C12H1:
(SEQ ID NO: 61)
GAAGTGCAGCTGGTCGAGTCTGGGGGAGGGCTGGTGCAGCCCGGCGGGTCACTGCGACTGAGCT

GCGCAGCTTCCGGATTCGCCTTTAGCTCCTACGACATGTCCTGGGTGCGACAGGCACCAGGAAAG

GGACTGGATTGGGTCGCTACTATCTCAGGAGGCGGGAGATACACCTACTATCCTGACAGCGTCAA

GGGCCGGTTCACAATCTCTAGAGATAACAGTAAGAACAATCTGTATCTGCAGATGAACAGCCTG

AGGGCTGAGGACACCGCACTGTACTATTGTGCCAACCGCTACGGGGAAGCATGGTTTGCCTATTG

GGGGCAGGGAACCCTGGTGACAGTCTCTAGT

Amino acid sequence of 14C12H1:
(SEQ ID NO: 62)
EVQLVESGGGLVQPGGSLRLSCAASGFAFSSYDMSWVRQAPGKGLDWVATISGGGRYTYYPDSVKG Nucleotide sequence of 14C12L1:
(SEQ ID NO: 63)
GACATTCAGATGACTCAGAGCCCCTCCTCCATGTCCGCCTCTGTGGGCGACAGGGTCACCTTCAC

ATGCCGCGCTAGTCAGGATATCAACACCTACCTGAGCTGGTTTCAGCAGAAGCCAGGGAAAAGC

CCCAAGACACTGATCTACCGGGCTAATAGACTGGTGTCTGGAGTCCCAAGTCGGTTCAGTGGCTC

AGGGAGCGGACAGGACTACACTCTGACCATCAGCTCCCTGCAGCCTGAGGACATGGCAACCTAC

TATTGCCTGCAGTATGATGAGTTCCCACTGACCTTTGGCGCCGGGACAAAACTGGAGCTGAAG

Amino acid sequence of 14C12L1:
(SEQ ID NO: 64)
DIQMTQSPSSMSASVGDRVTFTCRASQDINTYLSWFQQKPGKSPKTLIYRANRLVSGVPSRFSGSGSG

QDYTLTTSSLQPEDMATYYCLQYDEFPLTFGAGTKLELK

Nucleotide sequence of 14C12H1L1 heavy chain
(SEQ ID NO: 65)
GAAGTGCAGCTGGTCGAGTCTGGGGGAGGGCTGGTGCAGCCCGGCGGGTCACTGCGACTGAGCT

GCGCAGCTTCCGGATTCGCCTTTAGCTCCTACGACATGTCCTGGGTGCGACAGGCACCAGGAAAG

GGACTGGATTGGGTCGCTACTATCTCAGGAGGCGGGAGATACACCTACTATCCTGACAGCGTCAA

-continued

GGGCCGGTTCACAATCTCTAGAGATAACAGTAAGAACAATCTGTATCTGCAGATGAACAGCCTG

AGGGCTGAGGACACCGCACTGTACTATTGTGCCAACCGCTACGGGGAAGCATGGTTTGCCTATTG

GGGGCAGGGAACCCTGGTGACAGTCTCTAGTGCCAGCACCAAAGGACCTAGCGTGTTTCCTCTCG

CCCCCTCCTCCAAAAGCACCAGCGGAGGAACCGCTGCTCTCGGATGTCTGGTGAAGGACTACTTC

CCTGAACCCGTCACCGTGAGCTGGAATAGCGGCGCTCTGACAAGCGGAGTCCATACATTCCCTGC

TGTGCTGCAAAGCAGCGGACTCTATTCCCTGTCCAGCGTCGTCACAGTGCCCAGCAGCAGCCTGG

GCACCCAGACCTACATCTGTAACGTCAACCACAAGCCCTCCAACACCAAGGTGGACAAGAAAGT

GGAGCCCAAATCCTGCGACAAGACACACACCTGTCCCCCCTGTCCTGCTCCCGAACTCCTCGGAG

GCCCTAGCGTCTTCCTCTTTCCTCCCAAACCCAAGGACACCCTCATGATCAGCAGAACCCCTGAA

GTCACCTGTGTCGTCGTGGATGTCAGCCATGAGGACCCCGAGGTGAAATTCAACTGGTATGTCGA

TGGCGTCGAGGTGCACAACGCCAAAACCAAGCCCAGGGAGGAACAGTACAACTCCACCTACAGG

GTGGTGTCCGTGCTGACAGTCCTCCACCAGGACTGGCTGAACGGCAAGGAGTACAAGTGCAAGG

TGTCCAACAAGGCTCTCCCTGCCCCCATTGAGAAGACCATCAGCAAGGCCAAAGGCCAACCCAG

GGAGCCCCAGGTCTATACACTGCCTCCCTCCAGGGACGAACTCACCAAGAACCAGGTGTCCCTGA

CCTGCCTGGTCAAGGGCTTTTATCCCAGCGACATCGCCGTCGAGTGGGAGTCCAACGGACAGCCC

GAGAATAACTACAAGACCACCCCTCCTGTCCTCGACTCCGACGGCTCCTTCTTCCTGTACAGCAA

GCTGACCGTGGACAAAAGCAGGTGGCAGCAGGGAAACGTGTTCTCCTGCAGCGTGATGCACGAA

GCCCTCCACAACCACTACACCCAGAAAAGCCTGTCCCTGAGCCCCGGCAAA

Amino add sequence of 14C12H1L1 heavy chain variable region:
(SEQ ID NO: 66)
EVQLVESGGGLVQPGGSLRLSCAASGFAFSSYDMSWVRQAPGKGLDWVATISGGGRYTYYPDSVKG

RFTISRDNSKNNLYLQMNSLRAEDTALYYCANRYGEAWFAYWGQGTLVTVSSASTKGPSVFPLAPSS

KSTSGGTAALGCLVKDYFPEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

Nucleotide sequence of 14C12H1L1 light chain
(SEQ ID NO: 67)
GACATTCAGATGACTCAGAGCCCCTCCTCCATGTCCGCCTCTGTGGGCGACAGGGTCACCTTCAC

ATGCCGCGCTAGTCAGGATATCAACACCTACCTGAGCTGGTTTCAGCAGAAGCCAGGGAAAAGC

CCCAAGACACTGATCTACCGGGCTAATAGACTGGTGTCTGGAGTCCCAAGTCGGTTCAGTGGCTC

AGGGAGCGGACAGGACTACACTCTGACCATCAGCTCCCTGCAGCCTGAGGACATGGCAACCTAC

TATTGCCTGCAGTATGATGAGTTCCCACTGACCTTTGGCGCCGGGACAAAACTGGAGCTGAAGCG

AACTGTGGCCGCTCCCTCCGTCTTCATTTTTCCCCCTTCTGACGAACAGCTGAAATCAGGCACAGC

CAGCGTGGTCTGTCTGCTGAACAATTTCTACCCTAGAGAGGCAAAAGTGCAGTGGAAGGTCGATA

ACGCCCTGCAGTCCGGCAACAGCCAGGAGAGTGTGACTGAACAGGACTCAAAAGATAGCACCTA

TTCCCTGTCTAGTACACTGACTCTGTCCAAGGCTGATTACGAGAAGCACAAAGTGTATGCATGCG

AAGTGACACATCAGGGACTGTCAAGCCCCGTGACTAAGTCTTTTAACCGGGGCGAATGT

Amino acid sequence of 14C12H1L1 light chain:
(SEQ ID NO: 68)
DIQMTQSPSSMSASVGDRVTFTCRASQDINTYLSWFQQKPGKSPKTLIYRANRLVSGVPSRFSGSGSG

QDYTLTISSLQPEDMATYYCLQYDEFPLTFGAGTKLELKRTVAAPSVFIFPPSDEQLKSGTASVVCLLN

-continued

NFYPREAKVQWKVDNALQSGNSQESVTEQDSKDSTYSLSSTLTLSKADYEKHKVYACEVTHQGLSSP

VTKSFNRGEC

Nucleotide sequence of 14C12H1L1(G1TM) heavy chain
(SEQ ID NO: 69)
GAAGTGCAGCTGGTCGAGTCTGGGGGAGGGCTGGTGCAGCCCGGCGGGTCACTGCGACTGAGCT

GCGCAGCTTCCGGATTCGCCTTTAGCTCCTACGACATGTCCTGGGTGCGACAGGCACCAGGAAAG

GGACTGGATTGGGTCGCTACTATCTCAGGAGGCGGGAGATACACCTACTATCCTGACAGCGTCAA

GGGCCGGTTCACAATCTCTAGAGATAACAGTAAGAACAATCTGTATCTGCAGATGAACAGCCTG

AGGGCTGAGGACACCGCACTGTACTATTGTGCCAACCGCTACGGGGAAGCATGGTTTGCCTATTG

GGGGCAGGGAACCCTGGTGACAGTCTCTAGTGCCAGCACCAAAGGGCCCAGCGTGTTTCCTCTCG

CCCCCTCCTCCAAAAGCACCAGCGGAGGAACCGCTGCTCTCGGATGTCTGGTGAAGGACTACTTC

CCTGAACCCGTCACCGTGAGCTGGAATAGCGGCGCTCTGACAAGCGGAGTCCATACATTCCCTGC

TGTGCTGCAAAGCAGCGGACTCTATTCCCTGTCCAGCGTCGTCACAGTGCCCAGCAGCAGCCTGG

GCACCCAGACCTACATCTGTAACGTCAACCACAAGCCCTCCAACACCAAGGTGGACAAGAAAGT

GGAGCCCAAATCCTGCGACAAGACACACACCTGTCCCCCCTGTCCTGCTCCCGAAGCTGCTGGAG

CCCCTAGCGTCTTCCTCTTTCCTCCCAAACCCAAGGACACCCTCATGATCAGCAGAACCCCTGAA

GTCACCTGTGTCGTCGTGGATGTCAGCCATGAGGACCCCGAGGTGAAATTCAACTGGTATGTCGA

TGGCGTCGAGGTGCACAACGCCAAAACCAAGCCCAGGGAGGAACAGTACAACTCCACCTACAGG

GTGGTGTCCGTGCTGACAGTCCTCCACCAGGACTGGCTGAACGGCAAGGAGTACAAGTGCAAGG

TGTCCAACAAGGCTCTCCCTGCCCCCATTGAGAAGACCATCAGCAAGGCCAAAGGCCAACCCAG

GGAGCCCCAGGTCTATACACTGCCTCCCTCCAGGGACGAACTCACCAAGAACCAGGTGTCCCTGA

CCTGCCTGGTCAAGGGCTTTTATCCCAGCGACATCGCCGTCGAGTGGGAGTCCAACGGACAGCCC

GAGAATAACTACAAGACCACCCCTCCTGTCCTCGACTCCGACGGCTCCTTCTTCCTGTACAGCAA

GCTGACCGTGGACAAAAGCAGGTGGCAGCAGGGAAACGTGTTCTCCTGCAGCGTGATGCACGAA

GCCCTCCACAACCACTACACCCAGAAAAGCCTGTCCCTGAGCCCCGGCAAA

Amino acid sequence of 14C12H1L1(G1TM) heavy chain variable region:
(SEQ ID NO: 70)
EVQLVESGGGLVQPGGSLRLSCAASGFAFSSYDMSWVRQAPGKGLDWVATISGGGRYTYYPDSVKG

RFTISRDNSKNNLYLQMNSLRAEDTALYYCANRYGEAWFAYWGQGTLVTVSSASTKGPSVFPLAPSS

KSTSGGTAALGCLVKDYFPEPVTVSWNSGALTSGVHTFPAVLQSSGLYSLSSVVTVPSSSLGTQTYIC

NVNHKPSNTKVDKKVEPKSCDKTHTCPPCPAPEAAGAPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

Amino acid sequences of 14C12H1 heavy chain framework regions:
FR-H1:
(SEQ ID NO: 71)
EVQLVESGGGLVQPGGSLRLSCAAS

FR-H2:
(SEQ ID NO: 72)
MSWVRQAPGKGLDWVAT

FR-H3:
(SEQ ID NO: 73)
YYPDSVKGRFTISRDNSKNNLYLQMNSLRAEDTALYYC

FR-H4:
(SEQ ID NO: 74)
WGQGTLVTVSS

-continued

Amino acid sequences of 14C12L1 light chain framework regions:
FR-L1:
(SEQ ID NO: 75)
DIQMTQSPSSMSASVGDRVTFTCRAS

FR-L2:
(SEQ ID NO: 76)
LSWFQQKPGKSPKTIIY

FR-L3:
(SEQ ID NO: 77)
RLVSGVPSRFSGSGSGQDYTLTISSLQPEDMATYYC

FR-L4:
(SEQ ID NO: 78)
FGAGTKLELK

Amino acid sequence of Linker1:
(SEQ ID NO: 79)
GGGGSGGGGSGGGGSGGGGS

Nucleotide sequence of Linker:
(SEQ ID NO: 80)
GGCGGCGGCGGCAGCGGCGGCGGCGGCTCCGGAGGAGGCGGCTCTGGCGGCGGCGGCAGC Amino acid sequence of Linker2:
(SEQ ID NO: 81)
GGGGSGGGGSGGGGS Nucleotide sequence of Linker2:
(SEQ ID NO: 82)
GGCGGCGGCGGCTCCGGAGGAGGCGGCTCTGGCGGCGGCGGCAGC The amino acid sequence of the heavy chain of NTPDV2 and NTPDV4
(SEQ ID NO: 83):
wherein the CDR regions of 19F3H2(hG1TM) in the immunoglobulin moiety are marked in bold underlines, the CDR regions of 14C12H1V-Linker1-14C12L1V in the scFv part are marked in bold underlines, the mutated amino acids in the heavy chain region are marked in bold italics, and the linker regions are marked in bold:
QVQLVQSGAEVVKPGASVKVSCKASGYSFTGYTMNWVRQAPGQNLEWIGLINPYNAGTSYNQKFQ

GKVTLTVDKSTSTAYMELSSLRSEDTAVYYCARSEYRYGGDYFDYWGQGTTLTVSSASTKGPSVFP

LAPSSKSTSGGTAALGCLVKDYFPEPVTVSWNSGALTSGVHTFPAVLQSSGLYSLSSVVTVPSSSLGTQ

TYICNVNHKPSNTKVDKKVEPKSCDKTHTCPPCPAPE*AA*G*A*PSVFLFPPKPKDTLMISRTPEVTCVVVD

VSHEDPEVKFNWYVDGVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVEWESNGQPENNYKTTPPVLD

SDGSFFLYSLKTVDKSRWQQGNVFSCSVMHEALHNHYTQKSLSLSPGKGGGGSGGGGSGGGGSGG

GGS*EVQLVESGGGLVQPGGSLRLSCAAS*GFAFSSYD*MSWVRQAPGKGLDWVAT*ISGGGRYT*YYPDSVKG*

*RFTISRDNSKNNLYLQMNSLRAEDTALYYC*ANRYGEAWFAY*WGQGTLVLVSS*GGGGSGGGGSGGGGS

GGGGS*DIQMTQSPSSMSASVGDRVTFTCRAS*QDINTY*LSWFQQKPGKSPKTLIY*RAN*RLVSGVPSRFSGSG*]

*SGQDYTLTISSLQPEDMATYYC*LQYDEFPLT*FGAGTKLELKR*

Nucleotide sequence of the heavy chain of NTPDV2 and NTPDV4:
(SEQ ID NO: 84)
CAGGTGCAGCTGGTGCAGTCTGGAGCAGAGGTGGTGAAGCCAGGAGCCTCTGTGAAGGTGAGCT

GTAAGGCCAGCGGCTACTCCTTCACCGGCTATACAATGAACTGGGTGAGGCAGGCACCAGGACA

GAATCTGGAGTGGATCGGCCTGATCAACCCTTACAATGCCGGCACCTCTTATAACCAGAAGTTTC

AGGGCAAGGTGACCCTGACAGTGGACAAGTCCACCTCTACAGCCTACATGGAGCTGAGCTCCCT

GCGGAGCGAGGATACAGCCGTGTACTATTGCGCCCGGTCCGAGTACAGATATGGCGGCGACTAC

TTTGATTATTGGGGCCAGGGCACCACACTGACCGTGTCTAGCgcctccacaaaggggcccagcgtgtttcctctcgccc cctcctccaaaagcaccagcggaggaaccgctgctctcggatgtctggtgaaggactacttccctgaacccgtcaccgt gagctggaatagcggcgctctgacaagcggagtccatacattccctgctgtgctgcaaagcagcggactctattccctg tccagcgtcgtcacagtgcccagcagcagcctgggcacccagacctacatctgtaacgtcaaccacaagccctccaaca -continued ccaaggtggacaagaaagtggagcccaaatcctgcgacaagacacacacctgtccccctgtcctgctcccgaaGCTGC TggagCccctagcgtcttcctctttcctcccaaacccaaggacaccctcatgatcagcagaacccctgaagtcacctgt gtcgtcgtggatgtcagccatgaggaccccgaggtgaaattcaactggtatgtcgatggcgtcgaggtgcacaacgcca aaaccaagcccagggaggaacagtacaactccacctacagggtggtgtccgtgctgacagtcctccaccaggactggct gaacggcaaggagtacaagtgcaaggtgtccaacaaggctctccctgcccccattgagaagaccatcagcaaggccaaa ggccaacccagggagccccaggtctatacactgcctccctccagggacgaactcaccaagaaccaggtgtccctgacct gcctggtcaagggcttttatcccagcgacatcgccgtcgagtgggagtccaacggacagcccgagaataactacaagac cacccctcctgtcctcgactccgacggctccttcttcctgtacagcaaactgaccgtcgataaatctaggtggcagcag ggcaacgtgttctcttgttccgtgatgcatgaagcactgcacaaccattatacccagaagtctctga gcctgtcccccggcaagGGCGGCGGCGGCTCTGGAGGAGGAGGCAGCGGCGGAGGAGGCTCCGGAG

GCGGCGGCTCTGAGGTGCAGCTGGTGGAGTCTGGAGGAGGACTGGTGCAGCCTGGAGGCTCCCT

GAGGCTGTCTTGCGCAGCAAGCGGATTCGCCTTTAGCTCCTACGACATGAGCTGGGTGCGGCAGG

CACCTGGCAAGggtCTGGATTGGGTGGCAACCATCAGCGGAGGCGGCAGATACACATACTATCCC

GACTCCGTGAAGGGCAGGTTCACCATCTCCCGCGATAACTCTAAGAACAATCTGTATCTGCAGAT

GAACAGCCTGAGGGCCGAGGACACAGCCCTGTACTATTGCGCCAACCGCTACGGCGAGGCCTGG

TTTGCCTATTGGGGCCAGGGCACCCTGGTGACAGTGTCTAGCGGCGGCGGCGGCAGCGGCGGCG

GCGGCTCCGGAGGAGGCGGCTCTGGCGGCGGCGGCAGCGATATCCAGATGACCCAGTCCCCCTC

CTCTATGTCTGCCAGCGTGGGCGACCGGGTGACCTTCACATGTAGAGCCTCCCAGGATATCAACA

CCTACCTGTCTTGGTTTCAGCAGAAGCCCGGCAAGAGCCCTAAGACACTGATCTATCGGGCCAAT

AGACTGGTGAGCGGAGTGCCTTCCCGGTTCTCCGGCTCTGGCAGCGGACAGGACTATACCCTGAC

AATCAGCTCCCTGCAGCCAGAGGATATGGCCACATACTATTGCCTGCAGTATGACGAGTTCCCCC

TGACCTTCGGGgctGGCACTAAGCTGGAGCTGAAAAGA

The amino acid sequence of the heavy chain of NTPDV1 and NTPDV3 (SEQ ID NO: 85):
wherein the CDR regions of 19F3H2(hG1TM) is the immunoglobulin moiety are marked in bold underlines, the CDR regions of 14C12H1V-Linker2-14C12L1V in the scFv part are marked in bold underlines, the mutated amino acids in the heavy chain region are marked in bold italics, and the linker regions are marked in bold:
QVQLVQSGAEVVKPGASVKVSCKASGYSFTGYTMNWVRQAPGQNLEWIGLINPYNAGTSYNQKFQ

GKVTLTVDKSTSTAYMELSSLRSEDTAVYYCARSEYRYGGDYFDYWGQGTTLTVSSASTKGPSVFP

LAPSSKSTSGGTAALGCLVKDYFPEPVTVSWNSGALTSGVHTFPAVLQSSGLYSLSSVVTVPSSSLGTQ

TYICNVNHKPSNTKVDKKVEPKSCDKTHTCPPCPAPE*AA*G*A*PSVFLFPPKPKDTLMISRTPEVTCVVVD

VSHEDPEVKFNWYVDGVEVHNAKTKPREEQYNSTYRVVSVLTVLHQDWLNGKEYACKVSNKALPA

PIEKTISKAKGQPREPQVYTLPPSRDELTKNQVSLTCLVKGFYPSDIAVEWESNGQPENNYKTTPPVLD

SDGSFFLYSLKTVDKSRWQQGNVFSCSVMHEALHNHYTQKSLSLSPGKGGGGSGGGGSGGGGSGG

GGS_EVQLVESGGGLVQPGGSLRLSCAAS_GFAFSSYD_MSWVRQAPGKGLDWVAT_ISGGGRYT_YYPDSVKG_

_RFTISRDNSKNNLYLQMNSLRAEDTALYYC_ANRYGEAWFAY_WGQGTLVLVSS_GGGGSGGGGSGGGGS

_DIQMTQSPSSMSASVGDRVTFTCRAS_QDINTY_LSWFQQKPGKSPKTLIY_RAN_RLVSGVPSRFSGSGSGQDYT_

_LTISSLQPEDMATYYC_LQYDEFPLT_FGAGTKLELKR_

Nucleotide sequence of the heavy chain of NTPDV1 and NTPDV3:
(SEQ ID NO: 86)
CAGGTGCAGCTGGTGCAGTCTGGAGCAGAGGTGGTGAAGCCAGGAGCCTCTGTGAAGGTGAGCT

GTAAGGCCAGCGGCTACTCCTTCACCGGCTATACAATGAACTGGGTGAGGCAGGCACCAGGACA

GAATCTGGAGTGGATCGGCCTGATCAACCCTTACAATGCCGGCACCTCTTATAACCAGAAGTTTC

-continued

AGGGCAAGGTGACCCTGACAGTGGACAAGTCCACCTCTACAGCCTACATGGAGCTGAGCTCCCT

GCGGAGCGAGGATACAGCCGTGTACTATTGCGCCCGGTCCGAGTACAGATATGGCGGCGACTAC

TTTGATTATTGGGGCCAGGGCACCACACTGACCGTGTCTAGCGCCTCCACAAaggggcccagcgtgtttcctct cgcccccctcctccaaaagcaccagcggaggaaccgctgctctcggatgtctggtgaaggactacttccctgaacccgtc accgtgagctggaatagcggcgctctgacaagcggagtccatacattccctgctgtgctgcaaagcagcggactctatt ccctgtccagcgtcgtcacagtgcccagcagcagcctgggcacccagacctacatctgtaacgtcaaccacaagccctc caacaccaaggtggacaagaaagtggagcccaaatcctgcgacaagacacacacctgtccccccctgtcctgctcccgaa GCTGCTggagCccctagcgtcttcctctttcctcccaaacccaaggacaccctcatgatcagcagaaccCCTGAAGTCA

CCTGTGTCGTCGTGGATGTCAGCCATGAGGACCCCGAGGTGAAATTCAACTGGTATGTCGATGGCGTCGAG

GTGCACAACGCCAAAACCAAGCCCAGGGAGGAACAGTACAACTCCACCTACAGGGTGGTGTCCG

TGCTGACAGTCCTCCACCAGGACTGGCTGAACGGCAAGGAGTACAAGTGCAAGGTGTCCAACAA

GGCTCTCCCTGCCCCCATTGAGAAGACCATCAGCAAGGCCAAAGGCCAACCCAGGGAGCCCCAG

GTCTATACACTGCCTCCCTCCAGGGACGAACTCACCAAGAACCAGGTGTCCCTGACCTGCCTGGT

CAAGGGCTTTTATCCCAGCGACATCGCCGTCGAGTGGGAGTCCAACGGACAGCCCGAGAATAAC

TACAAGACCACCCCTCCTGTCCTCGACTCCGACGGCTCCTTCTTCCTGTACAGCAAACTGACCGTC

GATAAATCTAGGTGGCAGCAGGGCAACGTGTTCTCTTGTTCCGTGATGCATGAAGCACTGCACAA

CCATTATACCCAGAAGTCTCTGAGCCTGTCCCCCGGCAAGGGCGGCGGCGGCTCTGGAGGAGGA

GGCAGCGGCGGAGGAGGCTCCGGAGGCGGCGGCTCTGAGGTGCAGCTGGTGGAGTCTGGAGGA

GGACTGGTGCAGCCTGGAGGCTCCCTGAGGCTGTCTTGCGCAGCAAGCGGATTCGCCTTTAGCTC

CTACGACATGAGCTGGGTGCGGCAGGCACCTGGCAAGGGTCTGGATTGGGTGGCAACCATCAGC

GGAGGCGGCAGATACACATACTATCCCGACTCCGTGAAGGGCAGGTTCACCATCTCCCGCGATA

ACTCTAAGAACAATCTGTATCTGCAGATGAACAGCCTGAGGGCCGAGGACACAGCCCTGTACTAT

TGCGCCAACCGCTACGGCGAGGCCTGGTTTGCCTATTGGGGCCAGGGCACCCTGGTGACAGTGTC

TAGCGGCGGCGGCGGCTCCGGAGGAGGCGGCTCTGGCGGCGGCGGCAGCGATATCCAGATGACC

CAGTCCCCCTCCTCTATGTCTGCCAGCGTGGGCGACCGGGTGACCTTCACATGTAGAGCCTCCCA

GGATATCAACACCTACCTGTCTTGGTTTCAGCAGAAGCCCGGCAAGAGCCCTAAGACACTGATCT

ATCGGGCCAATAGACTGGTGAGCGGAGTGCCTTCCCGGTTCTCCGGCTCTGGCAGCGGACAGGAC

TATACCCTGACAATCAGCTCCCTGCAGCCAGAGGATATGGCCACATACTATTGCCTGCAGTATGA

CGAGTTCCCCCTGACCTTCGGGGCTGGCACTAAGCTGGAGCTGAAAAGATGATAAGAATTC

Amino acid sequence of NT5E(1-552)-his
(SEQ ID NO: 87)
MCPRAARAPATLLLALGAVLWPAAGAWELTILHTNDVHSRLEQTSEDSSKCVNASRCMGGVARLFT

KVQQIRRAEPNVLLLDAGDQYQGTIWFTVYKGAEVAHFMNALRYDAMALGNHEFDNGVEGLIEPLL

KEAKFPILSANIKAKGPLASQISGLYLPYKVLPVGDEVVGIVGYTSKETPFLSNPGTNLVFEDEITALQP

EVDKLKTLNVNKIIALGHSGFEMDKLIAQKVRGVDVVVGGHSNTFLYTGNPPSKEVPAGKYPFIVTSD

DGRKVPVVQAYAFGKYLGYLKIEFDERGNVISSHGNPILLNSSIPEDPSIKADINKWRIKLDNYSTQEL

GKTIVYLDGSSQSCRFRECNMGNLICDAMINNNLRHTDEMFWNHVSMCILNGGGIRSPIDERNNGTIT

WENLAAVLPFGGTFDLVQLKGSTLKKAFEHSVHRYGQSTGEFLQVGGIHVVYDLSRKPGDRVVKLD

VLCTKCRVPSYDPLKMDEVYKVILPNFLANGGDGFQMIKDELLRHDSGDQDINVVSTYISKMKVIYP

AVEGRIKFSTGSHHHHHH

-continued

Nucleotide sequence of NT5E(1-552)-his
(SEQ ID NO: 88)
ATGTGTCCTAGAGCCGCCAGAGCTCCAGCTACACTGCTGCTGGCTCTGGGAGCAGTCCTCTGGCC

AGCAGCAGGAGCTTGGGAACTGACCATCCTGCACACCAACGACGTGCACAGCAGGCTGGAACAG

ACCAGCGAGGACAGCAGCAAGTGCGTGAACGCCAGTCGCTGTATGGGAGGAGTGGCAAGGCTGT

TCACCAAGGTGCAGCAGATCCGGAGAGCCGAACCTAACGTGCTGCTGCTGGACGCCGGAGATCA

GTATCAGGGAACCATCTGGTTCACCGTGTACAAGGGCGCCGAAGTGGCCCACTTCATGAACGCTC

TGCGCTACGACGCTATGGCCCTGGGCAATCACGAGTTCGATAACGGCGTGGAGGGACTGATCGA

GCCTCTGCTGAAGGAGGCCAAGTTCCCCATCCTGAGCGCCAACATCAAGGCCAAGGGACCTCTG

GCTAGCCAGATTAGCGGCCTGTACCTGCCTTACAAGGTGCTGCCCGTGGGAGACGAAGTGGTGG

GAATCGTGGGCTACACCAGCAAGGAGACCCCTTTCCTGAGCAACCCAGGCACCAACCTGGTGTTC

GAGGACGAGATCACCGCTCTGCAGCCAGAGGTGGACAAGCTGAAGACCCTGAACGTGAACAAGA

TCATCGCCCTGGGACACAGCGGCTTCGAGATGGACAAGCTGATCGCCCAGAAAGTGCGAGGAGT

GGACGTGGTCGTGGGCGGACACAGCAACACCTTCCTGTACACCGGCAACCCTCCTTCTAAGGAAG

TGCCAGCCGGCAAGTACCCCTTCATCGTGACCAGCGACGACGGAAGAAAGGTGCCAGTGGTGCA

GGCTTACGCCTTCGGCAAGTACCTGGGCTACCTGAAGATCGAGTTCGACGAGCGGGGCAACGTG

ATCTCTAGCCACGGCAACCCCATCCTGCTGAACAGCAGCATCCCAGAGGACCCCAGCATCAAGG

CCGACATCAACAAGTGGCGGATCAAGCTGGACAACTACAGCACCCAGGAGCTGGGAAAGACCAT

CGTGTACCTGGACGGCAGCTCTCAGTCTTGCCGGTTCCGCGAGTGCAACATGGGCAACCTGATTT

GCGACGCCATGATCAACAACAACCTGCGGCACACCGACGAGATGTTTTGGAACCACGTCAGCAT

GTGCATCCTGAACGGCGGAGGCATCAGAAGCCCTATTGACGAGCGGAACAACGGCACCATCACT

TGGGAGAACCTGGCAGCAGTGCTGCCTTTTGGCGGAACATTCGACCTGGTGCAGCTGAAGGGCA

GCACACTGAAGAAGGCCTTCGAGCACAGCGTGCACAGATACGGCCAGAGCACAGGCGAGTTCCT

GCAGGTCGGAGGAATCCACGTGGTGTACGACCTGAGCAGGAAGCCAGGAGACAGAGTGGTGAA

GCTGGACGTGCTCTGCACCAAGTGTCGGGTGCCAAGCTACGACCCCCTGAAGATGGACGAGGTG

TACAAGGTCATCCTGCCCAACTTCCTGGCTAACGGAGGAGACGGCTTCCAGATGATCAAGGACG

AGCTGCTGAGGCACGACAGCGGAGACCAGGACATCAACGTCGTGTCCACCTACATCAGCAAGAT

GAAGGTCATCTACCCCGCCGTGGAAGGCAGGATCAAGTTCAGCACCGGCTCTCACCACCACCATC

ACCAC

Amino acid sequence of mFc:
(SEQ ID NO: 89)
PRGPTIKPCPPCKCPAPNLLGGPSVFIFPPKIKDVLMISLSPIVTCVVVDVSEDDPDVQISWFVNNVEVH

TAQTQTHREDYNSTLRVVSALPIQHQDWMSGKEEKCKVNNKDLPAPIERTISKPKGSVRAPQVYVLPP

PEEEMTKKQVTLTCMVTDFMPEDIYVEWTNNGKTELNYKNTEPVLDSDGSYFMYSKLRVEKKNWV

ERNSYSCSVVHEGLHNHHTTKSFSRTPGK

Amino acid sequence of 19F3H1V-Linker-19F3L2V:
(SEQ ID NO: 90)
QVQLQQSGAEVVKPGASMKMSCKASGYSFTGYTMNWVKQAHGQNLEWIGLINPYNAGTSYNQKFQ

GKATLTVDKSTSTAYMELSSLRSEDTAVYYCARSEYRYGGDYFDYWGQGTTLTVSSGGGGSGGGGS

VPDRFSGSGSGTDFTLTISSVQAEDVADYYCQQHYDTPYTFGGGTKLEIK

Nucleotide sequence of 19F3H1V-Linker2-19F3L2V:
(SEQ ID NO: 91)
CAGGTGCAGCTGCAGCAGTCTGGAGCAGAGGTGGTGAAGCCAGGAGCCTCTATGAAGATGAGCT

GTAAGGCCAGCGGCTACTCCTTCACCGGCTATACAATGAACTGGGTGAAGCAGGCCCACGGCCA

GAATCTGGAGTGGATCGGCCTGATCAACCCTTACAATGCCGGCACCTCTTATAACCAGAAGTTTC

-continued

AGGGCAAGGCCACCCTGACAGTGGACAAGTCCACCTCTACAGCCTACATGGAGCTGAGCTCCCT

GCGGAGCGAGGATACAGCCGTGTACTATTGCGCCCGGTCCGAGTACAGATATGGCGGCGACTAC

TTTGATTATTGGGGCCAGGGCACCACACTGACCGTGTCTAGC

GGCCTGTACGGCCTGTACGGCCTGTACGGCCTGTACAGCGAGAGGGGCCTGTACGGCCTGTACGG

CCTGTACGGCCTGTACAGCGAGAGGGGCCTGTACGGCCTGTACGGCCTGTACGGCCTGTACAGCG

AGAGGGACATCGTGATGACCCAGTCCCCAAGCTCCCTGGCCGTGTCTGTGGGAGAGCGGGTGAC

AATCTCCTGTAAGTCTAGCCAGTCTCTGCTGAACTCCTCTAATCAGAAGAACTACCTGGCCTGGT

ATCAGCAGAAGCCCGGCCAGGCCCCTAAGCTGCTGATCTACTTCGCCTCTACCAGGGAGAGCGG

AGTGCCAGACAGATTCTCTGGCAGCGGCTCCGGCACAGACTTCACCCTGACAATCAGCTCCGTGC

AGGCAGAGGACGTGGCAGATTACTATTGCCAGCAGCACTACGATACCCCCTATACATTTGGCGGC

GGCACCAAGCTGGAGATCAAG

Nucleotide sequence of 19F3H1:
(SEQ ID NO: 92)
CAGGTGCAGCTGCAGCAGTCTGGAGCAGAGGTGGTGAAGCCAGGAGCCTCTATGAAGATGAGCT

GTAAGGCCAGCGGCTACTCCTTCACCGGCTATACAATGAACTGGGTGAAGCAGGCCCACGGCCA

GAATCTGGAGTGGATCGGCCTGATCAACCCTTACAATGCCGGCACCTCTTATAACCAGAAGTTTC

AGGGCAAGGCCACCCTGACAGTGGACAAGTCCACCTCTACAGCCTACATGGAGCTGAGCTCCCT

GCGGAGCGAGGATACAGCCGTGTACTATTGCGCCCGGTCCGAGTACAGATATGGCGGCGACTAC

TTTGATTATTGGGGCCAGGGCACCACACTGACCGTGTCTAGC

Amino acid sequence of 19F3H1:
(SEQ ID NO: 93)
QVQLQQSGAEVVKPGASMKMSCKASGYSFTGYTMNWVKQAHGQNLEWIGLINPYNAGTSYNQKFQ

GKATLTVDKSTSTAYMELSSLRSEDTAVYYCARSEYRYGGDYFDYWGQGTTLTVSS

Nucleotide sequence of 19F3L1:
(SEQ ID NO: 94)
GACATCGTGATGACCCAGTCCCCAAGCTCCCTGGCAATGTCTGTGGGAGAGAGGGTGACAATGTC

CTGTAAGTCTAGCCAGTCTCTGCTGAACTCCTCTAATCAGAAGAACTACCTGGCCTGGTATCAGC

AGAAGCCCGGCCAGGCCCCTAAGCTGCTGGTGTACTTTGCCTCTACCAGGGAGAGCGGAGTGCC

AGACAGATTCTCTGGCAGCGGCTCCGGCACAGACTTCACCCTGACAATCAGCTCCGTGCAGGCAG

AGGACCTGGCAGATTATTTCTGCCAGCAGCACTACGATACCCCCTATACATTTGGCGGCGGCACC

AAGCTGGAGATCAAG

Amino acid sequence of 19F3L1:
(SEQ ID NO: 95)
DIVMTQSPSSLAMSVGERVTMSCKSSQSLLNSSNQKNYLAWYQQKPGQAPKLLVYFASTRESGVPDR

FSGSGSGTDFTLTISSVQAEDLADYFCQQHYDTPVTFGGGTKLEIK

Amino acid of 19F3L2 light chain (full length)
(SEQ ID NO: 96, with non-variable region sequences
underlined)
DIVMTQSPSSLAVSVGERVTISCKSSQSLLNSSNQKNYLAWYQQKPGQAPKLLIYFASTRESGVPDRFS

GSGSGTDFTLTISSVQAEDVADYYCQQHYDTPYTFGGGTKLEIKRTVAAPSVFIFPPSDEQLESGTASVV

CLLNNFYPREAKVQWKVDNALQSGNSQESVTEQDSKDSTYSLSSTLTLSKADYEKHKVYACEVTHQGLSSPVTK

SFNRGEC

Amino acid sequence of 19F3H2 heavy chain variable region with CDR sequences
underlined:
(SEQ ID NO: 97)
QVQLVQSGAEVVKPGASVKVSCKASGYSFTGYTMNWVRQAPGQNLEWIGLINPYNAGTSYNQKFQ

GKVTLTVDKSTSTAYMELSSLRSEDTAVYYCARSEYRYGGDYFDYWGQGTTLTVSS

-continued

Amino acid sequence of 19F3L2 heavy chain variable region with CDR sequences underlined:
(SEQ ID NO: 98)
DIVMTQSPSSLAVSVGERVTISCKSSQSLLNSSNQKNYLAWYQQKPGQAPKLLIYFASTRESGVPDRFS

GSGSGTDFTLTISSVQAEDVADYYCQQHYDTPYTFGGGTKLEIK

Amino acid sequence of 19F3L3 heavy chain variable region with CDR sequences underlined:
(SEQ ID NO: 99)
DIVMTQSPSSLAVSVGERVTISCKSSQSLLNSSNQKNYLAWYQQKPGQAPKLLIYFASTRESGVPDRFS

GSGSGTDFTLTISSLQAEDVAVYYCQQHYDTPYTFGGGTKLEIK

Nucleotide sequence of 19F3L2 light chain (full length)
(SEQ ID NO: 100)
GACATCGTGATGACCCAGTCCCCAAGCTCCCTGGCCGTGTCTGTGGGAGAGCGGGTGACAATCTCCTGTAAGTC

TAGCCAGTCTCTGCTGAACTCCTCTAATCAGAAGAACTACCTGGCCTGGTATCAGCAGAAGCCCGGCCAGGCCC

CTAAGCTGCTGATCTACTTCGCCTCTACCAGGGAGAGCGGAGTGCCAGACAGATTCTCTGGCAGCGGCTCCGGC

ACAGACTTCACCCTGACAATCAGCTCCGTGCAGGCAGAGGACGTGGCAGATTACTATTGCCAGCAGCACTACGA

TACCCCCTATACATTTGGCGGCGGCACCAAGCTGGAGATCAAGCGTACGGTGGCAGCCCCATCTGTCTTCATTT

TTCCCCCTAGTGACGAGCAGCTGAAATCCGGAACAGCCTCTGTGGTCTGTCTGCTGAACAATTTCTACCCTCGC

GAAGCCAAGGTGCAGTGGAAAGTCGATAACGCTCTGCAGAGTGGCAATTCACAGGAGAGCGTGACTGAACAGGA

CTCCAAGGATTCTACCTATAGTCTGAGCTCCACTCTGACCCTGTCCAAAGCAGATTACGAAAAGCACAAAGTGT

ATGCCTGTGAGGTCACCCACCAGGGGCTGAGTTCTCCAGTCACCAAATCCTTCAACAGAGGCGAATGT

---

The invention claimed is:

1. An anti-CD73/anti-PD-1 bispecific antibody comprising:

a first protein functional region targeting PD-1, and a second protein functional region targeting CD73, wherein according to Kabat, Chothia or IMGT numbering system, the first protein functional region comprises: heavy chain complementarity determining region (HCDR)1, HCDR2 and HCDR3 contained in a heavy chain variable region having the amino acid sequence set forth in SEQ ID NO: 44; and light chain complementarity determining region (LCDR)1, LCDR2 and LCDR3 contained in a light chain variable region having the amino acid sequence set forth in SEQ ID NO: 49;

and the second protein functional region comprises: HCDR1, HCDR2 and HCDR3 contained in a heavy chain variable region having the amino acid sequence set forth in SEQ ID NO: 2; and LCDR1, LCDR2 and LCDR3 contained in a light chain variable region having the amino acid sequence set forth in SEQ ID NO: 7.

2. The anti-CD73/anti-PD-1 bispecific antibody according to claim 1, wherein:

the first protein functional region comprises:

a sequence having the amino acid sequence set forth in SEQ ID NO: 44, or a sequence having at least 89% sequence identity to the sequence set forth in SEQ ID NO: 44; and a sequence having the amino acid sequence set forth in SEQ ID NO: 49, or a sequence having at least 90% sequence identity to the sequence set forth in SEQ ID NO: 49; or the first protein functional region comprises:

a sequence having the amino acid sequence set forth in SEQ ID NO: 62, or a sequence having at least 89% sequence identity to the sequence set forth in SEQ ID NO: 62; and a sequence having the amino acid sequence set forth in SEQ ID NO: 64, or a sequence having at least 90% sequence identity to the sequence set forth in SEQ ID NO: 64;

or, the second protein functional region comprises a sequence having the amino acid sequence set forth in SEQ ID NO: 2, or a sequence having at least 86% sequence identity to the sequence set forth in SEQ ID NO: 2; and a sequence having the amino acid sequence set forth in SEQ ID NO: 7, or a sequence having at least 90% sequence identity to the sequence set forth in SEQ ID NO: 7;

or the second protein functional region comprises a sequence having the amino acid sequence set forth in SEQ ID NO: 20, or a sequence having at least 86% sequence identity to the sequence set forth in SEQ ID NO: 20; and a sequence having the amino acid sequence set forth in SEQ ID NO: 22, or a sequence having at least 90% sequence identity to the sequence set forth in SEQ ID NO: 22;

or the second protein functional region comprises a sequence having the amino acid sequence set forth in SEQ ID NO: 20, or a sequence having at least 86% sequence identity to the sequence set forth in SEQ ID NO: 20; and a sequence having the amino acid sequence set forth in SEQ ID NO: 24, or a sequence having at least 90% sequence identity to the sequence set forth in SEQ ID NO: 24, or the second protein functional region comprises a sequence having the amino acid sequence set forth in SEQ ID NO: 93, or a sequence having at least 91% sequence identity to the sequence set forth in SEQ ID NO: 93; and a sequence having the amino acid sequence set forth in SEQ ID NO: 95, or a sequence having at least 94% sequence identity to the sequence set forth in SEQ ID NO: 95.

3. The anti-CD73/anti-PD-1 bispecific antibody according to claim 1, wherein:

the first protein functional region is an immunoglobulin and the second protein functional region is a single chain variable fragment (scFv); or the first protein functional region is a scFv and the second protein functional region is an immunoglobulin, wherein the bispecific antibody is comprised of one immunoglobulin and one or two scFvs.

4. The anti-CD73/anti-PD-1 bispecific antibody according to claim 1 wherein: the first protein functional region and the second protein functional region are linked directly or via a linker.

5. The anti-CD73/anti-PD-1 bispecific antibody according to claim 1, wherein: the first protein functional region and the second protein functional region are independently an immunoglobulin or an antigen-binding fragment, wherein the antigen-binding fragment is Fab, $F(ab')_2$ or a single-chain variable fragment (scFv).

6. The anti-CD73/anti-PD-1 bispecific antibody according to claim 5, wherein:

(i) N terminus of a heavy chain variable region of the antigen-binding fragment is linked directly or via a linker to C terminus of a heavy chain constant region CH1 of the immunoglobulin, and N terminus of a light chain variable region of the antigen-binding fragment is linked directly or via a linker to C terminus of a light chain constant region CL of the immunoglobulin; or (ii) N terminus of a heavy chain variable region of the antigen-binding fragment is linked directly or via a linker to C terminus of a light chain constant region CL of the immunoglobulin, and N terminus of a light chain variable region of the antigen-binding fragment is linked directly or via a linker to C terminus of a heavy chain constant region CH1 of the immunoglobulin; or (ii) C terminus of a heavy chain variable region of the antigen-binding fragment is linked directly or via a linker to N terminus of a heavy chain of the immunoglobulin, and C terminus of a light chain variable region of the antigen-binding fragment is linked directly or via a linker to N terminus of a light chain of the immunoglobulin; or (iv) C terminus of a heavy chain variable region of the antigen-binding fragment is linked directly or via a linker to N terminus of a light chain of the immunoglobulin, and C terminus of a light chain variable region of the antigen-binding fragment is linked directly or via a linker to N terminus of a heavy chain of the immunoglobulin.

7. The anti-CD73/anti-PD-1 bispecific antibody according to claim 6, wherein: the antigen-binding fragment is a single-chain variable fragment; and the first protein functional region is an immunoglobulin and the second protein functional region is a single-chain variable fragment; or the first protein functional region is a single-chain variable fragment and the second protein functional region is an immunoglobulin, wherein the single-chain variable fragment has the following structure: $NH_2$-$V_L$-linker-$V_H$-COOH or $NH_2$-$V_H$-linker-$V_L$-COOH.

8. The anti-CD73/anti-PD-1 bispecific antibody according to claim 7, wherein: when the single-chain variable fragment is linked to C terminus of a heavy chain of the immunoglobulin ($C_H$) or is linked to N terminus of a heavy chain, or is linked to C terminus of CH1 of a heavy chain constant region via a linker, the antibody heavy chain variable region ($V_H$) of the single-chain variable fragment is firstly linked, or the antibody light chain variable region ($V_L$) of the single-chain variable fragment is firstly linked.

9. The anti-CD73/anti-PD-1 bispecific antibody according to claim 7, wherein: the immunoglobulin is IgG, IgA, IgD, IgE or IgM.

10. The anti-CD73/anti-PD-1 bispecific antibody according to claim 7, wherein: a heavy chain variable region of the immunoglobulin has the amino acid sequence set forth in SEQ ID NO: 44, and a light chain variable region of the immunoglobulin has the amino acid sequence set forth in SEQ ID NO: 49; or a heavy chain variable region of the immunoglobulin has the amino acid sequence set forth in SEQ ID NO: 62, and a light chain variable region of the immunoglobulin has the amino acid sequence set forth in SEQ ID NO: 64; or a heavy chain variable region of the single-chain variable fragment has the amino acid sequence set forth in SEQ ID NO: 2, and a light chain variable region of the single-chain variable fragment has the amino acid sequence set forth in SEQ ID NO: 7; or a heavy chain variable region of the single-chain variable fragment has the amino acid sequence set forth in SEQ ID NO: 20, and a light chain variable region of the single-chain variable fragment has the amino acid sequence set forth in by SEQ ID NO: 22; or a heavy chain variable region of the single-chain variable fragment has the amino acid sequence set forth in SEQ ID NO: 20, and a light chain variable region of the single-chain variable fragment has the amino acid sequence set forth in by SEQ ID NO: 24; or a heavy chain variable region of the single-chain variable fragment has the amino acid sequence set forth in SEQ ID NO: 93, and a light chain variable region of the single-chain variable fragment has the amino acid sequence set forth in by SEQ ID NO: 95;

wherein, when the single-chain variable fragment is linked to C terminus of a heavy chain of the immunoglobulin via a linker, the heavy chain variable region ($V_H$) of the single-chain variable fragment may be firstly linked, or the light chain variable region ($V_L$) of the single-chain variable fragment may be firstly linked.

11. The anti-CD73/anti-PD-1 bispecific antibody according to claim 7, wherein:

a heavy chain variable region of the immunoglobulin has the amino acid sequence set forth in SEQ ID NO: 2, and a light chain variable region of the immunoglobulin has the amino acid sequence set forth in SEQ ID NO: 7;

or a heavy chain variable region of the immunoglobulin has the amino acid sequence set forth in SEQ ID NO:

20, and a light chain variable region of the immunoglobulin has the amino acid sequence set forth in SEQ ID NO: 22;

or a heavy chain variable region of the single-chain variable fragment has the amino acid sequence set forth in SEQ ID NO: 20, and a light chain variable region of the single-chain variable fragment has the amino acid sequence set forth in SEQ ID NO: 24;

or a heavy chain variable region of the immunoglobulin has the amino acid sequence set forth in SEQ ID NO: 93, and a light chain variable region of the immunoglobulin has the amino acid sequence set forth in SEQ ID NO: 95;

and/or, a heavy chain variable region of the single-chain variable fragment has the amino acid sequence set forth in SEQ ID NO: 44, and a light chain variable region of the single-chain variable fragment has the amino acid sequence set forth in SEQ ID NO: 49, or a heavy chain variable region of the single-chain variable fragment has the amino acid sequence represented by SEQ ID NO: 62, and a light chain variable region of the single-chain variable fragment has the amino acid sequence set forth in SEQ ID NO: 64, wherein, when the single-chain variable fragment is linked to C terminus of a heavy chain of the immunoglobulin via a linker, the antibody heavy chain variable region ($V_H$) of the single-chain variable fragment may be firstly linked, or, the antibody light chain variable region ($V_L$) may be linked firstly.

12. The anti-CD73/anti-PD-1 bispecific antibody according to claim 7, wherein:

(i) a heavy chain constant region of the immunoglobulin is an Ig gamma-1 chain C region, ACCESSION: P01857; and a light chain constant region of the immunoglobulin is an Ig kappa chain C region, ACCESSION: P01834, or (ii) a heavy chain constant region of the immunoglobulin mutates at any 2 or 3 of positions 234, 235 and 237 based on Ig gamma-1 chain C region, ACCESSION: P01857, and after the mutation, the bispecific antibody has a reduced affinity constant to FcγRIa, FcγRIIIa and/or C1q compared with that before the mutation.

13. A nucleic acid encoding the anti-CD73/anti-PD-1 bispecific antibody according to claim 1.

14. A method of treating a tumor comprising administering the anti-CD73/anti-PD-1 bispecific antibody according to claim 1.

15. An in vivo or in vitro method comprising: administering to a cell or administering to a subject in need thereof an effective amount of the anti-CD73/anti-PD-1 bispecific antibody according to claim 1.

16. A hybridoma cell line deposited at China Center for Type Culture Collection (CCTCC) on Jun. 19, 2018 as LT014 with an accession number of CCTCC NO: C2018137, wherein the hybridoma produces an antibody that binds to CD73.

17. An anti-CD73 monoclonal antibody, wherein the antibody is 19F3H2L3(hG1TM) and has a heavy chain amino acid sequence set forth in SEQ ID NO: 30 and a light chain amino acid sequence set forth in SEQ ID NO: 28.

18. The anti-CD73/anti-PD-1 bispecific antibody according to claim 1, wherein the first protein functional region comprises HCDR1 set forth in SEQ ID NO: 45, HCDR2 set forth in SEQ ID NO: 46, HCDR3 set forth in SEQ ID NO: 47, LCDR1 set forth in SEQ ID NO: 50, LCDR2 set forth in SEQ ID NO: 51 and LCDR3 set forth in SEQ ID NO: 52 respectively;

or the second protein functional region comprises: HCDR1 set forth in SEQ ID NO: 3, HCDR2 set forth in SEQ ID NO: 4, HCDR3 set forth in SEQ ID NO: 5, LCDR1 set forth in SEQ ID NO: 8, LCDR2 set forth in SEQ ID NO: 9 and LCDR3 set forth in SEQ ID NO: 10, respectively.

19. The anti-CD73/anti-PD-1 bispecific antibody according to claim 4, wherein: the linker is (GGGGS)n, as set forth in SEQ ID NO: 101, and n is 1, 2, 3, or 4.

20. The anti-CD73/anti-PD-1 bispecific antibody according to claim 8, wherein (i) a heavy chain variable region of the immunoglobulin comprises complementary determining regions having amino acid sequences set forth in SEQ ID NOs: 3-5, and a light chain variable region of the immunoglobulin comprises complementary determining regions having amino acid sequences set forth in SEQ ID NOs: 8-10;

a heavy chain variable region of the single-chain variable fragment comprises complementary determining regions having amino acid sequences set forth in SEQ ID NOs: 45-47, and a light chain variable region of the single-chain variable fragment comprises complementary determining regions having amino acid sequences set forth in SEQ ID NOs: 50-52, or (ii) a heavy chain variable region of the immunoglobulin comprises complementary determining regions having amino acid sequences set forth in SEQ ID NOs: 45-47, and a light chain variable region of the immunoglobulin comprises complementary determining regions having amino acid sequences set forth in SEQ ID NOs: 50-52;

a heavy chain variable region of the single-chain variable fragment comprises complementary determining regions having amino acid sequences set forth in SEQ ID NOs: 3-5, and a light chain variable region of the single-chain variable fragment comprises complementary determining regions having amino acid sequences set forth in SEQ ID NOs: 8-10.

21. The anti-CD73/anti-PD-1 bispecific antibody according to claim 20, wherein when the single-chain variable fragment $NH_2$-$V_L$-linker-$V_H$-COOH or $NH_2$-$V_H$-linker-$V_L$-COOH is linked to C terminus of the heavy chain of the immunoglobulin via a linker, the antibody heavy chain variable region ($V_H$) of the single-chain variable fragment comprising complementary determining regions having amino acid sequences set forth in SEQ ID NOs: 45-47 may be firstly linked, or the antibody light chain variable region ($V_L$) of the single-chain variable fragment comprising complementary determining regions having amino acid sequences set forth in SEQ ID NOs: 50-52 may be firstly linked, or wherein, when the single-chain variable fragment $NH_2$-$V_L$-linker-$V_H$-COOH or $NH_2$-$V_H$-linker-$V_L$-COOH is linked to C terminus of the heavy chain of the immunoglobulin via a linker, the antibody heavy chain variable region ($V_H$) of the single-chain variable fragment comprising complementary determining regions having amino acid sequences set forth in SEQ ID NOs: 3-5 may be firstly linked, or the antibody light chain variable region ($V_L$) of the single-chain variable fragment comprising complementary determining regions having amino acid sequences set forth in SEQ ID NOs: 8-10 may be firstly linked.

22. The anti-CD73/anti-PD-1 bispecific antibody according to claim 7, wherein:

according to the EU numbering system, a heavy chain constant region of the immunoglobulin has the following mutations at positions 234, 235 and/or 237 based on Ig gamma-1 chain C region, ACCESSION: P01857:

L234A and L235A;

L234A and G237A;

L235A and G237A;

or

L234A, L235A and G237A.

23. The anti-CD73/anti-PD-1 bispecific antibody according to claim 7, wherein: a heavy chain constant region of the immunoglobulin also has one or more mutations selected from the following mutations:

N297A, D265A, D270A, P238D, L328E, E233D, H268D, P271G, A330R, C226S, C229S, E233P, P331S, S267E, L328F, A330L, M252Y, S254T, T256E, N297Q, P238S, P238A, A327Q, A327G, P329A, K322A, T394D, G236R, G236A, L328R, A330S, P331S, H268A, E318A and K320A.

24. The anti-CD73/anti-PD-1 bispecific antibody according to claim 7, wherein: the anti-CD73/anti-PD-1 bispecific antibody is selected from the group consisting of:

(i) P1D7V01, of which a heavy chain in the immunoglobulin has the amino acid sequence set forth in SEQ ID NO: 66, a light chain in the immunoglobulin has the amino acid sequence set forth in SEQ ID NO: 68, linker 1 has the amino acid sequence set forth in SEQ ID NO: 79, the scFv consists of a heavy chain variable region having the amino acid set forth in SEQ ID NO: 20, linker 1 having the amino acid sequence set forth in SEQ ID NO: 79, and a light chain variable region having the amino acid set forth in SEQ ID NO: 24, (ii) P1D7V02R, of which a heavy chain in the immunoglobulin has the amino acid sequence set forth in SEQ ID NO: 66, a light chain in the immunoglobulin has the amino acid sequence set forth in SEQ ID NO: 68, linker 1 has the amino acid sequence set forth in SEQ ID NO: 79, the scFv consists of a light chain variable region having the amino acid set forth in SEQ ID NO: 24, linker 1 having the amino acid sequence set forth in SEQ ID NO: 79, and a heavy chain variable region having the amino acid set forth in SEQ ID NO: 20, (iii) P1D7V03, of which a heavy chain in the immunoglobulin has the amino acid sequence set forth in SEQ ID NO: 66, a light chain in the immunoglobulin has the amino acid sequence set forth in SEQ ID NO: 68, linker 1 has the amino acid sequence set forth in SEQ ID NO: 81, the scFv has a heavy chain variable region having the amino acid set forth in SEQ ID NO: 20, linker 1 having the amino acid sequence set forth in SEQ ID NO: 79, and a light chain variable region having the amino acid set forth in SEQ ID NO: 24, (iv) P1D7V04R, of which a heavy chain in the immunoglobulin has the amino acid sequence set forth in SEQ ID NO: 66, a light chain in the immunoglobulin has the amino acid sequence set forth in SEQ ID NO: 68, linker 1 has the amino acid sequence set forth in SEQ ID NO: 81, the scFv consists of a light chain variable region having the amino acid set forth in SEQ ID NO: 24, linker 1 having the amino acid sequence set forth in SEQ ID NO: 79, and a heavy chain variable region having the amino acid set forth in SEQ ID NO: 20.

25. The anti-CD73/anti-PD-1 bispecific antibody according to claim 7, wherein: the anti-CD73/anti-PD-1 bispecific antibody has a structure shown as heavy chain-light chain-linker 1-scFv, and the scFv is selected from 14C12H1V-linker 2-14C12L1V, 14C12H1V-linker 1-14C12L1V, particularly selected from the group consisting of:

(i) NTPDV1, of which a heavy chain has the amino acid sequence set forth in SEQ ID NO: 85, a light chain has the amino acid sequence set forth in SEQ ID NO: 28, linker 1 has the amino acid sequence set forth in SEQ ID NO: 79, 14C12H1V has the amino acid sequence set forth in SEQ ID NO: 62, linker 2 has the amino acid sequence set forth in SEQ ID NO: 81, and 14C12L1V has the amino acid sequence set forth in SEQ ID NO: 64;

(ii) NTPDV2, of which a heavy chain has the amino acid sequence set forth in SEQ ID NO: 83, a light chain has the amino acid sequence set forth in SEQ ID NO: 28, linker 1 has the amino acid sequence set forth in SEQ ID NO: 79, 14C12H1V has the amino acid sequence set forth in SEQ ID NO: 62, linker 1 has the amino acid sequence set forth in SEQ ID NO: 79, and 14C12L1V has the amino acid sequence set forth in SEQ ID NO: 64;

(iii) NTPDV3, of which a heavy chain has the amino acid sequence set forth in SEQ ID NO: 85, a light chain has the amino acid sequence set forth in SEQ ID NO: 96, linker 1 has the amino acid sequence set forth in SEQ ID NO: 79, 14C12H1V has the amino acid sequence set forth in SEQ ID NO: 62, linker 2 has the amino acid sequence set forth in SEQ ID NO: 81, and 14C12L1V has the amino acid sequence set forth in SEQ ID NO: 64; and (iv) NTPDV4, of which a heavy chain has the amino acid sequence set forth in SEQ ID NO: 83, a light chain has the amino acid sequence set forth in SEQ ID NO: 96, linker 1 has the amino acid sequence set forth in SEQ ID NO: 79, 14C12H1V has the amino acid sequence set forth in SEQ ID NO: 62, linker 1 has the amino acid sequence set forth in SEQ ID NO: 79, and 14C12L1V has the amino acid sequence set forth in SEQ ID NO: 64.

* * * * *